US012706184B2

(12) United States Patent
Soli

(10) Patent No.: US 12,706,184 B2
(45) Date of Patent: Aug. 11, 2026

(54) SYSTEMS AND METHODS FOR DISPLAYING AGGREGATED HEALTH RECORDS

(71) Applicant: Apple Inc., Cupertino, CA (US)

(72) Inventor: Christopher D Soli, Santa Cruz, CA (US)

(73) Assignee: Apple Inc., Cupertino, CA (US)

( * ) Notice: Subject to any disclaimer, the term of this patent is extended or adjusted under 35 U.S.C. 154(b) by 113 days.

(21) Appl. No.: 16/249,627

(22) Filed: Jan. 16, 2019

(65) Prior Publication Data

US 2019/0228847 A1 Jul. 25, 2019

Related U.S. Application Data

(60) Provisional application No. 62/620,455, filed on Jan. 22, 2018.

(51) Int. Cl.
*G16H 10/60* (2018.01)
*G06F 3/0482* (2013.01)
*G16H 40/20* (2018.01)

(52) U.S. Cl.
CPC .......... *G16H 10/60* (2018.01); *G06F 3/0482* (2013.01); *G16H 40/20* (2018.01)

(58) Field of Classification Search
None
See application file for complete search history.

(56) References Cited

U.S. PATENT DOCUMENTS

| | | |
|---|---|---|
| 5,515,344 A | 5/1996 | Ng |
| 6,600,696 B1 | 7/2003 | Lynn |
| 6,603,477 B1 | 8/2003 | Tittle |

(Continued)

FOREIGN PATENT DOCUMENTS

| | | |
|---|---|---|
| CN | 1585943 A | 2/2005 |
| CN | 1752973 A | 3/2006 |

(Continued)

OTHER PUBLICATIONS

Office Action received for Chinese Patent Application No. 201380081349.6, mailed on Jan. 5, 2021, 16 pages (7 pages of English Translation and 9 pages of Official Copy).

(Continued)

*Primary Examiner* — Lena Najarian
(74) *Attorney, Agent, or Firm* — YHE Law LLP

(57) ABSTRACT

The present disclosure generally relates to displaying aggregated health records on an electronic device. The method includes receiving a request to display health records for a user while the device is associated with one health care provider. The method also includes displaying categories of health records in response to receiving the first request, where selection of a category while the device is associated with the health care provider causes the device to display health records of the category from the health care provider. The method also includes receiving a second request to display health records for the user while the device is associated with two health care providers, where selection of a category while the device is associated with both health care providers causes the device to display health records in the selected category that is from both health care providers.

51 Claims, 83 Drawing Sheets

(56) References Cited

U.S. PATENT DOCUMENTS 6,950,839 B1 9/2005 Green et al.
7,107,546 B2 9/2006 Coulthard
7,166,078 B2 1/2007 Saini et al.
8,725,527 B1 5/2014 Kahn et al.
8,888,707 B2 11/2014 Shirasaki et al.
9,224,291 B2 12/2015 Moll-Carrillo et al.
9,579,060 B1 2/2017 Lisy et al.
9,589,445 B2 3/2017 White et al.
9,606,695 B2 3/2017 Matas
9,672,715 B2 6/2017 Roberts et al.
9,712,629 B2 7/2017 Molettiere et al.
9,721,066 B1 8/2017 Funaro et al.
9,730,621 B2 8/2017 Cohen et al.
9,740,825 B2 8/2017 Sansale et al.
9,808,206 B1 11/2017 Zhao et al.
9,940,682 B2 4/2018 Hoffman et al.
10,004,451 B1 6/2018 Proud
10,150,002 B2 12/2018 Kass et al.
10,254,911 B2 4/2019 Yang
10,275,262 B1 4/2019 Bull et al.
10,339,830 B2 7/2019 Han et al.
10,365,811 B2 7/2019 Robinson et al.
10,576,327 B2 3/2020 Kim et al.
10,592,088 B2 3/2020 Robinson et al.
10,602,964 B2 3/2020 Kerber
10,635,267 B2 4/2020 Williams
10,674,942 B2 6/2020 Williams et al.
10,692,593 B1* 6/2020 Young .................... G16H 10/60
10,762,990 B1 9/2020 Schilling et al.
10,777,314 B1 9/2020 Williams et al.
10,796,549 B2 10/2020 Roberts et al.
10,978,195 B2 4/2021 Blahnik et al.
11,103,161 B2 8/2021 Williams et al.
11,107,580 B1 8/2021 Felton et al.
11,209,957 B2 12/2021 Dryer et al.
2001/0039503 A1 11/2001 Chan et al.
2002/0095292 A1 7/2002 Mittal et al.
2003/0126114 A1 7/2003 Tedesco
2003/0130867 A1 7/2003 Coelho et al.
2003/0140044 A1 7/2003 Mok et al.
2003/0200483 A1 10/2003 Sutton
2004/0034288 A1* 2/2004 Hennessy .............. G16H 50/20
600/300
2004/0077958 A1 4/2004 Kato et al.
2004/0081024 A1 4/2004 Weng
2004/0193069 A1 9/2004 Takehara
2004/0210117 A1 10/2004 Ueno et al.
2005/0027208 A1 2/2005 Shiraishi et al.
2005/0079905 A1 4/2005 Martens
2005/0149362 A1 7/2005 Peterson et al.
2005/0165627 A1 7/2005 Fotsch et al.
2005/0187794 A1 8/2005 Kimak
2006/0074863 A1 4/2006 Kishore et al.
2006/0094969 A1 5/2006 Nissila
2006/0117014 A1 6/2006 Qi
2006/0136173 A1 6/2006 Case, Jr. et al.
2006/0205564 A1 9/2006 Peterson
2007/0016440 A1 1/2007 Stroup
2007/0033066 A1 2/2007 Ammer et al.
2007/0179434 A1 8/2007 Weinert et al.
2007/0250505 A1 10/2007 Yang et al.
2007/0250613 A1 10/2007 Gulledge
2008/0005106 A1 1/2008 Schumacher et al.
2008/0012701 A1 1/2008 Kass et al.
2008/0021884 A1 1/2008 Jones et al.
2008/0133742 A1 6/2008 Southiere et al.
2008/0146892 A1 6/2008 Leboeuf et al.
2008/0172361 A1 7/2008 Wong et al.
2008/0228045 A1 9/2008 Gao et al.
2008/0243885 A1 10/2008 Harger et al.
2009/0012821 A1 1/2009 Besson et al.
2009/0054743 A1 2/2009 Stewart
2009/0065578 A1 3/2009 Peterson et al.
2009/0105552 A1 4/2009 Nishiyama et al.
2009/0172773 A1 7/2009 Moore
2009/0192823 A1 7/2009 Hawkins et al.
2009/0216556 A1 8/2009 Martin et al.
2009/0235253 A1 9/2009 Hope
2009/0240521 A1 9/2009 Simons et al.
2009/0249076 A1 10/2009 Reed et al.
2009/0292561 A1 11/2009 Itoh
2009/0307105 A1* 12/2009 Lemay ................ G06F 3/04817
705/26.1
2009/0319243 A1 12/2009 Suarez-Rivera et al.
2010/0042949 A1 2/2010 Chen
2010/0094658 A1* 4/2010 Mok ...................... G16H 10/60
705/3
2010/0099539 A1 4/2010 Haataja
2010/0103101 A1 4/2010 Song et al.
2010/0119093 A1 5/2010 Uzuanis et al.
2010/0132044 A1 5/2010 Kogan et al.
2010/0161353 A1 6/2010 Mayaud
2010/0179832 A1 7/2010 Van et al.
2010/0222645 A1 9/2010 Nadler et al.
2010/0269157 A1 10/2010 Experton
2010/0292600 A1 11/2010 Dibenedetto et al.
2010/0305965 A1 12/2010 Benjamin et al.
2010/0312138 A1 12/2010 Regas
2011/0010195 A1 1/2011 Cohn
2011/0071765 A1 3/2011 Yodfat et al.
2011/0093481 A1 4/2011 Hussam
2011/0106553 A1 5/2011 Tanaka et al.
2011/0106557 A1* 5/2011 Gazula ................... G06Q 10/10
715/740
2011/0119088 A1 5/2011 Gunn et al.
2011/0137678 A1 6/2011 Williams
2011/0152656 A1 6/2011 Weinert et al.
2011/0166631 A1 7/2011 Breining
2011/0195383 A1 8/2011 Weiss
2011/0201911 A1 8/2011 Johnson et al.
2011/0214162 A1 9/2011 Brakensiek et al.
2011/0218407 A1 9/2011 Haberman et al.
2011/0246509 A1 10/2011 Migita et al.
2011/0306389 A1 12/2011 Nagayama
2012/0015778 A1 1/2012 Lee et al.
2012/0023586 A1 1/2012 Flickner et al.
2012/0041767 A1 2/2012 Hoffman et al.
2012/0059664 A1 3/2012 Georgiev et al.
2012/0112908 A1 5/2012 Prykaeri et al.
2012/0185267 A1 7/2012 Kamen et al.
2012/0203124 A1 8/2012 Lim
2012/0215115 A1 8/2012 Takahashi
2012/0232929 A1 9/2012 Experton
2012/0245447 A1 9/2012 Karan et al.
2012/0272186 A1 10/2012 Kraut
2012/0283524 A1 11/2012 Kiani et al.
2012/0283855 A1 11/2012 Hoffman et al.
2012/0302840 A1 11/2012 Kubo
2012/0302843 A1 11/2012 Otsubo et al.
2012/0311585 A1 12/2012 Gruber et al.
2012/0316455 A1 12/2012 Rahman et al.
2013/0011819 A1 1/2013 Horseman
2013/0012788 A1 1/2013 Horseman
2013/0013331 A1 1/2013 Horseman
2013/0054150 A1 2/2013 Sacks et al.
2013/0072765 A1 3/2013 Kahn et al.
2013/0095459 A1 4/2013 Tran
2013/0106603 A1 5/2013 Weast et al.
2013/0106684 A1 5/2013 Weast et al.
2013/0141233 A1 6/2013 Jacobs et al.
2013/0144653 A1 6/2013 Poe et al.
2013/0158367 A1 6/2013 Pacione et al.
2013/0187923 A1 7/2013 Yoshimoto et al.
2013/0191647 A1 7/2013 Ferrara et al.
2013/0262155 A1 10/2013 Hinkamp
2013/0268398 A1 10/2013 Agami et al.
2013/0274628 A1 10/2013 Fausti et al.
2013/0304510 A1 11/2013 Chen et al.
2013/0304616 A1 11/2013 Raleigh et al.
2013/0310726 A1 11/2013 Miller et al.
2013/0325396 A1 12/2013 Yuen et al.
2013/0325493 A1* 12/2013 Wong ..................... G16Z 99/00
705/2
2013/0325511 A1 12/2013 Neagle et al.

(56) References Cited

U.S. PATENT DOCUMENTS

2014/0005947 A1 1/2014 Jeon et al.
2014/0019162 A1* 1/2014 Skowronski ........... G16H 50/20 705/3
2014/0046926 A1 2/2014 Walton
2014/0073486 A1 3/2014 Ahmed et al.
2014/0088995 A1 3/2014 Damani
2014/0100885 A1* 4/2014 Stern ..................... G16H 50/30 705/3
2014/0127996 A1 5/2014 Park et al.
2014/0129007 A1 5/2014 Utter, II
2014/0129243 A1 5/2014 Utter, II
2014/0135592 A1 5/2014 Ohnemus et al.
2014/0142403 A1 5/2014 Brumback et al.
2014/0143678 A1 5/2014 Mistry et al.
2014/0156292 A1 6/2014 Kozicki et al.
2014/0164611 A1 6/2014 Molettiere et al.
2014/0176335 A1 6/2014 Brumback et al.
2014/0180595 A1 6/2014 Brumback et al.
2014/0184422 A1 7/2014 Mensinger et al.
2014/0197946 A1 7/2014 Park et al.
2014/0200426 A1 7/2014 Taub et al.
2014/0222446 A1 8/2014 Ash et al.
2014/0266776 A1 9/2014 Miller et al.
2014/0278220 A1 9/2014 Yuen
2014/0297217 A1 10/2014 Yuen
2014/0310643 A1 10/2014 Karmanenko et al.
2014/0344687 A1 11/2014 Durham et al.
2014/0354494 A1 12/2014 Katz
2014/0358012 A1 12/2014 Richards et al.
2014/0358584 A1 12/2014 Worden et al.
2015/0089536 A1 3/2015 Byerley
2015/0100245 A1 4/2015 Huang et al.
2015/0100348 A1 4/2015 Connery et al.
2015/0106025 A1 4/2015 Keller et al.
2015/0120633 A1 4/2015 Norlander et al.
2015/0125832 A1 5/2015 Tran
2015/0164349 A1 6/2015 Gopalakrishnan et al.
2015/0173686 A1 6/2015 Furuta et al.
2015/0182843 A1 7/2015 Esposito et al.
2015/0186602 A1 7/2015 Pipke et al.
2015/0193217 A1 7/2015 Xiang et al.
2015/0205930 A1 7/2015 Shaanan et al.
2015/0205947 A1 7/2015 Berman et al.
2015/0230717 A1 8/2015 Wan
2015/0261918 A1 9/2015 Thornbury, Jr.
2015/0262499 A1 9/2015 Wicka et al.
2015/0286800 A1 10/2015 Kanagala et al.
2015/0288797 A1 10/2015 Vincent
2015/0289823 A1 10/2015 Rack-Gomer et al.
2015/0324751 A1 11/2015 Orenstein et al.
2015/0343709 A1 12/2015 Gerstle et al.
2015/0347690 A1 12/2015 Keen et al.
2015/0347711 A1 12/2015 Soli et al.
2015/0350861 A1 12/2015 Soli et al.
2016/0019360 A1 1/2016 Pahwa et al.
2016/0027282 A1 1/2016 Lee
2016/0055420 A1 2/2016 Karanam et al.
2016/0058336 A1 3/2016 Blahnik et al.
2016/0058337 A1 3/2016 Blahnik et al.
2016/0062540 A1 3/2016 Yang et al.
2016/0063215 A1 3/2016 Zamer
2016/0066842 A1 3/2016 Kokkoneva et al.
2016/0078778 A1 3/2016 Holland
2016/0086500 A1 3/2016 Kaleal, III
2016/0089569 A1 3/2016 Blahnik
2016/0098522 A1 4/2016 Weinstein
2016/0103985 A1 4/2016 Shim et al.
2016/0106398 A1 4/2016 Kuppuswami
2016/0107031 A1 4/2016 Palatsi et al.
2016/0110523 A1 4/2016 Francois
2016/0132645 A1* 5/2016 Charpentier ........... G16H 10/60 705/3
2016/0135719 A1 5/2016 Von Kraus et al.
2016/0135731 A1 5/2016 Drennan
2016/0150978 A1 6/2016 Yuen et al.
2016/0166181 A1 6/2016 Shennib
2016/0166195 A1 6/2016 Radecka et al.
2016/0180026 A1 6/2016 Kim et al.
2016/0189051 A1 6/2016 Mahmood
2016/0210099 A1 7/2016 Hampapuram et al.
2016/0210434 A1 7/2016 Al-Sharif
2016/0235374 A1 8/2016 Miller et al.
2016/0256741 A1 9/2016 Holma et al.
2016/0270717 A1 9/2016 Luna et al.
2016/0270740 A1 9/2016 Raisoni et al.
2016/0275310 A1 9/2016 Edwards et al.
2016/0285985 A1 9/2016 Molettiere et al.
2016/0287177 A1 10/2016 Huppert et al.
2016/0296210 A1 10/2016 Matsushima
2016/0313869 A1 10/2016 Jang et al.
2016/0314670 A1 10/2016 Roberts et al.
2016/0317341 A1 11/2016 Galvan
2016/0324488 A1 11/2016 Olsen
2016/0328991 A1 11/2016 Simpson et al.
2016/0332025 A1 11/2016 Repka
2016/0357403 A1 12/2016 Chang et al.
2016/0357616 A1 12/2016 Yu et al.
2016/0360972 A1 12/2016 Kusakabe et al.
2016/0367138 A1 12/2016 Kim et al.
2016/0379511 A1 12/2016 Dawson et al.
2017/0000348 A1 1/2017 Karsten et al.
2017/0039327 A1 2/2017 Bitran et al.
2017/0042485 A1 2/2017 Chung et al.
2017/0043214 A1 2/2017 Higashi
2017/0046052 A1 2/2017 Lee et al.
2017/0046108 A1 2/2017 Kang et al.
2017/0053542 A1 2/2017 Wilson et al.
2017/0071551 A1 3/2017 Jain et al.
2017/0075551 A1 3/2017 Robinson et al.
2017/0084196 A1 3/2017 Nusbaum et al.
2017/0128003 A1 5/2017 Lim
2017/0132395 A1 5/2017 Futch
2017/0136297 A1 5/2017 Penie
2017/0140143 A1 5/2017 Ahmad et al.
2017/0147197 A1 5/2017 Yang et al.
2017/0150917 A1 6/2017 Brief et al.
2017/0156593 A1 6/2017 Ferber et al.
2017/0177797 A1 6/2017 Kurniawan et al.
2017/0181645 A1 6/2017 Mahalingam et al.
2017/0181678 A1 6/2017 Newberry
2017/0188893 A1 7/2017 Venkatraman et al.
2017/0188979 A1 7/2017 Volpe
2017/0215811 A1 8/2017 Newberry
2017/0225034 A1 8/2017 Kass et al.
2017/0235443 A1 8/2017 Suzuki
2017/0258455 A1 9/2017 Qi
2017/0274267 A1 9/2017 Blahnik
2017/0281057 A1 10/2017 Blahnik et al.
2017/0300643 A1* 10/2017 Bezark .................. G16H 20/70
2017/0319184 A1 11/2017 Sano
2017/0329933 A1 11/2017 Brust et al.
2017/0332980 A1 11/2017 Fifield et al.
2017/0354845 A1 12/2017 Williams et al.
2017/0364637 A1 12/2017 Kshepakaran et al.
2018/0042559 A1 2/2018 Cabrera et al.
2018/0055490 A1 3/2018 Lee et al.
2018/0056130 A1 3/2018 Bitran et al.
2018/0064388 A1 3/2018 Heneghan et al.
2018/0070861 A1 3/2018 Eastman et al.
2018/0078182 A1 3/2018 Chen et al.
2018/0078197 A1 3/2018 Ware et al.
2018/0081918 A1 3/2018 Gravenites et al.
2018/0096739 A1 4/2018 Sano
2018/0107962 A1 4/2018 Lundin et al.
2018/0110465 A1 4/2018 Naima
2018/0117414 A1 5/2018 Miyasaka et al.
2018/0120985 A1 5/2018 Wallace et al.
2018/0132768 A1 5/2018 Sasahara et al.
2018/0137937 A1 5/2018 Gass et al.
2018/0140211 A1 5/2018 Nakazawa et al.
2018/0140927 A1 5/2018 Kito et al.
2018/0154212 A1 6/2018 Park et al.
2018/0157864 A1 6/2018 Tribble et al.
2018/0189343 A1 7/2018 Embiricos et al.

(56) References Cited

U.S. PATENT DOCUMENTS

2018/0211020 A1 7/2018 Fukuda
2018/0226150 A1 8/2018 Hayter et al.
2018/0232494 A1 8/2018 Leppala et al.
2018/0239869 A1 8/2018 Laing et al.
2018/0255159 A1 9/2018 Cohen et al.
2018/0256036 A1 9/2018 Kogure et al.
2018/0256078 A1 9/2018 Vaterlaus
2018/0256095 A1 9/2018 Arnold et al.
2018/0263510 A1 9/2018 Cronin et al.
2018/0263517 A1 9/2018 Kubo
2018/0279885 A1 10/2018 Bulut
2018/0294053 A1 10/2018 Runyon et al.
2018/0329584 A1 11/2018 Williams et al.
2018/0336530 A1 11/2018 Johnson et al.
2018/0345078 A1 12/2018 Blahnik et al.
2018/0350451 A1 12/2018 Ohnemus et al.
2018/0350453 A1 12/2018 Nag et al.
2018/0368814 A1 12/2018 Kudtarkar
2018/0376107 A1 12/2018 Shibaev et al.
2019/0014205 A1 1/2019 Miloseski et al.
2019/0018588 A1 1/2019 Debates et al.
2019/0034050 A1 1/2019 Williams et al.
2019/0034494 A1 1/2019 Bradley et al.
2019/0090800 A1 3/2019 Bosworth et al.
2019/0090816 A1 3/2019 Horseman
2019/0108908 A1 4/2019 Faulks et al.
2019/0122523 A1 4/2019 Roberts et al.
2019/0138696 A1 5/2019 Carpenter et al.
2019/0150854 A1 5/2019 Chung et al.
2019/0192086 A1 6/2019 Menon et al.
2019/0206538 A1 7/2019 Xing et al.
2019/0223843 A1 7/2019 Vitti
2019/0228179 A1 7/2019 Rakshit et al.
2019/0240534 A1 8/2019 Black
2019/0252054 A1 8/2019 Dirani et al.
2019/0274563 A1 9/2019 Soli et al.
2019/0274565 A1 9/2019 Soli et al.
2019/0298230 A1 10/2019 Nicholson et al.
2019/0302995 A1 10/2019 Robinson et al.
2019/0333614 A1 10/2019 Burger et al.
2019/0341027 A1 11/2019 Vescovi et al.
2019/0365332 A1 12/2019 Fedichev et al.
2019/0380624 A1 12/2019 Ota et al.
2019/0380653 A1 12/2019 Benson et al.
2019/0385708 A1 12/2019 Hong et al.
2020/0000441 A1 1/2020 Lafon et al.
2020/0054931 A1 2/2020 Martin et al.
2020/0069258 A1 3/2020 Grinberg
2020/0100693 A1 4/2020 Velo
2020/0126673 A1 4/2020 Tanabe et al.
2020/0203012 A1 6/2020 Kamath et al.
2020/0214650 A1 7/2020 Lee et al.
2020/0245928 A1 8/2020 Kang et al.
2020/0261011 A1 8/2020 Seppänen et al.
2020/0273566 A1 8/2020 Bhowmik et al.
2020/0315544 A1 10/2020 Levine
2020/0323441 A1 10/2020 Deno et al.
2020/0350052 A1 11/2020 Saint et al.
2020/0356687 A1 11/2020 Salzman et al.
2020/0357522 A1 11/2020 Pahwa et al.
2020/0374682 A1 11/2020 Newman et al.
2020/0379611 A1 12/2020 Dryer et al.
2020/0381099 A1 12/2020 Crowley et al.
2020/0381100 A1 12/2020 Williams et al.
2020/0381123 A1 12/2020 Dryer et al.
2020/0384314 A1 12/2020 Lee et al.
2021/0019713 A1 1/2021 Vangala et al.
2021/0068714 A1 3/2021 Crowley et al.
2021/0204815 A1 7/2021 Koskela et al.
2021/0210182 A1 7/2021 Nag et al.
2021/0225482 A1 7/2021 Crowley et al.
2021/0257091 A1 8/2021 Spang et al.
2021/0369130 A1 12/2021 Felton et al.
2021/0373746 A1 12/2021 Felton et al.
2021/0373747 A1 12/2021 Felton et al.
2021/0373748 A1 12/2021 Felton et al.
2021/0375157 A1 12/2021 Sundstrom et al.
2021/0375450 A1 12/2021 Felton et al.
2021/0401378 A1 12/2021 Pho et al.
2022/0047212 A1 2/2022 Balsamo et al.
2022/0047250 A1 2/2022 Clements et al.
2022/0066902 A1 3/2022 Narra et al.
2022/0142515 A1 5/2022 Crowley
2022/0157143 A1 5/2022 Panneer Selvam et al.
2022/0262509 A1 8/2022 Pahwa et al.
2022/0273204 A1 9/2022 Kamath et al.
2022/0328161 A1 10/2022 Gilravi et al.
2023/0014290 A1 1/2023 Davydov et al.
2023/0016144 A1 1/2023 Dryer et al.
2023/0020517 A1 1/2023 Narra et al.
2023/0025724 A1 1/2023 Gilravi et al.
2023/0027358 A1 1/2023 Williams et al.
2023/0114054 A1 4/2023 Crowley et al.
2024/0013889 A1 1/2024 Crowley et al.
2024/0053862 A1 2/2024 Narra et al.

FOREIGN PATENT DOCUMENTS

CN 101107619 A 1/2008
CN 101150810 A 3/2008
CN 101651870 A 2/2010
CN 102339201 A 2/2012
CN 102790761 A 11/2012
CN 103250158 A 8/2013
CN 103370924 A 10/2013
CN 105260078 A 1/2016
CN 105388998 A 3/2016
CN 105721667 A 6/2016
CN 106415559 A 2/2017
CN 106537397 A 3/2017
CN 108604327 A 9/2018
CN 111344796 A 6/2020
EP 1077046 A1 2/2001
EP 2568409 A1 3/2013
EP 2921899 A2 9/2015
EP 3096235 A1 11/2016
EP 3101882 A2 12/2016
EP 3557590 A1 10/2019
JP 6-187118 A 7/1994
JP 2001-76078 A 3/2001
JP 2003-337863 A 11/2003
JP 2004-102609 A 4/2004
JP 2004-113466 A 4/2004
JP 2004-318503 A 11/2004
JP 2006-155104 A 6/2006
JP 2006-230679 A 9/2006
JP 2008-183339 A 8/2008
JP 2009-282670 A 12/2009
JP 2010-12335 A 1/2010
JP 2010-122901 A 6/2010
JP 2010-186249 A 8/2010
JP 2011-125633 A 6/2011
JP 2011-183101 A 9/2011
JP 2011-192126 A 9/2011
JP 2011-210119 A 10/2011
JP 2011-259253 A 12/2011
JP 2012-59264 A 3/2012
JP 2011-200575 A 11/2012
JP 2012-239808 A 12/2012
JP 2013-117690 A 6/2013
JP 2015-213686 A 12/2015
JP 2016-538926 A 12/2016
JP 2017-529880 A 10/2017
JP 2017-532069 A 11/2017
KR 10-2006-0117570 A 11/2006
KR 10-2011-0017076 A 2/2011
KR 10-2012-0076559 A 7/2012
KR 10-2013-0043698 A 5/2013
KR 10-2013-0093837 A 8/2013
KR 10-2013-0135282 A 12/2013
KR 10-2016-0028351 A 3/2016
KR 10-2016-0076264 A 6/2016
KR 10-2017-0019040 A 2/2017
KR 10-2017-0019745 A 2/2017

(56) References Cited

FOREIGN PATENT DOCUMENTS

| | | | | |
|---|---|---|---|---|
| KR | 10-2017-0020085 A | 2/2017 | | |
| KR | 10-2018-0129188 A | 12/2018 | | |
| KR | 10-2019-0094795 A | 8/2019 | | |
| WO | 1999/41682 A2 | 8/1999 | | |
| WO | 2001/96986 A2 | 12/2001 | | |
| WO | 2002/27530 A2 | 4/2002 | | |
| WO | WO-0241134 A2 * | 5/2002 | ............ G06Q 10/10 | |
| WO | 2008/073359 A2 | 6/2008 | | |
| WO | 2009/095908 A2 | 8/2009 | | |
| WO | 2012/048832 A1 | 4/2012 | | |
| WO | 2012/078079 A2 | 6/2012 | | |
| WO | 2012/086910 A1 | 6/2012 | | |
| WO | 2013/052789 A1 | 4/2013 | | |
| WO | 2013/109916 A1 | 7/2013 | | |
| WO | 2014/006862 A1 | 1/2014 | | |
| WO | 2014/207875 A1 | 12/2014 | | |
| WO | 2015/084353 A1 | 6/2015 | | |
| WO | 2015/164845 A1 | 10/2015 | | |
| WO | 2015/183828 A1 | 12/2015 | | |
| WO | 2016/036472 A1 | 3/2016 | | |
| WO | 2016/036582 A2 | 3/2016 | | |
| WO | 2016/179559 A2 | 11/2016 | | |
| WO | 2017/054277 A1 | 4/2017 | | |
| WO | 2017/172046 A1 | 10/2017 | | |
| WO | 2018/132507 A1 | 7/2018 | | |
| WO | 2018/222313 A1 | 12/2018 | | |
| WO | 2019/017508 A1 | 1/2019 | | |
| WO | 2019/099553 A1 | 5/2019 | | |
| WO | 2019/168956 A1 | 9/2019 | | |
| WO | 2019/240513 A1 | 12/2019 | | |
| WO | 2021/212112 A1 | 10/2021 | | |
| WO | 2022/010573 A1 | 1/2022 | | |

OTHER PUBLICATIONS

Epstein et al., "Examining Menstrual Tracking to Inform the Design of Personal Informatics Tools", Proceedings of the 2017 CHI Conference on Human Factors in Computing Systems, CHI '17, ACM Press, Denver, CO, USA, May 6-11, 2017, pp. 6876-6888.

Moglia et al., "Evaluation of Smartphone Menstrual Cycle Tracking Applications Using an Adapted Applications Scoring System", Obstetrics and Gynecology, vol. 127, No. 6, Jun. 2016, pp. 1153-1160.

Bagala et al., "Evaluation of Accelerometer-Based Fall Detection Algorithms on Real-World Falls", PloS ONE, vol. 7, No. 5, May 16, 2012, 9 pages.

Office Action received for Korean Patent Application No. 10-2019-7025781, mailed on Oct. 30, 2020, 10 pages (4 pages of English Translation and 6 pages of Official Copy).

International Search Report and Written Opinion received for PCT Patent Application No. PCT/US2020/042439, mailed on Oct. 9, 2020, 14 pages.

Lovejoy Ben, "Apple Watch blood sugar measurement coming in Series 7, claims report", Available Online at: https://9to5mac.com/2021/01/25/apple-watch-blood-sugar-measurement/, Jan. 25, 2021, 6 pages.

Office Action received for Japanese Patent Application No. 2020-000492, mailed on Dec. 11, 2020, 6 pages (3 pages English Translation and 3 pages of Official Copy).

Applicant Initiated Interview Summary received for U.S. Appl. No. 16/586,154, mailed on Mar. 11, 2020, 4 pages.

Final Office Action received for U.S. Appl. No. 16/586,154, mailed on Jul. 6, 2020, 27 pages.

International Search Report and Written Opinion received for PCT Patent Application No. PCT/US2020/035462, mailed on Sep. 11, 2020, 17 pages.

Invitation to Pay Additional Fees and Partial International Search Report received for PCT Patent Application No. PCT/US2020/035164, mailed on Oct. 16, 2020, 14 pages.

Non-Final Office Action received for U.S. Appl. No. 16/586,154, mailed on Dec. 9, 2019, 23 pages.

Non-Final Office Action received for U.S. Appl. No. 16/880,714, mailed on Oct. 28, 2020, 11 pages.

International Search Report and Written Opinion mailed Jun. 4, 2019 in International Patent Application No. PCT/US2019/014215.

Invitation to Pay Additional Fees and Partial Search Report received for PCT Patent Application No. PCT/US2020/070280, mailed on Oct. 7, 2020, 12 pages.

Non-Final Office Action received for U.S. Appl. No. 16/586,154, mailed on Dec. 28, 2020, 26 pages.

Search Report and Opinion received for Danish Patent Application No. PA202070620, mailed on Dec. 11, 2020, 9 pages.

Applicant-Initiated Interview Summary received for U.S. Appl. No. 16/586,154, mailed on Dec. 11, 2020, 5 pages.

Board Decision received for Chinese Patent Application No. 201380081349.6, mailed on Nov. 23, 2020, 2 pages (1 page of English Translation and 1 page of Official Copy).

Non-Final Office Action received for U.S. Appl. No. 16/820,383, mailed on Dec. 14, 2020, 11 pages.

Tech, Kalyani, "I See Some problems in Honor Band 5", Retrieved from: https://www.youtube.com/watch?v=5XPnYJFqajl, May 19, 2020, 1 page.

Ticks, Smartwatch, "Senbono S10 IP67 Waterproof Multi-Function Blood Pressure Sports Smartwatch: One Minute Overview", Retrieved from: https://www.youtube.com/watch?v=rMxLJvKIVBs, Oct. 30, 2019, 1 page.

Advisory Action received for U.S. Appl. No. 14/732,773, mailed on Aug. 23, 2019, 6 pages.

Advisory Action received for U.S. Appl. No. 14/732,773, mailed on Nov. 9, 2018, 6 pages.

Cho, H.S., "Satisfactory Innovative Smart-watch (fitbit force) . . . review after seven days of use, such as the amount of sleep and movement (improving sleep is the object of X-Blue", Online Available at: https://x-blueuv.blogspot.com/2013/12/fitbit-force.html, Dec. 3, 2013, 8 pages (2 pages of English Translation and 6 pages of Official Copy).

Corrected Notice of Allowance received for U.S. Appl. No. 14/732,773, mailed on Feb. 10, 2020, 3 pages.

Corrected Notice of Allowance received for U.S. Appl. No. 14/732,773, mailed on Mar. 24, 2020, 3 pages.

Cyclespeed Tours, "The Most Useful Data Fields to Display on Your Garmin", Online Available at: https://www.youtube.com/watch?v=AN0Eo50yxdg, Nov. 16, 2016, 3 pages.

Decision to Refuse received for European Patent Application No. 13811085.3, mailed on Sep. 11, 2018, 21 pages.

Final Office Action received for U.S. Appl. No. 14/732,773, mailed on Jul. 13, 2018, 48 pages.

Final Office Action received for U.S. Appl. No. 14/732,773, mailed on Jun. 21, 2019, 32 pages.

Final Office Action received for U.S. Appl. No. 15/167,699, mailed on Jun. 30, 2017, 8 pages.

International Preliminary Report on Patentability received for PCT Patent Application No. PCT/US2013/073188, mailed on Jun. 16, 2016, 6 pages.

International Preliminary Report on Patentability received for PCT Patent Application No. PCT/US2013/073195, mailed on Jun. 16, 2016, 10 pages.

International Search Report and Written Opinion received for PCT Patent Application No. PCT/US2013/073188 mailed on Feb. 24, 2014, 8 pages.

International Search Report and Written Opinion received for PCT Patent Application No. PCT/US2020/025997, mailed on Jul. 1, 2020, 16 pages.

International Search Report and Written Opinion received for PCT Patent Application No. PCT/US2020/025997, mailed on Jul. 14, 2020, 15 pages.

International Search Report received for PCT Patent Application No. PCT/US2013/073195, mailed on Jun. 23, 2014, 3 pages.

International Written Opinion received for PCT Patent Application No. PCT/US2013/073195, mailed on Jun. 23, 2014, 8 pages.

Jenbsjourney, "Wondering About a Fitbit?", Available at: https://jenbsjourney.blogspot.kr/2013/08/wondering-about-fitbit.html, Aug. 6, 2013, 12 pages.

(56) References Cited

OTHER PUBLICATIONS

Minutes of Oral Proceedings received for European Patent Application No. 13811085.3, mailed on Sep. 11, 2018, 3 pages.
Myflo App, "Functional Medicine Period Tracker and Hormone Balancing App", Available online at: https://web.archive.org/web/20170127104125/https://myflotracker.com/, Jan. 27, 2017, 14 pages.
Myflo Tutorial, "How to change the start date of your current period", Available online at: https://www.youtube.com/watch?v=uQQ-odIBJB4, Jan. 23, 2017, 3 pages.
Myflo Tutorial, "Setting and changing the end date of your period", Available online at: https://www.youtube.com/watch?v=UvAA4OgqL3E, Jan. 23, 2017, 3 pages.
Non-Final Office Action received for U.S. Appl. No. 14/732,773, mailed on Feb. 8, 2019, 32 pages.
Non-Final Office Action received for U.S. Appl. No. 14/732,773, mailed on Jan. 19, 2018., 45 pages.
Non-Final Office Action received for U.S. Appl. No. 15/167,699, mailed on Oct. 21, 2016, 13 pages.
Non-Final Office Action received for U.S. Appl. No. 15/885,448, mailed on Apr. 16, 2020, 9 pages.
Notice from the European Patent Office dated Oct. 1, 2007 Concerning Business Methods, Official Journal EPO, Available online at: http://archive.epo.org/epo/pubs/oj007/11_07/11_5927.pdf, Nov. 2007, pp. 592-593.
Notice of Acceptance received for Australian Patent Application No. 2013406817, mailed on Nov. 21, 2017, 3 pages.
Notice of Acceptance received for Australian Patent Application No. 2018201260, mailed on Jan. 15, 2020, 3 pages.
Notice of Allowance received for Chinese Patent Application No. 201380081315.7, mailed on Jan. 4, 2019, 2 pages (1 page of English Translation and 1 page of Official Copy).
Notice of Allowance received for Japanese Patent Application No. 2016-535045, mailed on Mar. 2, 2018, 4 pages (1 page of English Translation and 3 pages of Official Copy).
Notice of Allowance received for Japanese Patent Application No. 2018-068846, mailed on Dec. 9, 2019, 4 pages (1 page of English Translation and 3 pages of Official Copy).
Notice of Allowance received for Korean Patent Application No. 10-2016-7014353, mailed on Aug. 2, 2018, 3 pages (Official Copy Only) (See Communication under 37 CFR § 1.98(a) (3)).
Notice of Allowance received for Korean Patent Application No. 10-2016-7014577, mailed on May 30, 2019, 5 pages (2 pages of English Translation and 3 pages of Official Copy).
Notice of Allowance received for Korean Patent Application No. 10-2018-7032096, mailed on Dec. 12, 2018, 4 pages (1 page of English Translation and 3 pages of Official Copy).
Notice of Allowance received for U.S. Appl. No. 14/732,773, mailed on Dec. 18, 2019, 21 pages.
Notice of Allowance received for U.S. Appl. No. 15/167,699, mailed on Oct. 27, 2017, 8 pages.
Notice of Allowance received for U.S. Appl. No. 15/885,448, mailed on Jun. 16, 2020, 5 pages.
Notice of Allowance received for U.S. Appl. No. 16/588,950, mailed on Feb. 10, 2020, 9 pages.
Notice of Allowance received for U.S. Appl. No. 16/588,950, mailed on May 5, 2020, 9 pages.
Office Action received for Australian Patent Application No. 2013406817, mailed on Aug. 1, 2017, 3 pages.
Office Action received for Australian Patent Application No. 2013406817, mailed on Nov. 14, 2016, 4 pages.
Office Action received for Australian Patent Application No. 2018201260, mailed on Feb. 12, 2019, 6 pages.
Office Action received for Australian Patent Application No. 2018201260, mailed on Jul. 17, 2019, 3 pages.
Office Action received for Australian Patent Application No. 2018201260, mailed on Sep. 5, 2019, 5 pages.
Office Action received for Chinese Patent Application No. 201380081315.7, mailed on Aug. 16, 2018, 6 pages (3 pages of English Translation and 3 pages of Official Copy).
Office Action received for Chinese Patent Application No. 201380081315.7, mailed on Mar. 2, 2018, 12 pages (5 pages of English Translation and 7 pages of Official Copy).
Office Action received for Chinese Patent Application No. 201380081349.6, mailed on Feb. 26, 2019, 12 pages (6 pages of English Translation and 6 pages of Official Copy).
Office Action received for Chinese Patent Application No. 201380081349.6, mailed on Jan. 16, 2020, 11 pages (6 pages of English Translation and 5 pages of Official Copy).
Office Action received for Chinese Patent Application No. 201380081349.6, mailed on Jul. 15, 2019, 10 pages (5 pages of English Translation and 5 pages of Official Copy).
Office Action received for Chinese Patent Application No. 201380081349.6, mailed on Jul. 15, 2020, 9 pages (4 pages of English Translation and 5 pages of Official Copy).
Office Action received for Danish Patent Application No. PA201970532, mailed on May 29, 2020, 3 pages.
Office Action received for European Patent Application No. 13811085.3, mailed on Apr. 20, 2018, 15 pages.
Office Action received for European Patent Application No. 13812320.3, mailed on Mar. 28, 2018, 7 pages.
Office Action received for Indian Patent Application No. 201617016494, mailed on Apr. 27, 2020, 7 pages.
Office Action received for Japanese Patent Application No. 2016-535045, mailed on May 12, 2017, 10 pages (5 pages of English Translation and 5 pages of Official Copy).
Office Action received for Japanese Patent Application No. 2018-068846, mailed on Jan. 8, 2019, 6 pages (3 pages of English Translation and 3 pages of Official copy).
Office Action received for Korean Patent Application No. 10-2016-7014353, mailed on Mar. 21, 2018, 11 pages (5 pages of English Translation and 6 pages of Official Copy).
Office Action received for Korean Patent Application No. 10-2016-7014577, mailed on Dec. 26, 2017, 14 pages (6 pages of English Translation and 8 pages of Official Copy).
Office Action received for Korean Patent Application No. 10-2016-7014577, mailed on Oct. 31, 2018, 11 pages (5 pages of English Translation and 6 pages of Official Copy).
Office Action received for Korean Patent Application No. 10-2019-7025781, mailed on Nov. 26, 2019, 10 pages (4 pages of English Translation and 6 pages of Official Copy).
Search Report and Opinion received for Danish Patent Application No. PA201970532, mailed on Nov. 8, 2019, 9 pages.
Summons to Attend Oral Proceedings received for European Patent Application No. 13811085.3, mailed on Jan. 26, 2018., 14 pages.
Supplemental Notice of Allowance received for U.S. Appl. No. 16/588,950, mailed on Apr. 1, 2020, 2 pages.
Supplemental Notice of Allowance received for U.S. Appl. No. 16/588,950, mailed on Jul. 29, 2020, 2 pages.
Supplemental Notice of Allowance received for U.S. Appl. No. 16/588,950, mailed on Jun. 18, 2020, 2 pages.
Utilization of Galaxy S4-S Health, ChatOn and Samsung Hub, Available at: http://seeit.kr/1263, Jun. 12, 2013, 25 pages (Official Copy Only) (See Communication under 37 CFR § 1.98(a) (3)).
Wei-Yu et al., "A Multi-identities Authentication and Authorization Schema in Cloud Computing", Aug. 20, 2012, pp. 7-10 (English Abstract Submitted).
International Preliminary Report on Patentability received for PCT Patent Application No. PCT/US2019/014215, mailed on Aug. 6, 2020, 14 pages.
Invitation to Pay Addition Fees and Partial International Search Report received for PCT Patent Application No. PCT/US2019/014215, mailed on Apr. 12, 2019, 13 pages.
Applicant-Initiated Interview Summary received for U.S. Appl. No. 16/586,154, mailed on Apr. 14, 2021, 4 pages.
Non-Final Office Action received for U.S. Appl. No. 16/994,352, mailed on Jul. 30, 2021, 11 pages.
Notice of Allowance received for U.S. Appl. No. 16/820,383, mailed on Jul. 21, 2021, 11 pages.
Office Action received for Australian Patent Application No. 2020239692, mailed on Jul. 20, 2021, 5 pages.

(56) References Cited

OTHER PUBLICATIONS

Office Action received for Chinese Patent Application No. 201380081349.6, mailed on Jun. 2, 2021, 17 pages (8 pages of English Translation and 9 pages of Official Copy).
FAQ|SleepScore, Available Online at: https://www.sleepscore.com/sleepscore-app/faq/, Retrieved on May 26, 2021, 31 pages.
Notice of Allowance received for U.S. Appl. No. 16/880,714, mailed on Jun. 9, 2021, 6 pages.
Office Action received for Australian Patent Application No. 2019210192, mailed on May 25, 2021, 4 pages.
Cook, James, "German Period Tracking App Clue Has Over 2.5 Million Active Users—But It's Still Not Sure How It's Going to Make Money", Available online at: https://www.businessinsider.in/tech/german-period-tracking-app-clue-has-over-2-5-million-active-users-but-its-still-not-sure-how-its-going-to-make-money/articleshow/50511307.cms, Jan. 9, 2016, 9 pages.
Final Office Action received for U.S. Appl. No. 16/586,154, mailed on May 24, 2021, 29 pages.
Non-Final Office Action received for U.S. Appl. No. 16/990,846, mailed on May 10, 2021, 16 pages.
Office Action received for Danish Patent Application No. PA202070620, mailed on May 10, 2021, 5 pages.
Notice of Allowance received for U.S. Appl. No. 16/820,383, mailed on Mar. 31, 2021, 11 pages.
Notice of Allowance received for U.S. Appl. No. 16/880,714, mailed on Mar. 19, 2021, 7 pages.
Applicant-Initiated Interview Summary received for U.S. Appl. No. 16/820,383, mailed on Mar. 11, 2021, 2 pages.
International Search Report and Written Opinion received for PCT Patent Application No. PCT/US2020/070280, mailed on Nov. 30, 2020, 20 pages.
Search Report and Opinion received for Danish Patent Application No. PA202070815, mailed on Mar. 16, 2021, 8 pages.
Summons to Attend Oral Proceedings received for European Patent Application No. 13812320.3, mailed on Mar. 12, 2021, 9 pages.
Notice of Allowance received for Korean Patent Application No. 10-2019-7025781, mailed on Jun. 29, 2021, 5 pages (2 pages of English Translation and 3 pages of Official Copy).
Applicant-Initiated Interview Summary received for U.S. Appl. No. 16/880,714, mailed on Feb. 26, 2021, 5 pages.
International Search Report and Written Opinion received for PCT Patent Application No. PCT/US2020/035164, mailed on Feb. 8, 2021, 26 pages.
Decision to Refuse received for European Patent Application No. 13812320.3, mailed on Oct. 14, 2021, 4 pages.
Notice of Allowance received for U.S. Appl. No. 16/586,154, mailed on Oct. 15, 2021, 8 pages.
Office Action received for Australian Patent Application No. 2020239740, mailed on Sep. 28, 2021, 5 pages.
Applicant Initiated Interview Summary received for U.S. Appl. No. 16/994,352, mailed on Nov. 2, 2021, 4 pages.
Corrected Notice of Allowance received for U.S. Appl. No. 16/586,154, mailed on Oct. 27, 2021, 2 pages.
Corrected Notice of Allowance received for U.S. Appl. No. 17/031,704, mailed on Nov. 2, 2021, 7 pages.
International Search Report and Written Opinion received for PCT Patent Application No. PCT/US2021/035227, mailed on Oct. 6, 2021, 17 pages.
Office Action received for Danish Patent Application No. PA202070619, mailed on Oct. 14, 2021, 3 pages.
Office Action received for Danish Patent Application No. PA202070815, mailed on Oct. 18, 2021, 2 pages.
Non-Final Office Action received for U.S. Appl. No. 16/820,383, mailed on Jan. 10, 2022, 18 pages.
Non-Final Office Action received for U.S. Appl. No. 17/031,723, mailed on Jan. 24, 2022, 17 pages.
Notice of Allowance received for U.S. Appl. No. 16/990,846, mailed on Jan. 20, 2022, 6 pages.
Office Action received for Japanese Patent Application No. 2020-160023, mailed on Jan. 17, 2022, 11 pages (06 pages of English Translation and 05 pages of Official Copy).
Office Action received for Japanese Patent Application No. 2020-551585, mailed on Jan. 6, 2022, 11 pages (5 pages of English Translation and 6 pages of Official Copy).
International Preliminary Report on Patentability received for PCT Patent Application No. PCT/US2020/025997, mailed on Nov. 18, 2021, 10 pages.
Office Action received for Danish Patent Application No. PA202070620, mailed on Nov. 19, 2021, 2 pages.
Applicant-Initiated Interview Summary received for U.S. Appl. No. 17/031,717, mailed on Nov. 4, 2021, 5 pages.
Notice of Allowance received for Japanese Patent Application No. 2020-560883, mailed on Oct. 29, 2021, 4 pages (1 page of English Translation and 3 pages of Official Copy).
Office Action received for European Patent Application No. 20721342.2, mailed on Nov. 4, 2021, 9 pages.
Final Office Action received for U.S. Appl. No. 16/994,352, mailed on Dec. 6, 2021, 14 pages.
International Preliminary Report on Patentability received for PCT Patent Application No. PCT/US2020/035164, mailed on Dec. 16, 2021, 19 pages.
International Preliminary Report on Patentability received for PCT Patent Application No. PCT/US2020/035462, mailed on Dec. 16, 2021, 16 pages.
Notice of Acceptance received for Australian Patent Application No. 2019210192, mailed on Dec. 2, 2021, 3 pages.
Office Action received for Indian Patent Application No. 202014041484, mailed on Dec. 8, 2021, 8 pages.
Applicant-Initiated Interview Summary received for U.S. Appl. No. 16/586,154, mailed on Sep. 3, 2021, 4 pages.
Non-Final Office Action received for U.S. Appl. No. 17/031,717, mailed on Sep. 14, 2021, 35 pages.
Office Action received for Danish Patent Application No. PA202070619, mailed on Aug. 27, 2021, 12 pages.
Office Action received for Korean Patent Application No. 10-2021-7026284, mailed on Aug. 31, 2021, 10 pages (4 pages of English Translation and 6 pages of Official Copy).
Applicant-Initiated Interview Summary received for U.S. Appl. No. 15/978,126, mailed on Jan. 19, 2021, 4 pages.
Applicant-Initiated Interview Summary received for U.S. Appl. No. 15/978,126, mailed on Jul. 1, 2020, 6 pages.
Brief Communication Regarding Oral Proceedings received for European Patent Application No. 13812320.3, mailed on Sep. 16, 2021, 2 pages.
Corrected Notice of Allowance received for U.S. Appl. No. 16/820,383, mailed on Oct. 5, 2021, 2 pages.
Final Office Action received for U.S. Appl. No. 15/978,126, mailed on Sep. 30, 2020, 23 pages.
International Preliminary Report on Patentability received for PCT Patent Application No. PCT/US2018/023303, mailed on Dec. 12, 2019, 8 pages.
International Search Report and Written Opinion received for PCT Patent Application No. PCT/US2018/023303, mailed on Jun. 19, 2018, 10 pages.
Non-Final Office Action received for U.S. Appl. No. 15/978,126, mailed on Mar. 26, 2020, 16 pages.
Notice of Allowance received for U.S. Appl. No. 15/978,126, mailed on Feb. 4, 2021, 10 pages.
Notice of Allowance received for U.S. Appl. No. 16/990,846, mailed on Sep. 22, 2021, 9 pages.
Office Action received for Australian Patent Application No. 2019210192, mailed on Sep. 9, 2021, 4 pages.
Supplemental Notice of Allowance received for U.S. Appl. No. 16/880,714, mailed on Sep. 16, 2021, 2 pages.
Applicant-Initiated Interview Summary received for U.S. Appl. No. 17/031,704, mailed on Feb. 9, 2021, 3 pages.
Applicant-Initiated Interview Summary received for U.S. Appl. No. 17/031,704, mailed on Jun. 25, 2021, 3 pages.
Applicant-Initiated Interview Summary received for U.S. Appl. No. 17/031,717, mailed on Jan. 29, 2021, 5 pages.

(56) References Cited

OTHER PUBLICATIONS

Applicant-Initiated Interview Summary received for U.S. Appl. No. 17/031,717, mailed on May 17, 2021, 5 pages.
Corrected Notice of Allowance received for U.S. Appl. No. 16/820,383, mailed on Aug. 13, 2021, 2 pages.
Corrected Notice of Allowance received for U.S. Appl. No. 16/820,383, mailed on Aug. 19, 2021, 2 pages.
Final Office Action received for U.S. Appl. No. 17/031,704, mailed on Apr. 1, 2021, 31 pages.
Final Office Action received for U.S. Appl. No. 17/031,717, mailed on Feb. 24, 2021, 23 pages.
Non-Final Office Action received for U.S. Appl. No. 17/031,704, mailed on Dec. 10, 2020, 30 pages.
Non-Final Office Action received for U.S. Appl. No. 17/031,717, mailed on Nov. 19, 2020, 22 pages.
Notice of Allowance received for U.S. Appl. No. 17/031,704, mailed on Jul. 21, 2021, 10 pages.
Notice of Allowance received for U.S. Appl. No. 17/031,727, mailed on Dec. 24, 2020, 12 pages.
Notice of Allowance received for U.S. Appl. No. 17/031,727, mailed on Jun. 25, 2021, 6 pages.
Notice of Allowance received for U.S. Appl. No. 17/031,727, mailed on Mar. 12, 2021, 7 pages.
Office Action received for Australian Patent Application No. 2020239740, mailed on Jul. 9, 2021, 4 pages.
Search Report and Opinion received for Danish Patent Application No. PA202070619, mailed on Dec. 2, 2020, 11 pages.
Supplemental Notice of Allowance received for U.S. Appl. No. 17/031,727, mailed on Jan. 15, 2021, 2 pages.
Notice of Allowance received for Chinese Patent Application No. 201380081349.6, mailed on Dec. 17, 2021, 2 pages (1 page of English Translation and 1 page of Official Copy).
Office Action received for Chinese Patent Application No. 202110363565.6, mailed on Nov. 16, 2021, 16 pages (9 pages of English Translation and 7 pages of Official Copy).
Corrected Notice of Allowance received for U.S. Appl. No. 17/031,717, mailed on Apr. 15, 2022, 3 pages.
Non-Final Office Action received for U.S. Appl. No. 16/888,780, mailed on Apr. 20, 2022, 22 pages.
Notice of Acceptance received for Australian Patent Application No. 2020239692, mailed on Apr. 6, 2022, 3 pages.
Notice of Allowance received for Japanese Patent Application No. 2020-160023, mailed on Apr. 11, 2022, 4 pages (1 page of English Translation and 3 pages of Official Copy).
Applicant-Initiated Interview Summary received for U.S. Appl. No. 16/820,383, mailed on May 10, 2022, 2 pages.
Corrected Notice of Allowance received for U.S. Appl. No. 17/031,717, mailed on May 19, 2022, 3 pages.
Garmin Edge 520, Owner's Manual, Online available at: https://www8.garmin.com/manuals/webhelp/edge520/EN-US/Edge_520_OM_EN-US.pdf, 2015, 24 pages.
Non-Final Office Action received for U.S. Appl. No. 16/851,451, mailed on May 9, 2022, 26 pages.
Summons to Attend Oral Proceedings received for European Patent Application No. 20721342.2, mailed on May 20, 2022, 11 pages.
Office Action received for Korean Patent Application No. 10-2020-7023277, mailed on Jan. 26, 2022, 11 pages (5 pages of English Translation and 6 pages of Official Copy).
Final Office Action received for U.S. Appl. No. 16/820,383, mailed on Jun. 22, 2022, 21 pages.
Notice of Allowance received for U.S. Appl. No. 16/994,352, mailed on Jun. 3, 2022, 9 pages.
Office Action received for Chinese Patent Application No. 202111611270.2, mailed on May 10, 2022, 16 pages (8 pages of English Translation and 8 pages of Official Copy).
Office Action received for Danish Patent Application No. PA202070815, mailed on Jun. 14, 2022, 3 pages.
Supplemental Notice of Allowance received for U.S. Appl. No. 16/994,352, mailed on Jun. 20, 2022, 2 pages.
Applicant-Initiated Interview Summary received for U.S. Appl. No. 17/041,415, mailed on Jun. 29, 2022, 2 pages.
Final Office Action received for U.S. Appl. No. 17/031,723, mailed on Jul. 12, 2022, 25 pages.
Notice of Allowance received for U.S. Appl. No. 17/031,717, mailed on Jul. 7, 2022, 12 pages.
Office Action received for Chinese Patent Application No. 202110363565.6, mailed on May 7, 2022, 12 pages (7 pages of English Translation and 5 pages of Official Copy).
Applicant-Initiated Interview Summary received for U.S. Appl. No. 17/031,723, mailed on Mar. 21, 2021, 5 pages.
Applicant-Initiated Interview Summary received for U.S. Appl. No. 17/031,779, mailed on Mar. 10, 2022, 2 pages.
Corrected Notice of Allowance received for U.S. Appl. No. 16/990,846, mailed on Feb. 9, 2022, 3 pages.
Intention to Grant received for Danish Patent Application No. PA202070619, mailed on Jan. 17, 2022, 2 pages.
International Preliminary Report on Patentability received for PCT Patent Application No. PCT/US2020/042439, mailed on Jan. 27, 2022, 10 pages.
International Preliminary Report on Patentability received for PCT Patent Application No. PCT/US2020/070280, mailed on Mar. 17, 2022, 15 pages.
International Search Report and Written Opinion received for PCT Patent Application No. PCT/US2021/045375, mailed on Jan. 10, 2022, 21 pages.
International Search Report and Written Opinion received for PCT Patent Application No. PCT/US2021/048568, mailed on Jan. 7, 2022, 14 pages.
Invitation to Pay Additional Fees received for PCT Patent Application No. PCT/US2021/045375, mailed on Nov. 16, 2021, 12 pages.
Non-Final Office Action received for U.S. Appl. No. 17/031,779, mailed on Feb. 16, 2022, 17 pages.
Non-Final Office Action received for U.S. Appl. No. 17/041,415, mailed on Mar. 29, 2022, 11 pages.
Notice of Acceptance received for Australian Patent Application No. 2020239740, mailed on Feb. 22, 2022, 3 pages.
Notice of Allowance received for U.S. Appl. No. 16/994,352, mailed on Mar. 2, 2022, 14 pages.
Notice of Allowance received for U.S. Appl. No. 17/031,717, mailed on Mar. 16, 2022, 12 pages.
Office Action received for Australian Patent Application No. 2020239692, mailed on Jan. 27, 2022, 3 pages.
Summons to Attend Oral Proceedings received for European Patent Application No. 13811085.3, mailed on Mar. 3, 2022, 3 pages.
Applicant-Initiated Interview Summary received for U.S. Appl. No. 16/820,383, mailed on Aug. 12, 2022, 2 pages.
Decision to Grant received for Danish Patent Application No. PA202070619, mailed on Aug. 11, 2022, 2 pages.
Notice of Allowance received for Korean Patent Application No. 10-2021-7026284, mailed on Jul. 28, 2022, 6 pages (2 pages of English Translation and 4 pages of Official Copy).
Notice of Allowance received for Chinese Patent Application No. 202111611270.2, mailed on Sep. 21, 2022, 4 pages (1 page of English Translation and 3 pages of Official Copy).
Advisory Action received for U.S. Appl. No. 17/031,779, mailed on Oct. 20, 2022, 5 pages.
Brief Communication Regarding Oral Proceedings received for European Patent Application No. 20721342.2, mailed on Oct. 18, 2022, 1 page.
Final Office Action received for U.S. Appl. No. 16/851,451, mailed on Oct. 20, 2022, 31 pages.
Result of Consultation received for European Patent Application No. 20721342.2, mailed on Oct. 18, 2022, 3 pages.
Supplemental Notice of Allowance received for U.S. Appl. No. 17/041,415, mailed on Oct. 13, 2022, 2 pages.
Applicant-Initiated Interview Summary received for U.S. Appl. No. 17/031,723, mailed on Aug. 30, 2022, 4 pages.
Applicant-Initiated Interview Summary received for U.S. Appl. No. 17/031,779, mailed on Aug. 29, 2022, 2 pages.
Notice of Allowance received for U.S. Appl. No. 17/041,415, mailed on Aug. 31, 2022, 7 pages.

(56) References Cited

OTHER PUBLICATIONS

Notice of Allowance received for U.S. Appl. No. 17/317,084, mailed on Aug. 29, 2022, 10 pages.
Office Action received for Japanese Patent Application No. 2021-131726, mailed on Aug. 22, 2022, 8 pages (4 pages of English Translation and 4 pages of Official Copy).
Applicant-Initiated Interview Summary received for U.S. Appl. No. 16/851,451, mailed on Aug. 5, 2022, 3 pages.
Applicant-Initiated Interview Summary received for U.S. Appl. No. 16/888,780, mailed on Aug. 2, 2022, 4 pages.
Communication of the Board of Appeal received for European Patent Application No. 13811085.3, mailed on Jul. 28, 2022, 13 pages.
Notice of Allowance received for Japanese Patent Application No. 2020-551585, mailed on Jul. 22, 2022, 4 pages (1 page of English Translation and 3 pages of Official Copy).
Notice of Allowance received for Korean Patent Application No. 10-2020-7023277, mailed on Jul. 18, 2022, 5 pages (2 pages of English Translation and 3 pages of Official Copy).
Office Action received for Korean Patent Application No. 10-2020-0124134, mailed on Jul. 28, 2022, 22 pages (11 pages of English Translation and 11 pages of Official Copy).
International Preliminary Report on Patentability received for PCT Patent Application No. PCT/US2021/035227, mailed on Dec. 15, 2022, 10 pages.
Office Action received for Japanese Patent Application No. 2021-131726, mailed on Dec. 2, 2022, 4 pages (2 pages of English Translation and 2 pages of Official Copy).
Applicant-Initiated Interview Summary received for U.S. Appl. No. 16/953,781, mailed on Oct. 31, 2022, 12 pages.
Decision to Refuse received for European Patent Application No. 20721342.2, mailed on Nov. 10, 2022, 14 pages.
Minutes of Oral Proceedings received for European Patent Application No. 20721342.2, mailed on Nov. 8, 2022, 5 pages.
Notice of Allowance received for U.S. Appl. No. 16/953,781, mailed on Nov. 9, 2022, 7 pages.
Office Action received for Australian Patent Application No. 2020268150, mailed on Nov. 3, 2022, 4 pages.
Garmin,"Edge 520 Plus Owner's Manual", Online Available at: https://www8.garmin.com/manuals/webhelp/edge520plus/EN-US/Edge_520_Plus_OM_EN-US.pdf, 2018, 30 pages.
Intention to Grant received for Danish Patent Application No. PA202070815, mailed on Sep. 13, 2022, 2 pages.
Invitation to Pay Search Fees received for European Patent Application No. 19703582.7, mailed on Sep. 12, 2022, 3 pages.
Office Action received for Korean Patent Application No. 10-2020-7033395, mailed on Aug. 29, 2022, 11 pages (4 pages of English Translation and 7 pages of Official Copy).
Supplemental Notice of Allowance received for U.S. Appl. No. 17/041,415, mailed on Sep. 20, 2022, 2 pages.
Supplemental Notice of Allowance received for U.S. Appl. No. 17/317,084, mailed on Sep. 20, 2022, 2 pages.
Applicant-Initiated Interview Summary received for U.S. Appl. No. 16/851,451, mailed on Nov. 29, 2022, 4 pages.
Final Office Action received for U.S. Appl. No. 16/888,780, mailed on Nov. 25, 2022, 10 pages.
Invitation to Pay Search Fees received for European Patent Application No. 20760607.0, mailed on Nov. 21, 2022, 3 pages.
Non-Final Office Action received for U.S. Appl. No. 17/031,723, mailed on Dec. 5, 2022, 27 pages.
Notice of Allowance received for U.S. Appl. No. 16/820,383, mailed on Nov. 22, 2022, 16 pages.
Final Office Action received for U.S. Appl. No. 17/031,779, mailed on Jul. 14, 2022, 19 pages.
Non-Final Office Action received for U.S. Appl. No. 16/953,781, mailed on Jul. 26, 2022, 9 pages.
Applicant-Initiated Interview Summary received for U.S. Appl. No. 17/952,053, mailed on Apr. 5, 2023, 6 pages.
Corrected Notice of Allowance received for U.S. Appl. No. 16/953,781, mailed on Mar. 30, 2023, 2 pages.
Extended European Search Report received for European Patent Application No. 23150297.2, mailed on Mar. 28, 2023, 8 pages.
Notice of Allowance received for Japanese Patent Application No. 2021-131726, mailed on Mar. 17, 2023, 4 pages (1 page of English Translation and 3 pages of Official Copy).
Office Action received for Japanese Patent Application No. 2022-502594, mailed on Mar. 20, 2023, 10 pages (5 pages of English Translation and 5 pages of Official Copy).
Office Action received for Korean Patent Application No. 10-2020-0124134, mailed on Mar. 28, 2023, 9 pages (4 pages of English Translation and 5 pages of Official Copy).
Extended European Search Report received for European Patent Application No. 22194355.8, mailed on Dec. 23, 2022, 10 pages.
Office Action received for Australian Patent Application No. 2020313970, mailed on Dec. 22, 2022, 3 pages.
Office Action received for Japanese Patent Application No. 2021-192437, mailed on Dec. 16, 2022, 4 pages (2 pages of English Translation and 2 pages of Official Copy).
International Preliminary Report on Patentability received for PCT Patent Application No. PCT/US2021/045375, mailed on Feb. 23, 2023, 15 pages.
International Preliminary Report on Patentability received for PCT Patent Application No. PCT/US2021/048568, mailed on Mar. 9, 2023, 11 pages.
Non-Final Office Action received for U.S. Appl. No. 16/851,451, mailed on Feb. 24, 2023, 28 pages.
Notice of Allowance received for U.S. Appl. No. 16/820,383, mailed on Mar. 8, 2023, 13 pages.
Notice of Allowance received for U.S. Appl. No. 16/953,781, mailed on Feb. 27, 2023, 5 pages.
Office Action received for Australian Patent Application No. 2022201823, mailed on Mar. 9, 2023, 3 pages.
Office Action received for Australian Patent Application No. 2022204568, mailed on Mar. 11, 2023, 4 pages.
Final Office Action received for U.S. Appl. No. 16/851,451, mailed on Jun. 1, 2023, 35 pages.
Final Office Action received for U.S. Appl. No. 17/951,945, mailed on May 18, 2023, 18 pages.
Notice of Allowance received for Japanese Patent Application No. 2021-192437, mailed on May 19, 2023, 4 pages (1 page of English Translation and 3 pages of Official Copy).
Notice of Allowance received for U.S. Appl. No. 17/031,779, mailed on May 26, 2023, 9 pages.
Office Action received for Australian Patent Application No. 2022203508, mailed on May 19, 2023, 2 pages.
Office Action received for Australian Patent Application No. 2022204568, mailed on May 22, 2023, 4 pages.
Non-Final Office Action received for U.S. Appl. No. 17/735,395, mailed on Feb. 10, 2023, 28 pages.
Office Action received for Australian Patent Application No. 2020268150, mailed on Feb. 6, 2023, 5 pages.
Office Action received for European Patent Application No. 20760607.0, mailed on Feb. 1, 2023, 13 pages.
Applicant-Initiated Interview Summary received for U.S. Appl. No. 16/851,451, mailed on Apr. 20, 2023, 4 pages.
Notice of Allowance received for U.S. Appl. No. 17/952,053, mailed on Apr. 17, 2023, 6 pages.
Non-Final Office Action received for U.S. Appl. No. 17/951,945, mailed on Mar. 24, 2023, 14 pages.
Non-Final Office Action received for U.S. Appl. No. 17/952,182, mailed on Mar. 28, 2023, 9 pages.
Office Action received for Australian Patent Application No. 2020313970, mailed on Mar. 22, 2023, 4 pages.
Office Action received for Japanese Patent Application No. 2022-076722, mailed on Mar. 13, 2023, 6 pages (3 pages of English Translation and 3 pages of Official Copy).
Decision to Grant received for Danish Patent Application No. PA202070815, mailed on Dec. 23, 2022, 1 page.
Non-Final Office Action received for U.S. Appl. No. 17/952,053, mailed on Jan. 12, 2023, 12 pages.
Notice of Allowance received for U.S. Appl. No. 17/317,084, mailed on Jan. 6, 2023, 6 pages.

(56) References Cited

OTHER PUBLICATIONS

Office Action received for Chinese Patent Application No. 201910204981.4, mailed on Nov. 29, 2022, 14 pages (5 pages of English Translation and 9 pages of Official Copy).
Office Action received for European Patent Application No. 19703582.7, mailed on Jan. 11, 2023, 11 pages.
Applicant-Initiated Interview Summary received for U.S. Appl. No. 17/031,723, mailed on Jan. 23, 2023, 4 pages.
Notice of Allowance received for U.S. Appl. No. 17/031,779, mailed on Feb. 1, 2023, 11 pages.
Office Action received for Japanese Patent Application No. 2021-565912, mailed on Jan. 12, 2023, 9 pages (5 pages of English Translation and 4 pages of Official Copy).
Office Action received for Korean Patent Application No. 10-2022-7036381, mailed on Jan. 6, 2023, 10 pages (5 pages of English Translation and 5 pages of Official Copy).
Supplemental Notice of Allowance received for U.S. Appl. No. 17/317,084, mailed on Jan. 19, 2023, 2 pages.
Non-Final Office Action received for U.S. Appl. No. 17/735,395, mailed on Sep. 20, 2023, 29 pages.
Non-Final Office Action received for U.S. Appl. No. 17/951,945, mailed on Sep. 20, 2023, 19 pages.
Notice of Allowance received for U.S. Appl. No. 18/078,444, mailed on Aug. 31, 2023, 6 pages.
Non-Final Office Action received for U.S. Appl. No. 16/888,780, mailed on Aug. 17, 2023, 12 pages.
Notice of Allowance received for U.S. Appl. No. 17/952,185, mailed on Aug. 30, 2023, 12 pages.
Office Action received for Australian Patent Application No. 2020268150, mailed on Aug. 24, 2023, 5 pages.
Office Action received for European Patent Application No. 20760607.0, mailed on Aug. 17, 2023, 7 pages.
Non-Final Office Action received for U.S. Appl. No. 17/952,181, mailed on Aug. 7, 2023, 18 pages.
Notice of Acceptance received for Australian Patent Application No. 2022204568, mailed on Jul. 27, 2023, 3 pages.
Supplemental Notice of Allowance received for U.S. Appl. No. 17/852,020, mailed on Aug. 4, 2023, 2 pages.
Office Action received for Australian Patent Application No. 2022201823, mailed on Jun. 26, 2023, 6 pages.
Dabek et al., "A timeline-based framework for aggregating and summarizing electronic health records", IEEE Workshop on Visual Analytics in Healthcare (VAHC), available online at: https://www.researchgate.net/publication/325833364_A_timeline-based_framework_for_aggregating_and_summarizing_electronic_health_records, 2017, 7 pages.
Applicant-Initiated Interview Summary received for U.S. Appl. No. 17/031,723, mailed on Jun. 22, 2023, 2 pages.
Applicant-Initiated Interview Summary received for U.S. Appl. No. 17/398,810, mailed on Jun. 28, 2023, 5 pages.
Applicant-Initiated Interview Summary received for U.S. Appl. No. 17/735,395, mailed on Apr. 28, 2023, 2 pages.
Applicant-Initiated Interview Summary received for U.S. Appl. No. 17/735,395, mailed on Aug. 1, 2023, 2 pages.
Applicant-Initiated Interview Summary received for U.S. Appl. No. 17/951,945, mailed on Apr. 28, 2023, 2 pages.
Applicant-Initiated Interview Summary received for U.S. Appl. No. 17/951,945, mailed on Aug. 1, 2023, 2 pages.
Corrected Notice of Allowance received for U.S. Appl. No. 16/820,383, mailed on Apr. 28, 2023, 2 pages.
Corrected Notice of Allowance received for U.S. Appl. No. 17/031,779, mailed on Jun. 14, 2023, 2 pages.
Final Office Action received for U.S. Appl. No. 17/735,395, mailed on May 17, 2023, 31 pages.
Non-Final Office Action received for U.S. Appl. No. 17/031,723, mailed on Jun. 2, 2023, 23 pages.
Non-Final Office Action received for U.S. Appl. No. 17/398,810, mailed on Jun. 2, 2023, 19 pages.
Notice of Acceptance received for Australian Patent Application No. 2020313970, mailed on Jun. 22, 2023, 3 pages.
Notice of Acceptance received for Australian Patent Application No. 2022203508, mailed on Jun. 27, 2023, 3 pages.
Notice of Allowance received for Japanese Patent Application No. 2022-502594, mailed on Jul. 7, 2023, 4 pages (1 page of English Translation and 3 pages of Official Copy).
Notice of Allowance received for Korean Patent Application No. 10-2022-7036381, mailed on Jul. 12, 2023, 7 pages (2 pages of English Translation and 5 pages of Official Copy).
Notice of Allowance received for U.S. Appl. No. 16/820,383, mailed on Aug. 2, 2023, 14 pages.
Notice of Allowance received for U.S. Appl. No. 17/852,020, mailed on Jul. 12, 2023, 9 pages.
Notice of Allowance received for U.S. Appl. No. 18/078,444, mailed on May 12, 2023, 9 pages.
Notice of Hearing received for Indian Patent Application No. 201617016494, mailed on Apr. 10, 2023, 2 pages.
Office Action received for Australian Patent Application No. 2020268150, mailed on May 8, 2023, 4 pages.
Office Action received for Chinese Patent Application No. 201910204981.4, mailed on Apr. 29, 2023, 12 pages (4 pages of English Translation and 8 pages of Official Copy).
Office Action received for German Patent Application No. 112020002566.7, mailed on Mar. 24, 2023, 32 pages (14 pages of English Translation and 18 pages of official copy).
Office Action received for Indian Patent Application No. 202215032692, mailed on Jun. 15, 2023, 3 pages.
Office Action received for Japanese Patent Application No. 2021-565912, mailed on Jun. 26, 2023, 3 pages (1 page of English Translation and 2 pages of Official Copy).
Office Action received for Japanese Patent Application No. 2022-078280, mailed on Jul. 24, 2023, 8 pages (4 pages of English Translation and 4 pages of Official Copy).
Office Action received for Korean Patent Application No. 10-2020-0124134, mailed on Jun. 23, 2023, 8 pages (4 pages of English Translation and 4 pages of Official Copy).
Office Action received for Korean Patent Application No. 10-2022-7036278, mailed on Jun. 30, 2023, 10 pages (4 pages of English Translation and 6 pages of Official Copy).
Supplemental Notice of Allowance received for U.S. Appl. No. 18/078,444, mailed on Jun. 15, 2023, 2 pages.
Levy et al., "A good little tool to get to know yourself a bit better", a qualitative study on users' experiences of app-supported menstrual tracking in Europe., In: BMC Public Health, vol. 19, 2019, pp. 1-11.
Advisory Action received for U.S. Appl. No. 17/398,810, mailed on Dec. 11, 2023, 4 pages.
Applicant-Initiated Interview Summary received for U.S. Appl. No. 17/584,190, mailed on Dec. 4, 2023, 5 pages.
Decision on Appeal received for Korean Patent Application No. 10-2020-0124134, mailed on Oct. 20, 2023, 24 pages (4 pages of English Translation and 20 pages of Official Copy).
Final Office Action received for U.S. Appl. No. 17/735,395, mailed on Dec. 7, 2023, 29 pages.
Final Office Action received for U.S. Appl. No. 17/951,945, mailed on Dec. 7, 2023, 20 pages.
Luo et al., "Detection and Prediction of Ovulation From Body Temperature Measured by an In-Ear Wearable Thermometer", IEEE Transactions on Biomedical Engineering, Available online at: 10.1109/TBME.2019.2916823, vol. 67, No. 2, May 15, 2019, pp. 512-522.
Notice of Allowance received for Korean Patent Application No. 10-2020-0124134, mailed on Nov. 21, 2023, 8 pages (2 pages of English Translation and 6 pages of Official Copy).
Notice of Allowance received for U.S. Appl. No. 16/820,383, mailed on Dec. 7, 2023, 13 pages.
Notice of Allowance received for U.S. Appl. No. 17/952,185, mailed on Dec. 13, 2023, 9 pages.
Supplemental Notice of Allowance received for U.S. Appl. No. 17/952,185, mailed on Nov. 30, 2023, 2 pages.
Final Office Action received for U.S. Appl. No. 17/031,723, mailed on Oct. 4, 2023, 13 pages.
Final Office Action received for U.S. Appl. No. 17/398,810, mailed on Oct. 4, 2023, 17 pages.

(56) References Cited

OTHER PUBLICATIONS

Non-Final Office Action received for U.S. Appl. No. 17/210,920, mailed on Sep. 28, 2023, 22 pages.
Notice of Acceptance received for Australian Patent Application No. 2022201823, mailed on Sep. 26, 2023, 3 pages.
Notice of Allowance received for U.S. Appl. No. 17/952,181, mailed on Sep. 27, 2023, 9 pages.
Office Action received for Japanese Patent Application No. 2022-131993, mailed on Sep. 15, 2023, 6 pages (3 pages of English Translation and 3 pages of Official Copy).
Office Action received for Korean Patent Application No. 10-2021-7036242, mailed on Sep. 19, 2023, 13 pages (6 pages of English Translation and 7 pages of Official Copy).
Supplemental Notice of Allowance received for U.S. Appl. No. 17/952,185, mailed on Oct. 2, 2023, 2 pages.
Applicant-Initiated Interview Summary received for U.S. Appl. No. 17/031,723, mailed on Oct. 31, 2023, 4 pages.
Office Action received for Chinese Patent Application No. 202180053264.1, mailed on Sep. 23, 2023, 17 pages (9 pages of English Translation and 8 pages of Official Copy).
Office Action received for European Patent Application No. 20753659.0, mailed on Oct. 26, 2023, 9 pages.
Supplemental Notice of Allowance received for U.S. Appl. No. 17/952,181, mailed on Oct. 27, 2023, 2 pages.
Final Office Action received for U.S. Appl. No. 16/888,780, mailed on Feb. 29, 2024, 12 pages.
Office Action received for Chinese Patent Application No. 202180053264.1, mailed on Jan. 18, 2024, 14 pages (8 pages of English Translation and 6 pages of Official Copy).
Corrected Notice of Allowance received for U.S. Appl. No. 16/851,451, mailed on Feb. 20, 2024, 3 pages.
Notice of Allowance received for Korean Patent Application No. 10-2022-7036278, mailed on Jan. 30. 2024, 8 pages (2 pages of English Translation and 6 pages of Official Copy).
Office Action received for Chinese Patent Application No. 201980018078.7, mailed on Nov. 25, 2023, 20 pages (9 pages of English Translation and 11 pages of Official Copy).
Office Action received for Indian Patent Application No. 202315061713, mailed on Feb. 14, 2024, 8 pages.
Office Action received for Indian Patent Application No. 202315061718, mailed on Feb. 14, 2024, 8 pages.
Applicant-Initiated Interview Summary received for U.S. Appl. No. 16/888,780, mailed on Dec. 14, 2023, 3 pages.
Notice of Allowance received for Japanese Patent Application No. 2022-131993, mailed on Dec. 18, 2023, 4 pages (1 page of English Translation and 3 pages of Official Copy).
Supplemental Notice of Allowance received for U.S. Appl. No. 17/952,181, mailed on Dec. 20, 2023, 2 pages.
Non-Final Office Action received for U.S. Appl. No. 17/584,190, mailed on Oct. 5, 2023, 17 pages.
Office Action received for European Patent Application No. 20751022.3, mailed on Oct. 19, 2023, 8 pages.
Supplemental Notice of Allowance received for U.S. Appl. No. 17/952,181, mailed on Oct. 6, 2023, 2 pages.
Supplemental Notice of Allowance received for U.S. Appl. No. 18/078,444, mailed on Oct. 16, 2023, 4 pages.
Applicant-Initiated Interview Summary received for U.S. Appl. No. 17/735,395, mailed on Nov. 15, 2023, 2 pages.
Applicant-Initiated Interview Summary received for U.S. Appl. No. 17/951,945, mailed on Nov. 15, 2023, 2 pages.
Office Action received for Korean Patent Application No. 10-2023-7034892, mailed on Nov. 8, 2023, 5 pages (2 pages of English Translation and 3 pages of Official Copy).
Pre-Appeal Review Report received for Japanese Patent Application No. 2021-565912, mailed on Oct. 12, 2023, 5 pages (2 pages of English Translation and 3 pages of Official Copy).
Applicant-Initiated Interview Summary received for U.S. Appl. No. 17/210,920, mailed on Jan. 26, 2024, 3 pages.
Applicant-Initiated Interview Summary received for U.S. Appl. No. 17/735,395, mailed on Jan. 31, 2024, 2 pages.
Applicant-Initiated Interview Summary received for U.S. Appl. No. 17/951,945, mailed on Jan. 31, 2024, 2 pages.
Corrected Notice of Allowance received for U.S. Appl. No. 17/952,053, mailed on Jan. 25, 2024, 6 pages.
Notice of Allowance received for U.S. Appl. No. 16/851,451, mailed on Jan. 31, 2024, 13 pages.
Office Action received for Korean Patent Application No. 10-2023-7018399, mailed on Jan. 24, 2024, 11 pages (4 pages of English Translation and 7 pages of Official Copy).
Final Office Action received for U.S. Appl. No. 17/952,182, mailed on Jan. 4, 2024, 9 pages.
Office Action received for European Patent Application No. 20760607.0, mailed on Jan. 3, 2024, 7 pages.
Notice of Allowance received for Chinese Patent Application No. 201980018078.7, mailed on Mar. 28, 2024, 2 pages (1 page of English Translation and 1 page of Official Copy).
Extended European Search Report received for European Patent Application No. 25159768.8, mailed on May 27, 2025, 10 pages.

* cited by examiner

FIG. 1A

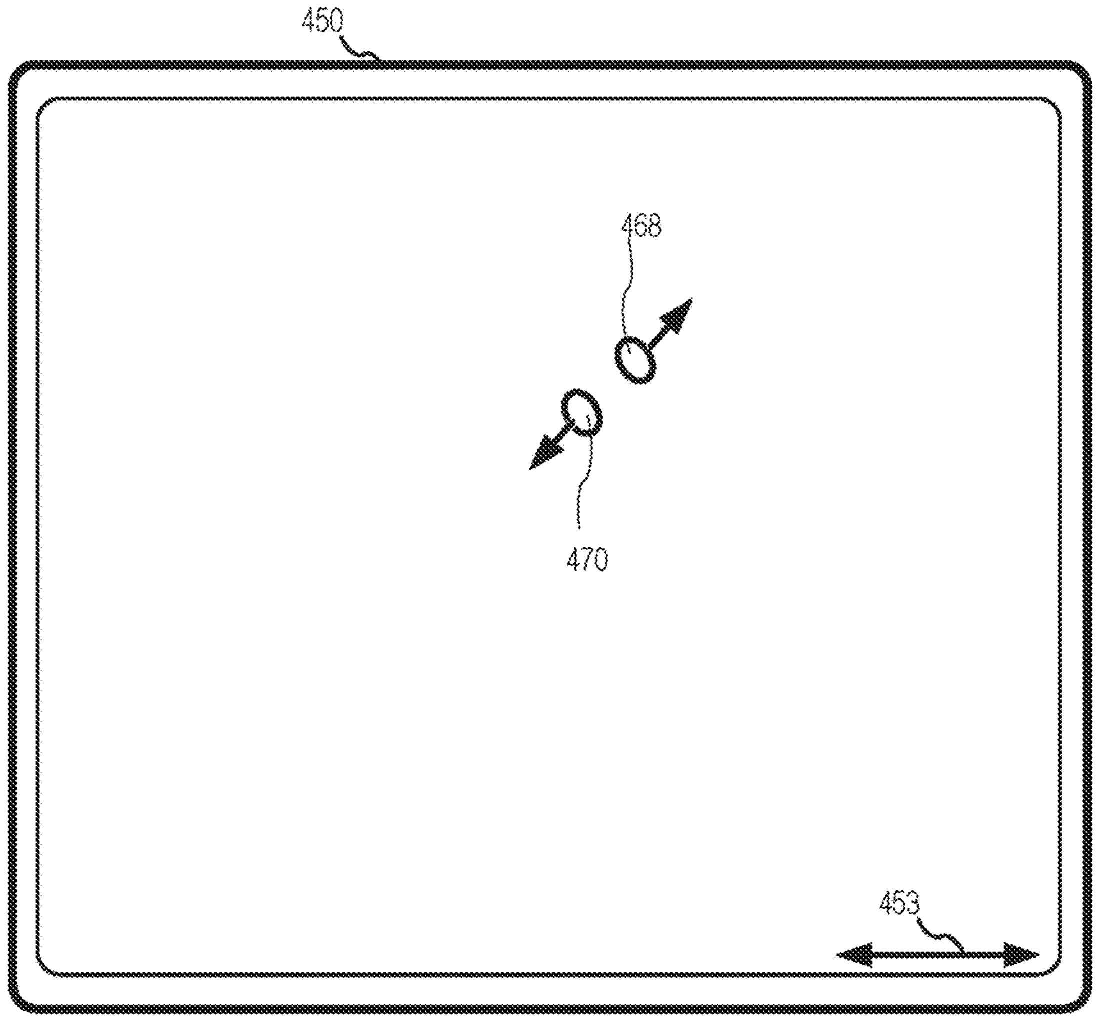
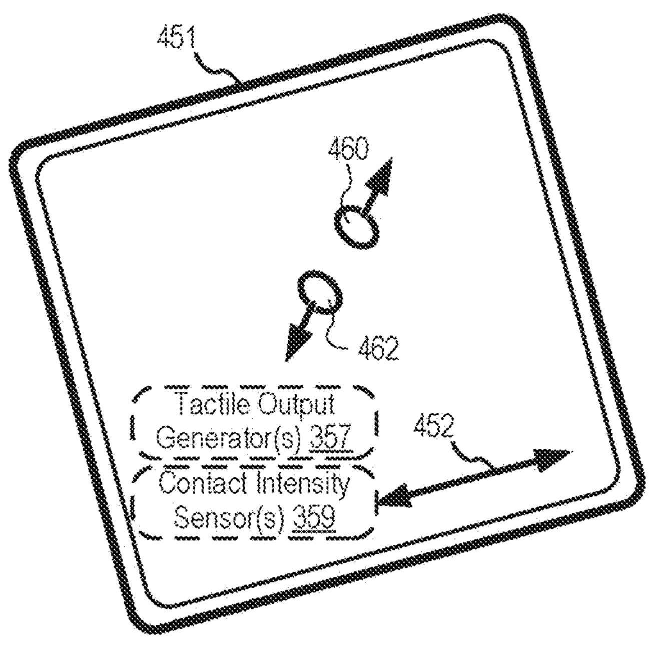
*FIG. 4B*

While the electronic device is associated with a first health care provider and not associated with a second health care provider, receive, via the one or more input devices, a first request to display health records for a first user
702

In response to receiving the first request to display health records for the first user, display, on the display, a plurality of representations of categories of health records, including:
704

A first representation of a first category of the plurality of categories, where selection of the first representation of the first category while the electronic device is associated with the first health care provider and not associated with the second health care provider causes the electronic device to display, on the display, a plurality of health records in the first category from the first health care provider, and
706

A second representation of a second category of the plurality of categories, where selection of the second representation of the second category while the electronic device is associated with the first health care provider and not associated with the second health care provider causes the electronic device to display, on the display, a plurality of health records in the second category from the first health care provider
708

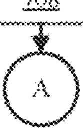

After displaying the plurality of representations of categories of health records and after the electronic device is associated with the second health care provider, receiving, via the one or more input devices, a second request to display health records for the first user
710

In response to receiving the second request to display health records for the first user, display, on the display, the plurality of representations of categories of health records, including:
712

The first representation of the first category of the plurality of categories, where selection of the first representation of the first category while the electronic device is associated with the first health care provider and the second health care provider causes the electronic device to display, on the display, one or more health records in the first category from the first health care provider and one or more health records in the first category from the second health care provider
714

The second representation of the second category of the plurality of categories, where selection of the second representation of the second category while the electronic device is associated with the first health care provider and the second health care provider causes the electronic device to display, on the display, one or more health records in the second category from the first health care provider and one or more health records in the second category from the second health care provider
716

FIG. 7A

Health records of a first type are displayed in a first color and health records of a second type are displayed in a second color that is different from the first color
718

Display, on the display, first content summarizing the first category and a first category information affordance associated with the first category, where selection of the first category information affordance causes the electronic device to display, on the display additional content associated with the first category that is not included in the first content, and
display, on the display, second content summarizing the second category and a second category information affordance of the second category, where selection of the second category information affordance causes the electronic device to display, on the display, additional content associated with the second category that is not included in the second content
720

The plurality of health records in the first category are displayed in a chronological order, and the plurality of health records in the second category are displayed in a chronological order
722

Detect selection of the first representation of the first category while the electronic device is associated with the first health care provider,
in response to detecting selection of the first representation of the first category while the electronic device is associated with the first health care provider display, on the display, a first representation of a first health record of the plurality of health records in the first category from the first health care provider,
where:
the first representation of the first health record includes a numerical value within a range of numerical values, and the numerical value is indicative of a health condition of the first user, and
where the range of values is indicative of normal range of values for the health condition
724

Display the numerical value with a color selected based on a severity of the health condition of the first user
726

FIG. 7B

Display a second representation of a second health record of the plurality of health records in the first category from the first health care provider, and wherein the second representation of the second health record comprises a graph indicative of a condition of the first user over a period of time
728

The plurality of health records in the first category from the first health care provider include a first health record in the first category from the first health care provider and a second health record in the first category from the first health care provider,
the plurality of health records in the second category from the first health care provider include a third health record in the second category from the first health care provider and a fourth health record in the second category from the first health care provider,
the first health record in the first category from the first health care provider and the third health record in the second category from the first health care provider are records of a first visit to the first health care provider, and the second health record in the first category from the first health care provider and the fourth health record in the second category from the first health care provider are records of a second visit to the first health care provider,
in response to receiving the first request to display health records for the first user, concurrently display, on the display, the first health record and the third health record in a first group, where the first group is identified on the display by a first date of the first visit, and
in response to receiving the first request to display health records for the first user, concurrently display, on the display, the second health record and the fourth health record in a second group, where the second group is identified on the display by a second date of the second visit, where the first date is different from the second date
730

The first health record in the first category from the first health care provider and the second health record in the first category from the first health care provider are displayed in a first color, and
the third health record in the second category from the first health care provider and the fourth health record in the second category from the first health care provider are displayed in a second color that is different from the first color
732

Receive an update to the first health record in the first category from the first health care provider, and display, on the display, a first update badge associated with the first health record of the first group, where the first update badge and the first health record are concurrently displayed in a first region of the display
734

FIG. 7C

Display a third representation of a third health record of the plurality of health records in the first category from the first health care provider, wherein the third representation of the third health record comprises an image indicative of a medical record of the first user
736

Receive an update to a health record of the first category of health records, and after receiving the update to the health record of the first category, and in response to receiving at least one of the first request to display the health records for the first user and the second request to display the health records for the first user, display, on the display, a second update badge associated with the first category, where the second update badge and the first representation of the first category are concurrently displayed in a first region of the display
738

Second update badge is visually associated with the first representation of the first category
740

Selection of the first representation of the first category while the electronic device is associated with the first health care provider causes the device to display, on the display, a representation of the health record of the first category of health records, and where the second update badge is visually associated with the representation of the health record of the first category of health records
742

The second update badge includes content of the update to the health record on the second update badge
744

Receive, via the one or more input devices, a request to select the second update badge, in response to receiving the request to select the second update badge, display, on the display, the update to the health record of the first category of health records
746

Concurrently display the update to the health record and a recommendation affordance associated with the health record
receive, via the one or more input devices, a request to select the recommendation affordance, and in response to receiving the request to select the recommendation affordance, display, on the display, a recommended action, where the recommended action is based on the update to the health record
748

The recommendation is a recommendation to schedule an appointment with the first health care provider, and where displaying the recommended action includes concurrently displaying the recommended action and a scheduling affordance
750

FIG. 7D

Receive an update to a health record of the first category of health records, and in response to receiving the update to the health record:
in accordance with a determination that a significance of the update is greater than a threshold value, displaying, on the display, a notification of the update.
in accordance with a determination that a significance of the update is less than the threshold value, forgoing displaying, on the display, the notification of the update
752

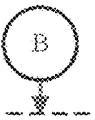

Receive, via the one or more input devices, a first selection of the first representation of the first category, in response to receiving the first selection, displaying, on the display, a plurality of representations of subcategories of health records of the first category, including:
a first representation of a first subcategory of the first category, where selection of the first representation of the first subcategory of the first category causes the electronic device to display, on the display, a plurality of health records in the first subcategory of the first category from the first health care provider, and
a second representation of a second subcategory of the first category, where selection of the second representation of the second subcategory of the first category causes the electronic device to display, on the display, a plurality of health records in the second subcategory of the first category from the first health care provider
754

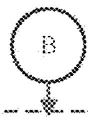

The plurality of health records in the first category from the second health care provider include a fifth health record in the first category from the second health care provider,
the plurality of health records in the second category from the second health care provider include a sixth health record in the second category from the second health care provider,
the fifth health record in the first category from the second health care provider and the sixth health record in the second category from the second health care provider are records of a third visit to the second health care provider, and
in response to receiving the second request to display health records for the first user, concurrently display, on the display, the fifth health record and the sixth health record in a third group, where:
the third group is identified on the display by a third date of the third visit to the second health care provider, and the first group, the second group, and the third group are concurrently displayed on the display.
756

FIG. 7E

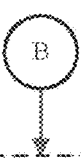

In response to receiving the first request to display health records for the first user, display, on the display, first content identifying an identity and location of the first health care provider, and
in response to receiving the second request to display health records for the first user, display, on the display, second content identifying an identity and location of the second health care provider
758

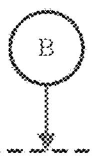

Where selection of the first representation of the first category while the electronic device is associated with the first health care provider and not associated with the second health care provider causes the electronic device to display, on the display, historical health records associated with the first category from the first health care provider, and where the historical health records associated with the first category include the plurality of health records in the first category from the first health care provider,
where selection of the second representation of the second category while the electronic device is associated with the first health care provider and not associated with the second health care provider causes the electronic device to display, on the display, historical health records associated with the second category from the first health care provider, and where the historical health records associated with the second category include the plurality of health records in the second category from the first health care provider,
where selection of the first representation of the first category while the electronic device is associated with the first health care provider and the second health care provider causes the electronic device to display, on the display, historical health records associated with the first category from the first health care provider and the second health care provider, and where the historical health records associated with the first category include the one or more health records in the first category from the first health care provider and the one or more health records in the first category from the second health care provider, and
where selection of the second representation of the second category while the electronic device is associated with the first health care provider and the second health care provider causes the electronic device to display, on the display, historical health records associated with the second category from the first health care provider and from the second health care provider, and where the historical health records associated with the second category are the one or more health records in the second category from the first health care provider and one or more health records in the second category from the second health care provider.
760

While the electronic device is associated with health data for a first user that includes a plurality of health record items of a first type and a plurality of health record items of a second type that is different from the first type, receive, via the one or more input devices, a request to display health record summary information for the first user
902

In response to receiving the request, display, on the display, health record summary information for the first user that includes concurrently displaying a plurality of health record items, including:
904

A first health record item of the first type that has a first date, where health record summary information excludes a plurality of health record items of the first type with dates earlier than the first date
906

The first health record item includes a representation of a severity of a condition of the first user
908

The first health record item includes a representation of a condition of the first user over a period of time
910

A second health record item of the second type that has a second date that is different from the first date, where health record summary information excludes a plurality of health record items of the second type that have a date that is earlier than the second date
912

The health data for the first user includes a plurality of health record items of a third type that is different from the first type and the second type, and
where displaying health record summary information further includes concurrently display the first health record item, the second health record item, and a third health record item of the third type that has a third date, where health record summary information excludes a plurality of health record items of the third type with dates earlier than the third date
914

The health data include health data associated with a plurality of health care providers of the first user, where the first health record item is associated with a first health care provider of the plurality of health care providers, and where the second health record item is associated with a second health care provider of the plurality of providers
916

The plurality of health record items include a fourth health record item of a fourth type that has a fourth date, where the first health record item and the fourth health record item are associated with a first health care provider, and where the first date and the fourth date are dates of first and second visits to the first health care provider
918

FIG. 9A

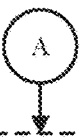

After displaying the health record that includes the first health record item and the second health record item: receive third health record item of the first type with a third date that is after the first date, after receiving the third health record item, receive, via the one or more input devices, a second request to display health record summary information for the first user, and in response to receiving the second request, display, on the display, an updated health record summary for the first user that includes concurrently displaying the second health record item and the third health record item without displaying the first health record item
920

After displaying the health record that includes the first health record item and the second health record item: receive a new health record item of the health data for the first user, where the new health record item has a date that is more recent than the first date and the second date, after receiving the new health record item, receive, via the one or more input devices, a third request to display health record summary information for the first user, and in response to receiving the third request, display on the display, an updated health record summary for the first user that includes concurrently displaying the first health record item, the second health record item, and the new health record item
922

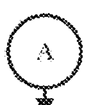

Receive, via the one or more input devices, a first request to display the plurality of health record items of the first type that are not displayed in the summary; and in response to receiving the first request to display the plurality of health record items of the first type that are not displayed in the summary, display on the display, a plurality of health record items of the first type with dates earlier than the first date
924

In response to receiving the first request to display the plurality of health record items of the first type that are not displayed in the summary, display, on the display, a health record archive for the first user that includes concurrently displaying a health record item of the first type with a most recent date and one or more of the plurality of health record items of the first type with dates earlier than the first date
926

In response to receiving the first request to display the plurality of health record items of the first type not displayed in the summary, display, on the display, a fourth health record item of the first type in the health record archive, where the fourth health record item includes a representation of a health metric measured on a fourth date earlier than the first date
928

FIG. 9B

After displaying health record summary information with the first health record and the second health record:
receive a third health record item of a third type that has a third date that is more recent than the first date and the second date, and
in response to a request to view health record summary information, update health record summary information to include the third health record item, where the first health record item, the second health record item, and the third health record item are concurrently displayed in health record summary information
930

In response to the request to display health record summary information, in accordance with a determination that a health record item of the health data for the first user is incomplete, display an incomplete record affordance in health record summary information
932

Receive, via the one or more input devices, a user verification of an accuracy of a health record item of the plurality of health record items displayed in health record summary information, and
in response to receiving the user verification of the accuracy of the health record item, provide the user verification to a health care provider associated with the health record item
934

FIG. 9C

Receive, via the one or more input devices, a first user indication that a health record item of the plurality of health record items included in health record summary information is inaccurate, and
in response to receiving the first user indication, exclude the health record item from health record summary information, where the health record item is no longer included in health record summary information after being excluded from health record summary information
936

In response to receiving the first user indication, automatically, without further user input, transmit to a request for updated information for the health record item from a health care provider computer system
938

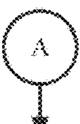

Receive, via the one or more input devices, information updating the first health record item,
and
after receiving the information updating the first health record item, receive a second request to display health record summary information for the first user, and
in response to receiving the request to display health record summary information for the first user, display an updated health record summary for the first user including concurrently display an updated first health record item that reflects the changes to the first health record item and the second health record item
940

FIG. 9D

While the electronic device is associated with one or more health care providers of a user, display a first representation of a first ongoing health condition of a plurality of ongoing health conditions of the user indicated by health record information from the one or more health care providers, where the plurality of ongoing health conditions include a second ongoing health condition and a third ongoing health condition
1102

While displaying the first representation of the first ongoing health condition, receive, via the one or more input devices, a request to mark the first ongoing health condition as inactive for the user
1104

After receiving the request to mark the first ongoing health condition as inactive, receive, via the one or more input devices, a request to display ongoing health conditions for the user
1106

In response to receiving the request to display ongoing health conditions for the user, concurrently display, on the display, a second representation of the second ongoing health condition of the user from the plurality of ongoing health conditions indicated by health record information from the one or more health care providers and a third representation of the third ongoing health condition of the user from the plurality of ongoing health conditions indicated by health record information from the one or more health care providers without displaying the first representation of the first ongoing health condition of the user as an active health condition
1108

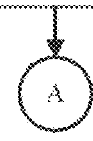

In response to receiving the request to mark the first ongoing health condition as inactive, display, on the display, a visual indication that the first ongoing health condition as inactive
1110

In response to receiving the request to display the plurality of ongoing health conditions for the user, concurrently display, on the display:
the visual indication that the first ongoing health condition is inactive,
the second ongoing health condition of the user, and
the third ongoing health condition of the user
1112

FIG. 11A

After receiving the request to mark the first ongoing health condition as inactive, receive, via the one or more input devices, a second request to mark the first health condition as active,
in response to receiving the second request to mark the first health condition as active, update the first representation of the first ongoing health condition to indicate that the first ongoing health condition is active,
after updating the first representation of the first ongoing health condition as active, receive a second request to display the plurality of ongoing health conditions for the user, and
in response to receiving the second request to display the plurality of ongoing health conditions for the user, concurrently display, on the display, a representation of the updated first ongoing health condition, the second representation of the second ongoing health condition, and the third representation of the third ongoing health condition
1114

In response to receiving the request to mark the first ongoing health condition as inactive, send, to a computer system associated with a health care provider that is associated with the first ongoing health condition, with information indicative of an inactive status of the first ongoing health condition
1116

After receiving an update to the first ongoing health condition, receive, via the one or more input devices, a third request to display ongoing health conditions for the user, and
in response to receiving the third request to display the plurality of ongoing health conditions for the user, concurrently display, on the display:
a representation of the updated first ongoing health condition,
the second representation of the second ongoing health condition, and
the third representation of the third ongoing health condition
1118

In response to receiving the update to the first ongoing health condition, mark the first ongoing health condition as an active health condition
1120

FIG. 11B

In response to receiving the update to the first ongoing health condition, send the update to a computer system associated with a health care provider that is associated with the first ongoing health condition
1122

In response to a determination of a set of dates associated with the second ongoing health condition, display, on the display, a notification regarding the second ongoing health condition on each date of the set of dates
1124

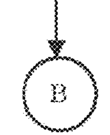

The set of dates associated with the second ongoing health condition includes a first date, where the first date is a date on which a prescription for the second ongoing health condition is scheduled to be refilled, and where the notification includes a reminder to refill the prescription
1126

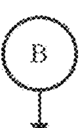

Anticipate a date when a remaining amount of a prescription for the second ongoing health condition will be below a threshold, where the set of dates associated with the second ongoing health condition includes a second date, where the second date is a date on which the prescription is anticipated to be below a threshold, and where the notification includes a reminder to refill the prescription
1128

Request, on the second date, a health care provider of the one or more health care providers to refill the prescription, where the health care provider is associated with the second ongoing health condition
1130

FIG. 11C

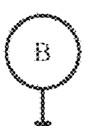

Receive, via the one or more input devices, an update to a remaining amount of a prescription for the second ongoing health condition, and
in accordance with a determination that the remaining amount of the prescription is below a threshold, display, on the display, a notification to refill the prescription
1132

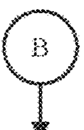

The set of dates associated with the second ongoing health condition includes a third date, where the third date is a scheduled date to visit a health care provider of the one or more health care providers, and where the health care provider is associated with the second ongoing health condition
1134

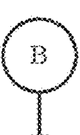

Display, on the display, a first reminder affordance associated with the second ongoing health condition, and while displaying the first reminder affordance, receive, via the one or more input devices, a request to select the first reminder affordance,
where the set of dates associated with the second ongoing health condition includes the set of dates associated with the second ongoing health condition
1136

FIG. 11D

In accordance with a determination that a reminder associated with the second ongoing health condition is also associated with a time,
displays, on the display and at the time, a notification regarding the reminder associated with the second ongoing health condition
1137

The reminder associated with the second ongoing health condition is a recurring reminder associated with an interval of time at which the user is instructed to take a prescription for the second ongoing health condition, and where the notification is a reminder to take a prescribed dosage of the prescription
1138

The notification includes a second reminder affordance associated with the reminder,
receive, via the one or more input devices, a request to select the second reminder affordance,
in response to receiving the request to select the second reminder affordance, calculate a remaining amount of the prescription, and
in accordance with a determination that the remaining amount of the prescription is below a threshold, display, on the display, a second notification regarding the second ongoing health condition, where the second notification is a reminder to refill the prescription
1140

The user is a patient and the electronic device is a patient device and where:
while the patient device is associated with one or more health care providers of the patient, display on the display of the patient device, the first representation of the first ongoing health condition,
while displaying the representation of the first ongoing health condition on the patient device, receive from the patient, via the one or more input devices, a request from the patient to mark the first ongoing health condition as inactive for the patient,
after receiving the request from the patient to mark the first ongoing health condition as inactive, receive, via the one or more input devices, a request from the patient to display ongoing health conditions for the patient, and
in response to receiving the request from the patient to display ongoing health conditions for the patient, concurrently display, on the display of the patient device, the second representation of the second ongoing health condition and the third representation of the third ongoing health condition, without displaying the representation of the first ongoing health condition
1142

FIG. 11E

SYSTEMS AND METHODS FOR DISPLAYING AGGREGATED HEALTH RECORDS

CLAIM FOR PRIORITY

This application claims benefit of U.S. Provisional Patent Application No. 62/620,455, entitled "SYSTEMS AND METHODS FOR DISPLAYING AGGREGATED HEALTH RECORDS," filed on Jan. 22, 2018, which is hereby incorporated by reference in its entirety.

FIELD

The present disclosure relates generally to computer user interfaces, and more specifically to techniques for displaying aggregated health records.

BACKGROUND

Health care providers sometimes provide patients with paper copies of their health records. Paper copies of health records are easily lost and are susceptible to deterioration. Some health care providers that have gone digital provide patients with electronic copies of their health records. However, current methods for displaying health records on electronic devices are outdated, cumbersome, and inefficient. For example, some existing methods use complex and time-consuming user interfaces, which may include multiple key presses or keystrokes to provide a limited amount of health records to the user. In addition, these methods take longer than necessary, thereby wasting energy. This latter consideration is particularly important in battery-operated devices.

It is well understood that the use of personally identifiable information should follow privacy policies and practices that are generally recognized as meeting or exceeding industry or governmental requirements for maintaining the privacy of users. In particular, personally identifiable information data should be managed and handled so as to minimize risks of unintentional or unauthorized access or use, and the nature of authorized use should be clearly indicated to users.

BRIEF SUMMARY

Accordingly, the present technique provides electronic devices with faster, more efficient methods and interfaces for displaying aggregated health records. Such methods and interfaces optionally complement or replace other methods for displaying health records. Such methods and interfaces reduce the number, extent, and/or nature of the inputs from a user, reduce the cognitive burden on the user, and produce a more efficient human-machine interface. For battery-operated computing devices, such methods and interfaces conserve power and increase the time between battery charges.

The above deficiencies and other problems associated with user interfaces for electronic devices (e.g., with touch-sensitive surfaces) are reduced or eliminated by the disclosed devices. In some embodiments, the device is a desktop computer. In some embodiments, the device is portable (e.g., a notebook computer, tablet computer, or handheld device). In some embodiments, the device is a personal electronic device (e.g., a wearable electronic device, such as a watch). In some embodiments, the device has a touchpad. In some embodiments, the device has a touch-sensitive display (also known as a "touch screen" or "touch-screen display"). In some embodiments, the device has a graphical user interface (GUI), one or more processors, memory and one or more modules, programs or sets of instructions stored in the memory for performing multiple functions. In some embodiments, the user interacts with the GUI primarily through stylus and/or finger contacts and gestures on the touch-sensitive surface. In some embodiments, the functions optionally include image editing, drawing, presenting, word processing, spreadsheet making, game playing, telephoning, video conferencing, e-mailing, instant messaging, workout support, digital photographing, digital videoing, web browsing, digital music playing, note taking, and/or digital video playing. Executable instructions for performing these functions are, optionally, included in a non-transitory computer readable storage medium or other computer program product configured for execution by one or more processors.

In accordance with some embodiments, a method is performed at an electronic device with a display and one or more input devices. The method includes receiving, via the one or more input devices, a first request to display health records for a first user while the electronic device is associated with a first health care provider and not associated with a second health care provider. In response to receiving the first request to display health records for the first user, the method also includes displaying, on the display, a plurality of representations of categories of health records. The plurality of representation of categories of health records include a first representation of a first category of the plurality of categories, wherein selection of the first representation of the first category while the electronic device is associated with the first health care provider and not associated with the second health care provider causes the electronic device to display, on the display, a plurality of health records in the first category from the first health care provider. The plurality of representations of categories of health records also include a second representation of a second category of the plurality of categories, wherein selection of the second representation of the second category while the electronic device is associated with the first health care provider and not associated with the second health care provider causes the electronic device to display, on the display, a plurality of health records in the second category from the first health care provider. The method also includes receiving, via the one or more input devices, a second request to display health records for the first user after displaying the plurality of representations of categories of health records and after the electronic device is associated with the second health care provider. In response to receiving the second request to display health records for the first user, the method also includes displaying, on the display, the plurality of representations of categories of health records. The plurality of representations of categories of health records include the first representation of the first category of the plurality of categories, wherein selection of the first representation of the first category while the electronic device is associated with the first health care provider and the second health care provider causes the electronic device to display, on the display, one or more health records in the first category from the first health care provider and one or more health records in the first category from the second health care provider. The plurality of representations of categories of health records also include the second representation of the second category of the plurality of categories, wherein selection of the second representation of the second category while the electronic device is associated with the first health care provider and the second health care provider causes the electronic device to display, on the display, one or more health records in the second category from the first health care provider and one or more health records in the second category from the second health care provider.

In accordance with some embodiments, a non-transitory computer readable storage medium storing one or more programs, the one or more programs comprising instructions, which when executed by one or more processors of an electronic device with a display and one or more input devices, cause the electronic device to receive, via the one or more input devices, a first request to display health records for a first user while the electronic device is associated with a first health care provider and not associated with a second health care provider. In response to receiving the first request to display health records for the first user, the instructions also cause the electronic device to include displaying, on the display, a plurality of representations of categories of health records. The plurality of representation of categories of health records include a first representation of a first category of the plurality of categories, wherein selection of the first representation of the first category while the electronic device is associated with the first health care provider and not associated with the second health care provider causes the electronic device to display, on the display, a plurality of health records in the first category from the first health care provider. The plurality of representations of categories of health records also include a second representation of a second category of the plurality of categories, wherein selection of the second representation of the second category while the electronic device is associated with the first health care provider and not associated with the second health care provider causes the electronic device to display, on the display, a plurality of health records in the second category from the first health care provider. The instructions, which when executed, also cause the electronic device to receive, via the one or more input devices, a second request to display health records for the first user after displaying the plurality of representations of categories of health records and after the electronic device is associated with the second health care provider. In response to receiving the second request to display health records for the first user, the instructions also cause the device to display, on the display, the plurality of representations of categories of health records. The plurality of representations of categories of health records include the first representation of the first category of the plurality of categories, wherein selection of the first representation of the first category while the electronic device is associated with the first health care provider and the second health care provider causes the electronic device to display, on the display, one or more health records in the first category from the first health care provider and one or more health records in the first category from the second health care provider. The plurality of representations of categories of health records also include the second representation of the second category of the plurality of categories, wherein selection of the second representation of the second category while the electronic device is associated with the first health care provider and the second health care provider causes the electronic device to display, on the display, one or more health records in the second category from the first health care provider and one or more health records in the second category from the second health care provider.

In accordance with some embodiments, a method is performed at an electronic device with a display and one or more input devices. The method includes receiving, via the one or more input devices, a request to display health record summary information for the first user while the electronic device is associated with health data for a first user that includes a plurality of health record items of a first type and a plurality of health record items of a second type that is different from the first type. The method also includes displaying, on the display, health record summary information for the first user that includes concurrently displaying a plurality of health record items in response to receiving the request. The plurality of health record items include a first health record item of the first type that has a first date, wherein health record summary information excludes a plurality of health record items of the first type with dates earlier than the first date. The plurality of health record items also include a second health record item of the second type that has a second date that is different from the first date, wherein health record summary information excludes a plurality of health record items of the second type that have a date that is earlier than the second date.

In accordance with some embodiments, a non-transitory computer readable storage medium storing one or more programs, the one or more programs comprising instructions, which when executed by one or more processors of an electronic device with a display and one or more input devices, cause the electronic device to receive, via the one or more input devices, a request to display health record summary information for the first user while the electronic device is associated with health data for a first user that includes a plurality of health record items of a first type and a plurality of health record items of a second type that is different from the first type. The instructions also cause the device to display, on the display, health record summary information for the first user that includes concurrently displaying a plurality of health record items in response to receiving the request. The plurality of health record items include a first health record item of the first type that has a first date, wherein health record summary information excludes a plurality of health record items of the first type with dates earlier than the first date. The plurality of health record items also include a second health record item of the second type that has a second date that is different from the first date, wherein health record summary information excludes a plurality of health record items of the second type that have a date that is earlier than the second date.

In accordance with some embodiments, a method is performed at an electronic device with a display and one or more input devices. The method includes displaying a first representation of a first ongoing health condition of a plurality of ongoing health conditions of the user indicated by health record information from the one or more health care providers while the electronic device is associated with one or more health care providers of a user. The method also includes, while displaying the first representation of the first ongoing health condition, receiving, via the one or more input devices, a request to mark the first ongoing health condition as inactive for the user. The method also includes, after receiving the request to mark the first ongoing health condition as inactive, receiving, via the one or more input devices, a request to display ongoing health conditions for the user. The method also includes in response to receiving the request to display ongoing health conditions for the user, concurrently displaying, on the display, a second representation of the second ongoing health condition of the user from the plurality of ongoing health conditions indicated by health record information from the one or more health care providers and a third representation of the third ongoing health condition of the user from the plurality of ongoing health conditions indicated by health record information from the one or more health care providers without displaying the first representation of the first ongoing health condition of the user as an active health condition.

In accordance with some embodiments, a non-transitory computer readable storage medium storing one or more programs, the one or more programs comprising instructions, which when executed by one or more processors of an electronic device with a display and one or more input devices, cause the electronic device to display a first representation of a first ongoing health condition of a plurality of ongoing health conditions of the user indicated by health record information from the one or more health care providers while the electronic device is associated with one or more health care providers of a user. The instructions also cause the electronic device to, while displaying the first representation of the first ongoing health condition, receive, via the one or more input devices, a request to mark the first ongoing health condition as inactive for the user. The instructions also cause the electronic device to, after receiving the request to mark the first ongoing health condition as inactive, receive, via the one or more input devices, a request to display ongoing health conditions for the user. The instructions also cause the electronic device to, in response to receiving the request to display ongoing health conditions for the user, concurrently displaying, on the display, a second representation of the second ongoing health condition of the user from the plurality of ongoing health conditions indicated by health record information from the one or more health care providers and a third representation of the third ongoing health condition of the user from the plurality of ongoing health conditions indicated by health record information from the one or more health care providers without displaying the first representation of the first ongoing health condition of the user as an active health condition.

In accordance with some embodiments, an electronic device includes a display, one or more input devices, one or more processors, and memory storing one or more programs; the one or more programs are configured to be executed by the one or more processors and the one or more programs include instructions for performing or causing performance of the operations of any of the methods described herein. In accordance with some embodiments, a computer readable storage medium has stored therein instructions, which, when executed by an electronic device with a display and one or more input devices, cause the device to perform or cause performance of the operations of any of the methods described herein. In accordance with some embodiments, a graphical user interface on an electronic device with a display and one or more input devices, a memory, and one or more processors to execute one or more programs stored in the memory includes one or more of the elements displayed in any of the methods described herein, which are updated in response to inputs, as described in any of the methods described herein. In accordance with some embodiments, an electronic device includes: a display, one or more input devices, and means for performing or causing performance of the operations of any of the methods described herein. In accordance with some embodiments, an information processing apparatus, for use in an electronic device with a display and one or more input devices, includes means for performing or causing performance of the operations of any of the methods described herein.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for displaying aggregated health records, thereby increasing the effectiveness, efficiency, and user satisfaction with such devices. Such methods and interfaces may complement or replace other methods for displaying aggregated health records.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 1A is a block diagram illustrating a portable multifunction device with a touch-sensitive display in accordance with some embodiments.

FIG. 4B illustrates an exemplary user interface for a multifunction device with a touch-sensitive surface that is separate from the display in accordance with some embodiments.

FIGS. 7A-7F are flow diagrams of a process for displaying aggregated health records in accordance with some embodiments.

FIGS. 9A-9D are flow diagrams of a process for displaying dashboard user interfaces having aggregated health records in accordance with some embodiments.

FIGS. 11A-11E are flow diagrams illustrating a method for displaying a health record manager that allows the user to designate the status of certain health records in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for displaying aggregated health records in a common interface. The use of such a common interface avoids the risk that a user may be viewing less than all of the health records relative to a particular concern or question in the interface. The use of such common interface also improves the user's efficiency while viewing the user's health records by reducing a need to navigate through multiple user interfaces in order to view the health records displayed in the interface. Such techniques can reduce the cognitive burden on a user who accesses the user's health records, thereby enhancing productivity. Further, such techniques can reduce processor and battery power otherwise wasted on redundant user inputs.

Figure 8A:
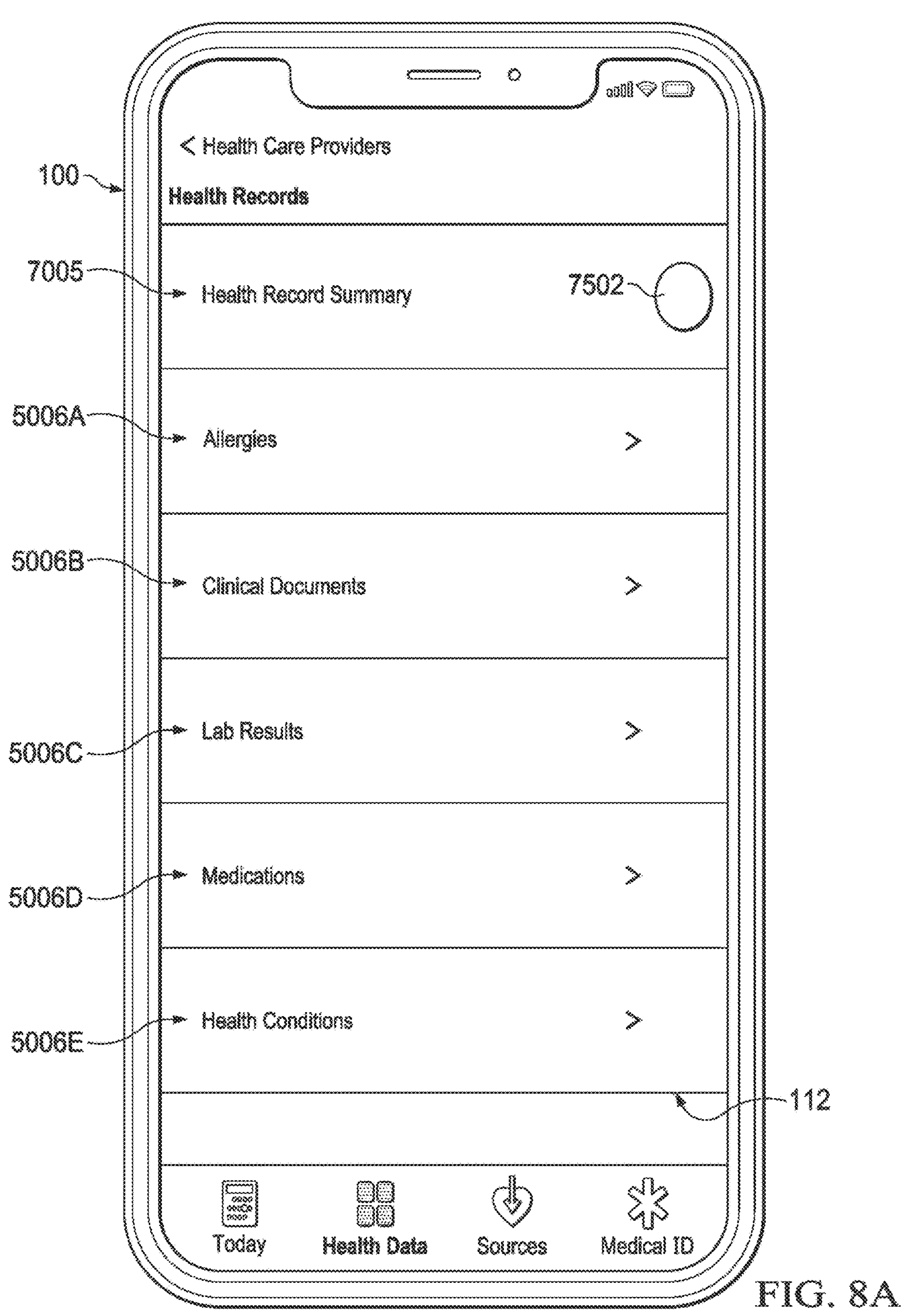
FIGS. 8A-8N illustrate exemplary dashboard user interfaces for displaying aggregated health records in accordance with some embodiments.
Figure 8B:
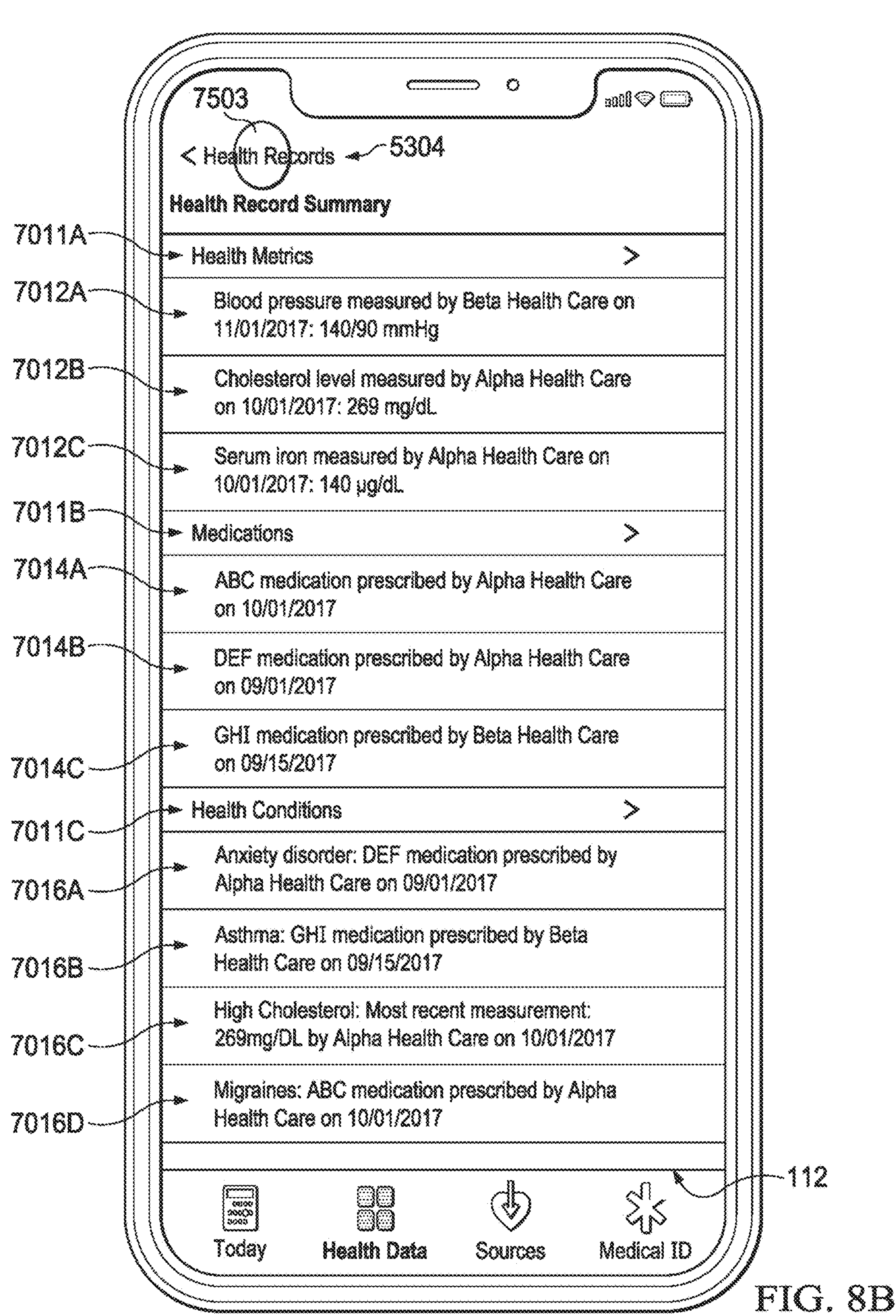
Figure 8B:
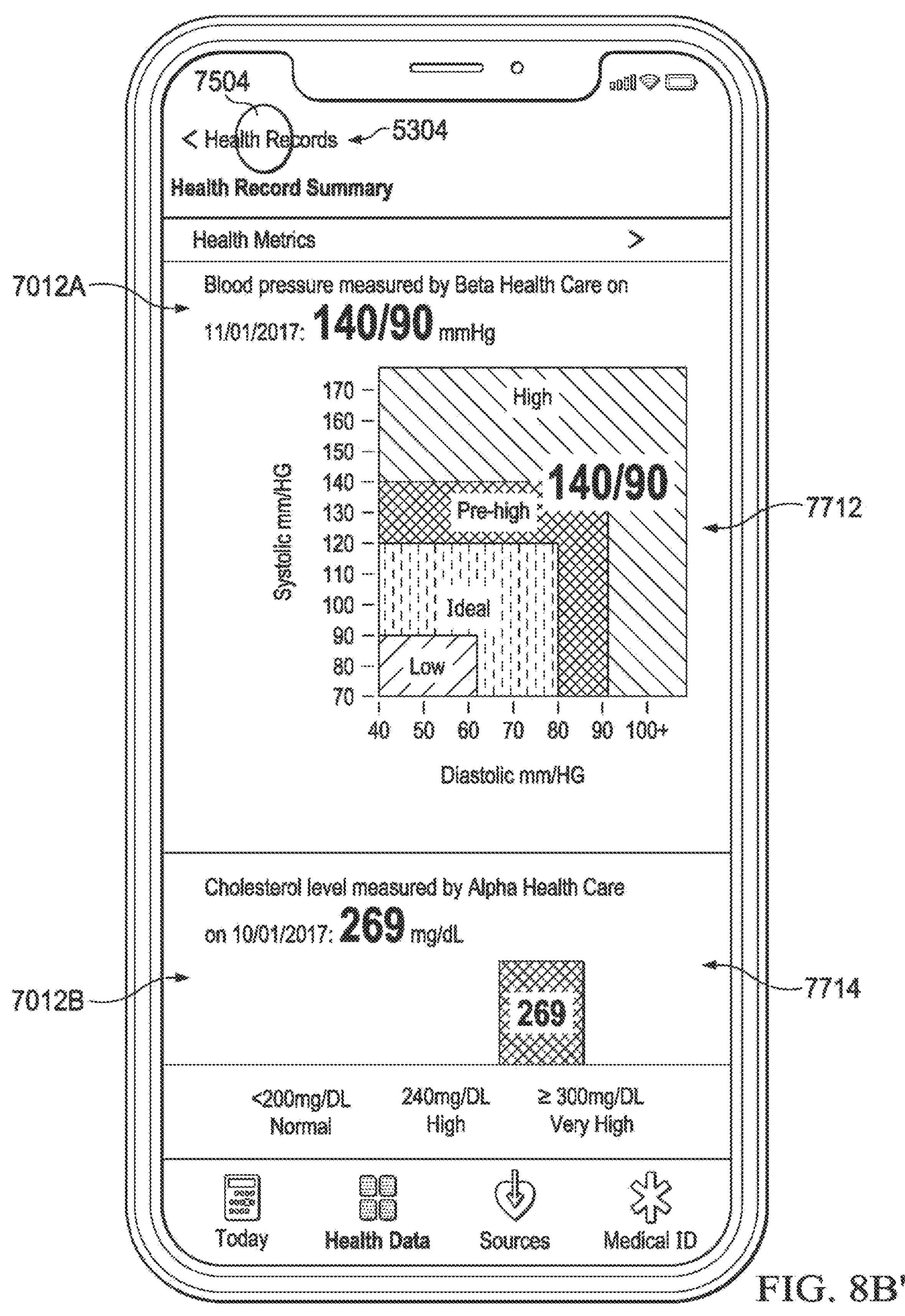
Figure 8C:
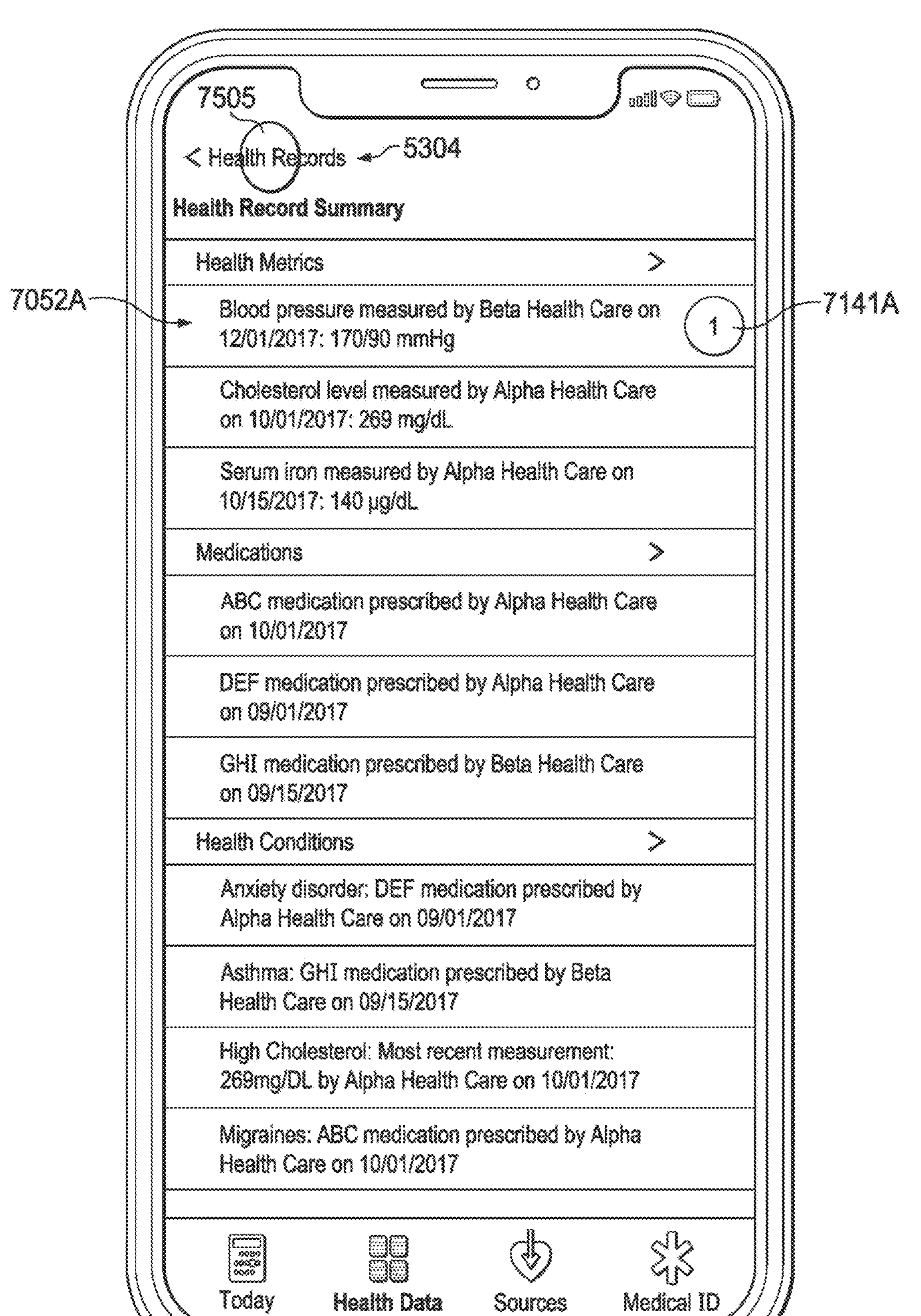
Figure 8C:
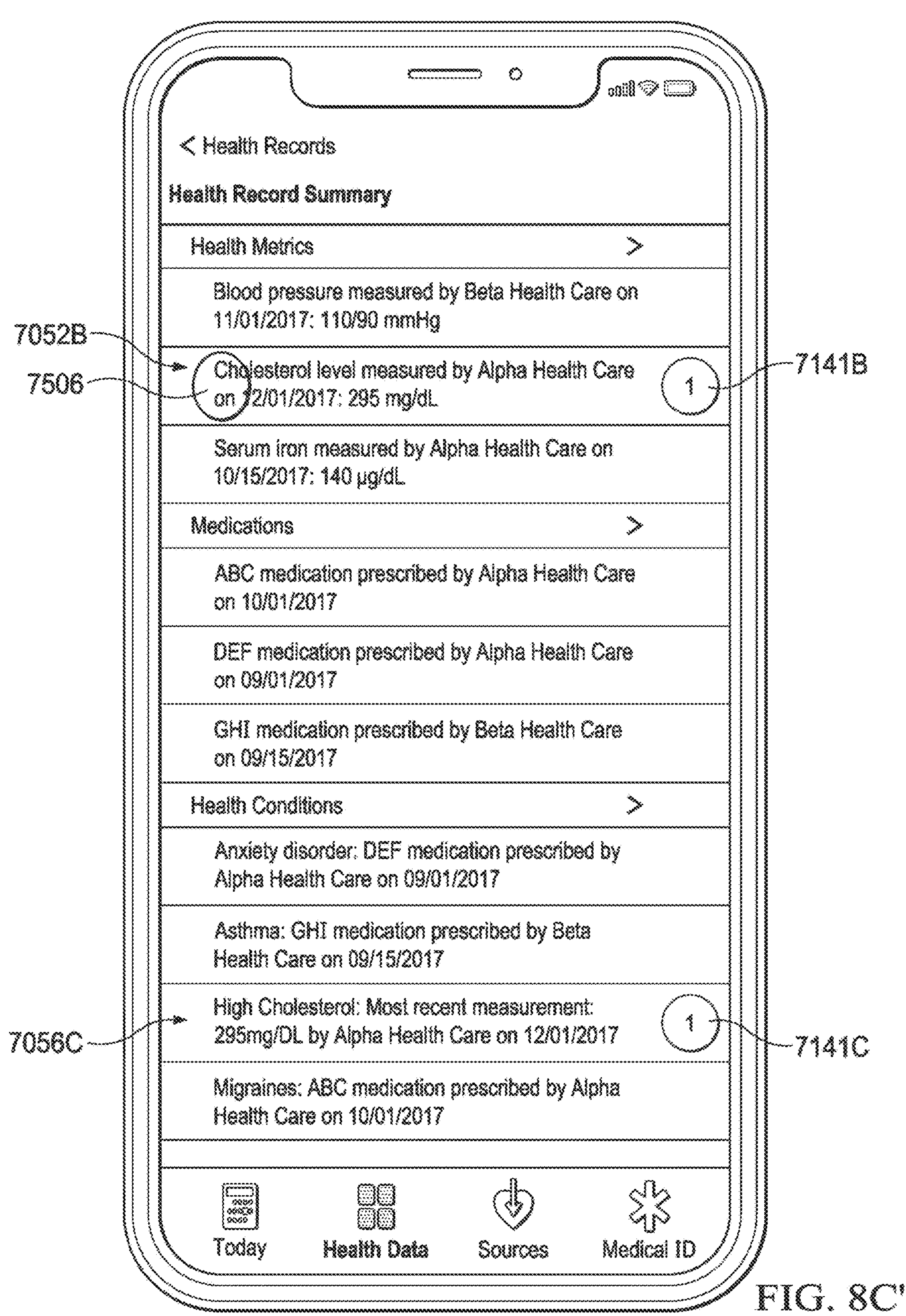
Figure 10A:
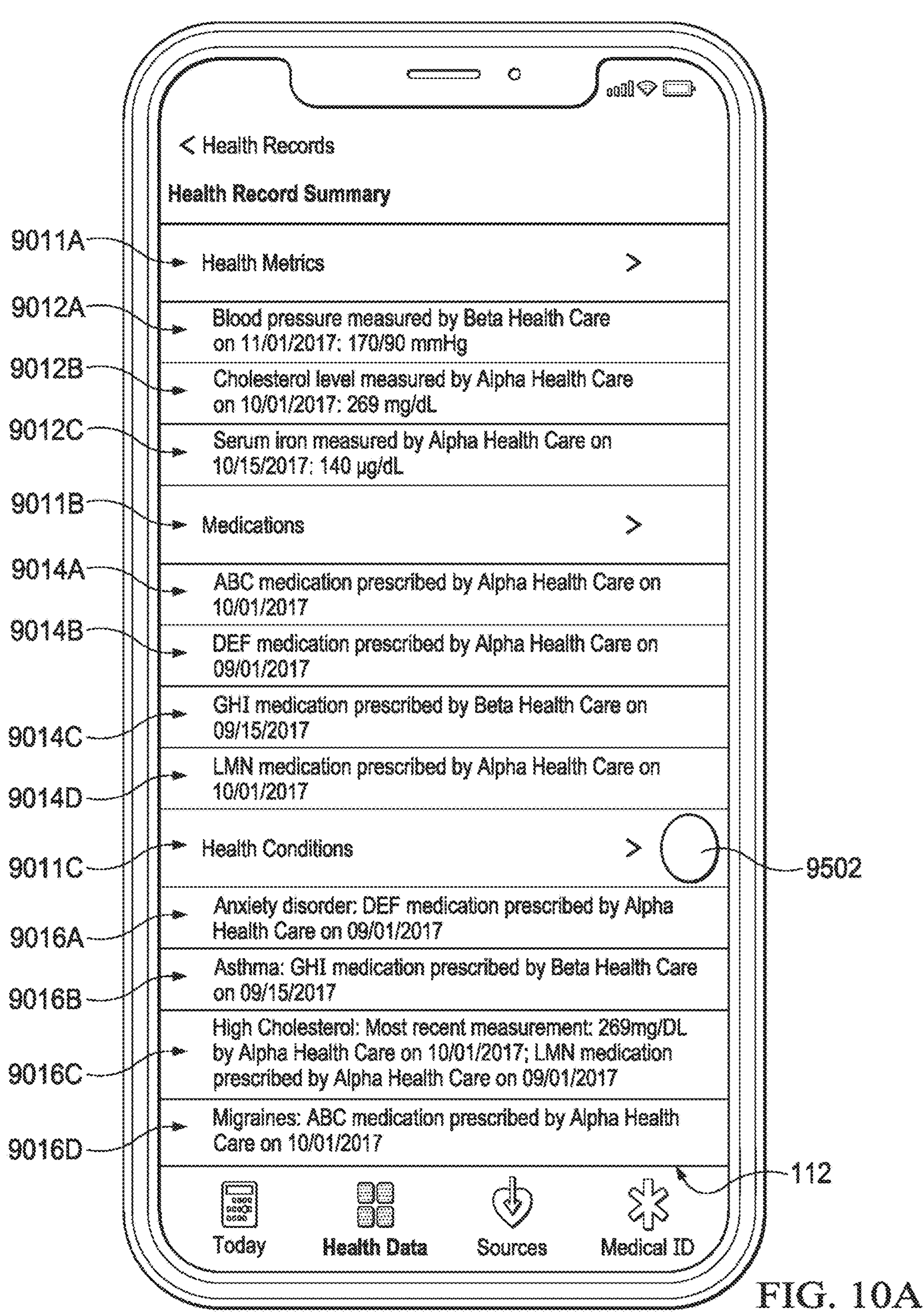
FIGS. 10A-10Q illustrate exemplary user interfaces for displaying a health record manager that allows the user to designate the status of certain health records in accordance with some embodiments.

Below, FIGS. 1A-1B, 2, 3, 4A-4B, and 5A-5B provide a description of exemplary devices for performing the techniques for displaying aggregated health records. FIGS. 6A-6Q' illustrate exemplary user interfaces for displaying aggregated health records. FIGS. 7A-7F are flow diagrams illustrating methods of displaying aggregated health records in accordance with some embodiments. The user interfaces in FIGS. 6A-6Q' are used to illustrate the processes described below, including the processes in FIGS. 7A-7F. FIGS. 8A-8N illustrate exemplary dashboard user interfaces for displaying aggregated health records. FIGS. 9A-9D are flow diagrams illustrating methods for displaying dashboard user interfaces having aggregated health records in accordance with some embodiments. The user interfaces in FIGS. 8A-8N are used to illustrate the processes described below, including the processes in FIGS. 9A-9D. FIGS. 10A-10Q illustrate exemplary user interfaces for displaying a health record manager that allows the user to designate the status of certain health records through the health record manager. FIGS. 11A-11E are flow diagrams illustrating methods for displaying a health record manager that allows the user to designate the status of certain health records through the health record manager in accordance with some embodiments. The user interfaces in FIGS. 10A-10Q are used to illustrate the processes described below, including the processes in FIGS. 11A-11E.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
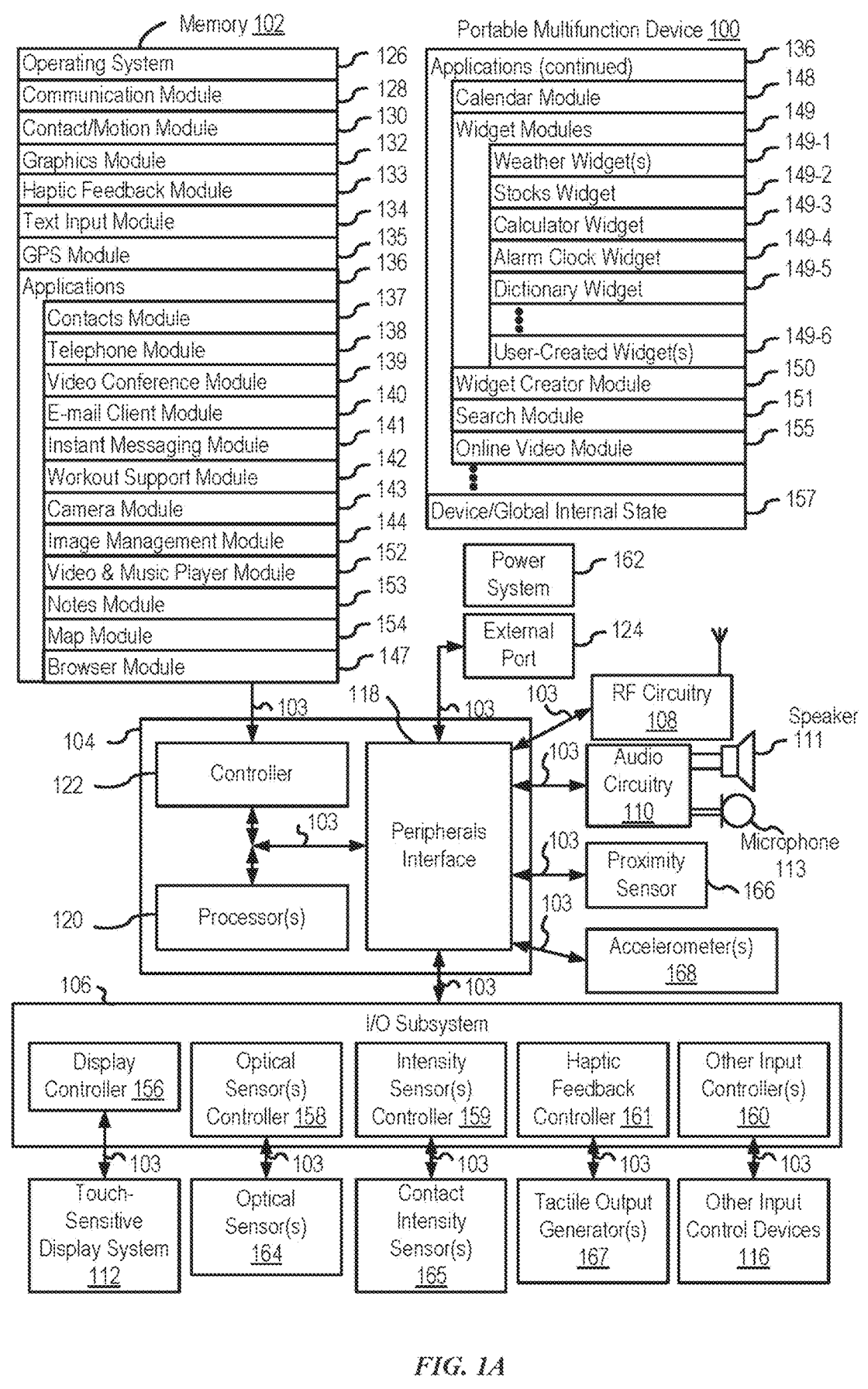

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/ output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; U.S. Ser. No. 11/240,788, "Proximity Detector In Handheld Device"; U.S. Ser. No. 11/620,702, "Using Ambient Light Sensor To Augment Proximity Sensor Output"; U.S. Ser. No. 11/586,862, "Automated Response To And Sensing Of User Activity In Portable Devices"; and U.S. Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
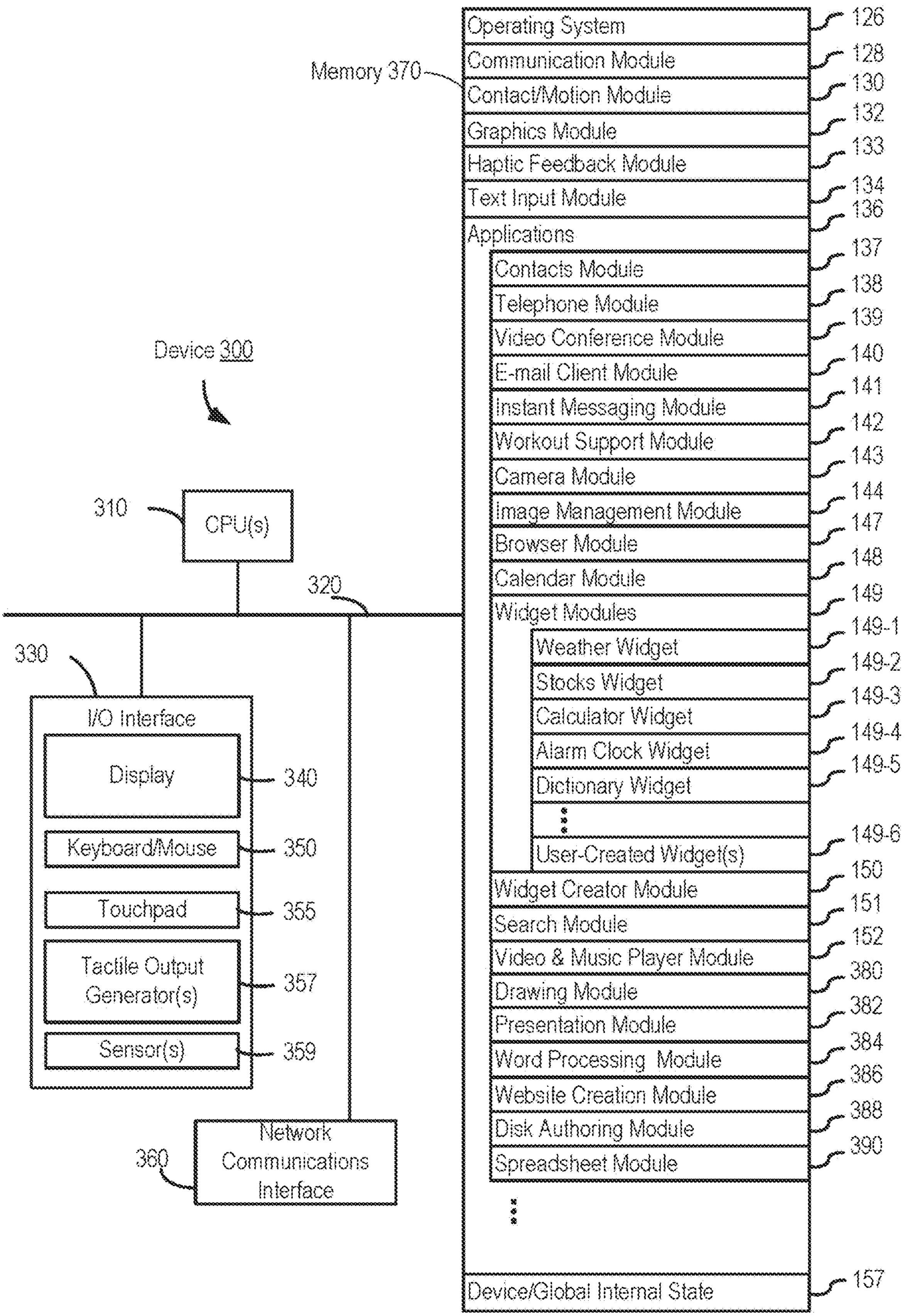
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:

- Contacts module 137 (sometimes called an address book or contact list);
- Telephone module 138;
- Video conference module 139;
- E-mail client module 140;
- Instant messaging (IM) module 141;
- Workout support module 142;
- Camera module 143 for still and/or video images;
- Image management module 144;
- Video player module;
- Music player module;
- Browser module 147;
- Calendar module 148;
- Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
- Widget creator module 150 for making user-created widgets 149-6;
- Search module 151;
- Video and music player module 152, which merges video player module and music player module;
- Notes module 153;
- Map module 154; and/or
- Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
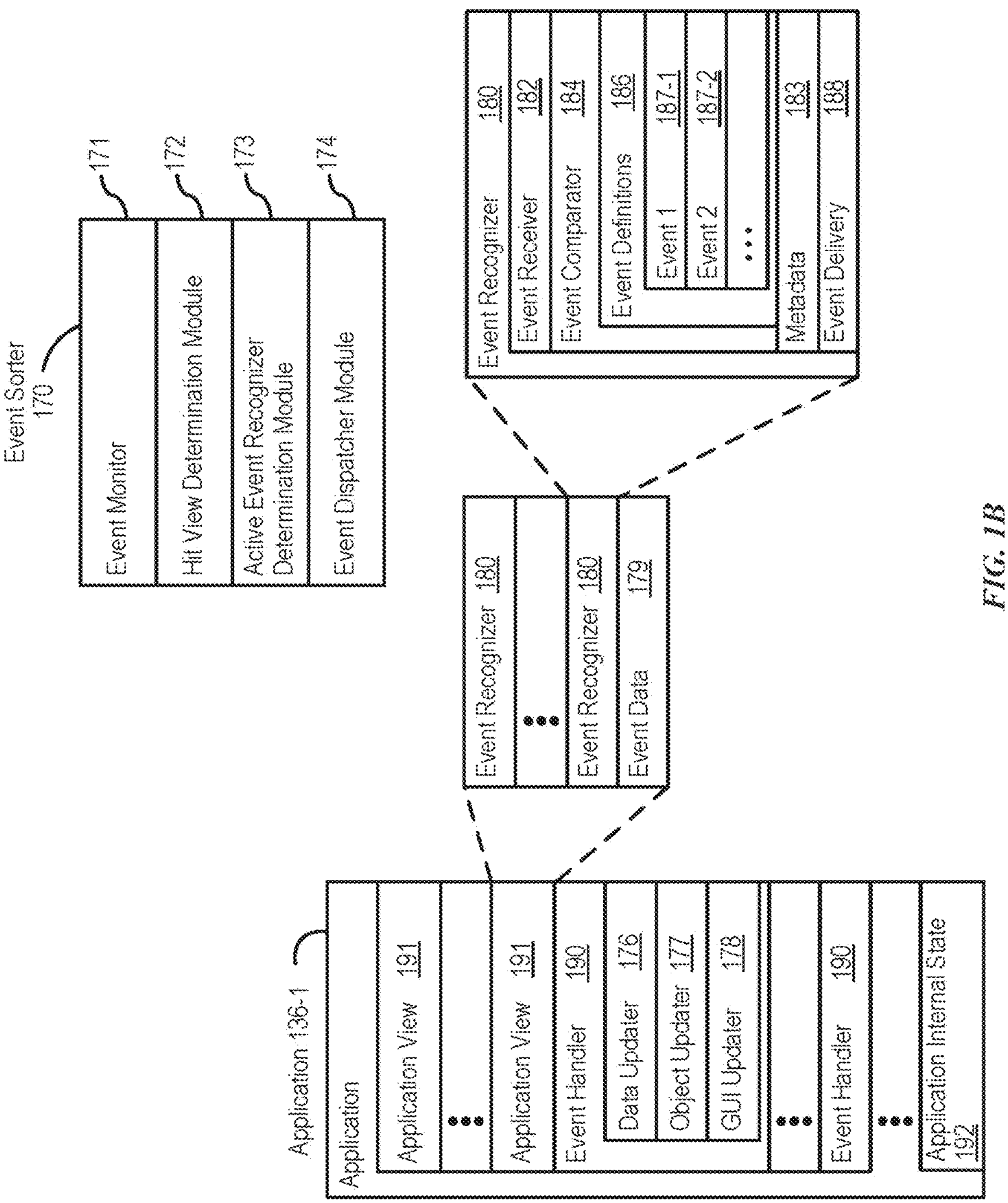
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of:

resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
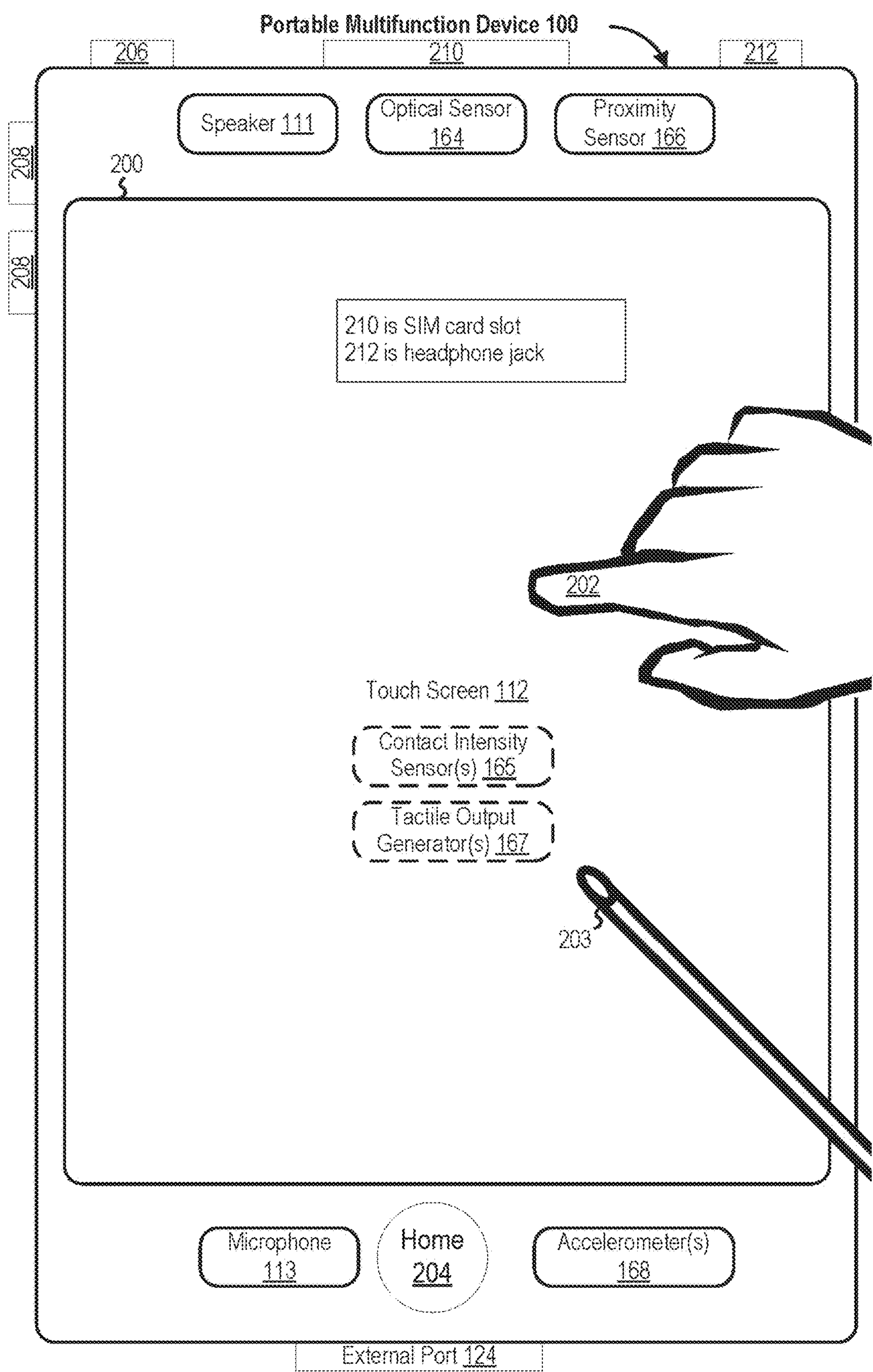
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
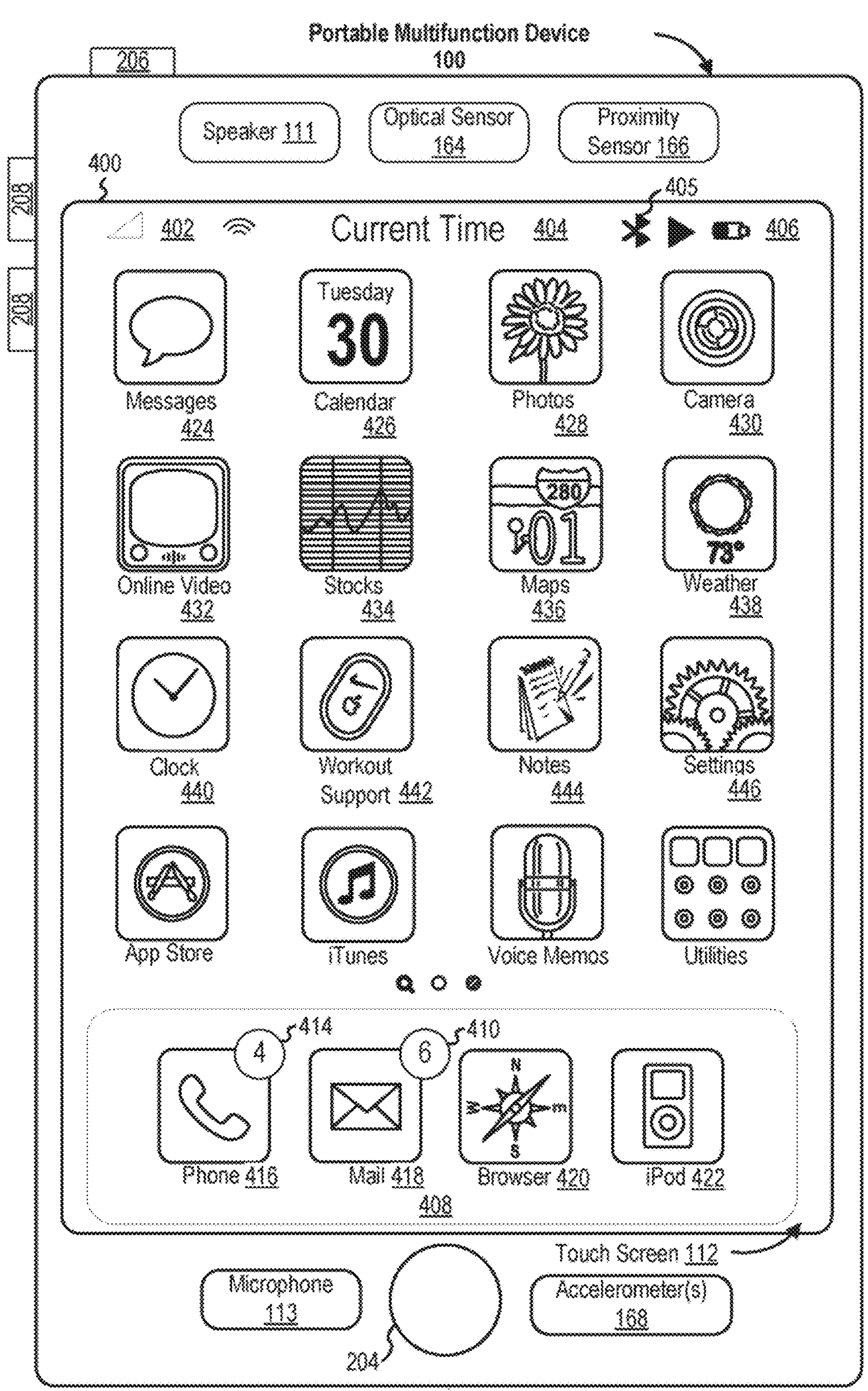
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

- Signal strength indicator(s) 402 for wireless communication(s), such as cellular and Wi-Fi signals;
- Time 404;
- Bluetooth indicator 405;
- Battery status indicator 406;
- Tray 408 with icons for frequently used applications, such as:
  - Icon 416 for telephone module 138, labeled "Phone," which optionally includes an indicator 414 of the number of missed calls or voicemail messages;
  - Icon 418 for e-mail client module 140, labeled "Mail," which optionally includes an indicator 410 of the number of unread e-mails;
  - Icon 420 for browser module 147, labeled "Browser;" and
  - Icon 422 for video and music player module 152, also referred to as iPod (trademark of Apple Inc.) module 152, labeled "iPod;" and
- Icons for other applications, such as:
  - Icon 424 for IM module 141, labeled "Messages;"
  - Icon 426 for calendar module 148, labeled "Calendar;"
  - Icon 428 for image management module 144, labeled "Photos;"
  - Icon 430 for camera module 143, labeled "Camera;"
  - Icon 432 for online video module 155, labeled "Online Video;"
  - Icon 434 for stocks widget 149-2, labeled "Stocks;"
  - Icon 436 for map module 154, labeled "Maps;"
  - Icon 438 for weather widget 149-1, labeled "Weather;"
  - Icon 440 for alarm clock widget 149-4, labeled "Clock;"
  - Icon 442 for workout support module 142, labeled "Workout Support;"
  - Icon 444 for notes module 153, labeled "Notes;" and
  - Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
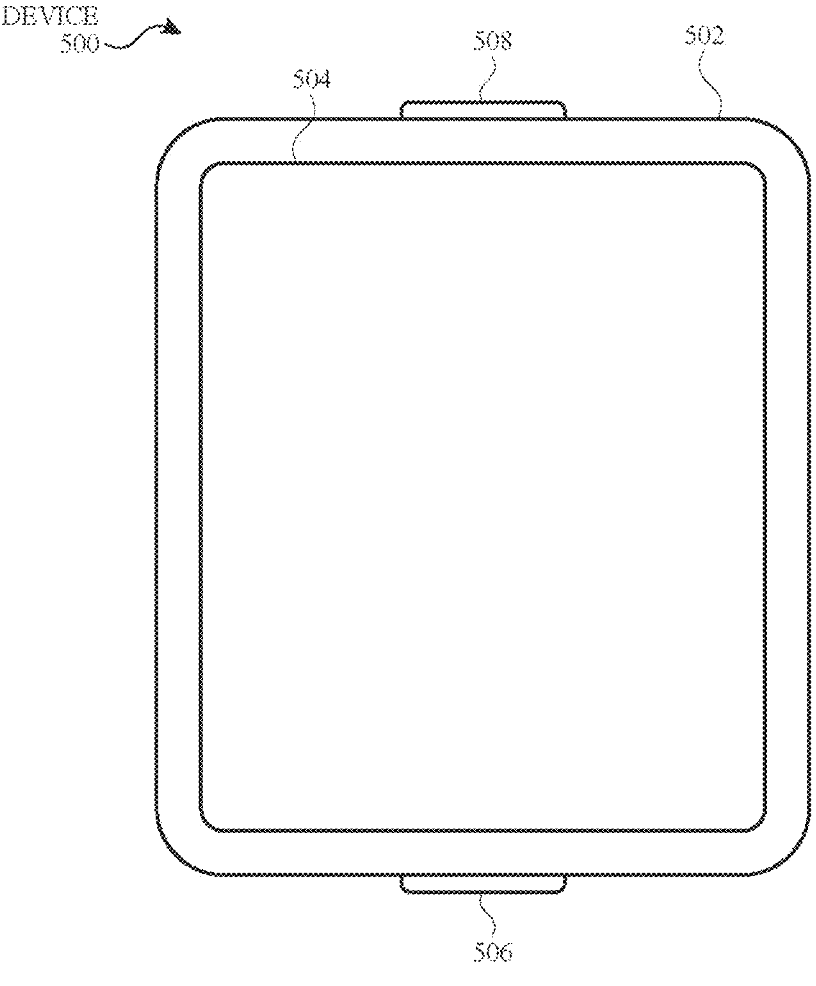
FIG. 5A illustrates a personal electronic device in accordance with some embodiments.
Figure 6A:
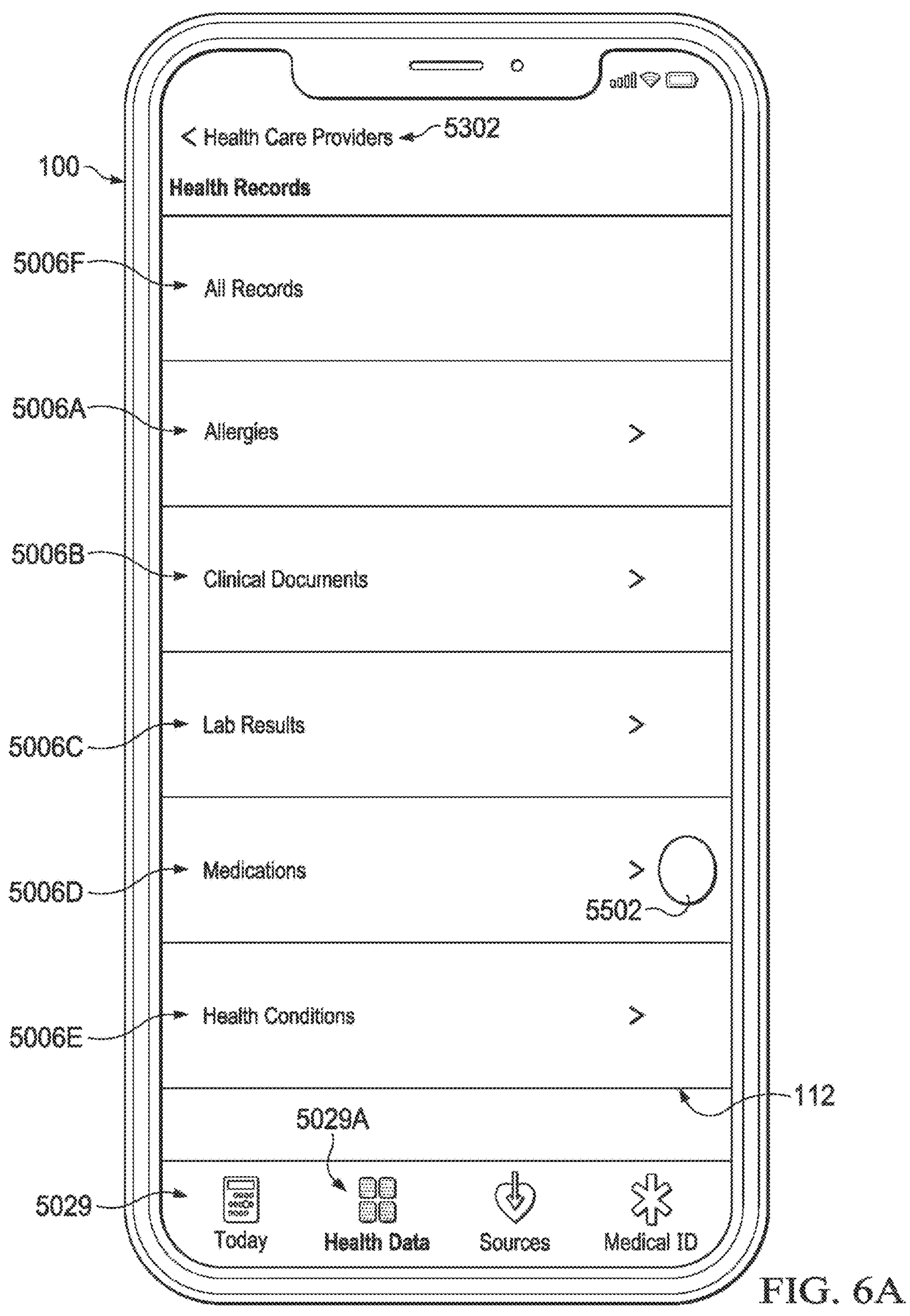
FIGS. 6A-6Q' illustrate exemplary user interfaces for displaying aggregated health records in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
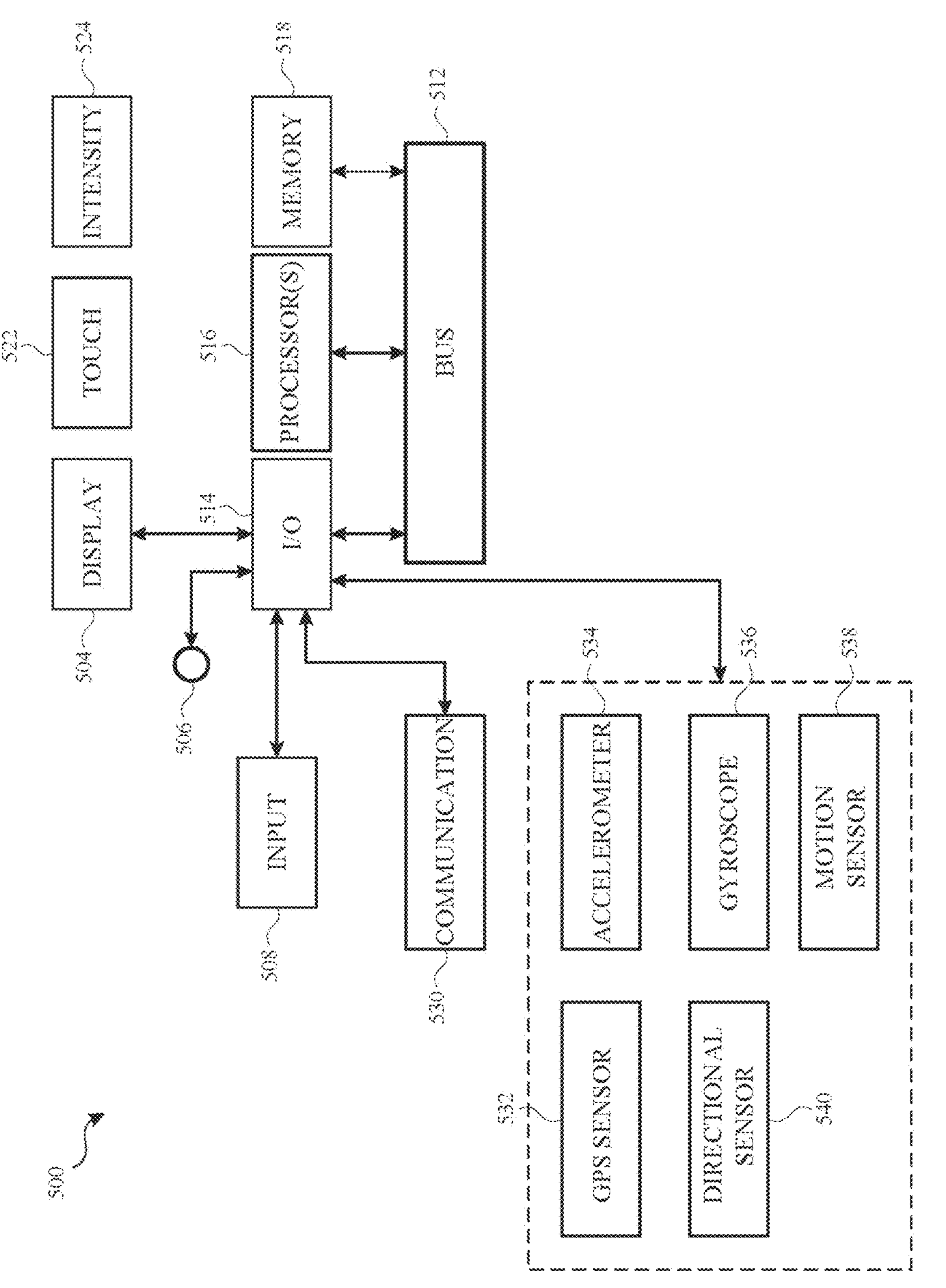
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 900, and 1100 (FIGS. 7A-7F, 9A-9D, and 11A-11E). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UI") and associated processes that are implemented on an electronic device, such as portable multifunction device 100, device 300, or device 500.

FIGS. 6A-6Q' illustrate exemplary user interfaces for displaying aggregated health records to a user, in accordance with some embodiments. For convenience, the health records will be described herein as health records of the user. However, the health records could be health records of a family member or other individuals associated with the user of the exemplary user interfaces. The user interfaces in these figures are used to illustrate the processes described below, including the processes in FIGS. 7A-7F.

Although some of the examples that follow will be given with reference to inputs on a touch-screen display (where the touch-sensitive surface and the display are combined), in some embodiments, the device detects inputs on a touch-sensitive surface 451 that is separate from the display 450, as shown in FIG. 4B. In other embodiments, the processes described herein may be implemented with devices having physical user interfaces, voice interfaces, or other suitable interfaces. For convenience of explanation, the embodiments described below will be discussed with reference to operations performed on a device with a touch-sensitive display system 112. In such embodiments, a focus selector is, optionally: a respective finger or stylus contact, a representative point corresponding to a finger or stylus contact (e.g., a centroid of a respective contact or a point associated with a respective contact), or a centroid of two or more contacts detected on the touch-sensitive display system 112. However, analogous operations are, optionally, performed on a device with a display 450 and a separate touch-sensitive surface 451 in response to detecting the contacts on the touch-sensitive surface 451 while displaying the user interfaces discussed below, along with a focus selector.

FIGS. 6A-6Q' illustrate exemplary user interfaces for displaying aggregated health information of a user in accordance with some embodiments. The user interfaces of FIGS. 6A-6Q' allow a user to review health records of the user from one or more health care providers. Such user interfaces present the health records of the user in an organized manner that allows the user to quickly and efficiently view the user's health records. More particularly, the health records in FIGS. 6A-6Q' are organized into categories. In the illustrated embodiments, such categories include allergies, clinical documents, lab results, medications, and health conditions. However, in alternative embodiments, additional or different categories or groupings may be utilized to organize the health records. The user interfaces also present updates to existing health records and new health records in an organized manner that integrates existing health records with updates to existing health records and new health records.

In one embodiment, to obtain health information of a user for display in the exemplary user interfaces illustrated in FIGS. 6A-6Q', the user accesses one or more user interfaces ("onboarding user interfaces") that are not illustrated herein to initiate, continue, or complete an onboarding process with a health care provider. In some embodiments, and while a user interface illustrated in FIG. 6A or a similar user interface is displayed on display 112, the user accesses the onboarding user interfaces by interacting with a health care providers affordance 5302. The user may periodically access the onboarding user interfaces to initiate the onboarding process of a new health care provider, to review information about an existing health care provider with whom the user has completed the onboarding process, to contact a health care provider, to update information about a health care provider, or to remove a health care provider. Once the onboarding process with the health care provider is complete, device 100 obtains access to the user's health records from the health care provider and displays the health records of the health care provider on display 112. In some embodiments, device 100, in response to a determination that the onboarding process is complete, displays the user interface illustrated in FIG. 6A on display 112. In other embodiments, onboarding user interfaces include a toolbar 5029 with a health data affordance 5029A as illustrated in FIG. 6A. In such embodiments, the user interacts with health data affordance 5029A to access FIG. 6A.

Figure 6B:
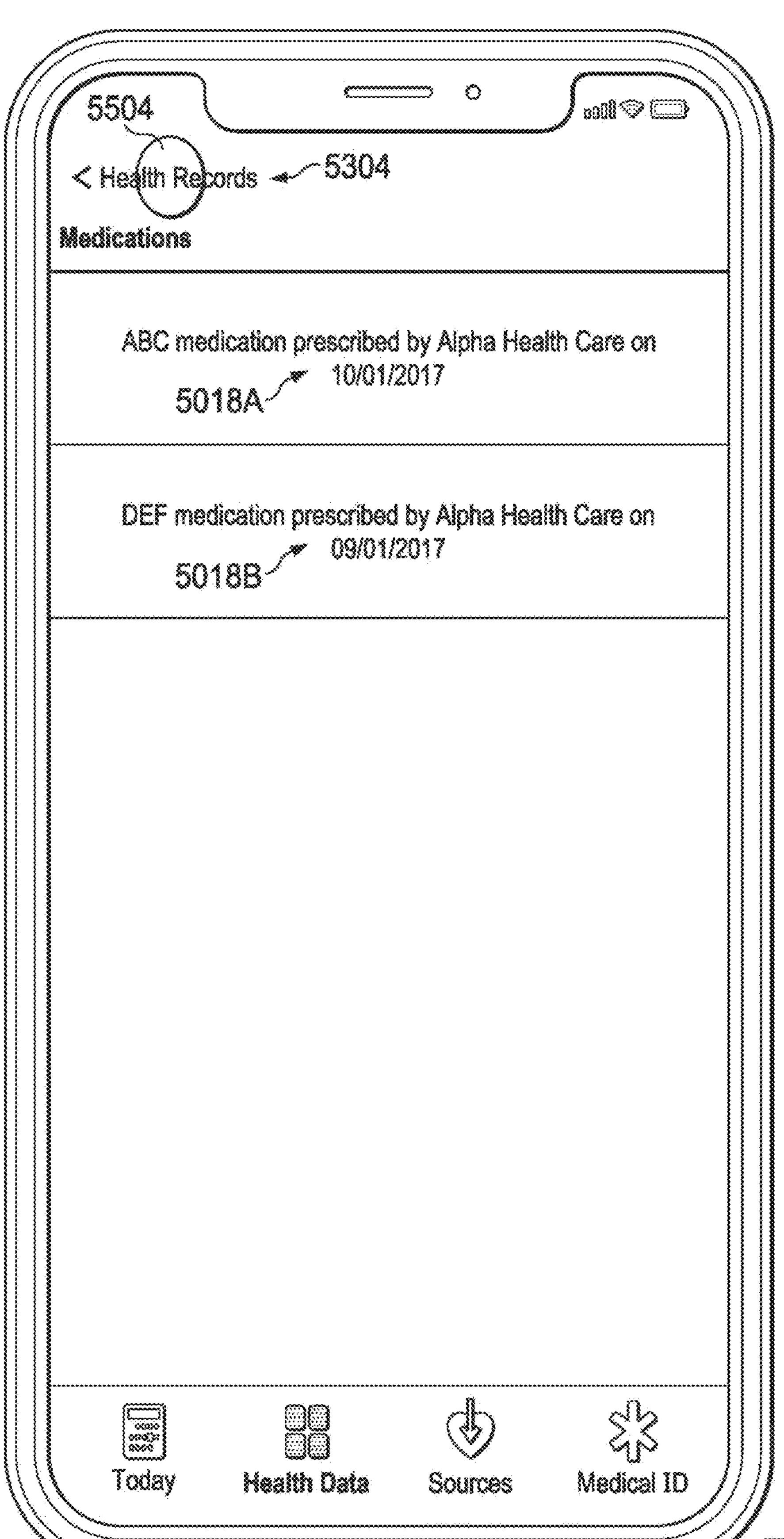
Figure 6B:
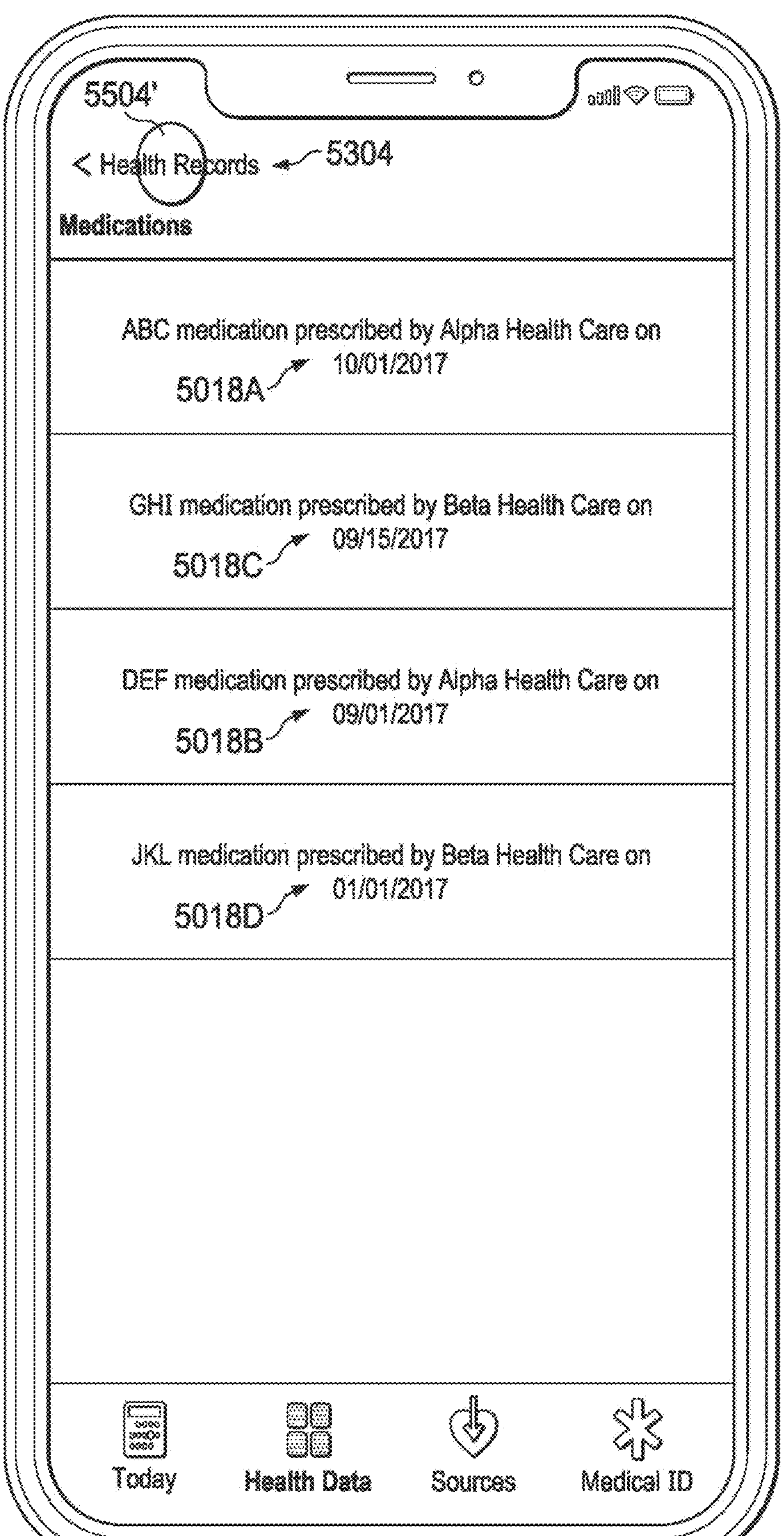

FIG. 6A illustrates one embodiment of displaying representations of categories of health records of a user from one or more health care providers. FIG. 6A includes category representations 5006A, 5006B, 5006C, 5006D, and 5006E, and an all records representation 5006F that is associated with all of the health records of the user. In the illustrated embodiment, category representation 5006A is associated with allergy health records, category representation 5006B is associated with clinical documents, category representation 5006C is associated with lab results, category representation 5006D is associated with medications, and category representation 5006E is associated with health conditions. Each of category representations 5006A-5006E is an affordance that includes text identifying that such affordance is associated with health records from a particular category. Each of category representations 5006A-5006E is selectable by the user to view health records of the user from the associated category. In some embodiments, category representations 5006A-5006E also include a description of the corresponding category, a summary of the health records included in the corresponding category, or other information regarding the corresponding category. For example, category representation 5006E may include information summarizing different ongoing health conditions of the user. All records representation 5006F is an affordance that includes text indicating that such affordance is associated with all health records. All records representation 5006F is selectable by a user to view all health records of the user. FIGS. 6A-6B illustrate detecting a tap gesture (e.g., tap gesture with contact 5502, FIG. 6A) on an affordance (category representation 5006D for medications), and in response to the tap gesture, displaying health records that correspond to the category of health records associated with the affordance (e.g., medication records 5018A and 5018B, FIG. 6B).

FIG. 6B illustrates the display of health records associated with category representation 5006D illustrated in FIG. 6A for medications. More particularly, medication records 5018A and 5018B (ABC medication and DEF medication) are displayed. In the illustrated embodiment, medication records 5018A and 5018B are health records of medication taken by the user and include text identifying the name of the medication (ABC and DEF medications respectively), the health care provider that prescribed the medication (Alpha Health Care for both records), and the date the medication was prescribed (Oct. 1, 2017 and Sep. 1, 2017, respectively). A health care provider may be a designation of one or more of an individual physician, the name of a healthcare organization such as a home health care organization or hospital group, or a specific facility or location at which treatment was obtained, such as a particular hospital or clinic location. In other embodiments, text or images representing additional information regarding medication may be displayed in medication records 5018A and 5018B such as the pharmacy dispensing the medication, the refill or expiration date of the medication, instructions or affordances to refill the medication, dosages, directions, warnings, adverse drug interactions, active ingredients, images of the medication, a fact sheet regarding the medication, or any other suitable information. In the illustrated embodiment, medication records 5018A and 5018B are arranged in order of most recent prescription date. In other embodiments, medication records 5018A and 5018B are arranged listing daily medications before other medications, in an alphabetical order, or in another suitable order for organizing medication. FIG. 6B also illustrates a health records affordance 5304, which is an affordance the user interacts with to view category representations 5006A-5006E (allergies, clinical documents, lab results, medications, and health conditions categories, respectively) illustrated in FIG. 6A. In that regard, FIG. 6B further illustrates detection of a tap gesture with contact 5504 over health records affordance 5304 to display category representations 5006A-5006E in FIG. 6C.

In FIG. 6B, medication records 5018A and 5018B (ABC medication and DEF medication) are both health records provided by Alpha Health Care. In some embodiments of FIGS. 6A-6Q', where the user has completed an onboarding process with two or more health care providers, medication records containing information about medications provided by all health care providers of the user are concurrently displayed on display 112. In that regard, FIG. 6B' illustrates an alternative embodiment where the user has completed the onboarding process with Alpha Health Care and Beta Health Care. In FIG. 6B', in response to detecting the tap gesture with contact 5502 over category representation 5006D in FIG. 6A, medication records 5018C and 5018D (for GHI and JKL medications, respectively) prescribed by Beta Health Care are concurrently displayed with medication records 5018A and 5018B prescribed by Alpha Health Care. In such a manner, a user may review all of the user's prescriptions from user's health care providers in one interface. In the illustrated embodiment, medication records 5018A-5018D are organized by prescription date. In other embodiments, medication records included in FIGS. 6A-6Q' may be organized by health care provider, by treated condition, or in any other suitable manner.

Figure 6C:
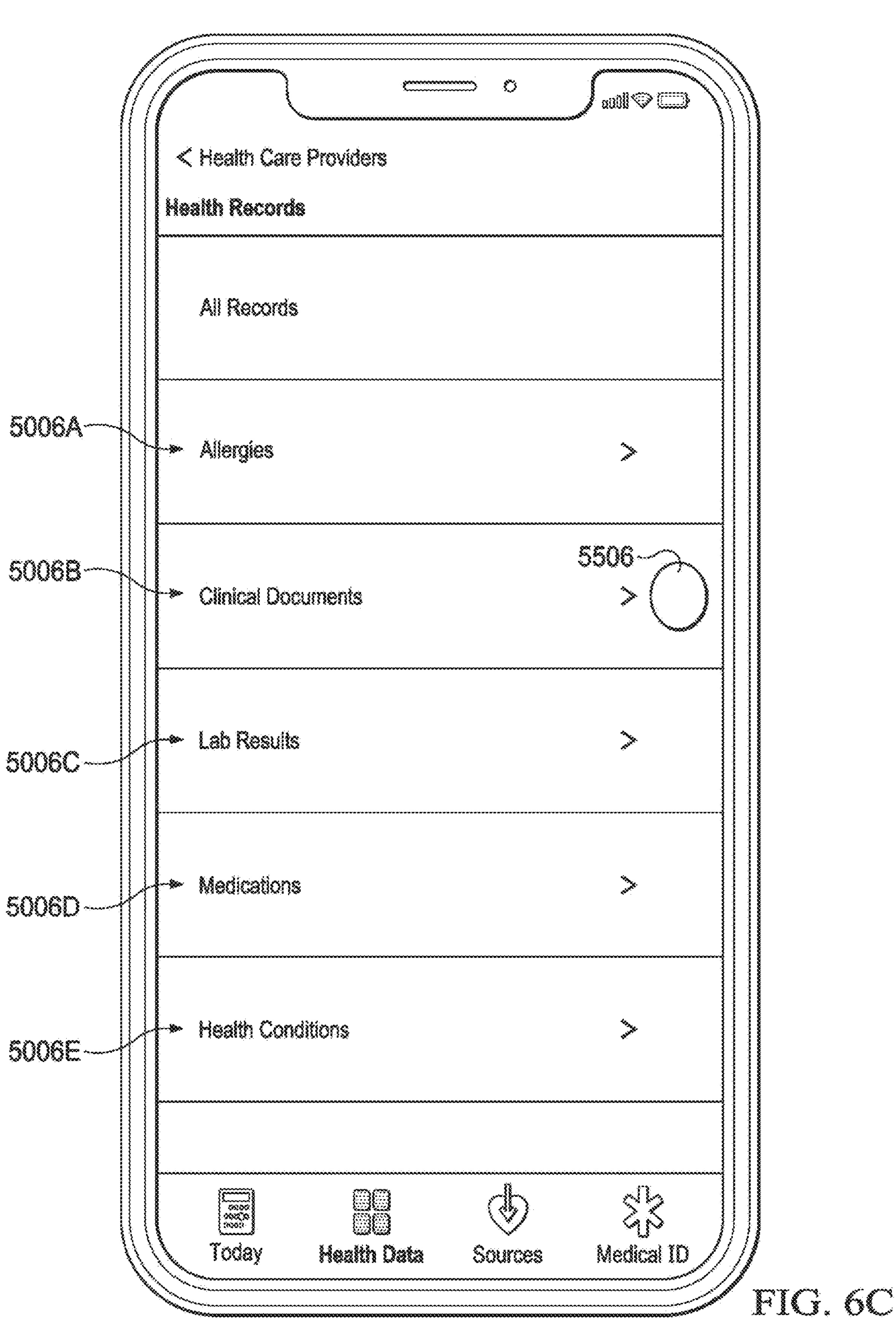

FIG. 6B' also illustrates detecting a tap gesture with contact 5504' over health records affordance 5304 to display category representations 5006A-5006E (allergies, clinical documents, lab results, medications, and health conditions categories, respectively) in FIG. 6C. FIG. 6C illustrates re-displaying category representations 5006A-5006E in response to detecting the tap gesture with contact 5504 or 5504' over health records affordance 5304. FIG. 6C further illustrates detecting a tap gesture with contact 5506 over category representation 5006B associated with clinical documents to display three representations of sub-categories 5015A-5015C of clinical documents (x-ray images, CT-scans, and ultrasound images sub-categories, respectively) in FIG. 6D.

Figure 6D:
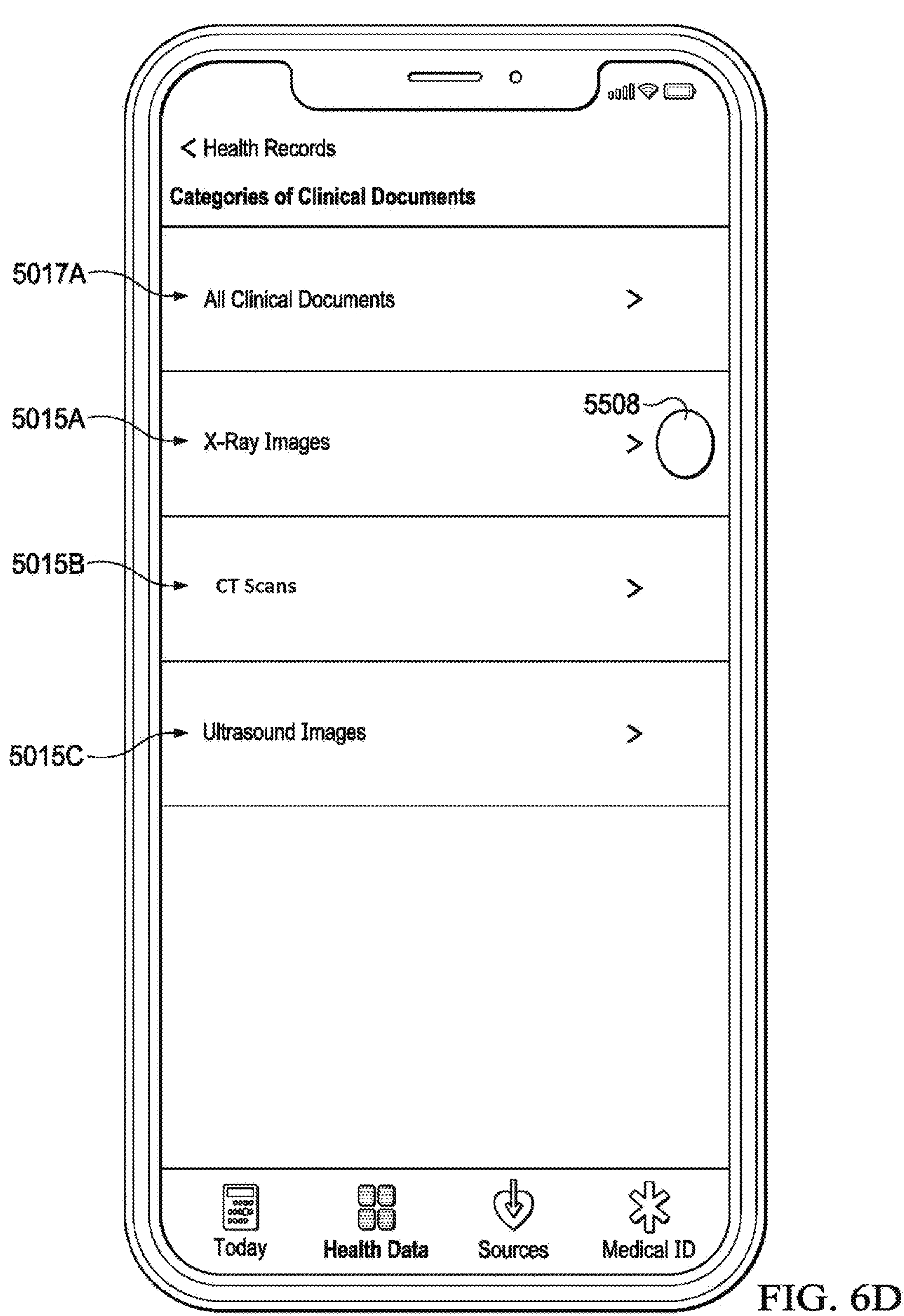
Figure 6E:
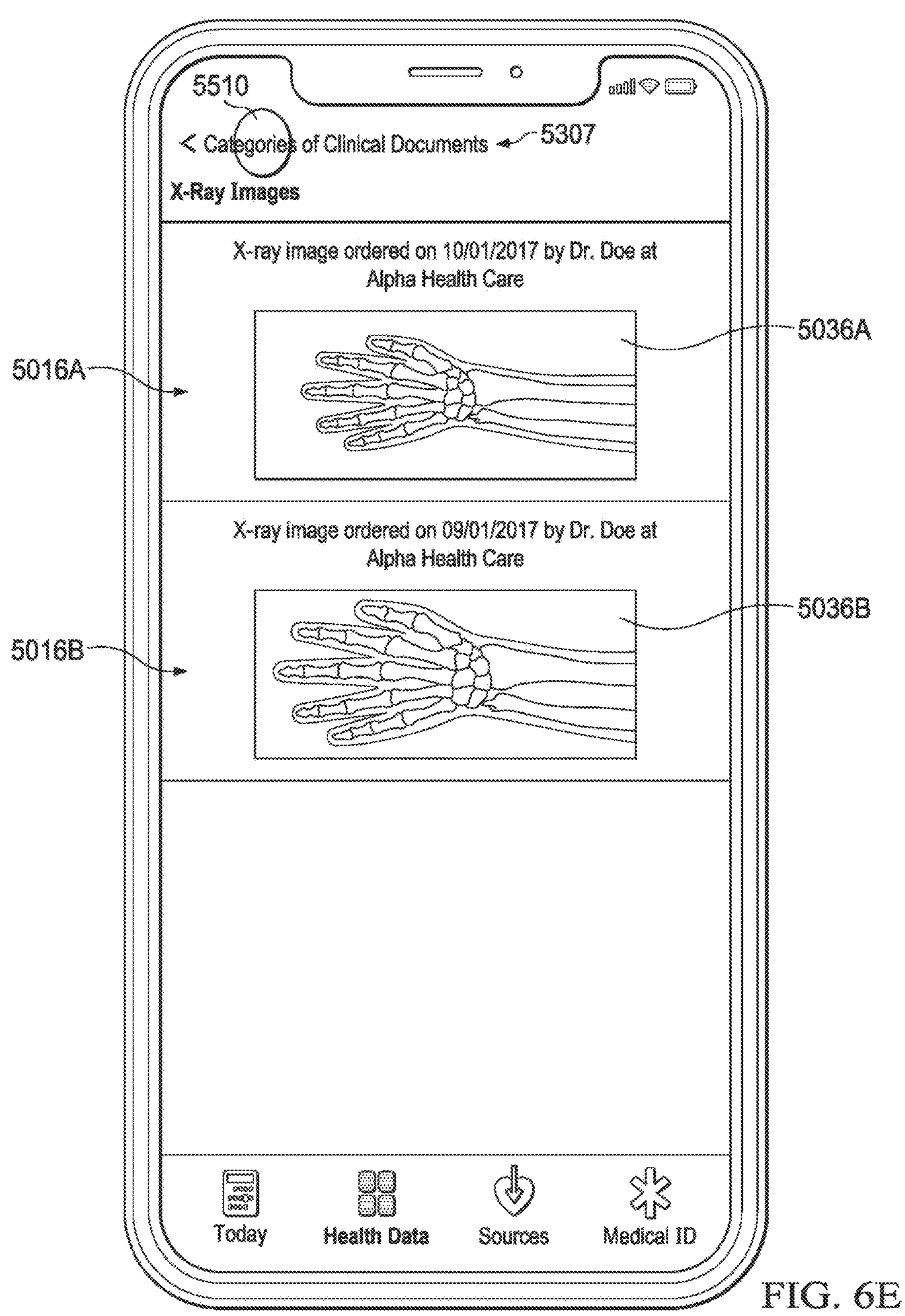
Figure 6E:
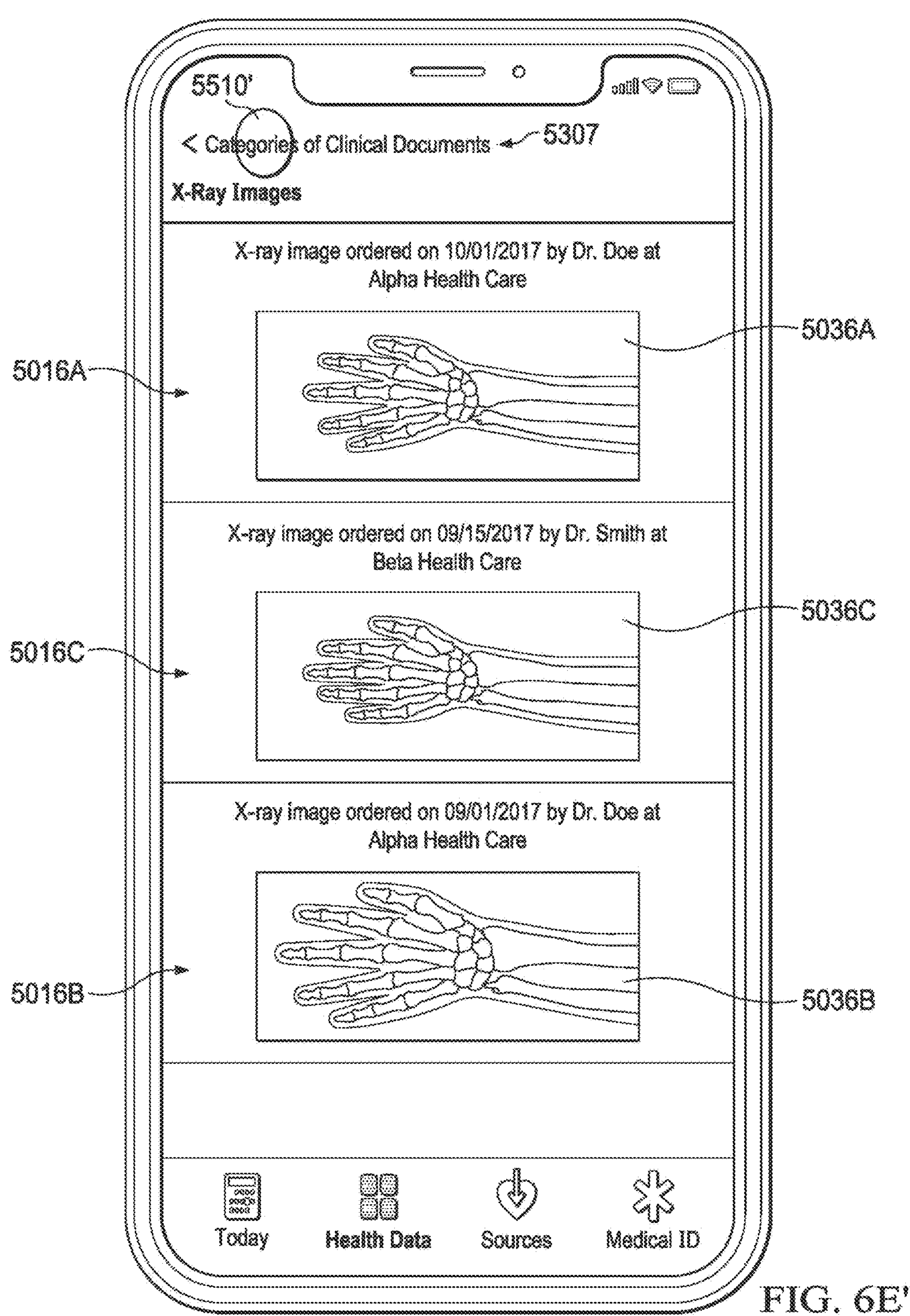

FIG. 6D illustrates the display of representations of sub-categories 5015A-5015C of clinical documents, as well as a representation of all clinical documents 5017A. In the illustrated embodiment, sub-category representation 5015A is associated with x-ray images, sub-category representation 5015B is associated with CT-scan images, and sub-category representation 5015C is associated with ultrasound images. As illustrated in FIG. 6D, each of sub-category representations 5015A-5015C is an affordance that includes text identifying that such affordance is associated with health records from a particular sub-category of clinical documents. Representation of all clinical documents 5017A is an affordance that includes text identifying that such affordance is associated with all health records of clinical documents. Further, each of sub-category representations 5015A-5015C is selectable by the user to view clinical documents of the user from the associated sub-category. In the illustrated embodiment, sub-categories of the clinical documents category are formed based on the type of clinical document. In other embodiments, clinical documents obtained during different periods of time (such as within a year, a quarter, a month, or another period of time) are grouped into different sub-categories of clinical documents based on such periods of time. In further embodiments, sub-categories of the health records of the user are sub-categorized based on other suitable means to organize the user's health records. FIG. 6D further illustrates detection of a tap gesture with contact 5508 over sub-category representation 5015A associated with x-ray images to display x-ray records 5016A and 5016B in FIG. 6E. FIG. 6E illustrates the display of health records associated with sub-category representation 5015A (e.g., sub-category of "X-Ray Images," FIG. 6D). More particularly, x-ray records 5016A and 5016B are displayed. In the illustrated embodiment, x-ray records 5016A and 5016B are records of x-ray images of the user and include text identifying the providers that ordered or conducted the x-ray exams (Dr. Doe and Alpha Health Care for both records). In the embodiment illustrated in FIG. 6E, both a physician (which may be a physician ordering or reviewing the x-ray image) and the facility are identified as providers. In such a manner, a health care professional and organization or facility associated with a health record may both be identified in a health record. In other embodiments, multiple physicians may be listed to identify the physician ordering the x-ray, or the physician reviewing the x-ray. In such embodiments, both a health care provider organization, and a facility are identified to give the user additional information. Each of x-ray records 5016A and 5016B also include text identifying the date the x-ray image was taken (Oct. 1, 2017 and Sep. 1, 2017 respectively) and an image file 5036A or 5036B containing a picture of the x-ray image. In some embodiments, the user may tap on one of image files 5036A or 5036B to overlay a full screen picture of the x-ray image, zoom in on the picture of the x-ray image, or to obtain additional information about the x-ray image such as the notes or diagnosis of a radiologist.

Similar to FIG. 6B, in FIG. 6E x-ray records 5016A and 5016B are both health records provided by Alpha Health Care. FIG. 6E' illustrates an alternative embodiment where the user has completed the onboarding process with Alpha Health Care and Beta Health Care. In FIG. 6E', in response to detecting the tap gesture with contact 5508 over sub-category representation 5015A (x-ray images sub-category) in FIG. 6D, x-ray record 5016C from Beta Health Care is concurrently displayed with x-ray records 5016A and 5016B from Alpha Health Care. In such a manner, similar to the user interface of FIG. 6C', a user may review all of the user's x-ray images from the user's health care providers in one interface. In the illustrated embodiment, x-ray record 5016C includes text identifying providers (Dr. Smith and Beta Health Care) and the date on which such x-ray image was taken (Sep. 15, 2017), as well as an image file 5036C containing a picture of the x-ray image. Although not illustrated in FIG. 6E', in one embodiment, health records from different subcategories of clinical documents from both Alpha Health Care and Beta Health Care can be displayed in a single user interface, for example, by a user selection of representation of all clinical documents 5017A illustrated in FIG. 6D.

Figure 6F:
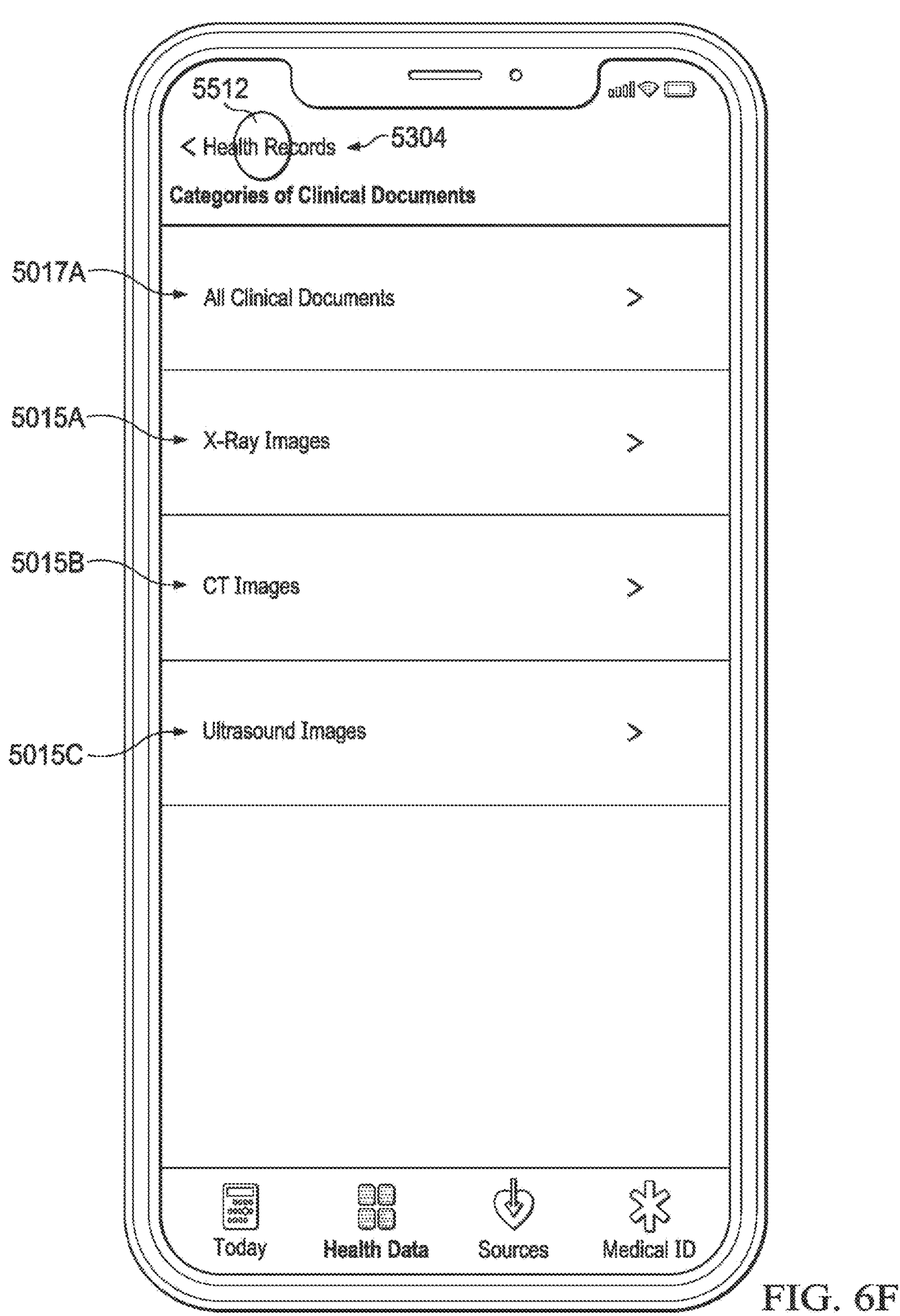
Figure 6G:
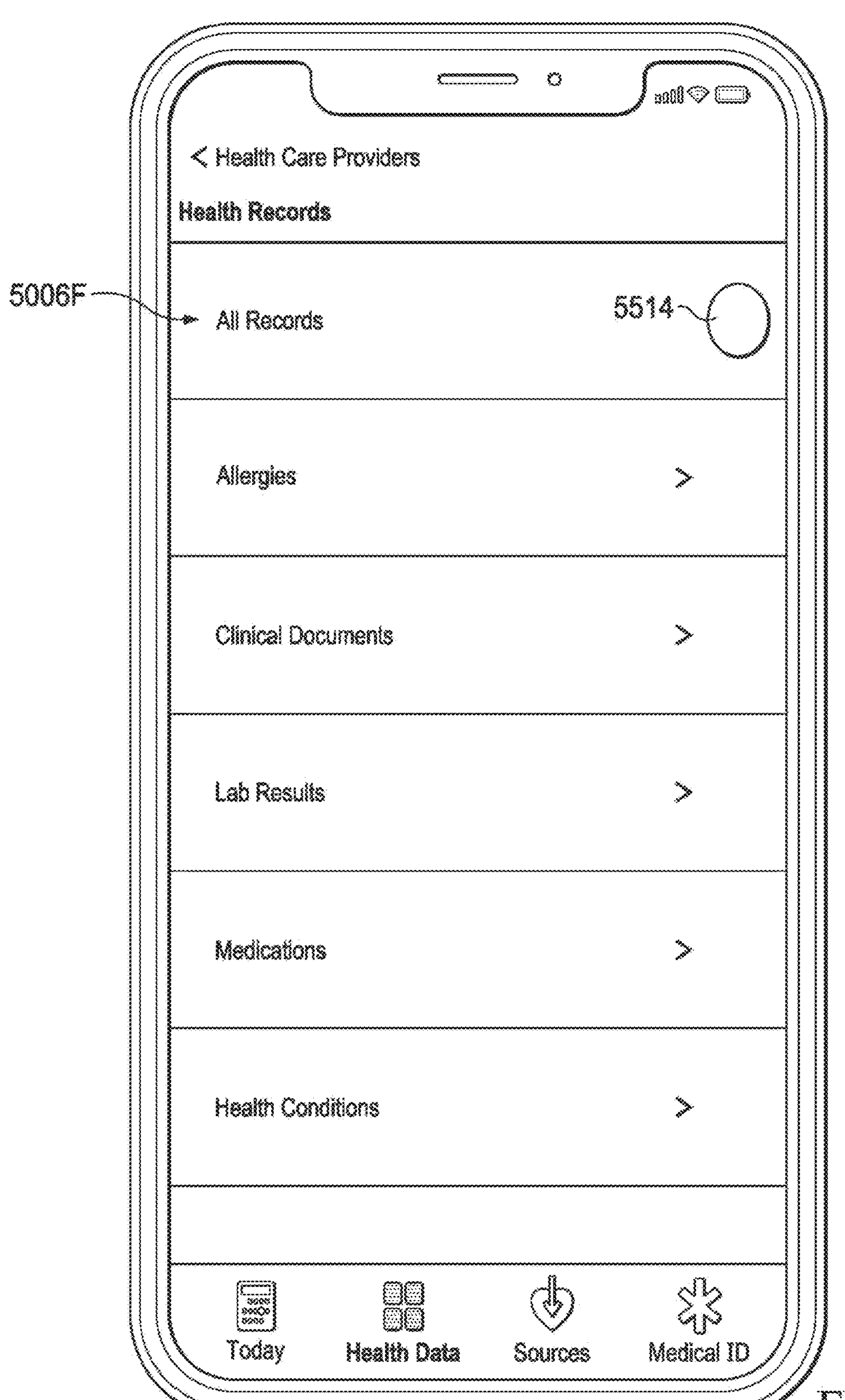

FIGS. 6E and 6E' each illustrate detecting a tap gesture with contact 5510 or 5510' respectively over a clinical documents affordance 5307 to display sub-category representations 5015A-5015C (x-ray images, CT-scans, and ultrasound images) in FIG. 6F. FIG. 6F illustrates re-displaying sub-categories 5015A-5015C in response to detecting the tap gesture with contact 5510 or 5510' over clinical documents affordance 5308. In some embodiments, the user may select sub-category representation 5015B or sub-category representation 5015C to view health records belonging to the such other sub-categories of health records. In the illustrated embodiment, the user performs a tap gesture with contact 5512 over health records affordance 5304 to view category representations 5006A-5006E (allergies, clinical documents, lab results, medications, and health conditions categories, respectively) in FIG. 6G. FIG. 6G illustrates re-displaying category representations 5006A-5006E in response to detecting the tap gesture with contact 5512 over health records affordance 5304 (e.g., as shown in FIG. 6F).

Figure 6H:
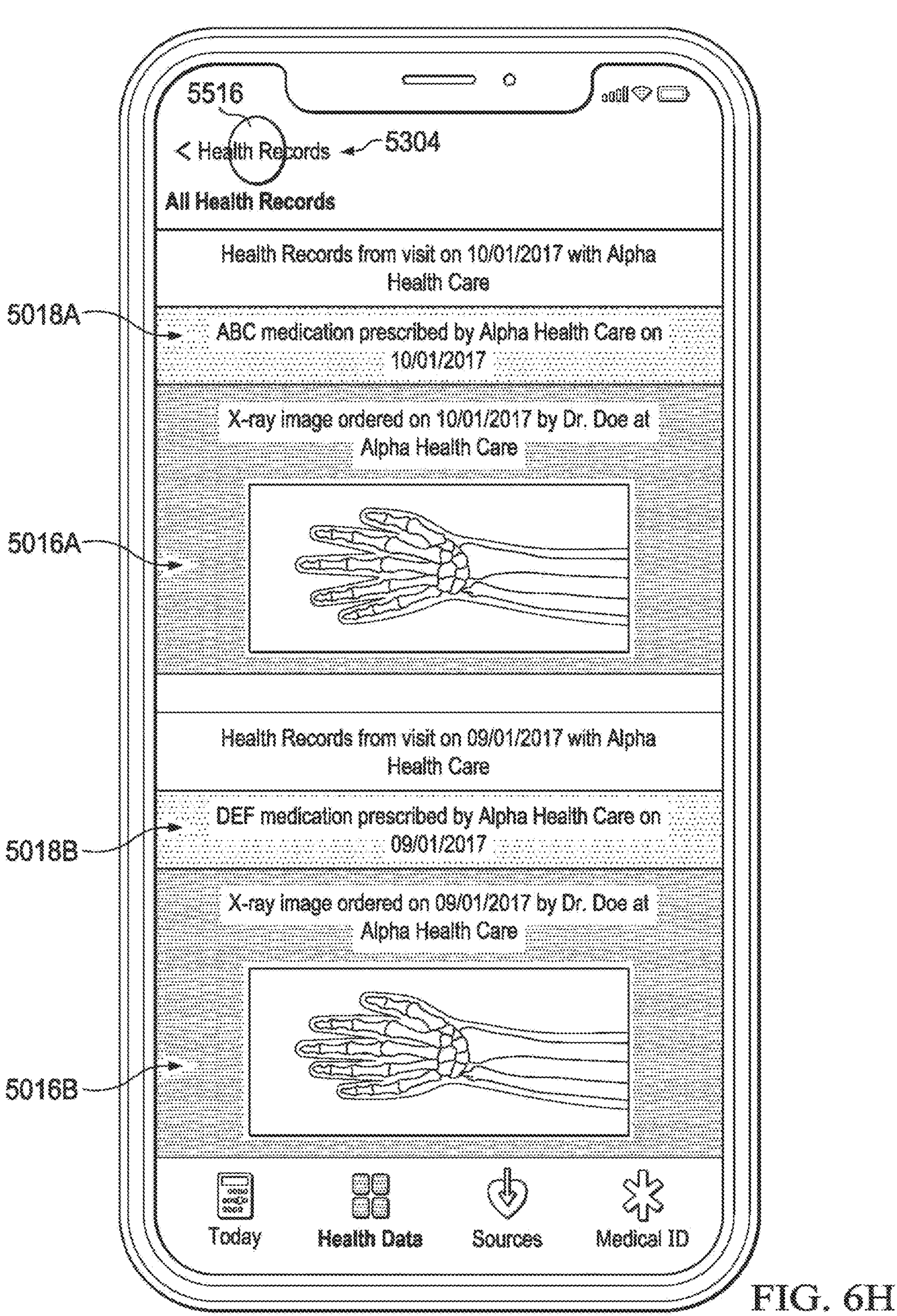
Figure 6H:
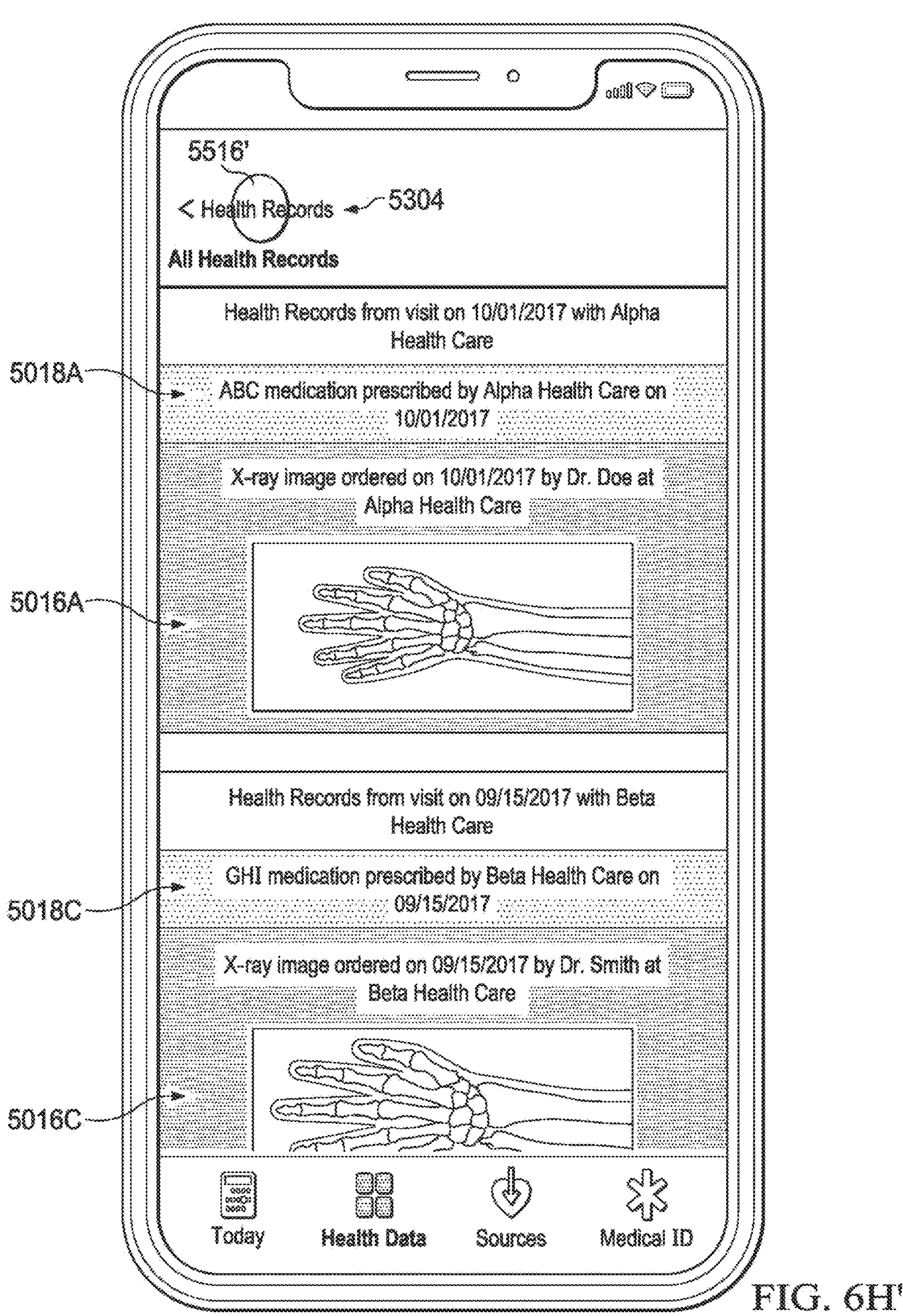

FIG. 6G also illustrates detecting a tap gesture with contact 5514 over all records representation 5006F to concurrently display health records from different categories in FIG. 6H. FIG. 6H illustrates displaying health records from multiple categories of health records. In the illustrated embodiment, medication records and x-ray records are concurrently displayed and are organized by date. More particularly, FIG. 6H illustrates the concurrent display of medication records 5018A and 5018B (ABC medication and DEF medication) and x-ray records 5016A and 5016B of x-ray images obtained on Oct. 1, 2017 and Sep. 1, 2017. In the illustrated embodiment, health records are grouped based on the date of visitation with a health care provider. Medication record 5018A and x-ray record 5016A are displayed in a first group of health records from a visit with Alpha Health Care on Oct. 1, 2017. Medication record 5018B and x-ray record 5016B are displayed in a second group of health records from a visit with Alpha Health Care on Sep. 1, 2017. In the illustrated embodiment, health records are displayed in different colors to differentiate between health records of different categories. Medication records 5018A and 5018B are displayed in a first color representative of medications and x-ray records 5016A and 5016B are displayed in a second color representative of clinical documents. In an alternative embodiment, x-ray records 5018A and 5018B are displayed in a color representative of the sub-category of x-ray images. In other embodiments, health records may be displayed in groups or colors may be assigned based on any characteristic such as time period, visit date, provider (where more than one provider has been onboarded as described relative to FIG. 6H'), category of health record, subcategory of health record, severity of condition, or any other suitable criteria. Characteristics such as health care provider may be further divided or differentiated by organization, physician, facility, or location. In such a manner, groups in which health records are displayed and the colors of such health records may be used to allow a user to quickly visualize and distinguish between health records having different characteristics. In other embodiments, health records satisfying a common criteria may be commonly displayed in particular fonts, in particular locations, with particular icons, alongside particular graphical elements, or otherwise with particular visual characteristics to allow a user to distinguish health records by more than the two criteria available when only display groups and color are utilized.

In FIG. 6H, x-ray records 5016A and 5016B of x-ray images obtained on Oct. 1, 2017 and Sep. 1, 2017, and medication records 5018A and 5018B (ABC medication and DEF medication) are all health records provided by Alpha Health Care. FIG. 6H' illustrates an alternative embodiment where the user has completed the onboarding process with Alpha Health Care and Beta Health Care. In FIG. 6H', in response to detecting the tap gesture with contact 5514 over all records representation 5016F in FIG. 6G, medication record 5018C (GHI medication) and x-ray record 5016C of for an x-ray image ordered on Sep. 15, 2017 are both obtained from Beta Health Care and are concurrently displayed with medication record 5018A and x-ray record 5016A from Alpha Health Care. In FIG. 6H', medication record 5018C and x-ray record 5016C are displayed in a group and represent health records of a Sep. 15, 2017 visit with Beta Health Care. In the illustrated embodiment, medication record 5018C and x-ray record 5016C are health records of a Sep. 15, 2017 visit and are more recent than the medication record 5018B and x-ray record 5016B, which are health records of a Sep. 1, 2017 visit. Thus, medication record 5018C and x-ray record 5016C are displayed instead of or ahead of medication record 5018B and x-ray record 5016B on display 112. In one embodiment, the user performs a swipe gesture (not shown) to view less recent health records, such as medication record 5018B and x-ray record 5016B. In other embodiments, display 112 concurrently displays health records from more than two visits.

Figure 6I:
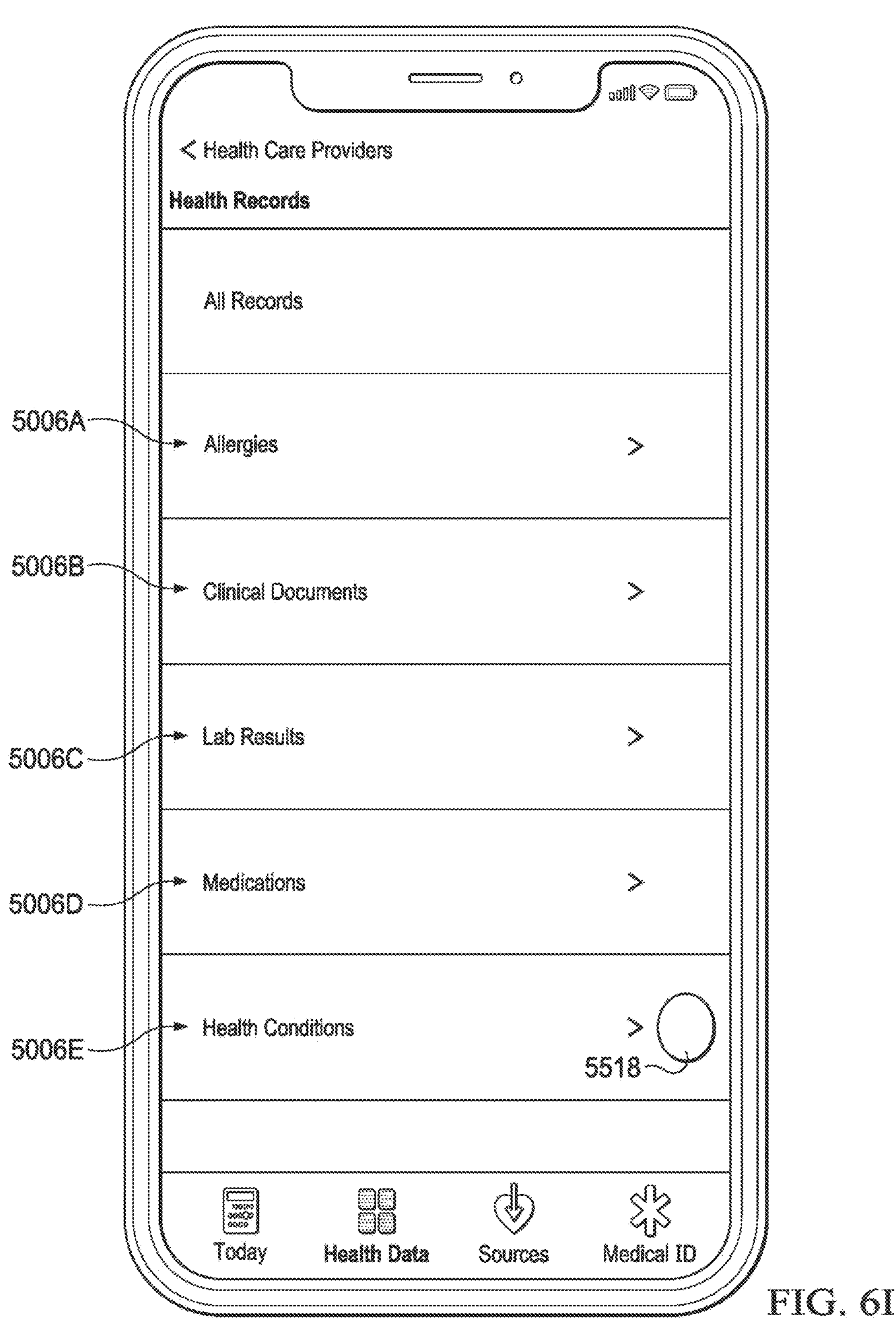

FIGS. 6H and 6H' each further illustrate detecting a tap gesture with contact 5516 or 5516' respectively over health records affordance 5304 to display category representations 5006A-5006E (allergies, clinical documents, lab results, medications, and health conditions categories respectively) in FIG. 6I. FIG. 6I illustrates re-displaying category representations 5006A-5006E in response to detecting the tap gesture with contact 5516 or 5516' over health records affordance 5304. FIG. 6I also illustrates detecting a tap gesture with contact 5518 over category representation 5006E to view health condition records 5020A, 5020B, and 5020C in FIG. 6J.

Figure 6J:
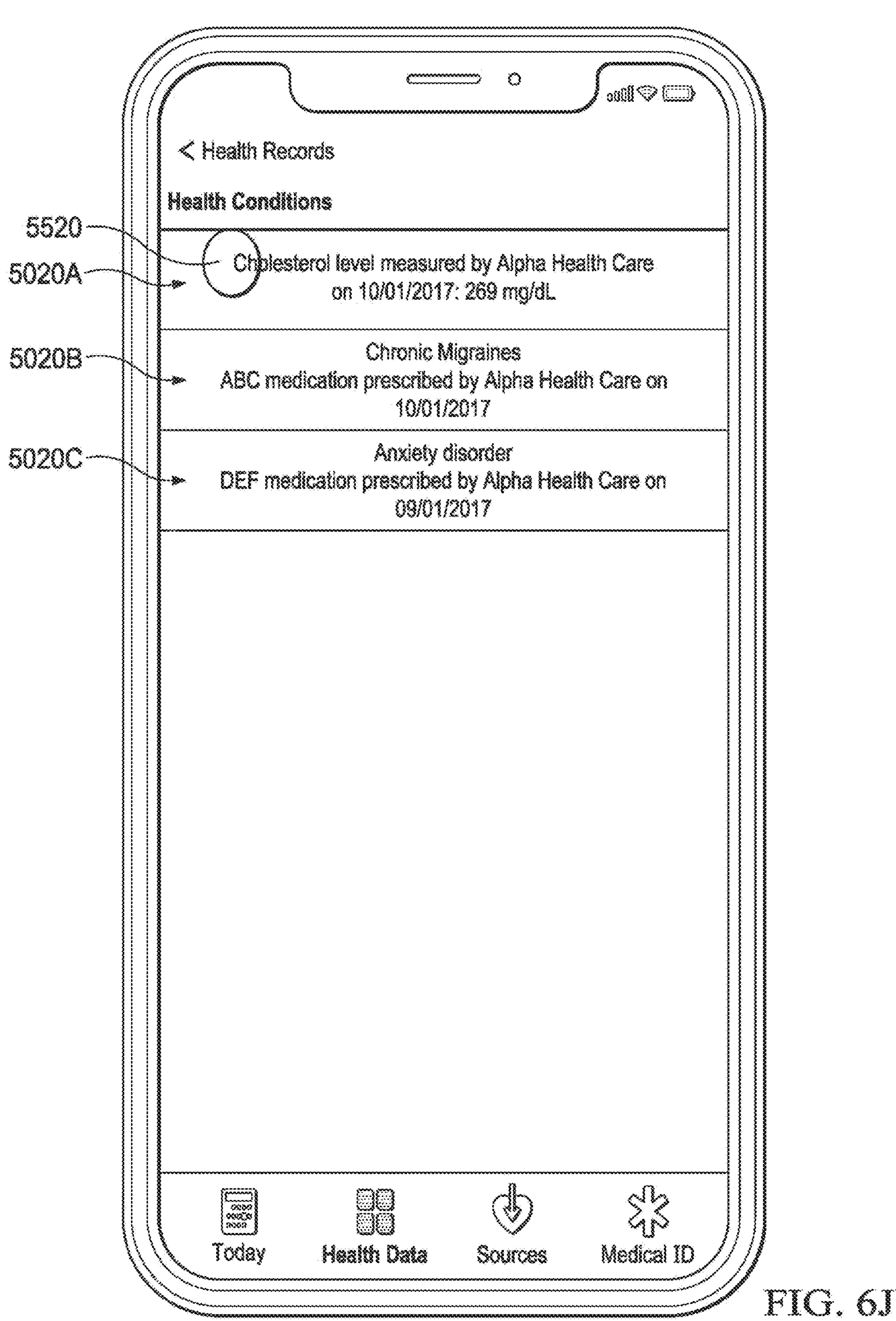
Figure 6J:
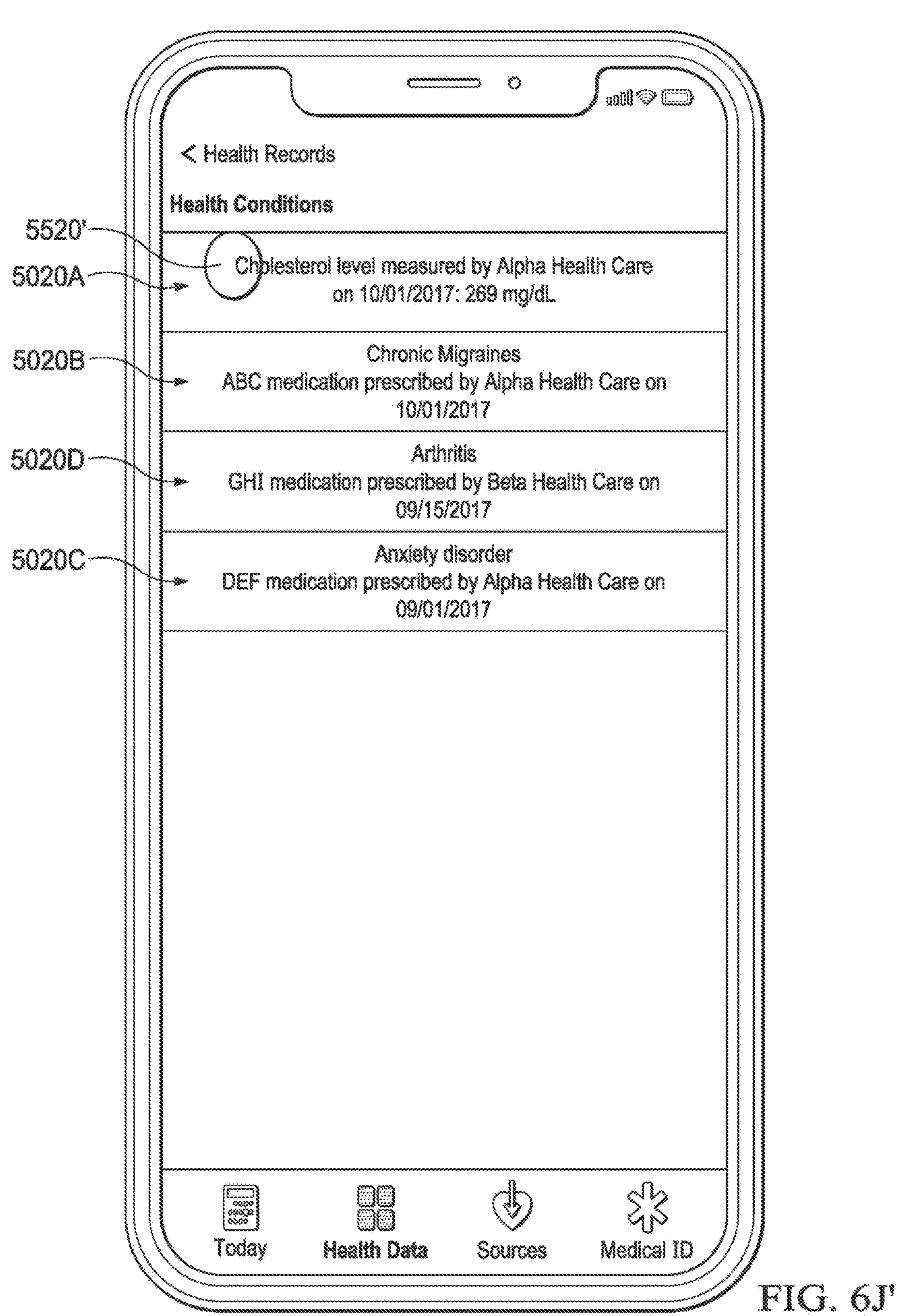

FIG. 6J illustrates displaying health condition records 5020A, 5020B, and 5020C of the user. In the illustrated embodiment, health condition record 5020A is a health record containing information about the user's cholesterol level, the date the user's cholesterol was measured, and the name of the health care provider that measured the user's cholesterol level. In some embodiments, the value of the user's cholesterol level is displayed in an enlarged font, underlined, highlighted, or is otherwise formatted to emphasize the cholesterol level of the user. In some embodiments, the value of the user's cholesterol level is also displayed in a color indicative of where the user's cholesterol level falls within a range of cholesterol levels. For example, the value of the user's cholesterol level may be displayed in green if the user's cholesterol level is below 200 mg/dL, in yellow if the user's cholesterol level is between 200 mg/dL and 300 md/dL, and in red if the user's cholesterol level is above 300 mg/dL. In one embodiment, the numerical value of the current cholesterol value is displayed within a range of numerical values. The numerical value is indicative of the severity of the cholesterol level of the user and the range of values is indicative of a normalcy or severity of the health condition. Similar numerical values and ranges of numerical values may be used with respect to other health conditions of the user to display the normalcy or severity of any condition. Graphical representations of such value and ranges may also be utilized. In the illustrated embodiment, health condition record 5020B is a health record containing information about the user's chronic migraines, the medication prescribed to the user, the date of the prescription, and the health care provider that provided the prescription to the user. Similarly, health condition record 5020C is a health record containing information about the user's anxiety disorder, the medication prescribed to the user, the date of the prescription, as well as the name of the health care provider that provided the prescription to the user.

In FIG. 6J, health condition records 5020A-5020C (cholesterol level, chronic migraines, and anxiety disorder, respectively), and are all health records provided by Alpha Health Care. FIG. 6J' illustrates an alternative embodiment where the user has completed the onboarding process with Alpha Health Care and Beta Health Care. In FIG. 6J', in response to detecting the tap gesture with contact 5518 over category representation 5006E (health conditions category) in FIG. 6I, health condition record 5020D from Beta Health Care is concurrently displayed with health condition records 5020A-5020C. Health condition record 5020D, similar to health condition records 5020B and 5020C, is a health record containing information about the medication prescribed to treat the health condition, the date the medication was prescribed to the user, and the name of the health care provider that provided the prescription to the user. In some embodiments, each health condition record also contains additional information about the respective health condition, such as a description of the health condition, symptoms, related health conditions, treatment options, lifestyle recommendations, and other suitable information about the respective health condition. In some embodiments, each health condition record is an affordance that the user selects to view additional information about the corresponding health condition. In that regard, FIGS. 6J and 6J' also illustrate detecting a tap gesture with contact 5520 or 5520', respectively, over health condition record 5020A to display such additional information in FIG. 6K or FIG. 6K' respectively.

Figure 6K:
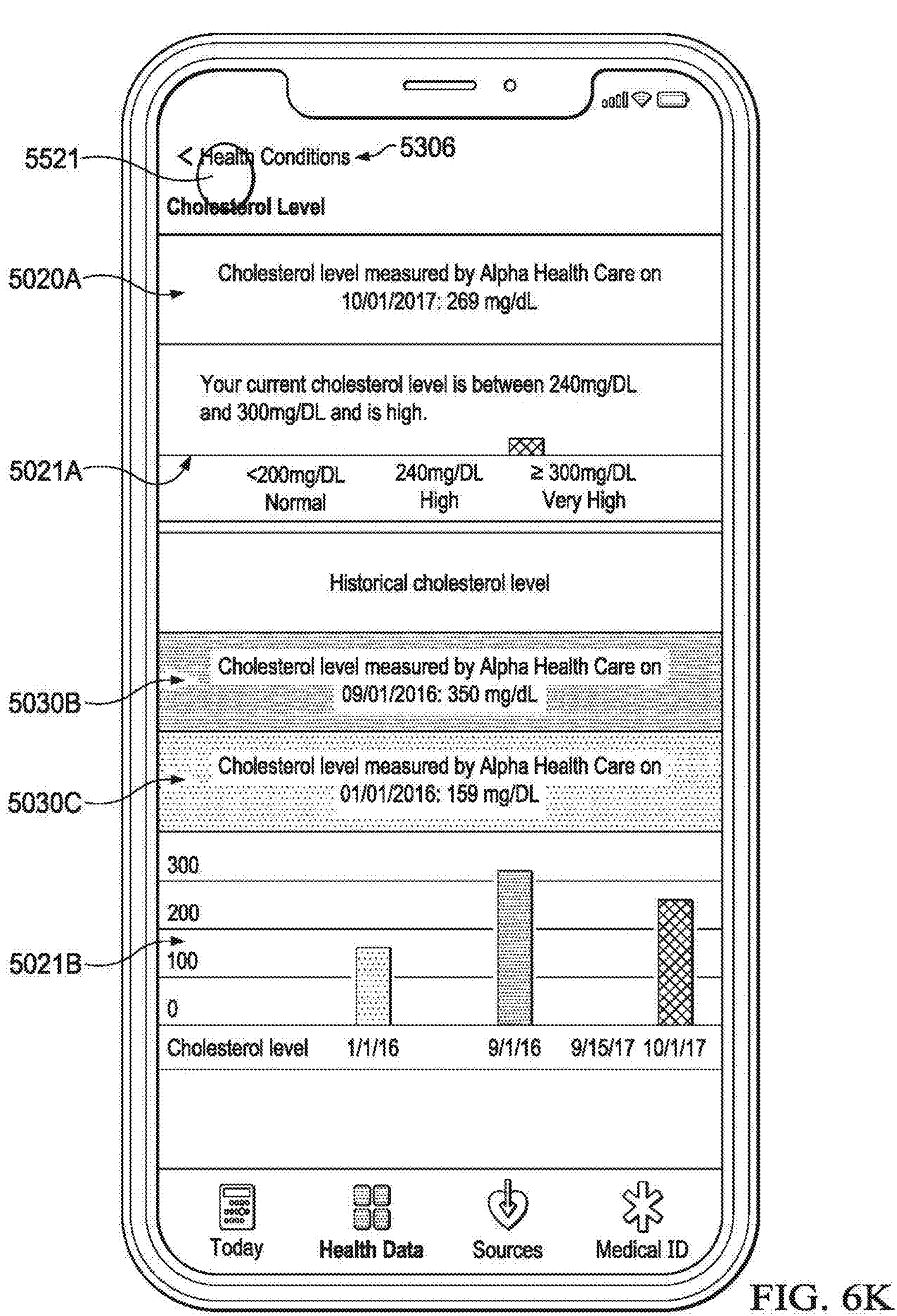
Figure 6K:
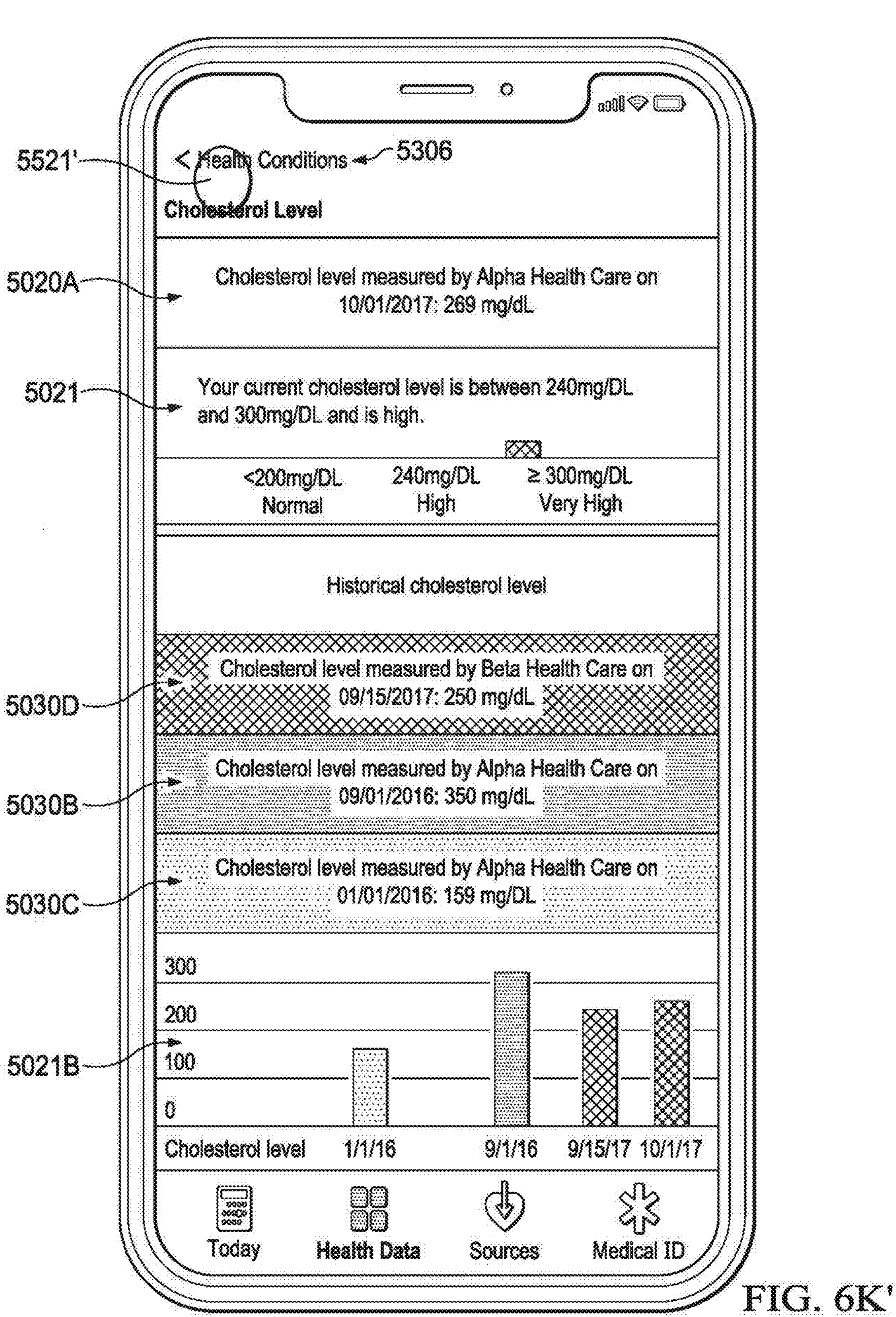

FIG. 6K illustrates displaying additional information regarding health condition record 5020A (the user's cholesterol level). As illustrated in FIG. 6K, a cholesterol representation 5021A is displayed containing an indication of the user's current cholesterol level and an indication of where the user's current cholesterol level falls within a range of cholesterol levels. More particularly, cholesterol representation 5021A graphically identifies the user's current cholesterol level within a range between 240 mg/dL and 300 mg/dL, thereby falling in a range between high cholesterol (240 mg/dL) and very high cholesterol (300 mg/dL). In the illustrated embodiment, a cholesterol representation 5021B is also displayed on display 112. As further illustrated in FIG. 6K, cholesterol representation 5021B is displayed containing a bar graph of the user's cholesterol level over time, where each bar represents a measurement of the user's cholesterol level. In the depicted embodiment, different bars representing cholesterol levels that fall within different ranges are displayed in different colors. In other embodiments, additional representations of the user's current and historical cholesterol level are displayed. FIG. 6K also illustrates displaying historical health records of the user's cholesterol level in health condition record 5030B and 5030C from Sep. 1, 2016 and Jan. 1, 2016 respectively. As used herein, a historical health record is a health record of any particular health information other than the current health record of such health information. For example, a medication record containing information about a medication that is no longer prescribed to the user is a historical health record. Additional examples of historical records are illustrated in at least FIGS. 8D and 8E and are discussed in the subsequent paragraphs. In the illustrated embodiment, the historical health records are also color coded based on the severity of the user's health condition relative to normalcy. In the illustrated embodiment, the cholesterol level measured on Jan. 1, 2016 is under 200 mg/dL and is assigned a first color (e.g., green), whereas the cholesterol level measured on Sep. 1, 2016 is over 300 mg/dL and is assigned a second color (e.g., red). In other embodiments, different colors that identify different severity levels of the user's health condition are assigned to different ranges of cholesterol levels.

FIG. 6K' illustrates displaying additional information regarding health condition record 5020A from both Alpha Health Care and Beta Health Care. In the illustrated embodiment, a historical health record 5030D obtained from Beta Health Care on Sep. 15, 2017 is displayed with historical health records 5030B and 5030C (the user's cholesterol levels measured on Sep. 1, 2016 and Jan. 1, 2016, respectively) previously described in FIG. 6K. In the illustrated embodiment, the user's cholesterol level measured on Sep. 15, 2017 is between 200 mg/dL and 300 mg/dL and is assigned a third color (e.g., orange). Further, cholesterol representation 5021B includes bar graphs of the user's historical cholesterol levels obtained from both Alpha Health Care and Beta Health Care.

Figure 6L:
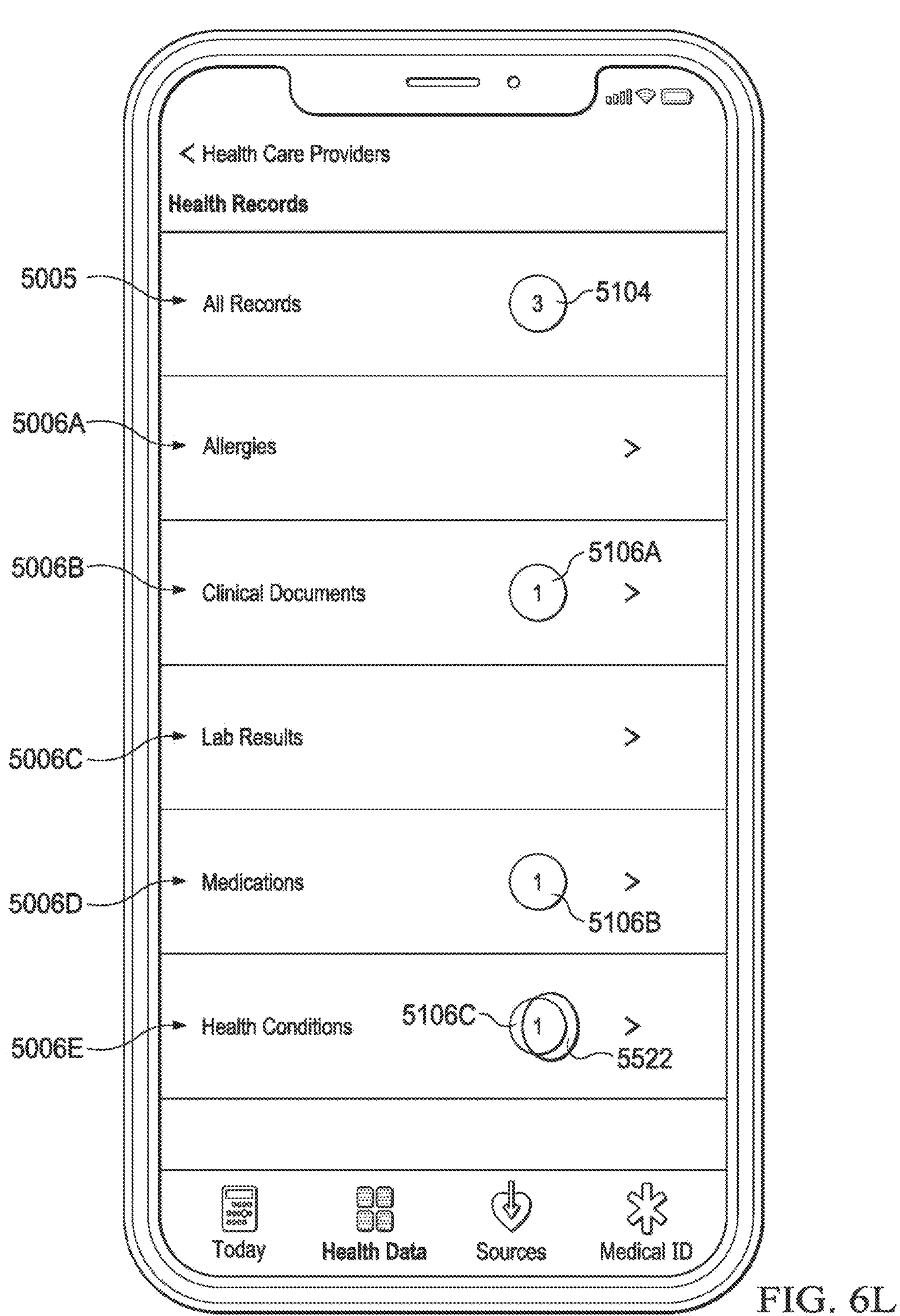
Figure 6L:
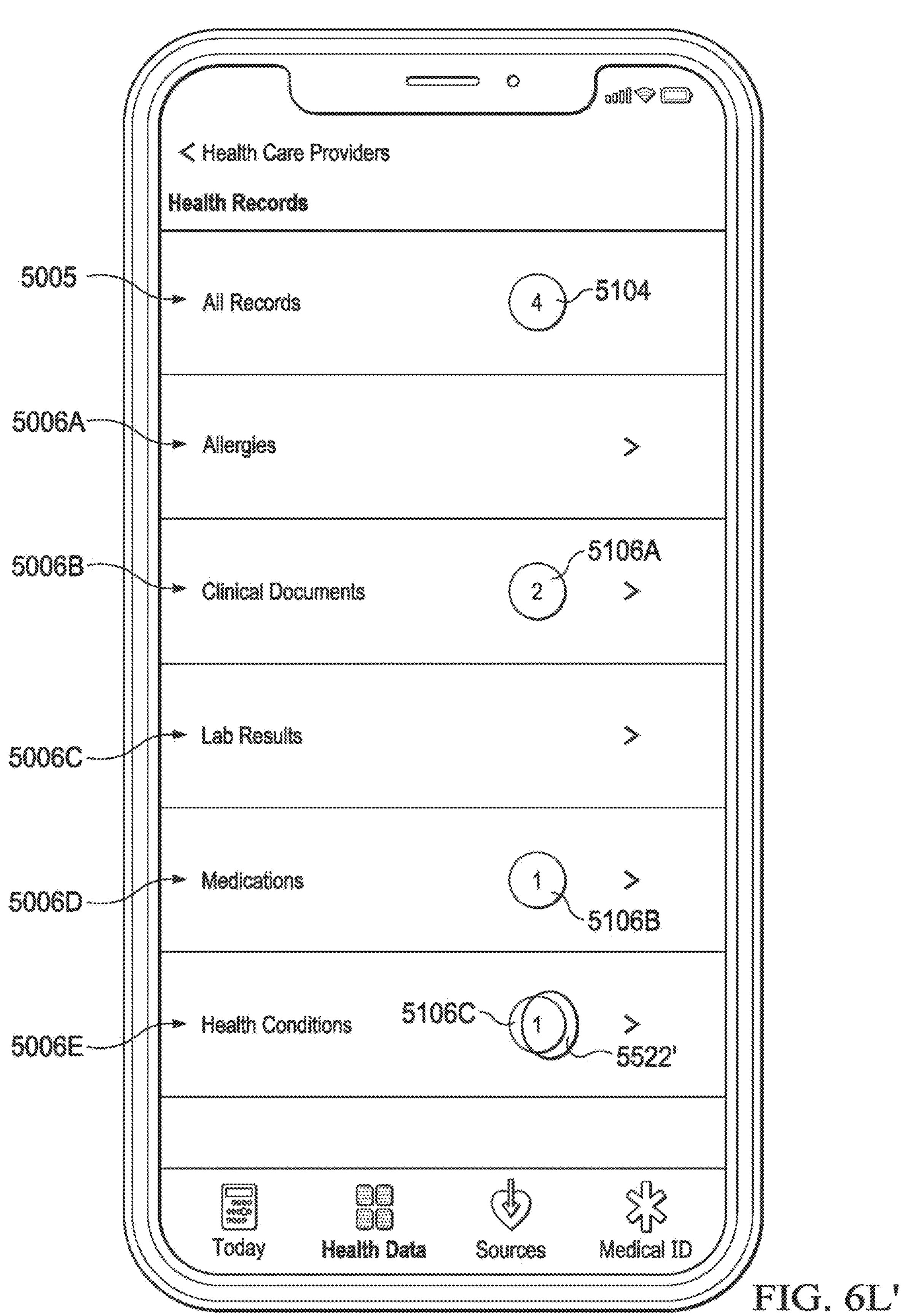
Figure 6M:
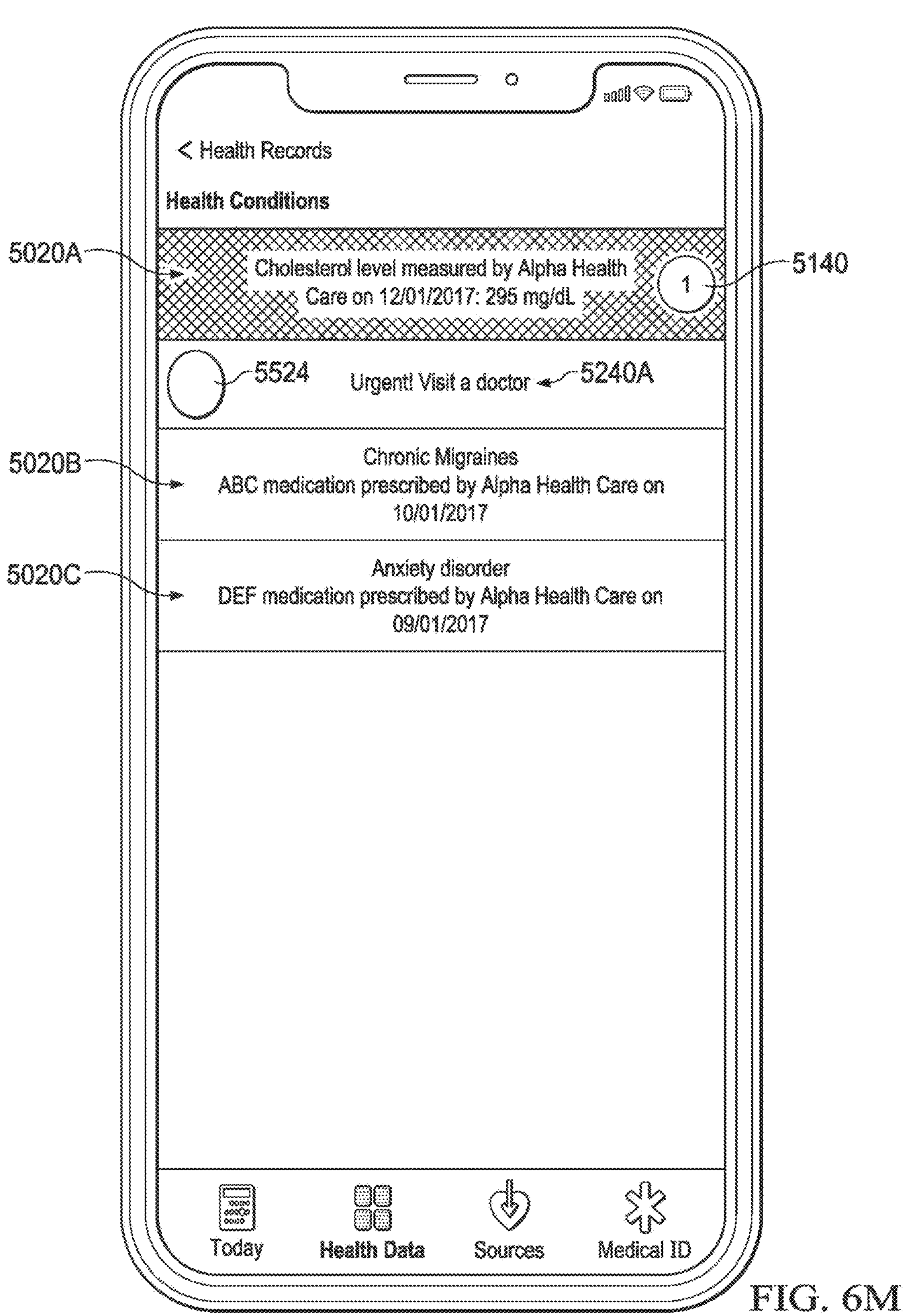
Figure 6M:
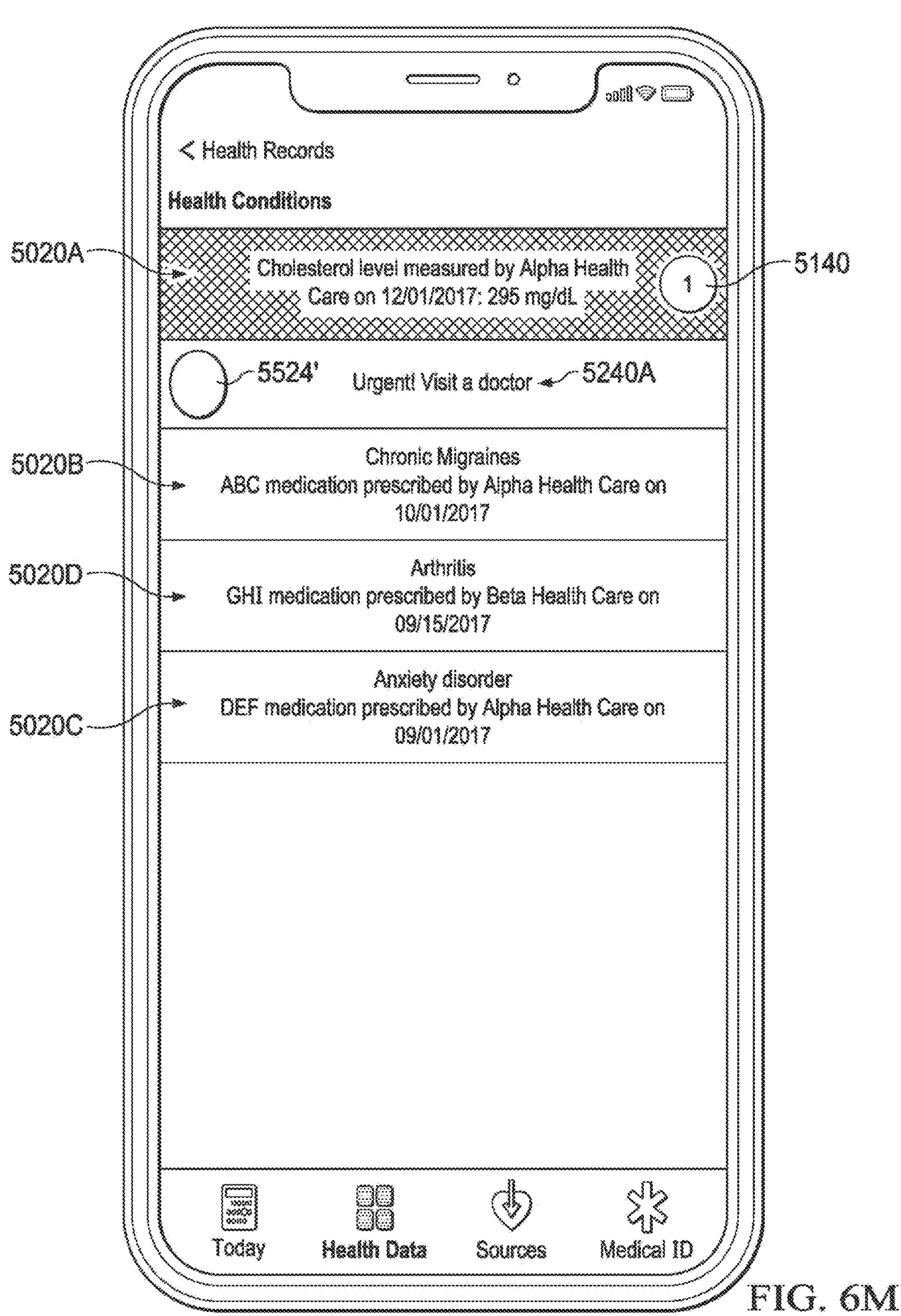
Figure 6N:
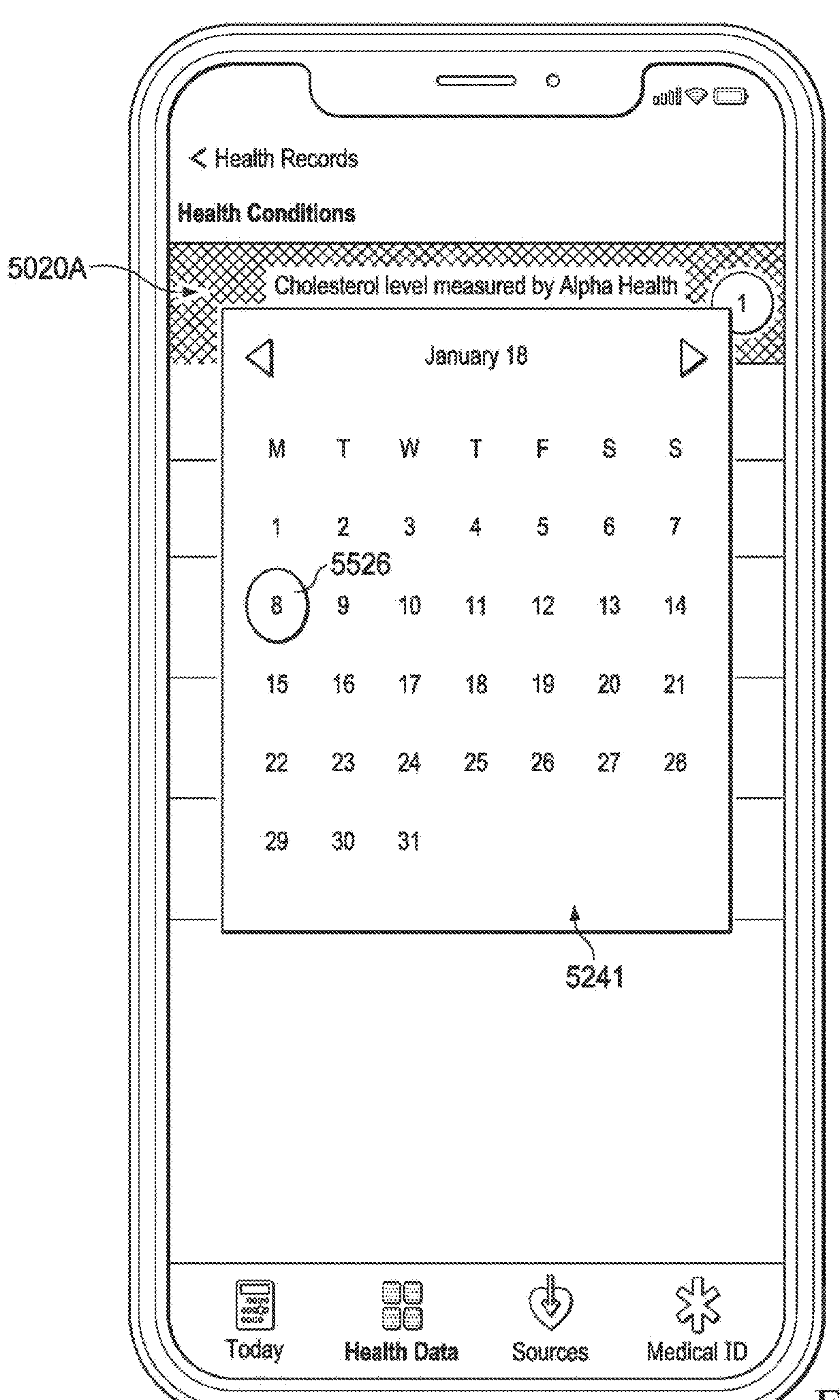
Figure 6O:
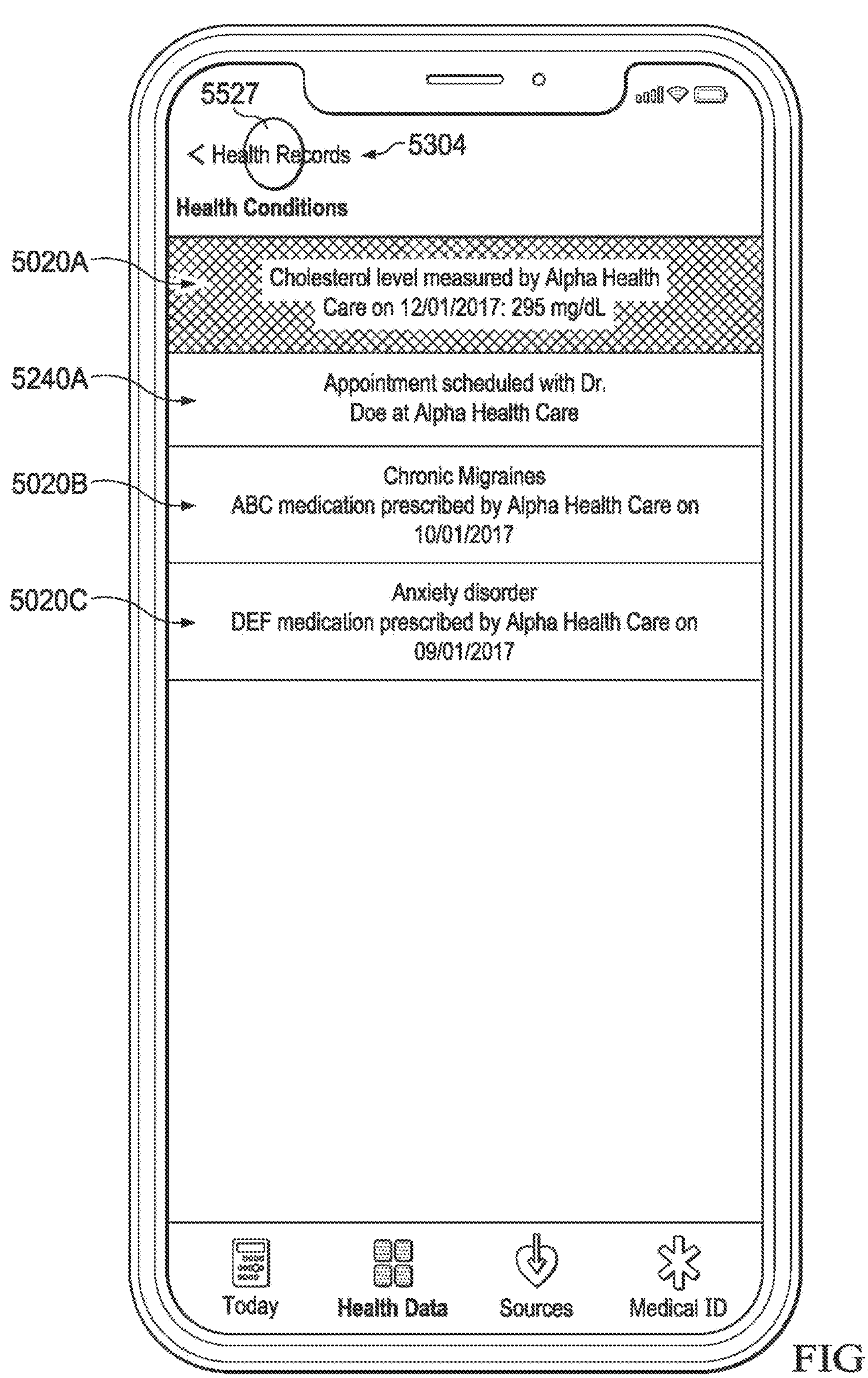
Figure 6O:
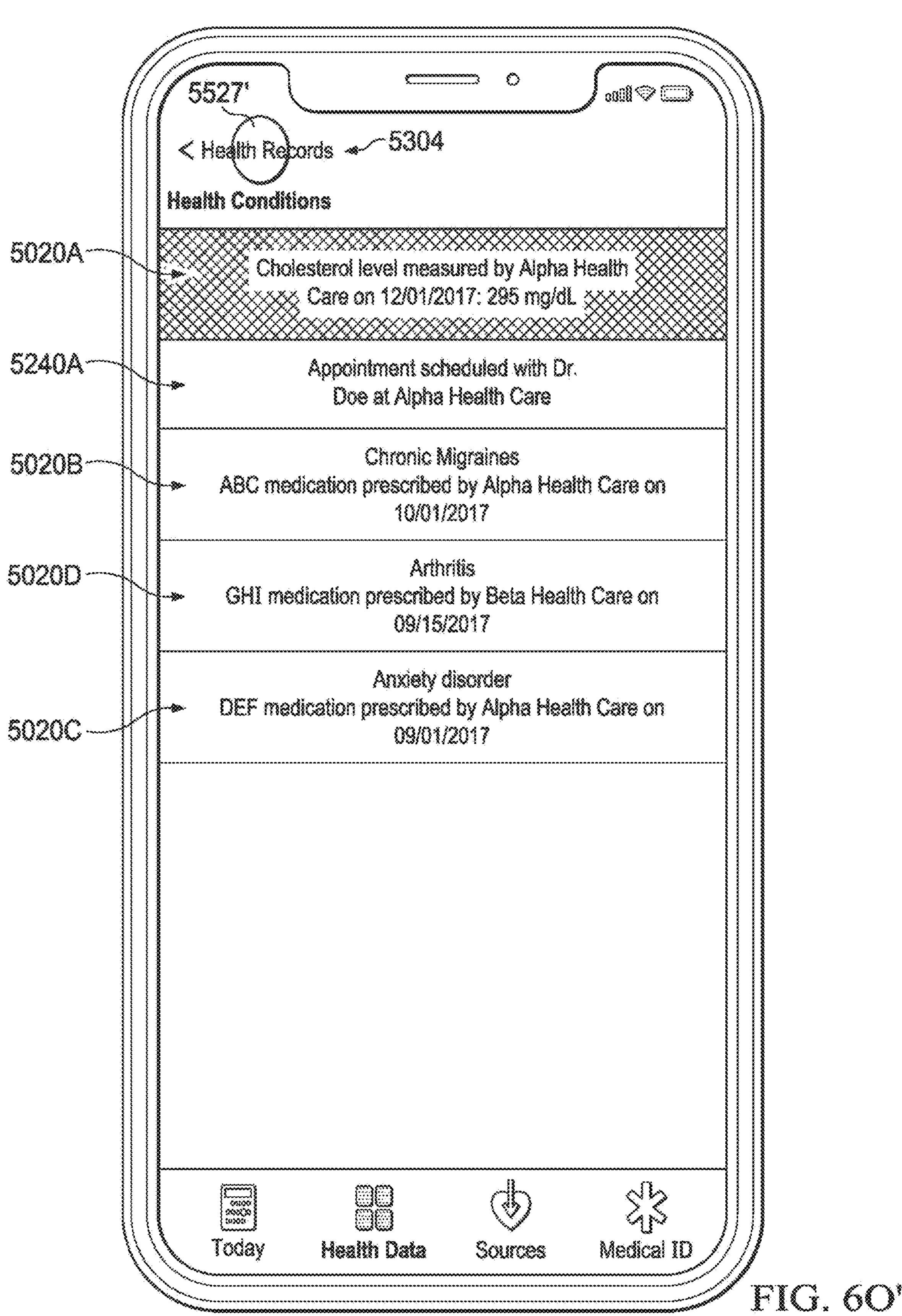
Figure 6P:
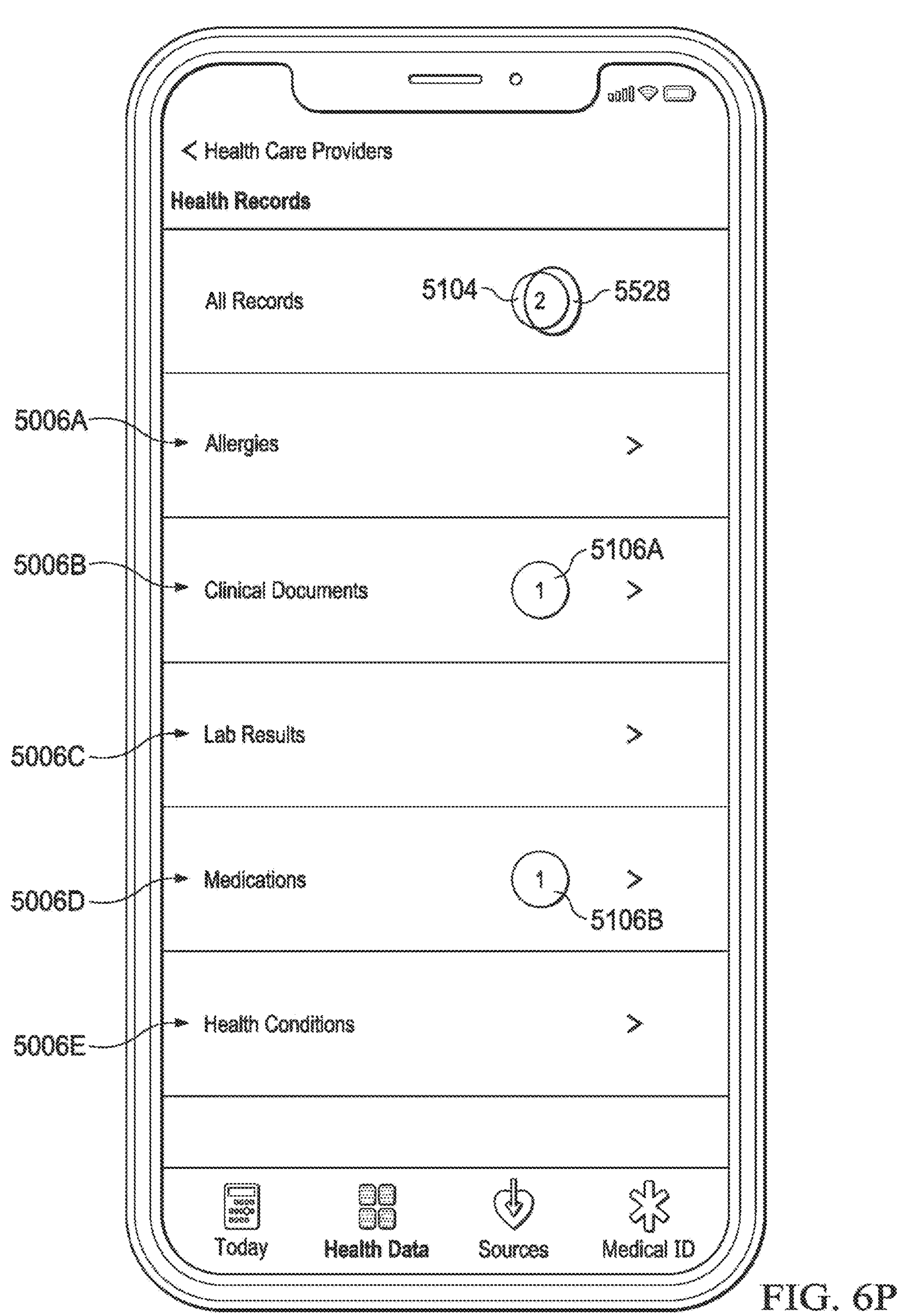
Figure 6P:
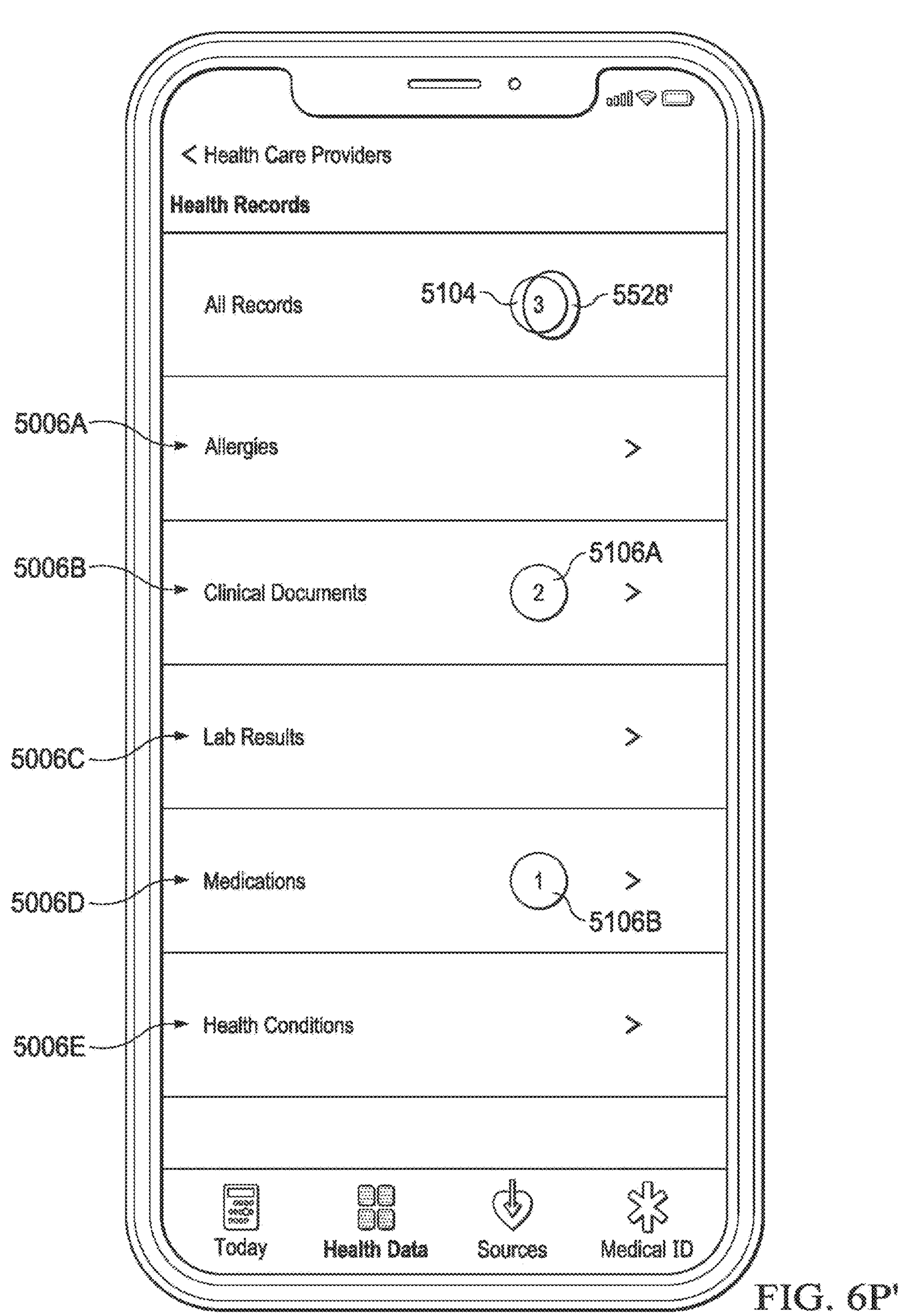
Figure 6Q:
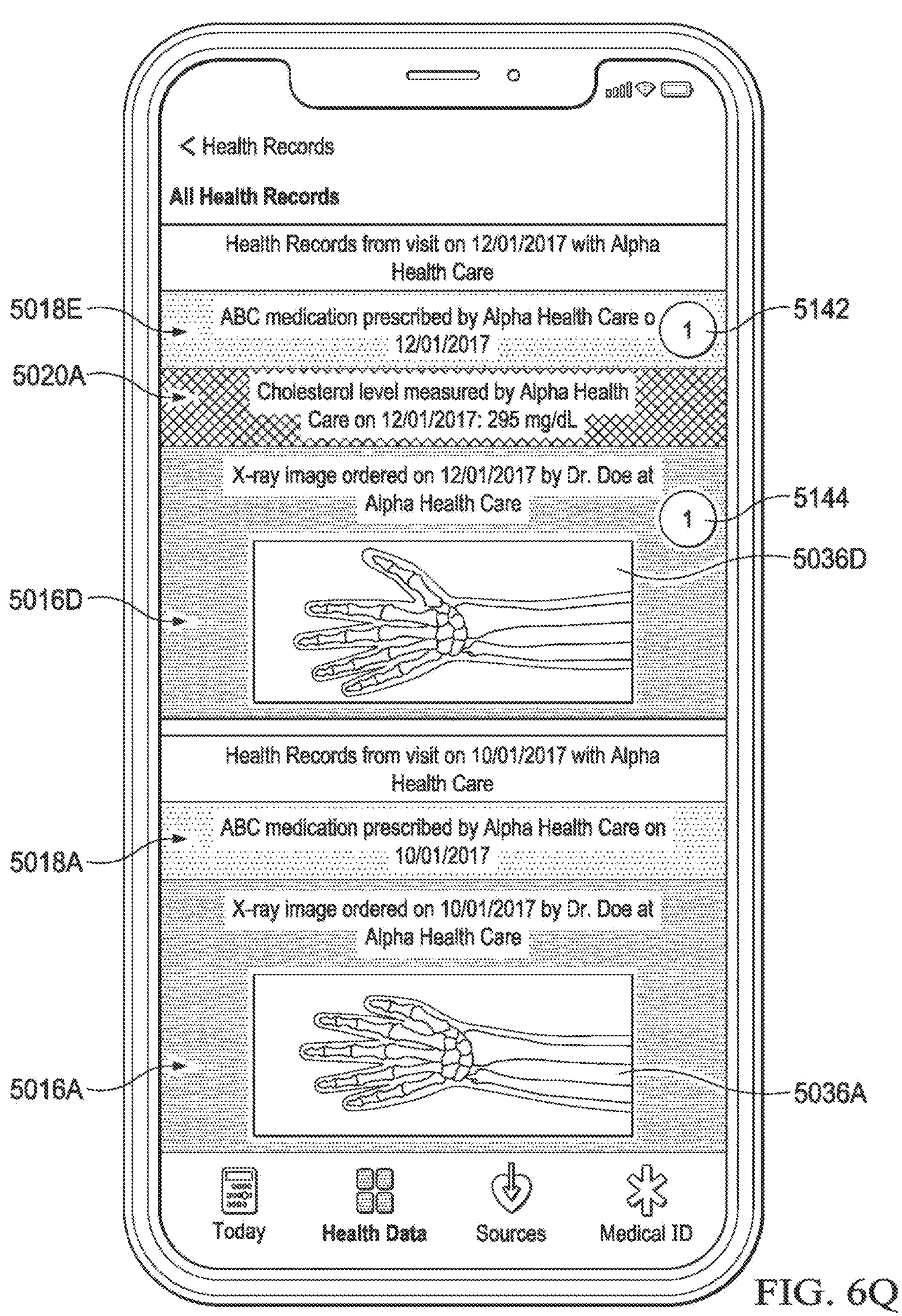
Figure 6Q:
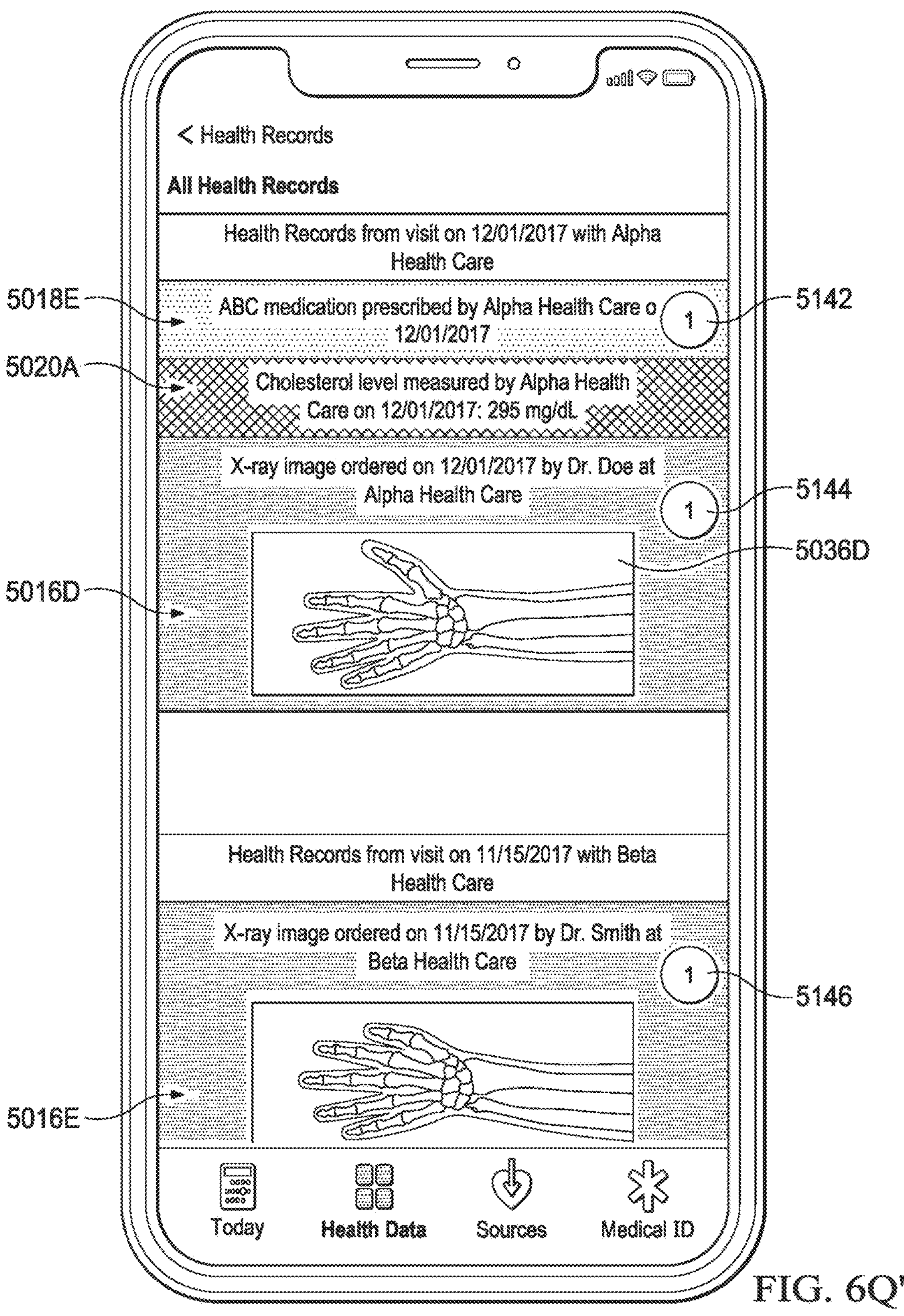

FIGS. 6L-6Q' illustrate user interfaces for displaying notifications of updates that have been made to user's health records on device 100. Updates to the user's health records may include updates to the user's existing health records or new health records. Similar to FIG. 6A, FIG. 6L illustrates displaying category representations 5006A-5006E (allergies, clinical documents, lab results, medications, and health conditions categories respectively) after updates to the health records of the user have been received by device 100. In the illustrated embodiment, three updates have been received by device 100 that have not yet been reviewed by the user. To notify the user of the three updates, a total update badge 5104 is displayed with all health records representation 5006F and category update badges 5106A, 5106B, and 5106C are displayed with category representations 5006B, 5006D, and 5006E, respectively. In the illustrated embodiment, total update badge 5104 is a circle including the number of total updates to the health records of the user. Similarly, category update badges 5106A, 5106B, and 5106C are circles including the number of updates to the health records within the health record category associated with category representations 5006B, 5006D, and 5006E, respectively. In the illustrated embodiment, total update badge 5104 indicates that three updates to health records have been received that have not been reviewed, and each of category updates 5106A-5106C indicates that one update to a health record within the corresponding health record category has been received that has not been reviewed. FIGS. 6K and 6K' each further illustrate detecting a tap gesture with contact 5521 or 5521' respectively over health conditions affordance 5306, which is an affordance the user selects to return to the user interface illustrated in FIGS. 6J and 6J'.

While FIG. 6L illustrates one embodiment of the display of update badges to indicate updates to a user's health records, other text, symbols, graphics, or displayed effect of any size, shape, color, or design may be used to indicate as an update badge to indicate an update or the number of updates. For example, an update badge may be a highlighted or flashing category representation or displaying the time or date of an update. In some embodiments, total update badge 5104 and category update badges, such as category update badges 5106A-5106C (indicating updates to clinical documents records, medication records, and health conditions records, respectively) are not concurrently displayed. In one or more of such embodiments, only category update badges are displayed on display 112. In one or more of such embodiments, only total update badge 5104 is displayed on display 112. In some embodiments, a summary or a portion of the content of an update is displayed on or with an update badge. In one embodiment, an update badge is an affordance separate from the affordance of a category, and the user selects the update badge to display an updated health record or a summary or portion of the updated health record. FIG. 6L further illustrates detecting a tap gesture with contact 5522 over category update badge 5106C to display an update to health condition record 5020A in FIG. 6M.

In some embodiments of FIGS. 6L-6Q', in addition to or in lieu of an update badge, a user may receive a notification of all updates via onscreen alerts, text messages, or audio or video notifications. In one embodiment, such notifications may be based on whether particular health records are designated by a user or health care provider as being urgent. In one embodiment, device 100 may be preconfigured with, or configurable by a user to set, one or more thresholds for one or more types of health records. If an update to a health record is received having a particular result, measurement, value, reading, or other measurable aspect that exceeds an established threshold or otherwise satisfies a criterion, one or more notifications to the user are automatically generated on device 100. In some embodiments, the method of notification may change based on the severity of a particular result, measurement, value, reading, or other measurable aspect, or based on the type or number of thresholds reached. For example, a text message may be generated for some updates while an audible alarm may be generated for other updates that is repeated at regular or escalated shorter intervals until the user completes a required action. In one embodiment, updates that are not urgent or do not exceed an established threshold do not trigger the generation of a notification.

FIG. 6L' illustrates an alternate embodiment of FIG. 6L after the user has completed the onboarding process with both Alpha Health Care and Beta Health Care. As illustrated in FIG. 6L', as a result of the inclusion of two health care providers instead of the single health care provider with respect to FIG. 6L, four updates are now displayed instead of the three updates in FIG. 6L. In the illustrated embodiment, total update badge 5104 indicates that four total updates have been received that have not been reviewed, category update badge 5106A indicates that two updates to clinical records have been received but not yet reviewed, category update badge 5106B indicates that one update to medication records has been received that has not been reviewed, and category update badge 5106C indicates that one update to health conditions records has been received that has not been reviewed. FIG. 6L' further illustrates detecting a tap gesture with contact 5522' over category update badge 5106C to display an update to health condition record 5020A in FIG. 6M'.

FIGS. 6M and 6M' illustrate displaying an update to health condition record 5020A (the user's cholesterol level) in response to detecting the tap gesture with contact 5522 or 5522' respectively over category update badge 5106C. In each of the illustrated embodiments, the user's cholesterol level has been updated to reflect a new measurement of cholesterol made by Alpha Health Care on Dec. 1, 2017. In each of the illustrated embodiments, a health record update badge 5140 is displayed with health condition record 5020A to indicate that health condition record 5020A has been updated. Health condition record 5020A is displayed in a color indicating a severity of the user's cholesterol level. In each of the illustrated embodiments, a recommendation affordance 5240A containing a recommended action to visit a doctor is displayed with health condition record 5020A. In some embodiments, the recommendation affordance is a recommendation to engage in exercise, change the user's diet, or engage in other suitable actions that reduce the user's cholesterol levels. In some embodiments, recommendation affordance 5240A also includes content indicating the importance of the update or the severity of the user's condition. In one or more of such embodiments, the user may self-designate the importance of certain types of health records as well as updates to certain types of health records. For example, the user may designate all updates to the user's cholesterol level as urgent updates. In one or more of such embodiments, the user designates the importance of certain types of health records based on the amount of positive or negative change to the user's health condition. For example, the user may designate the importance of an update to the user's cholesterol level based on the amount of change to the user's cholesterol level. In other embodiments, the health care provider may designate the importance of certain updates. Although the discussion of FIGS. 6M and 6M' above are directed to updates to and recommendations based on the user's cholesterol, the foregoing paragraphs also apply to other types of health records. For example, where the user has received a new measurement of serum iron, a recommendation affordance recommending the user to change the user's diet to increase sources of iron may be displayed on display 112.

FIGS. 6M and 6M' further illustrate detecting a tap gesture with contact 5524 or 5524' respectively over recommendation affordance 5240A, which contains a recommendation based on the user's cholesterol level, to display a calendar affordance 5241 in FIG. 6N. More particularly, FIG. 6N illustrates the display of calendar affordance 5241 overlaid on the user interface illustrated in FIG. 6M or 6M'. FIG. 6N also illustrates detection of a tap gesture with contact 5526 over the date January 8 on calendar affordance 5241. In such a manner, a user may select a date to schedule an appointment with a doctor consistent with the recommendation displayed in recommendation affordance 5240A. Additional affordances may be utilized to select the time of an appointment or display or enter additional information with respect to the appointment. In some embodiments, calendar affordance 5241 or additional affordances display dates and times based on the user's availability and the doctor's available appointments.

FIGS. 6O and 6O' each illustrate displaying an update to recommendation affordance 5240A. In each illustrated embodiment, recommendation affordance 5240A for health condition record 5020A has been updated to include text indicative of the date of the appointment and the name of the doctor the user is scheduled to meet. In some embodiments, device 100 will designate a time to display or otherwise announce a notification to remind the user about the upcoming appointment. FIGS. 6O and 6O' also illustrate detecting a tap gesture with contact 5527 or 5527' respectively over health records affordance 5304 to display any remaining updates to health records in FIGS. 6P and 6P' respectively.

FIGS. 6P and 6P' illustrate category representations 5006A-5006E (allergies, clinical documents, lab results, medications, and health conditions categories respectively) and the display of remaining updates to the user's health records. In the embodiment of FIG. 6P, where the user has onboarded only one health care provider, total update badge 5104, which indicates the total number of updates received by device 100 but have not been reviewed by the user, has been updated from three updates to two updates to indicate the remaining number of updates that the user has yet to review. Category update badge 5106C, which was previously displayed with representation category 5006E (health conditions category) in FIG. 6L, is no longer displayed since the user has reviewed the update to health condition record 5020A. Similarly, in the embodiment of FIG. 6P', where the user has onboarded two health care providers and more updates exist as a result thereof, total update badge 5104 has been updated from four updates to three updates to indicate the remaining number of updates that the user has yet to review. Similar to FIG. 6P, category update badge 5106C, which was previously displayed with representation category 5006E in FIG. 6L', is no longer displayed since the user has reviewed the update to health condition record 5020A. Each of FIGS. 6P and 6P' further illustrate detecting a tap gesture with contact 5528 or 5528', respectively, over total updates badge 5104 to display FIG. 6Q or 6Q' respectively.

FIGS. 6Q and 6Q' each display updates to multiple types of health records. The illustrated embodiment of FIG. 6Q displays a first update of a new medication record 5018E for a new prescription of ABC medication prescribed by Alpha Health Care on Dec. 1, 2017, and a second update of a new x-ray record 5016D of an x-ray taken at Alpha Health Care on Dec. 1, 2017 are displayed with update badges 5142 and 5144 respectively. In some embodiments, health record update badges that are for updates to existing health records and updates of new health records have different symbols, shapes, sizes, text fonts, text colors, or other visual differences to help the user differentiate between updates to existing health records and updates of new health records. The illustrated embodiment FIG. 6Q' also illustrates displaying medication record 5018E of ABC medication, health conditions record 5020A of the user's cholesterol level, and x-ray record 5016D of an x-ray image ordered on Dec. 1, 2017. In addition to the updates of new medication record 5018E and new x-ray record 5016D from Alpha Health Care on Dec. 1, 2017, FIG. 6Q' includes updates from Beta Health Care and therefore displays a third update of a new x-ray record 5016E taken at Beta Health Care on Nov. 15, 2017 with health record update badge 5146.

FIGS. 7A-7F are a flow diagrams illustrating a method for displaying aggregated health records of a user using an electronic device in accordance with some embodiments. FIGS. 7A-7F are flow diagrams illustrating a method for displaying aggregated health records for a user, using, for example, the user interfaces of FIGS. 6A-6Q'. As described in reference to FIGS. 6A-6Q', method 700 can be utilized to display aggregated health records from one or from multiple health care providers of the user. Method 700 is performed at a device, (e.g., device 100, 300, 500 illustrated in FIGS. 1, 3, and 5A, respectively). In one of such embodiments, display 112 is a touch screen display and the touch-sensitive surface is on or integrated with display 112. In some embodiments, display 112 is separate from the touch-sensitive surface. In other embodiments, the processes described herein may be implemented with devices having physical user-interfaces, voice interfaces, or other suitable interfaces. Some operations in the method 700 are, optionally, combined. Additionally, the order of some operations is, optionally, changed.

As described below, method 700 provides an intuitive way for displaying aggregated health records obtained from a health care provider of the user. Method 700 also provides an intuitive way for concurrently displaying aggregated health records obtained from multiple health care providers of the user. The method reduces the cognitive burden on a user when the user is viewing health records of the user obtained from the one or more health care providers of the user, thereby creating a more efficient human-machine interface. The method also increases efficiency of the user by concurrently displaying health records obtained from multiple health care providers. For battery-operated computing devices, enabling a user to review health records obtained from a health care provider or multiple health care providers faster and more efficiently conserves power and increases the time between battery charge Similar to FIGS. 6A-6Q', using method 700 a user can visualize health records in a common interface. The use of such a common interface avoids the risk that a user may be viewing less than all health information relative to a particular concern or question. For example, a user may be unaware that blood tests taken by two different providers tested for a particular condition and give a hospital or other subsequent provider inaccurate information. Similarly, the use of device 100 to store health records across multiple providers for viewing by a user in a common interface may offer the user a readily available source of comprehensive information regarding the user's health over a period of time even if a user has moved or changed providers. Often, prior health care providers may destroy health records after a certain period of time of a patient not seeing such health care provider and such information may be lost forever. Such health records may contain critical health history information and baseline data critical to diagnosing and treating subsequent illnesses. Additionally, the use of such a common interface avoids the need for a user to use device 100 to retrieve data from a variety of locations on device 100 or other websites, portals, and other information sources to piece together information on a particular health condition, with the risk that information is overlooked, not readily available, or available only after a lengthy electronic search using device 100. Further, storing such health records in device 100 and offering a single interface to allow a user to view and browse all of such health records avoids the need for a user to use device 100 to communicate with multiple health care providers with back-and-forth voice calls (often with lengthy hold times), interactive telephone systems, voice mails, emails, and other electronic messaging platforms in order to piece together health records from several sources. Half-a-day or more of required use of device 100 to piece together the foregoing information can now be substituted with a few clicks on device 100 by the user in the interface illustrated in FIG. 6B', resulting in a considerable savings of bandwidth, battery life, and energy that were previously wasted.

FIGS. 7A-7F are flow diagrams illustrating a method for displaying aggregated health records for a user, using, for example, the user interfaces of FIGS. 6A-6Q'. As described in reference to FIGS. 6A-6Q', method 700 can be utilized to display aggregated health records from one or from multiple health care providers of the user. Method 700 is performed at a device, (e.g., device 100, 300, 500). In one of such embodiments, display 112 is a touch screen display and the touch-sensitive surface is on or integrated with display 112. In some embodiments, display 112 is separate from the touch-sensitive surface. In other embodiments, the processes described herein may be implemented with devices having physical user-interfaces, voice interfaces, or other suitable interfaces. Some operations in the method 700 are, optionally, combined. Additionally, the order of some operations is, optionally, changed.

Similar to FIGS. 6A-6Q', using one or more embodiments of method 700 described below as being illustrated by FIGS. 7A-7F, a user can visualize health records in a common interface. The use of such a method avoids the risk that a user may be viewing less than all health information relative to a particular concern or question. For example, a user may be unaware that blood tests taken by two different providers tested for a particular condition and give a hospital or other subsequent provider inaccurate information. Similarly, the use of the method on a device such as device 100 to store health records across multiple providers for viewing by a user in a common interface may offer the user a readily available source of comprehensive information regarding the user's health over a period of time even if a user has moved or changed providers. Often, prior health care providers may destroy health records after a certain period of time of a patient not seeing such health care provider and such information may be lost forever. Such health records may contain critical health history information and baseline data critical to diagnosing and treating subsequent illnesses. Additionally, the use of such a method avoids the need for a user to use a device such as device 100 to retrieve data from a variety of locations on such device or other websites, portals, and other information sources to piece together information on a particular health condition, with the risk that information is overlooked, not readily available, or available only after a lengthy electronic search using the device. Further, storing and displaying such health records using such a method on a device such as device 100 and offering a single interface to allow a user to view and browse all of such health records avoids the need for a user to use the device to communicate with multiple health care providers with back-and-forth voice calls (often with lengthy hold times), interactive telephone systems, voice mails, emails, and other electronic messaging platforms in order to piece together health records from several source. Half-a-day or more of required use of such a device to piece together the foregoing information can now be substituted with the use of such a method requiring only a few clicks on a device by a user, resulting in a considerable savings of bandwidth, battery life, and energy that were previously wasted.

In some embodiments, while device 100 is associated with a first health care provider and not associated with a second health care provider, device 100 receives (702), via one or more input devices, a first request to display health records for a user. In some embodiments, once the user completes onboarding process with a health care provider, the request to display health records is automatically transmitted to device 100. In some embodiments, the user selects health data affordance 5029A illustrated in FIG. 6A or an affordance displayed in an onboarding user interface to request device 100 to display health records for the user. In some embodiments, the request to display health records is a request to display health records of multiple users, such as the health records of a family.

Device 100, in response to receiving the first request to display health records for the first user, displays (704), on display 112, a plurality of representations of categories of health records. FIG. 6A, for example, shows five categories of health records (e.g., category representations 5006A-5006E).

The plurality of representation of categories include a first representation of a first category of the plurality of categories (706). FIG. 6A, for example, shows category representation 5006D, which is associated with medications of the user. Further, selection of the first representation of the first category while device 100 is associated with the first health care provider and not associated with the second health care provider causes device 100 to display (706), on display 112, a plurality of health records in the first category from the first health care provider. In the embodiment illustrated in FIG. 6B, the user is only associated with Alpha Health Care and not associated with Beta Health Care. FIG. 6B, for example, shows an embodiment where only medication records 5018A-5018B (ABC medication and DEF medication) from only Alpha Health Care are displayed on device 100.

The plurality of representations also include a second representation of a second category of the plurality of categories (708). FIG. 6I, for example, shows category representation 5006E, which is associated with health conditions of the user. Further, selection of the second representation of the second category while device 100 is associated with the first health care provider and not associated with the second health care provider causes device 100 to display (708), on display 112, a plurality of health records in the second category from the first health care provider. FIG. 6J, for example, shows two health condition records 5020A and 5020B (cholesterol level and chronic migraines) in response to detecting the tap gesture shown in FIG. 6I over category representation 5006E.

In some embodiments, the health records of a first type are displayed in a first color and the health records of a second type are displayed in a second color that is different from the first color (718). FIG. 6H, for example, illustrates displaying x-ray records 5016A and 5016B (ordered on Oct. 1, 2017 and Sep. 1, 2017, respectively) in a first color and displaying medication records 5018A and 5018B (ABC medication and DEF medication) in a second color. Different types of health records are displayed in different colors to help the user differentiate health records that belong to different categories (or sub-categories). In some embodiments, where multiple health records belonging to different categories are concurrently displayed, the user may rely on colors alone to determine which category (or sub-category) a health record belongs to. In other embodiments, where multiple records from different health care providers are concurrently displayed, the user may also rely on colors to differentiate different health records from different health care providers. Further, displaying different types of health records in different colors also reduces user mistakes (such as incorrectly identifying a health record, or failing to identify a health record) when the user is browsing through the user's health records. The foregoing enhances the operability of the device and makes the user-device interface more efficient by allowing the user to differentiate different types of health records based on color. The method also increases efficiency of the user by allowing the user to identify a health record by a color assigned to the type of the health record. For battery-operated computing devices, enabling a user to browse through the user's health records faster and more efficiently conserves power and increases the time between battery charges.

In some embodiments, device 100 displays (720), on display 112, first content summarizing the first category and a first category information affordance associated with the first category, where selection of the first category information affordance causes device 100 to display, on display 112, additional content associated with the first category that is not included in the first content. In some embodiments, category representation 5006E (health conditions category) in FIG. 6I includes a summary affordance that contains content summarizing a particular health condition of the user. Further, device 100, in response to detecting a user selection of the summary affordance, displays additional information about the health conditions of the user, such as the cause of the health condition, how to identify symptoms of the health conditions, non-medicinal treatments to alleviate the health condition, as well as other helpful information about the health condition.

In some embodiments, device 100 also displays (720), on display 112, second content summarizing the second category and a second category information affordance of the second category, where selection of the second category information affordance causes device 100 to display, on display 112, additional content associated with the second category that is not included in the second content. In some embodiments, category representation 5006B (clinical documents category as shown in FIG. 6G) includes a summary affordance that contains content summarizing allergies the user suffers from. Further, device 100, in response to detecting a user selection of the summary affordance, displays additional information about the allergies the user suffers from, such as methods to reduce or prevent triggers of specific allergies, non-medicinal treatments to alleviate symptoms of allergies, as well as other helpful information about the allergies. Content containing descriptions of categories of health records are provided with category representations. The method increases efficiency of the user by allowing the user to make an informed selection of a category of health record based on the descriptions of different categories of health records. The method also enhances the operability of the device and makes the user-device interface more efficient by helping the user to provide proper inputs and by reducing the number of extraneous inputs caused by the user selecting the wrong category of health records. For battery-operated computing devices, enabling a user to browse through the user's health records faster and more efficiently conserves power and increases the time between battery charges.

In some embodiments, the plurality of health records in the first category are displayed in a chronological order (722). FIG. 6B', for example, shows medication records 5018A-5018B (ABC medication and DEF medication) arranged based on the prescription date. In some embodiments, the plurality of health records in the second category are displayed in a chronological order (722). FIG. 6J, for example, shows health condition records 5020A-5020C (associated with cholesterol level, chronic migraines, and anxiety disorder, respectively) arranged based on the prescription dates of medications prescribed for the health conditions. Presenting the health records in a chronological order allows a user to view health records of the user based on date increases efficiency of the user. For battery-operated computing devices, enabling a user to browse through the user's health records faster and more efficiently conserves power and increases the time between battery charges.

In some embodiments, device 100 detects (724) selection of the first representation of the first category while device 100 is associated with the first health care provider. FIG. 6I, for example, shows a tap gesture with contact 5518 over category representation 5006E (health conditions category). In some embodiments, device 100, in response to detecting selection of the first representation of the first category while device 100 is associated with the first health care provider displays (724), on display 112, a first representation of a first health record of the plurality of health records in the first category from the first health care provider. FIG. 6J, for example, shows health condition record 5020A, where health condition record 5020A contains the user's cholesterol level measured on Oct. 1, 2017 by Alpha Health Care. The first representation of the first health record includes a numerical value within a range of numerical values, and the numerical value is indicative of a health condition of the first user, where the range of values is indicative of normal range of values for the health condition (724). Health conditions record 5020A illustrated in FIG. 6J, contains a value of the user's cholesterol level, which is 269 mg/dL. In some embodiments, health condition record 5020A also includes values that represent a range of cholesterols, such as between 0-400 mg/dL. The method reduces the cognitive burden on a user by providing the user with a numerical value that allows the user to determine a severity of a health condition based on the numerical value, thereby creating a more efficient human-machine interface. The method also increases efficiency of the user by allowing the user to quickly identify the severity of the health condition from the numerical value. For battery-operated computing devices, enabling a user to identify a severity of a health condition, medical records associated with the health condition, as well as the health condition over time faster and more efficiently conserves power and increases the time between battery charges.

In some embodiments, device 100 displays (726) the numerical value with a color selected based on a severity of the health condition of the first user. In some embodiments, the value of the user's cholesterol is displayed in green if the value is below 200 mg/dL, is displayed in yellow if the value is between 200 mg/dL and 300 mg/dL, and is displayed in red if the value is above 300 mg/dL. Displaying the numerical value based on the severity of the user's health condition allows the user to determine a severity of a health condition without intricate knowledge on how to read the numerical value, thereby creating a more efficient human-machine interface. The method also increases efficiency of the user by allowing the user to quickly identify the severity of the health condition based on color associated with the numerical value. For battery-operated computing devices, enabling a user to identify a severity of a health condition time faster and more efficiently conserves power and increases the time between battery charges.

In some embodiments, device 100 displays (728) a second representation of a second health record of the plurality of health records in the first category from the first health care provider, and where the second representation of the second health record includes a graph indicative of a condition of the first user over a period of time. FIG. 6K, for example, shows cholesterol representation 5021B in response to detecting the tap gesture illustrated in FIG. 6J over health condition record 5020A (cholesterol level of the user). Cholesterol representation 5021B is a bar graph of the user's cholesterol level over time. The method also reduces the cognitive burden on a user by providing the user with an image of a medical record of the user, which provides the user with information on the user's condition over time, thereby creating a more efficient human-machine interface. The method also increases efficiency of the user by allowing the user to quickly identify the user's health condition over time in one common interface without having to navigate through multiple user interfaces. For battery-operated computing devices, enabling a user to identify the user's health condition over time faster and more efficiently conserves power and increases the time between battery charges.

In some embodiments, the plurality of health records in the first category from the first health care provider include a first health record in the first category from the first health care provider and a second health record in the first category from the first health care provider (730). FIG. 6B, for example, shows two medication records 5018A and 5018B (ABC medication and DEF medication) obtained from Alpha Health Care.

In some embodiments, the plurality of health records in the second category from the first health care provider include a third health record in the second category from the first health care provider and a fourth health record in the second category from the first health care provider (730). FIG. 6E, for example, shows two x-ray records 5016A and 5016B (ordered on Oct. 1, 2017 and Sep. 1, 2017, respectively) obtained from Alpha Health Care.

In some embodiments, the first health record in the first category from the first health care provider and the third health record in the second category from the first health care provider are records of a first visit to the first health care provider (730). FIGS. 6B and 6E, for example, show that medication record 5018A (ABC medication) and x-ray record 5016A are records of an Oct. 1, 2017 visit to Alpha Health Care.

In some embodiments, the second health record in the first category from the first health care provider and the fourth health record in the second category from the first health care provider are records of a second visit to the first health care provider (730). FIGS. 6B and 6E, for example, show that medication record 5018B (DEF medication) and x-ray record 5016B are records of a Sep. 1, 2017 visit to Alpha Health Care.

In some embodiments, and in response to receiving the first request to display health records for the first user, device 100 concurrently displays (730), on display 112, the first health record and the third health record in a first group, where the first group is identified on display 112 by a first date of the first visit. FIG. 6H, for example, shows grouping medication record 5018A (ABC medication) and x-ray record 5016A in a first group and concurrently display medication record 5018A and x-ray record 5016A on display 112.

In some embodiments, and in response to receiving the first request to display health records for the first user, device 100 concurrently displays (730), on display 112, the second health record and the fourth health record in a second group, where the second group is identified on display 112 by a second date of the second visit, where the first date is different from the second date. FIG. 6H, for example, show grouping medication record 5018B (DEF medication) and x-ray record 5016B in a second group. Further medication record 5018B and x-ray record 5016B are concurrently displayed on display 112. The method reduces the cognitive burden on a user when the user is viewing the health records by grouping health records based on an appointment date with a health care provider, and by arranging different groups based on the appointment date. Optionally, where the health records are from multiple health care providers, the health records are grouped by health care provider and appointment date, and the groups are arranged by appointment date. Optionally, the method reduces the cognitive burden on a user when the user is viewing the health records by displaying health records belonging to different categories in different colors to help the user differentiate different categories of health records. Optionally, the method also reduces the cognitive burden on a user when the user is viewing the health records by displaying update badges with updates to health records. Each of the foregoing creates a more efficient human-machine interface. The method also increases efficiency of the user by allowing the user to identify a health record based on an appointment date with a health care provider, and based on different appointment dates with different health care providers. The method also allows the user to view different health records from different health care providers in a common interface, thereby increasing the efficiency of the user and making the user-device interface more efficient. For battery-operated computing devices, enabling a user to browse through the user's health records faster and more efficiently conserves power and increases the time between battery charges.

In some embodiments, the first health record in the first category from the first health care provider and the second health record in the first category from the first health care provider are displayed in a first color (732). FIG. 6H, for example, shows medication record 5018A (ABC medication) and x-ray record 5016A ordered on Oct. 1, 2017 in a first color.

In some embodiments, the third health record in the second category from the first health care provider and the fourth health record in the second category from the first health care provider are displayed in a second color that is different from the first color (732). FIG. 6H, for example, shows medication record 5018B (DEF medication) and x-ray record 5016B ordered on Sep. 1, 2017 in a second color that is different than the first color. Displaying different categories of health records in different colors allows the user to quickly differentiate different health records, which creates a more efficient human-machine interface. The method also increases efficiency of the user by allowing the user to identify a health record based on color. For battery-operated computing devices, enabling a user to browse through the user's health records faster and more efficiently conserves power and increases the time between battery charges.

In some embodiments, device 100 receives (734) an update to the first health record in the first category from the first health care provider. FIG. 6L, for example, illustrates receiving multiple updates from Alpha Health Care (e.g., updates to category representation 5006B for clinical documents, category representation 5006D for medications, and category representation 5006E for health conditions). In some embodiments, device 100, displays, on display 112, a first update badge associated with the first health record of the first group, where the first update badge and the first health record are concurrently displayed in a first region of display 112. FIG. 6L, for example, shows category update badge 5106C and category representation 5006E in a region of display 112. In some embodiments, category update badge 5106C is appended to category representation 5006E. The method reduces the cognitive burden on a user by allowing the user to identify which health records have been updated, which creates a more efficient human-machine interface. The method also increases efficiency of the user by allowing the user to quickly identify which health records have been updated. For battery-operated computing devices, enabling a user to identify health records that have been updated faster and more efficiently conserves power and increases time between battery charges.

In some embodiments, device 100 displays (736) a third representation of a third health record of the plurality of health records in the first category from the first health care provider, where the third representation of the third health record includes an image indicative of a medical record of the first user. In some embodiments, an image of an x-ray associated with an x-ray record, such as x-ray record 5016A (ordered on Oct. 1, 2017) in FIG. 6E is displayed in response to a user selection of the x-ray record. In some embodiments, such as FIG. 6E, where x-ray record 5016A contains image file 5036A of the x-ray image, selection of image file 5036A causes device 100 to enlarge image file 5036A. The method reduces the cognitive burden on a user by providing the user with an image of a medical record of the user, which allows the user to quickly assess a health condition related to the medical record, thereby creating a more efficient human-machine interface. For battery-operated computing devices, enabling a user to assess the user's health condition faster and more efficiently conserves power and increases the time between battery charges.

In some embodiments, device 100 receives (738) an update to a health record of the first category of health records. FIG. 6L, for example, illustrates receiving multiple updates from Alpha Health Care (e.g., updates to category representation 5006B for clinical documents, category representation 5006D for medications, and category representation 5006E for health conditions). In some embodiments, after receiving the update to the health record of the first category, and in response to receiving at least one of the first request to display the health records for the first user and the second request to display the health records for the first user, device 100 displays (738), on display 112, a second update badge associated with the first category, where the second update badge and the first representation of the first category are concurrently displayed in a first region of display 112. FIG. 6M, for example, shows medication records 5020A-5020C (associated with cholesterol level, chronic migraines, and anxiety disorder of the user, respectively) in response to detecting the gesture in FIG. 6L over category representation 5006E. FIG. 6M also shows health record update badge 5140 with health condition record 5020A to indicate that health condition record 5020A has been updated. The method reduces the cognitive burden on a user by allowing the user to identify which health records have been updated, which creates a more efficient human-machine interface. The method also increases efficiency of the user by allowing the user to quickly identify which health records have been updated. For battery-operated computing devices, enabling a user to identify health records that have been updated faster and more efficiently conserves power and increases time between battery charges.

In some embodiments, the second update badge is visually associated with the first representation of the first category (740). FIG. 6L, for example, shows category update badge 5106C and category representation 5006E (health conditions category) in a region of display 112. In some embodiments, category update badge 5106C is appended to category representation 5006E. The method reduces the cognitive burden on a user by allowing the user to identify which categories contain updates to the user's health records, which creates a more efficient human-machine interface. The method also increases efficiency of the user by allowing the user to quickly identify which health records have been updated. For battery-operated computing devices, enabling a user to identify health records that have been updated faster and more efficiently conserves power and increases time between battery charges.

In some embodiments, selection of the first representation of the first category while device 100 is associated with the first health care provider causes device 100 to display (742), on display 112, a representation of the health record of the first category of health records, and where the second update badge is visually associated with the representation of the health record of the first category of health records. FIG. 6M, for example, shows health record update badge 5140 and health condition record 5020A (associated with the user's cholesterol level) in the same region. In one or more embodiments, health record update badge 5140 is appended to health condition record 5020A. The method reduces the cognitive burden on a user by allowing the user to identify which categories contain updates to the user's health records. The method reduces the cognitive burden on a user by allowing the user to identify which categories contain updates to the user's health records, which creates a more efficient human-machine interface. The method also increases efficiency of the user by allowing the user to quickly identify which health records have been updated. For battery-operated computing devices, enabling a user to identify health records that have been updated faster and more efficiently conserves power and increases time between battery charges.

In some embodiments, the second update badge includes content of the update to the health record on the second update badge (744). In some embodiments, content of an update, such as a summary of the update, is displayed on an update badge, such as category update badge 5106A, 5106B, or 5106C, health record update badge 5140, or total update badge 5104 shown in FIGS. 6L and 6M. The method reduces the cognitive burden on a user by allowing the user to identify the content of the update or a summary of the content of the update without having to perform further actions, which creates a more efficient human-machine interface. The method also increases efficiency of the user by allowing the user to quickly identify a change in a health condition associated with the updated health record. For battery-operated computing devices, enabling a user to identify a change in the user's health condition faster and more efficiently conserves power and increases time between battery charges.

In some embodiments, device 100 receives (746), via the one or more input devices, a request to select the second update badge. In some embodiments, total update badge 5104 shown in FIG. 6L and category update badges 5106A-5106C (each shown in FIG. 6L) include update affordances, which are affordances the user selects to view updates to the corresponding health records. FIG. 6L, for example, shows a tap gesture with contact 5522 over category update badge 5106C. In some embodiments, and in response to receiving the request to select the second update badge, device 100 displays (746), on display 112, the update to the health record of the first category of health records. FIG. 6M, for example, shows an update to health condition record 5020A (health record of the user's cholesterol level) in response to detecting the tap gesture illustrated in FIG. 6L. As illustrated in FIG. 6M, health condition record 5020A has been updated to indicate the user's cholesterol level on Dec. 1, 2017. The method reduces the cognitive burden on a user by allowing the user to identify which categories contain updates to the user's health records. The method reduces the cognitive burden on a user by allowing the user to access an update to a health record by selecting an update badge, which creates a more efficient human-machine interface. The method also increases efficiency of the user by allowing the user to easily access the update by selecting the update badge. For battery-operated computing devices, enabling a user to access updates to the user's health records that have been updated faster and more efficiently conserves power and increases time between battery charges.

In some embodiments, device 100 concurrently displays (748) the update to the health record and a recommendation affordance associated with the health record. FIG. 6M, for example, shows concurrently displaying health conditions record 5020A (health record of the user's cholesterol level) and recommendation affordance 5240A. In some embodiments, device 100 receives (748), via the one or more input devices, a request to select the recommendation affordance. FIG. 6M, for example, also shows a tap gesture with contact 5524 over recommendation affordance 5240A. In some embodiments, and in response to receiving the request to select the recommendation affordance, device 100 displays (748), on display 112, a recommended action, where the recommended action is based on the update to the health record. FIG. 6N, for example shows calendar affordance 5241 in response to the gesture illustrated in FIG. 6M. In the illustrated embodiment, the recommended action is to schedule an appointment with a doctor. In some embodiments, content describing or illustrating the recommended action is also displayed with recommendation affordance 5240A. FIG. 6M, for example, shows recommendation affordance 5240A containing a text of a recommended action to visit a doctor. The method reduces the cognitive burden on a user by providing recommendations without user input, thereby creating a more efficient human-machine interface. The method also increases efficiency of the user by automatically providing the user with response strategies. For battery-operated computing devices, enabling a user to determine whether the user should respond to an update to the user's health record, as well as how to respond to the update, faster and more efficiently conserves power and increases time between battery charges.

In some embodiments, the recommendation is a recommendation to schedule an appointment with the first health care provider (750). In such embodiments, displaying the recommended action includes concurrently displaying the recommended action and a scheduling affordance (750). FIG. 6N, for example shows calendar affordance 5241 in response to the gesture illustrated in FIG. 6M. In the illustrated embodiment, the recommended action is to schedule an appointment with a doctor. The method reduces the cognitive burden on a user by providing recommendations without user input, thereby creating a more efficient human-machine interface. The method also increases efficiency of the user by automatically providing the user with response strategies. For battery-operated computing devices, enabling a user to determine whether the user should respond to an update to the user's health record, as well as how to respond to the update, faster and more efficiently conserves power and increases time between battery charges.

In some embodiments, device 100 receives (752) an update to a health record of the first category of health records. FIG. 6L, for example, illustrates receiving multiple updates from Alpha Health Care (e.g., updates to category representation 5006B for clinical documents, category representation 5006D for medications, and category representation 5006E for health conditions). In some embodiments, device 100, in response to receiving the update to the health record and in accordance with a determination that a significance of the update is greater than a threshold value, displays (752), on display 112, a notification of the update. Recommendation affordance 5240A of FIG. 6M, for example, includes the text "Urgent!" to indicate the significance to the change in the user's cholesterol. In some embodiments, a notification of the update and the significance of the update overlays a portion of display 112 even when user interfaces illustrated in FIG. 6A-6Q' are not displayed on display. In one or more embodiments, the notification is a text based notification.

Device 100, in accordance with a determination that a significance of the update is less than the threshold value, forgoes (752) displaying, on display 112, the notification of the update. In some embodiments, where the user's cholesterol level did not significantly change or improve, or did not meet a threshold value for providing a notification about the update, then recommendation affordance 5240A of FIG. 6M or 6M' is not displayed on display 112. The method reduces the cognitive burden on a user by notifying the user about important updates, thereby creating a more efficient human-machine interface. The method also increases efficiency of the user by allowing the user to determine, based on the presence or lack of a notification, whether an update is an important update. For battery-operated computing devices, enabling a user to determine whether an update is an important update faster and more efficiently conserves power and increases time between battery charges.

Device 100, after displaying the plurality of representations of categories of health records, and after being associated with the second health care provider, receives (710), via the one or more input devices, a second request to display health records for the first user. In some embodiments, where the user has completed the onboarding process with multiple health care providers, the user requests device 100 to display health records obtained from two or more health care providers.

After device 100 has processed the user's request to display health records obtained from two or more health care providers, device 100, receives a second request from the user to display the user's health records. Device 100, in response to receiving the second request to display health records for the first user, displays (712), on display 112, the plurality of representations of categories of health records. FIG. 6A, for example, shows five category representations 5006A-5006E (allergies, clinical documents, lab results, medications, and health conditions categories, respectively).

The plurality of representations of categories include the first representation of the first category of the plurality of categories (714). FIG. 6A, for example, shows category representation 5006D (medications category), which is associated with medications of the user. Further, selection of the first representation of the first category while device 100 is associated with the first health care provider and the second health care provider causes device 100 to display (714), on display 112, one or more health records in the first category from the first health care provider and one or more health records in the first category from the second health care provider. FIG. 6B' for example, illustrates an alternative embodiment to FIG. 6B. In the embodiment of FIG. 6B', the user has completed the onboarding process with both Alpha Health Care and Beta Health Care. In this embodiment, the gesture with contact 5502 on category representation 5006D illustrated in FIG. 6A, or a similar gesture selecting category representation 5006D while device 100 is associated with Alpha Health Care and Beta Health Care causes device 100 to display medication records obtained from both Alpha Health Care and Beta Health Care. In that regard, FIG. 6B' shows medication records 5018A and 5018B (ABC medication and DEF medication) from Alpha Health Care and two medication records 5018C and 5018D (GHI medication and JKL medication) from Beta Health Care in response to detecting the tap gesture shown in FIG. 6A over category representation 5006D.

The plurality of representations of categories of health records also include the second representation of the second category of the plurality of categories (716). FIG. 6I, for example, shows category representation 5006E (health conditions category), which is associated with health conditions of the user.

Further, selection of the second representation of the second category while the device 100 is associated with the first health care provider and the second health care provider causes device 100 to display (716), on display 112, one or more health records in the second category from the first health care provider and one or more health records in the second category from the second health care provider. FIG. 6J' for example, illustrates an alternative embodiment to FIG. 6J. In the embodiment of FIG. 6J', the user has completed the onboarding process with both Alpha Health Care and Beta Health Care. In this embodiment, the gesture with contact 5518 on category representation 5006E (health conditions category) illustrated in FIG. 6I, or a similar gesture selecting category representation 5006E while device 100 is associated with Alpha Health Care and Beta Health Care, causes device 100 to display (716) health condition records obtained from both Alpha Health Care and Beta Health Care. In that regard, FIG. 6J' shows health condition records 5020A-5020C (cholesterol level, chronic migraines, and anxiety disorder) from Alpha Health Care and health condition record 5020D (arthritis) from Beta Health Care in response to detecting the tap gesture shown in FIG. 6I over category representation 5006E.

In some embodiments, device 100 receives (754), via the one or more input devices, a first selection of the first representation of the first category. FIG. 6C, for example, shows the tap gesture with contact 5506 over category representation 5006B (clinical documents category).

In some embodiments, and in response to receiving the first selection, device 100 displays (754), on display 112, a plurality of representations of subcategories of health records of the first category. FIG. 6D, for example, shows sub-category representations 5015A-5015C (x-ray images, CT-scans, and ultrasound images subcategories, respectively) in response to detecting the tap gesture shown in FIG. 6C over category representation 5006B (clinical documents category).

In some embodiments, the plurality of sub-categories of health records include a first representation of a first sub-category of the first category (754). FIG. 6D, for example, shows sub-category representation 5015A (x-ray images sub-category) in response to detecting the tap gesture shown in FIG. 6C over category representation 5006B. In the illustrated embodiment, representation of sub-category 5015A is associated with x-ray images. Further, selection of the first representation of the first subcategory of the first category causes device 100 to display (754), on display 112, a plurality of health records in the first subcategory of the first category from the first health care provider. FIG. 6E, for example, shows x-ray records 5016A and 5016B (ordered on Oct. 1, 2017 and Sep. 1, 2017, respectively) in response to detecting the tap gesture over sub-category representation 5015A shown in FIG. 6D.

In some embodiments, the plurality of sub-categories of health records include a second representation of a second subcategory of the first category (754). FIG. 6D, for example, shows sub-category representation 5015A (x-ray images sub-category) in response to detecting the tap gesture shown in FIG. 6C with contact 5506 over category representation 5006B (clinical documents category). Further, selection of the second representation of the second subcategory 5015B (CT-scans sub-category, FIG. 6D) of the first category causes device 100 to display (754), display 112, a plurality of health records in the second subcategory of the first category from the first health care provider. FIG. 6E' illustrates displaying x-ray records 5016A and 5016B obtained from Alpha Health Care and x-ray record 5016C obtained from Beta Health Care in response to detecting the tap gesture over sub-category representation 5015A shown in FIG. 6D. In a similar embodiment, where a tap gesture is detected over sub-category representation 5015B while the user has completed the onboarding process with both Alpha Health Care and Beta Health Care, health records of CT-scans obtained from both Alpha Health Care and Beta Health Care would be displayed on display 112. Ordering the user's health records into subcategories of categories (and additional levels of sub-categories) and providing only the health records that belong to the sub-category (or additional level of subcategory) in a common user interface avoids the need for the user to navigate through all of the health records of the category to find a particular health record, which reduces the amount of time which the user spends to search for the health record. Reducing the amount of time the user spends to search for health records results in less power usage and improves the battery life of the device by allowing the user to use the device more quickly and efficiently.

In some embodiments, the plurality of health records in the first category from the second health care provider include a fifth health record in the first category from the second health care provider (756). FIG. 6H', for example, shows medication record 5018C (GHI medication) obtained from Beta Health Care. In some embodiments, the plurality of health records in the second category from the second health care provider include a sixth health record in the second category from the second health care provider (756). FIG. 6H', for example, shows x-ray record 5016C obtained from Beta Health Care. In some embodiments, the fifth health record in the first category from the second health care provider and the sixth health record in the second category from the second health care provider are records of a third visit to the second health care provider (756). FIG. 6H', for example, shows that medication record 5018C and x-ray record 5016C were both obtained during the Sep. 15, 2017 visit to Beta Health Care. In some embodiments, and in response to receiving the second request to display health records for the first user, device 100 concurrently displays (756), on display 112, the fifth health record and the sixth health record in a third group where the third group is identified on display 112 by a third date of the third visit to the second health care provider, and where the first group, the second group, and the third group are concurrently displayed on display 112. FIG. 6H', for example, shows concurrently displaying medication record 5018C and x-ray record 5016C. Both health records were obtained during the Sep. 15, 2017 visit to Beta Health Care. FIG. 6H' also shows concurrently displaying first group and third group of health records (health records obtained during Oct. 1, 2017 visit with Alpha Health Care and during Sep. 15, 2017 visit with Beta Health Care, respectively). In some embodiments, where dimensions of display 112 is greater, device 100 would concurrently display first group, second group, and third group of health records. The method reduces the cognitive burden on a user when the user is viewing the health records from multiple health providers by grouping health records based on an appointment date with a health care provider, and by arranging different groups based on the appointment date. The method also increases efficiency of the user by allowing the user to identify a health record based on an appointment date with a health care provider. For battery-operated computing devices, enabling a user to browse through the user's health records faster and more efficiently conserves power and increases the time between battery charges.

In some embodiments, and in response to receiving the first request to display health records for the first user, device 100 displays (758), on display 112, first content identifying an identity and location of the first health care provider. FIG. 6B, for example, displays medication records 5018A and 5018B (ABC medication and DEF medication). Each medication record 5018A and 5018B identifies Alpha Health Care as the health care provider that prescribed the corresponding medication. In some embodiments, each medication record contains additional information about the corresponding medication, such as the dosage, instructions to take the medication, name of the doctor who prescribed the medication, the location of Alpha Health Care, the location of nearest pharmacies to pick-up or refill the medication, the medication's fact sheet, the date the medication is scheduled to run out, as well as other suitable content that provide information about the medication. In some embodiments, and in response to receiving the second request to display health records for the first user, device 100 displays (758), on display 112, second content identifying an identity and location of the second health care provider. FIG. 6J, for example displays health condition records 5020A and 5020B (cholesterol level and chronic migraines). Each health condition record 5020A and 5020B identifies Alpha Health Care as the health care provider that prescribed medication for the corresponding health condition. In some embodiments, each health condition record contains additional information about the corresponding health condition, such as Alpha Health Care's location. The method increases efficiency of the user by allowing the user to obtain information about the health care provider without having to contact the health care provider. The method also enhances the operability of the device and makes the user-device interface more efficient by helping the user to determine the location as well as other information about the provider without having to perform additional inputs. The method also reduces strain on existing network, and reduces the amount of telecommunication between the user and the health care provider. For battery-operated computing devices, enabling a user to browse through the user's health records faster and more efficiently conserves power and increases the time between battery charges.

In some embodiments, selection of the first representation of the first category while device 100 is associated with the first health care provider and not associated with the second health care provider causes device 100 to display (760), on display 112, historical health records associated with the first category from the first health care provider, and where the historical health records associated with the first category include the plurality of health records in the first category from the first health care provider. FIG. 6K, for example, shows historical health records of the user's cholesterol level obtained from Alpha Health Care (e.g., cholesterol representations 5030B-5030C of the user's cholesterol level measured on Sep. 1, 2016 and Jan. 1, 2016) in response to detecting the gesture illustrated in FIG. 6J.

In some embodiments, selection of the second representation of the second category while device 100 is associated with the first health care provider and not associated with the second health care provider causes device 100 to display (760), on display 112, historical health records associated with the second category from the first health care provider, and where the historical health records associated with the second category include the plurality of health records in the second category from the first health care provider. FIG. 6J, for example, shows health condition records 5020A-5020C (cholesterol level, chronic migraines, and anxiety disorder, respectively). In some embodiments, where the user selects health condition record 5020B, historical health records of the user's migraine history would be displayed.

In some embodiments, selection of the first representation of the first category while device 100 is associated with the first health care provider and the second health care provider causes the device 100 to display (760), on display 112, historical health records associated with the first category from the first health care provider and the second health care provider, and where the historical health records associated with the first category include the one or more health records in the first category from the first health care provider and the one or more health records in the first category from the second health care provider. FIG. 6K', for example, shows historical health records of the user's cholesterol level obtained from Alpha Health Care (e.g., cholesterol representations 5030B-5030C of the user's cholesterol level measured on Sep. 1, 2016 and Jan. 1, 2016) and Beta Health Care (e.g., cholesterol representation 5030D of the user's cholesterol level measured on Sep. 15, 2015) in response to detecting the gesture illustrated in FIG. 6J.

In some embodiments, selection of the second representation of the second category while device 100 is associated with the first health care provider and the second health care provider causes device 100 to display (760), on display 112, historical health records associated with the second category from the first health care provider and from the second health care provider, and where the historical health records associated with the second category are the one or more health records in the second category from the first health care provider and one or more health records in the second category from the second health care provider. In some embodiments, FIG. 6J, for example, shows health condition records 5020A-5020C (cholesterol level, chronic migraines, and anxiety disorder, respectively). In some embodiments, where the user selects health condition record 5020B, historical health records of the user's migraine history obtained from both Alpha Health Care and Beta Health Care would be displayed. The method reduces the number of inputs required to obtain historical health records by allowing the user to access the user's historical health records associated with a health record by allowing the user to access the historical health records by selecting the health record, thereby creating a more efficient human-machine interface. The method allows the user to easily access the user's historical health records for a particular record by selecting the health record, thereby increasing the user's efficiency. For battery-operated computing devices, allowing a user to view the user's historical health records faster and more efficiently conserves power and increases the time between battery charges.

The particular order in which the operations in FIGS. 7A-7F have been described is merely exemplary and is not intended to indicate that the described order is the only order in which the operations could be performed. One of ordinary skill in the art would recognize various ways to reorder the operations described herein. Additionally, details of the processes described above with respect to method 700 (e.g., FIGS. 7A-7F) are also applicable in an analogous manner to the methods described below. For example, methods 900 and 1100 optionally include one or more of the characteristics of the various methods described above with reference to method 700. For example, the methods for displaying aggregated health records described above with reference to 700 are optionally used by method 900 to display current and historical health records in a dashboard user interface. Similarly, the methods for displaying aggregated health records described above with reference to 700 are optionally used by method 1100 to display health records of certain health conditions that the user may designate as active or inactive in a health record manager. For brevity, these details are not repeated below.

FIGS. 8A-8N illustrate exemplary dashboard user interfaces having aggregated health records, in accordance with some embodiments. FIGS. 8A-8N allow the display of a single dashboard view of a comprehensive summary of a user's current health care data using health records obtained from each health care provider of such user. For convenience, the health records will be described herein as health records of a user of device 100. However, the health records could be health records of a family member or other individuals associated with the user of the exemplary user interfaces. For purposes of FIGS. 8A-8N, the user has completed the onboarding process with Alpha Health Care and Beta Health Care or otherwise has health records from Alpha Health Care and Beta Health Care that are managed using the dashboard user interfaces of FIGS. 8A-8N or that are otherwise stored on or accessible by device 100. The user interfaces in these figures are used to illustrate the processes described below, including the processes in FIGS. 9A-9D.

Although some of the examples that follow will be given with reference to inputs on a touch-screen display (where the touch-sensitive surface and the display are combined), in some embodiments, the device detects inputs on a touch-sensitive surface 451 that is separate from the display 450, as shown in FIG. 4B. In other embodiments, the processes described herein may be implemented with devices having physical user-interfaces, voice interfaces, or other suitable interfaces. For convenience of explanation, the embodiments described below will be discussed with reference to operations performed on a device with a touch-sensitive display system 112. In such embodiments, a focus selector is, optionally: a respective finger or stylus contact, a representative point corresponding to a finger or stylus contact (e.g., a centroid of a respective contact or a point associated with a respective contact), or a centroid of two or more contacts detected on the touch-sensitive display system 112. However, analogous operations are, optionally, performed on a device with a display 450 and a separate touch-sensitive surface 451 in response to detecting the contacts on the touch-sensitive surface 451 while displaying the user interfaces discussed below, along with a focus selector.

FIGS. 8A-8N illustrate a health record summary displayed in a dashboard that includes information derived from a user's current health records, such information being referred to hereafter as health record summary information. As used herein, a current health record refers to a health record of any health information that is more up-to-date than the other health records managed using the dashboard user interfaces of FIGS. 8A-8N or stored on or accessible by device 100. The dashboard user interfaces of FIGS. 8A-8N also allow a user to display information regarding the user's health records in different levels of detail. More particularly, a dashboard initially displays a health record summary that includes health record summary information, and then allows the user to interact with the dashboard to drill down and access additional information not included in the health record summary. Similarly, the user may also interact with the dashboard to review historical health records of the user. As device 100 receives updates to existing health records or of new health records, the health record summary displayed in the dashboard is periodically updated so that the user is presented with health record summary information based on the most recent health records and is not presented with out-of-date health records or other historical health records that may be no longer relevant.

FIG. 8A illustrates category representations 5006A-5006E (allergies, clinical documents, lab results, medications, and health conditions categories, respectively) and a health record summary representation 7005. Health record summary representation 7005 is an affordance that includes text indicating that such affordance is associated with a health record summary. Health record summary representation 7005 is selectable by the user to view the health record summary. FIGS. 8A-8B illustrate detecting a tap gesture with contact 7502 on health record summary representation 7005 in FIG. 8A and, in response to the tap gesture, displaying the health record summary on display 112 in the dashboard of FIG. 8B.

FIG. 8B illustrates displaying a dashboard of a health record summary that includes health record summary information containing multiple types of health records on display 112. Health records in the illustrated embodiment are current health records obtained from both Alpha Health Care and Beta Health Care. In the illustrated embodiment, all current health records are displayed for each category of health records, regardless of which health care provider the current health record is provided by. In such a manner, the most recent health information for the user is displayed in the dashboard. In the illustrated embodiment, the health metric summary includes health metric records 7012A-7012C, medication records 7014A-7014C, and health condition records 7016A-7016D. FIG. 8B also illustrates displaying a health metrics affordance 7011A, a medications affordance 7011B, and a health conditions affordance 7011C. In the illustrated embodiment, each of health metrics affordance 7011A, medications affordance 7011B, and health conditions affordance 7011C is selectable by the user to view historical health metric records, medication records, and health condition records of the user.

In the embodiment illustrated by FIG. 8B, health metric records 7012A-7012C are displayed in a group with health metrics affordance 7011A in alphabetical order based on the type of health metric record. Health metric record 7012A contains a current measurement of the user's blood pressure measured on Nov. 1, 2017 by Beta Health Care. In the illustrated embodiment, the Nov. 1, 2017 measurement is the user's most recent blood pressure measurement from both Alpha Health Care and Beta Health Care. In some embodiments, where historical health records of the user's blood pressure level measured prior to Nov. 1, 2017 are available, the user may access such historical health records by selecting health metrics affordance 7011A. Health metric record 7012B contains a current measurement of the user's cholesterol level measured on Oct. 1, 2017 by Alpha Health Care. Health metric record 7012C contains a current measurement of the user's serum iron level measured on Oct. 1, 2017 by Alpha Health Care.

In the embodiment illustrated by FIG. 8B, medication records 7014A-7014C are displayed in a group with medications affordance 7011B in alphabetical order based on the type of medication. Medication health records 7014A-7014C are the user's current medication prescriptions for ABC medication, DEF medication, and GHI medication respectively. Each of medication health records 7014A-7014C also identifies a prescription date for the corresponding medication and the health care provider that prescribed the medication.

In the embodiment illustrated by FIG. 8B, Health condition records 7016A-7016D are displayed in a group with health conditions affordance 7011C in alphabetical order based on the type of health condition. Health condition records 7016A-7016D are health records of the user's current health conditions of anxiety disorder, asthma, high cholesterol, and migraines respectively. In some embodiments, health condition records 7016A-7016B and 7016D also include information on medications most recently prescribed for the corresponding health conditions (anxiety disorder, asthma, and migraines), even if such medications are separately identified in a medications group.

Although the embodiment illustrated in FIG. 8B shows ten health records in the health record in the health records summary, in other embodiments, the health record summary may include a different number of current health records of the user. Further, in some embodiments, not all of the current health records included in the health record summary are concurrently displayed on display 112. In one or more of such embodiments, the user performs a gesture to scroll through the current health records displayed in the health record summary. Although health records displayed in the illustrated embodiments are grouped by category and arranged in an alphabetical order, in other embodiments, health records may be grouped or ordered by date, provider, similarity, criticality, relevant biologic function or system (for example, all cardiology measurements followed by all endocrine measurements), or any other suitable criteria or based on any suitable factor. In one embodiment, the order in which health records are displayed is configurable by a user or provider (such as by a primary care physician). FIG. 8B also illustrates detecting a tap gesture with contact 7503 on health records affordance 5304 to return to the user interface illustrated in FIG. 8A.

FIG. 8B' is an alternate embodiment of a dashboard of a health care summary displayed in response to detecting a tap gesture with contact 7502 on health record summary representation 7005 in FIG. 8A. FIG. 8B' includes health care summary information shown as graphical representations of health records. More particularly, FIG. 8B' illustrates health metric record 7012A (blood pressure level) and health metric record 7012B (cholesterol level). In the illustrated embodiment, health metric record 7012A contains a chart 7712 illustrating the user's blood pressure level (140/90 mmHg) within a range of blood pressure levels. In the illustrated embodiment, the numerical value of the user's blood pressure level is placed at a position on chart 7712 proximate to where the measured blood pressure falls within the range. In such a manner, chart 7712 may illustrate where the user's blood pressure level falls relative to a range of blood pressure levels indicative of the normalcy or severity of the user's blood pressure. In some embodiments, health metric record 7012A also includes a legend or other explanation of how to analyze chart 7712 or information about the significance of user's blood pressure level to help the user assess the user's blood pressure level.

Health metric record 7012B contains a bar graph 7714 illustrating the user's cholesterol level (269 md/dL) within a range of cholesterol levels. In the illustrated embodiment, the numerical value of the user's cholesterol level is placed at a position on chart 7714 proximate to where the measured cholesterol falls within the range. In the illustrated embodiment, the bar containing the numerical value of the user's cholesterol level is displayed in a color that indicates the normalcy or severity of the user's cholesterol level. For example, the bar may be green, yellow, or red if the user's cholesterol level is under 200 mg/dL, between 200 mg/dL and 300 mg/dL, or above 300 mg/dL, respectively.

In the embodiment illustrated in FIG. 8B', health metric record 7012A includes a blood pressure level that is displayed in a larger font of text than other text displayed in health metric record 7012A. In such a manner, important information such as testing measurements or lab results may be emphasized to highlight such information for the user. Similarly, in health metric record 7012B the measurement of the user's cholesterol level is also displayed in a larger font to help the user identify the most recent measurement of the user's cholesterol level. In other embodiments, text containing measurements of the user's health metrics are highlighted, displayed in a different color, bolded, italicized or formatted in other suitable ways to allow a user to quickly identify the user's health metrics. FIG. 8B' also illustrates detecting a tap gesture with contact 7504 on health records affordance 5304 to return to the user interface illustrated in FIG. 8A.

Device 100 periodically receives updates to the user's health records. FIG. 8C illustrates displaying a dashboard of a health record summary containing an update to health metric record 7012A of FIG. 8B that includes a blood pressure measurement of the user. As illustrated in FIG. 8C, a health metric record 7052A (blood pressure level measured on Dec. 1, 2017) is displayed in the health record summary in lieu of health metric record 7012A (blood pressure level measured on Nov. 1, 2017) of FIG. 8B that included a prior blood pressure measurement of the user. Further, an update badge 7141A is displayed with health metric record 7052A to indicate that health metric record 7052A is an updated health record and to draw the user's attention to health metric record 7052A. FIG. 8C also illustrates detecting a tap gesture with contact 7505 on health records affordance 5304 to return to the user interface illustrated in FIG. 8A.

FIG. 8C' illustrates an alternate embodiment of the dashboard of FIG. 8C. In the illustrated alternate embodiment, health metric record 7052A with a new blood pressure measurement that is illustrated in FIG. 8C has not been received by device 100. However, health metric record 7052B has been received by device 100 with a more recent cholesterol measurement than health metric record 7012B illustrated in FIG. 8B. FIG. 8C' therefore illustrates that health metric record 7052B is displayed in the health record summary in lieu of health metric record 7012B illustrated in FIG. 8B. In some embodiments, an update may affect multiple health records displayed in the health record summary. In such embodiments, all of the affected health records displayed in the health record summary may be updated. In the illustrated embodiment, health condition record 7016C of FIG. 8B (high cholesterol) is also updated with health condition record 7056C to reflect the current measurement of the user's cholesterol. Further, update badges 7141B and 7141C are displayed with health metric record 7052B and health condition record 7056C to indicate the updates and to draw the user's attention to the corresponding health records. FIG. 8C' further illustrates detecting a tap gesture with contact 7506 on health metric record 7052B and, in response to the tap gesture, displaying a health record archive 7058 in FIG. 8D.

Figure 8D:
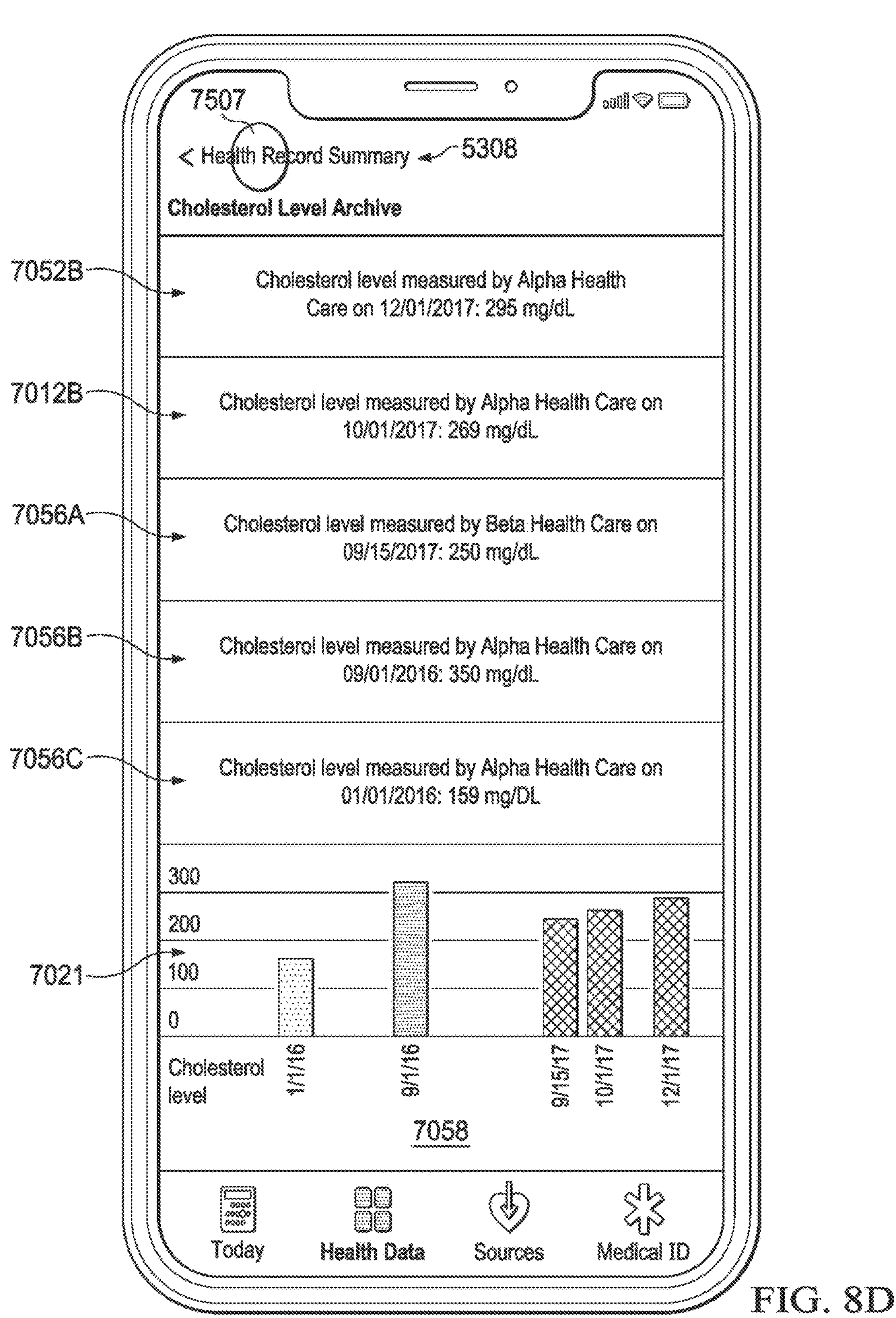

FIG. 8D illustrates one embodiment of health record archive 7058 containing historical health records of the user's cholesterol level. A health record archive is a user interface for the display of historical health records. In the illustrated embodiment, health record archive 7058 contains health metric record 7052B, which contains the current measurement of the user's cholesterol level, health metric record 7012B, displayed in the health record summary illustrated in FIG. 8B before device 100 received health metric record 7052B, and further health metric records 7056A-7056C. Health metric records 7056A-7056C contain measurements of the user's cholesterol level measured on Sep. 15, 2017, Sep. 1, 2016, and Jan. 1, 2016 by Alpha Health Care or Beta Health Care. A graph 7021 of the user's cholesterol level over time is also displayed in health record archive 7058. Graph 7021 contains several bars, each indicative of a different measurement of the cholesterol level of the user associated with health metric records 7052B, 7012B, and 7056A-7056C. The bars may be displayed in colors that indicate the normalcy of the user's cholesterol level. For example, bars that indicate measurements of cholesterol levels under 200 mg/dL may be displayed in a first color, bars that indicate measurements of cholesterol levels between 200 mg/dL and 300 mg/dL may be displayed in a second color, and bars that indicate measurements of cholesterol levels above 300 mg/dL may be displayed in a third color. Health metric records 7052B, 7012B, and 7056A-7056C and graph 7021 provide the user with information about the user's cholesterol level over time. FIG. 8D also illustrates detecting a tap gesture with contact 7507 on a health record summary affordance 5308 to display the dashboard of user's health record summary in FIG. 8E.

Figure 8E:
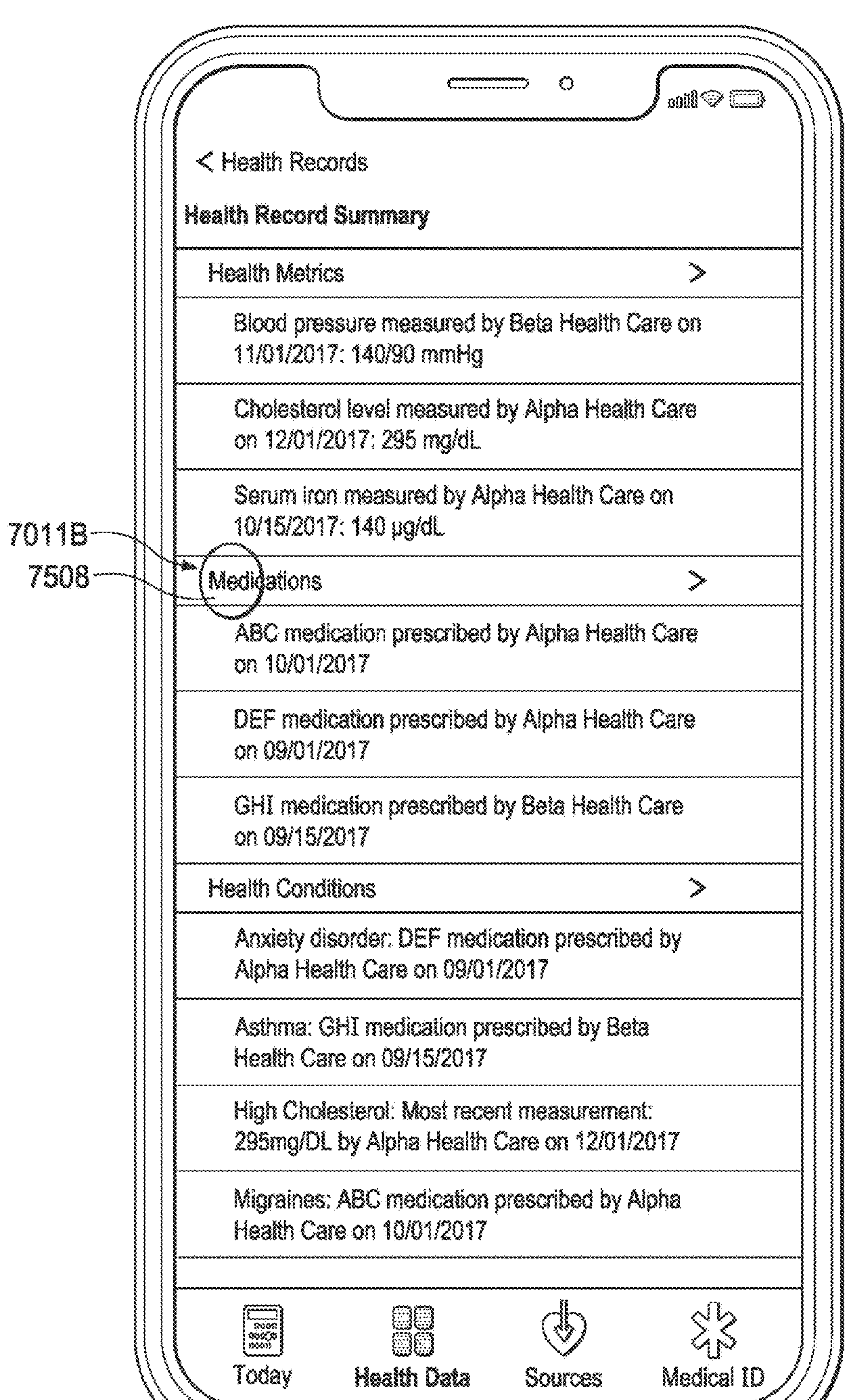

FIG. 8E illustrates one embodiment of the dashboard of the health record summary shown in FIG. 8C' after a user has viewed the update of new health record 7052B (cholesterol level) of FIG. 8C'. Update badges 7141B and 7141C (shown in FIG. 8C') are no longer displayed in FIG. 8E because the user has already reviewed the update of new health record 7052B. FIG. 8E further illustrates detecting a tap gesture with contact 7508 on medications affordance 7011B and, in response to the tap gesture, displaying a health record archive 7057 in FIG. 8F.

Figure 8F:
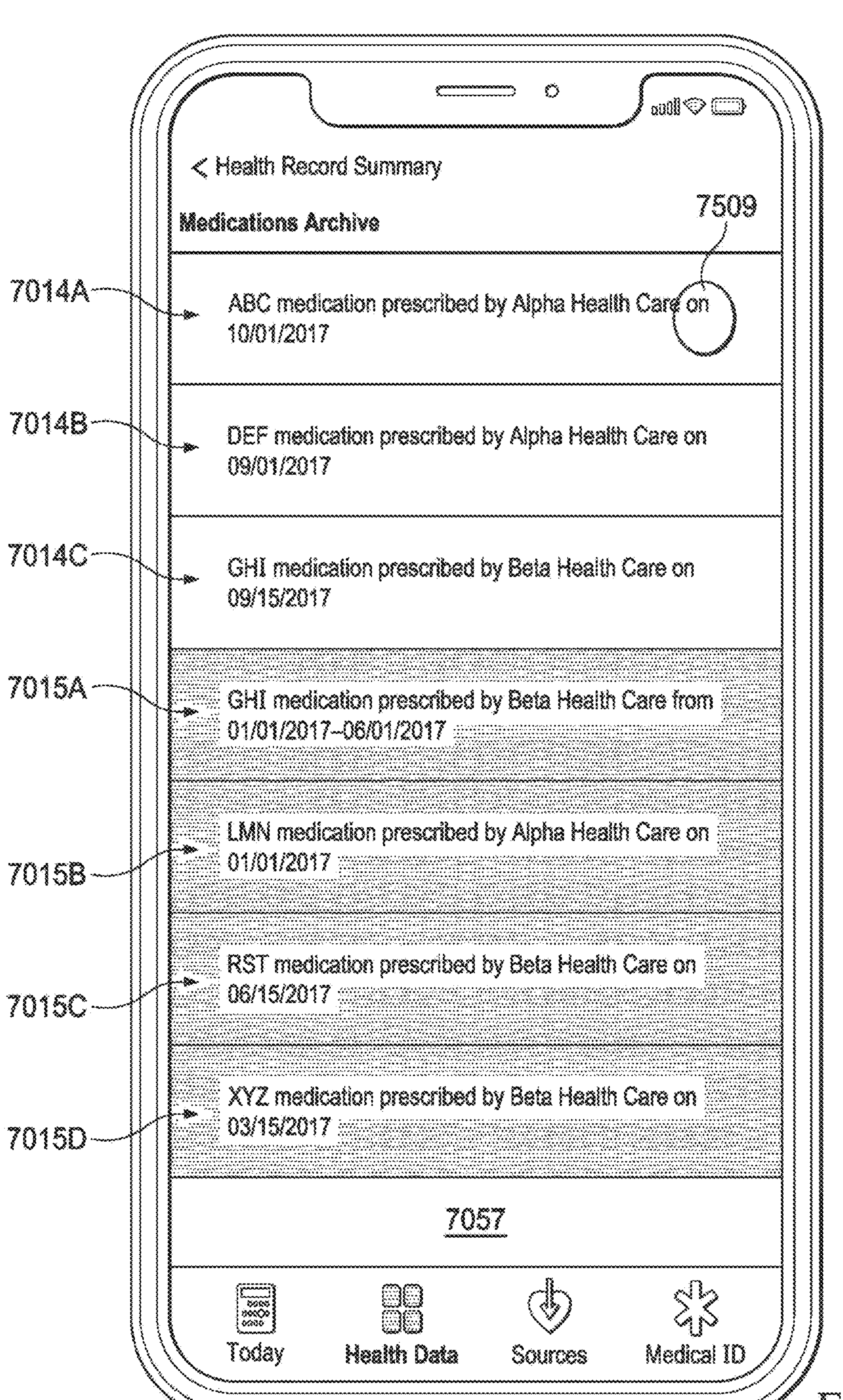

FIG. 8F illustrates an embodiment of health record archive 7057 containing historical health records of the user's medication. In the illustrated embodiment, health record archive 7057 contains current medication records 7014A-7014C (ABC medication, DEF medication, and GHI medication, respectively) and historical medication records 7015A-7015D. Historical medication record 7015A is an expired prescription of a currently prescribed GHI medication. Historical medication record 7015A also provides a prescription time period of the expired prescription and the name of the health care provider that prescribed the medication. Historical medication records 7015B-7015D are health records of medications (LMN, RST, and XYZ medications, respectively) that the user is no longer taking. In the illustrated embodiment, historical medication records 7015A-7015D are greyed out, are displayed in a smaller or lighter font, or are displayed in a different color than current medication records 7014A-7014C to allow the user to easily differentiate between current medications that the user is taking and expired medications. In some embodiments, historical medication record 7015A and current medication record 7014C, which both contain information about GHI medication, are not concurrently displayed in the health record archive. In some embodiments, the user selects a current medication record of a medication (such as ABC medication) to access historical medication records of the same medication that may have been taken by the user during an earlier time period or in different dosages. FIG. 8F further illustrates detecting a tap gesture with contact 7509 on medication record 7014A and, in response to the tap gesture, displaying additional information about ABC medication in FIG. 8G.

Figure 8G:
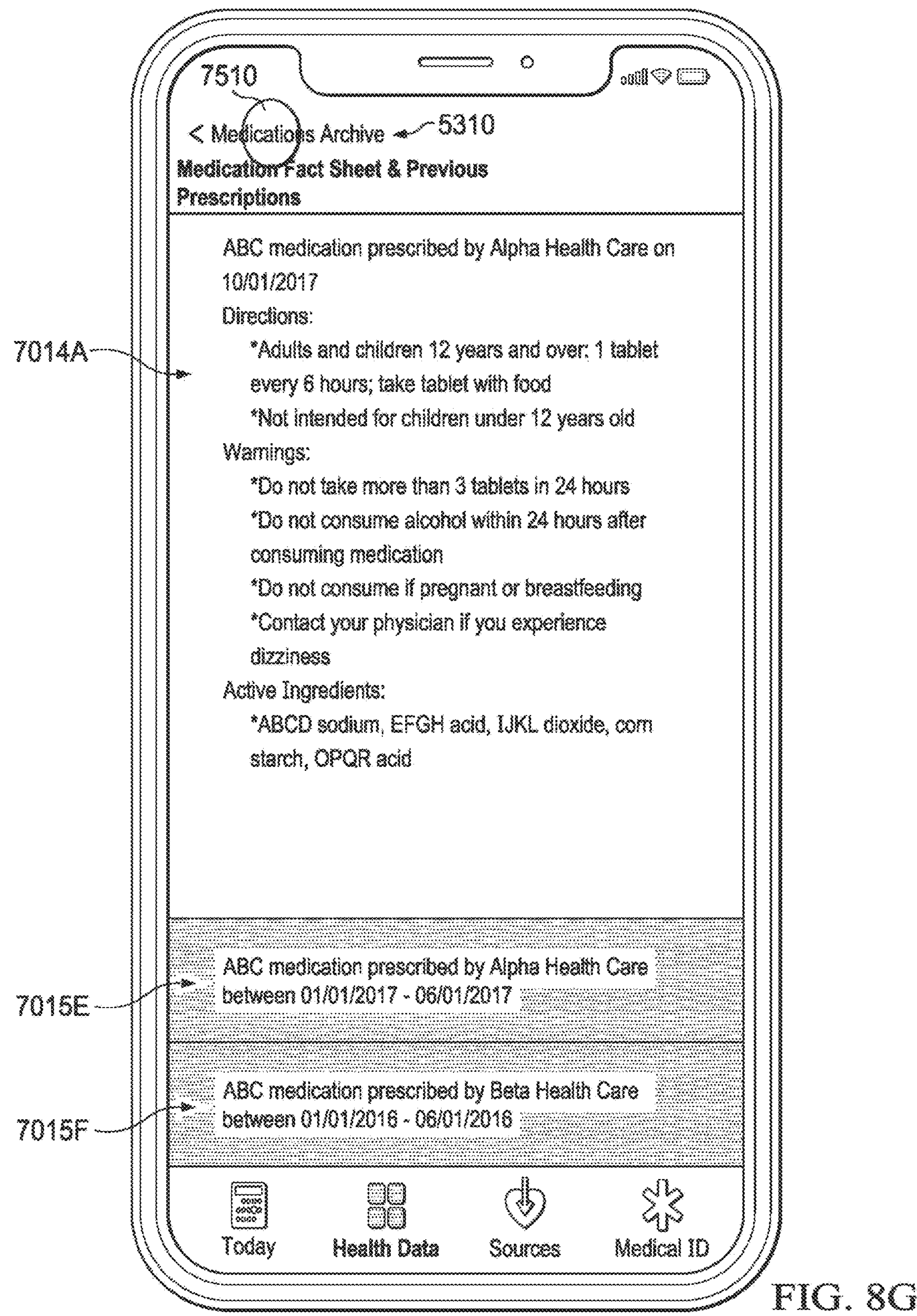

FIG. 8G illustrates displaying a fact sheet corresponding to medication record 7014A containing directions, warnings, and active ingredients of ABC medication. In other embodiments, additional information about ABC medication may also be displayed such as information regarding the pharmacy dispensing the medication, alternative sources for dispensing the medication (such as a pharmacy benefit manager), co-pay information, insurance coverage information, available generics, the refill or expiration date of the medication, instructions or affordances to refill the medication, dosages, adverse drug interactions, or images of the medication. Historical medication records 7015E and 7015F containing expired prescriptions of ABC medication are displayed in a different color to indicate that the prescriptions are not active. FIG. 8G further illustrates detecting a tap gesture with contact 7510 on a medications archive affordance 5310 to view health record archive 7057 illustrated in FIG. 8F.

Figure 8H:
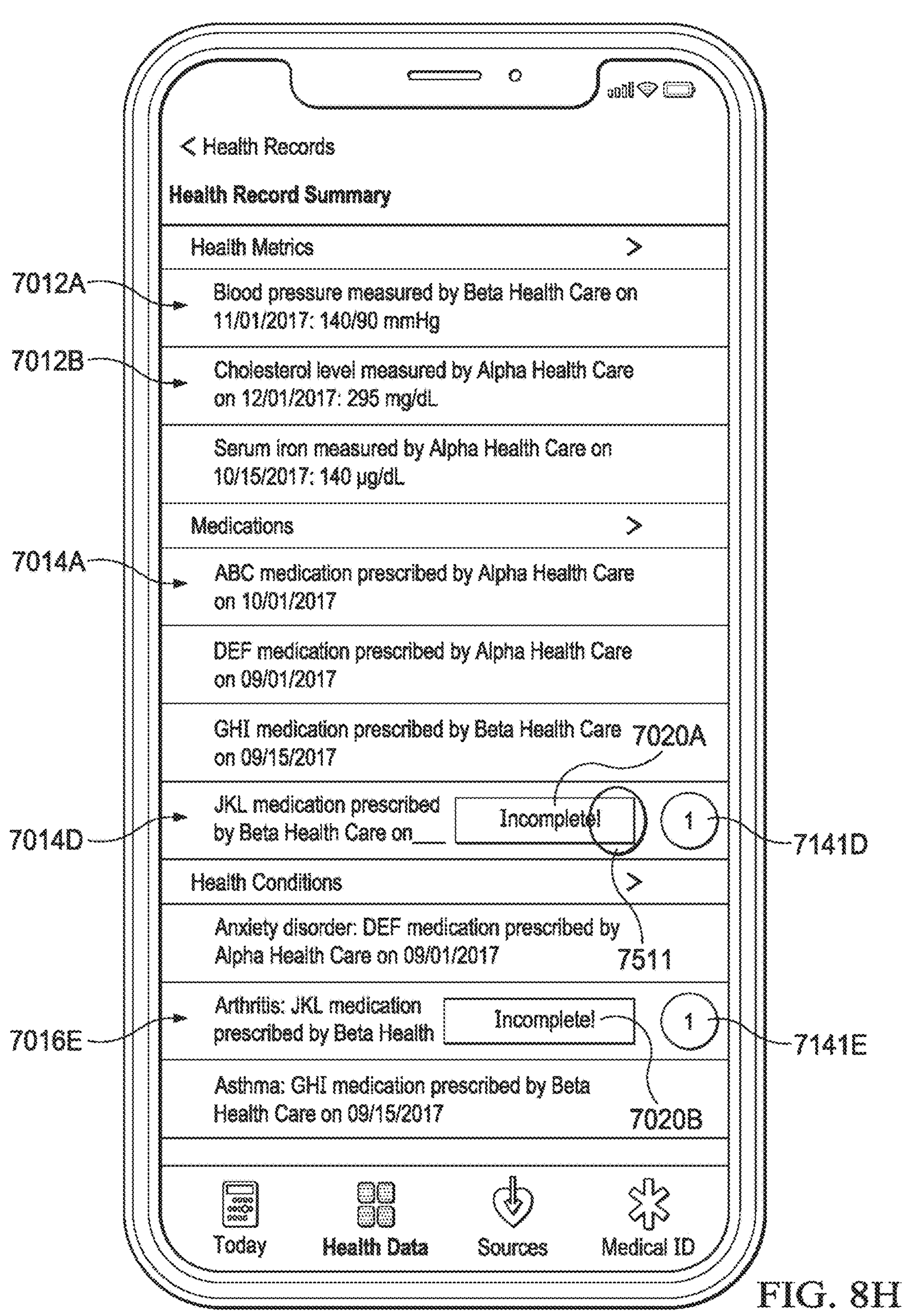

Similar to FIG. 8C', FIG. 8H also displays an embodiment of a dashboard of a health record summary after receiving an update to the user's health records. Occasionally, health records provided by health care providers are incomplete. An incomplete health record is a health record that is missing information, such as a hospital visitation date, the name of a physician, a prescription date, or other information that allows the user to adequately comprehend the health record. Health records may be flagged as incomplete by a health care provider, by a user directly, or automatically by device 100 in response to determining that a field in a received health record that is expected for the type of the received health record is missing. Such a determination by device 100 may be determined by parsing the health record, automatically searching for a particular string of text, interrogating the header file of a particular health record, determining that a required field is missing or that a number of fields for such health record less than the expected number has been received, or by any other suitable method.

In the embodiment illustrated in FIG. 8H, an update of new medication record 7014D for JKL medication and an update of new health condition record 7016E for arthritis are displayed in the health record summary, together with update badges 7141D and 7141E, respectively. Although medication record 7014D and health condition record 7016E both identify the name of the health care provider prescribing the medication and the name of the medication (JKL medication), the prescription date is missing from both medication record 7014D and health condition record 7016E. In the illustrated embodiment, incomplete affordances 7020A and 7020B are concurrently displayed with update badges 7141D and 7141E to notify the user about the updates to the user's health records and to notify the user that the health records that are the subject of the updates are missing information. Incomplete affordances 7020A and 7020B are affordances that the user selects to obtain more information about an incomplete health record.

Figure 8I:
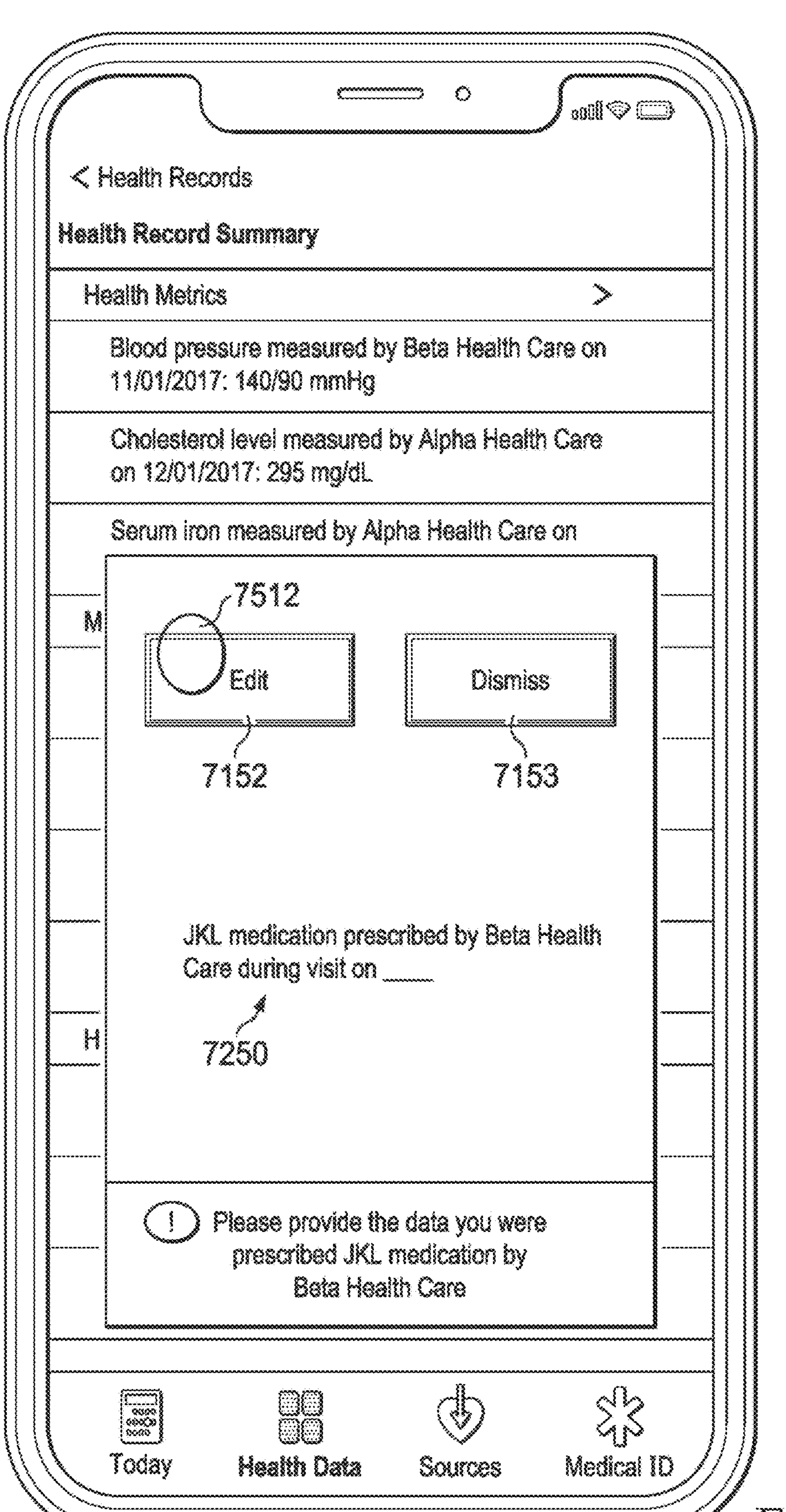

FIG. 8H further illustrates detecting a tap gesture with contact 7511 on incomplete affordance 7020A on medication record 7014D (JKL medication) and, in response to the tap gesture, displaying a notification 7250 in FIG. 8I about the information missing from medication record 7014D of FIG. 8H. In the illustrated embodiment, notification 7250 is overlaid on the dashboard of the health record summary shown in FIG. 8H. Notification 7250 contains text indicating that the prescription date of JKL medication is missing from medication record 7014D of FIG. 8H. Notification 7250 also contains an edit affordance 7152 and a dismiss affordance 7153. In some embodiments, the user is aware of the missing information (such as the prescription date missing from medication record 7014D and health condition record 7016E for arthritis of FIG. 8H) and may fill out the missing information. The user interacts with edit affordance 7152 to edit or add information about JKL medication such as the prescription date. In that regard, FIG. 8I also illustrates detecting a tap gesture with contact 7512 on edit affordance 7152. Once the user has added the information about JKL medication that was incomplete, the user selects dismiss affordance 7153.

In response to the user's selection of dismiss affordance 7153 and device 100 determining that the missing information was provided by the user, device 100 removes the display of notification 7020A from medication record 7014D (JKL medication) in FIG. 8H. Since notification 7020B was an indication that health condition record 7016E (arthritis) was incomplete for the same reason (the missing prescription date for JKL medication), device 100 also removes the display of notification 7020B from health condition record 7016E in FIG. 8H. In other embodiments, where device 100 determines that the user has not entered the correct information that was missing, or where the user has selected dismiss affordance 7153 without entering any information, then incomplete affordances 7020A and 7020B of FIG. 8H remain displayed with medication record 7014D and health condition record 7016E, respectively.

Figure 8J:
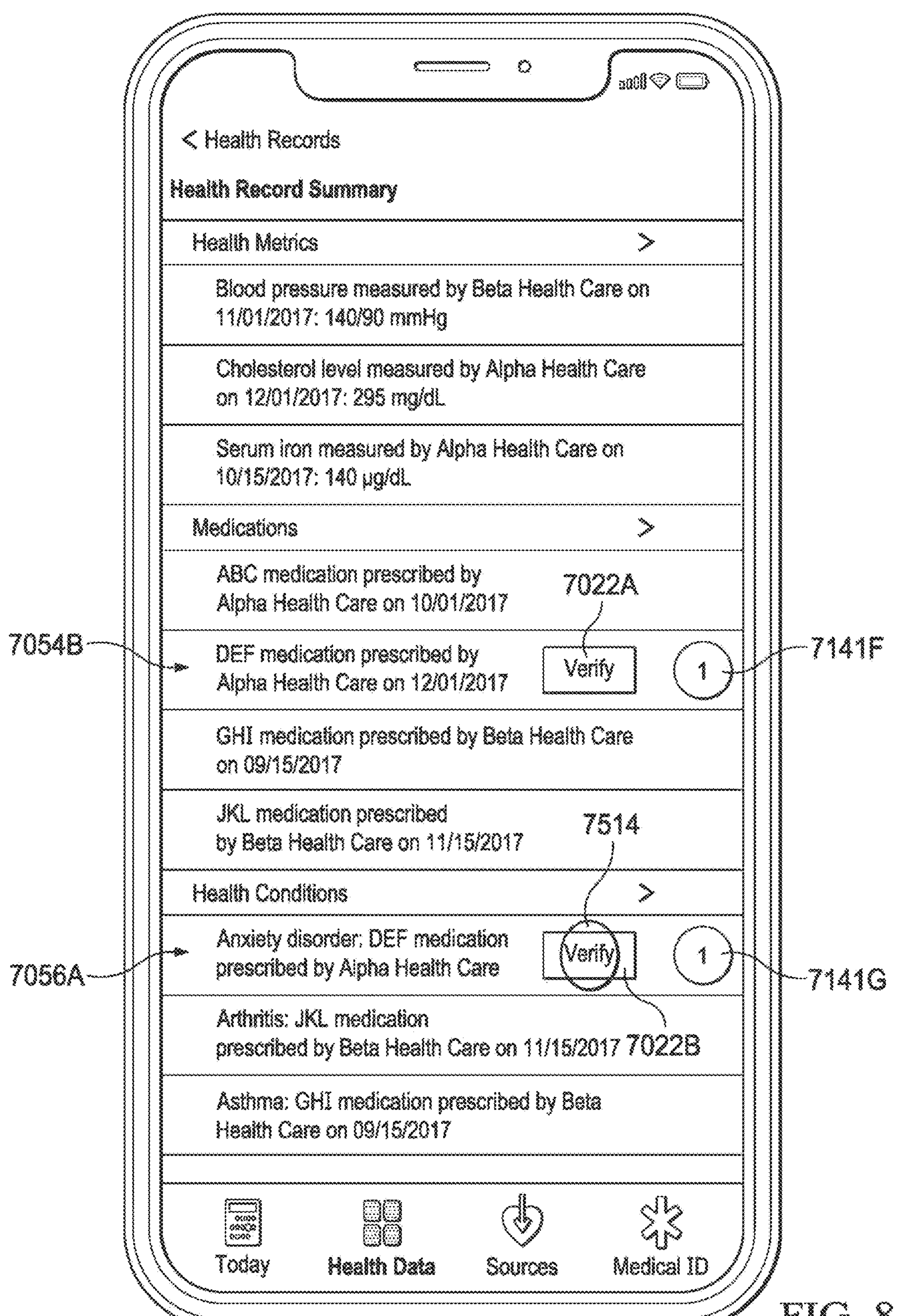

Similar to FIG. 8H, FIG. 8J also displays a health record summary after receiving an update to the user's health records. Device 100 occasionally determines that, although a health record is not missing any information, the authenticity or accuracy of a health record should be verified by the user. Device 100 may make such determination in response to a determination that information in the health record is unexpected or does not fall within an established range of values, includes data that varies drastically from data included in a prior health record, is from a health care provider that the user has not received a health record from for a long period of time, or for any other suitable reason. In still other embodiments, device 100 makes a determination that a health record should be verified if the health record appears to conflict or contradict other health records.

In the embodiment illustrated by FIG. 8J, updates of new medication record 7054B (DEF medication) and new health condition record 7056A (anxiety disorder) are received with the most recent prescription date of DEF medication and are displayed with update badges 7141F and 7141G respectively. Although neither medication record 7054B nor health condition record 7056A are missing any information, device 100, verification affordances 7022A and 7022B are concurrently displayed with update badges 7141F and 7141G to notify the user that the user should verify health condition records 7054B and 7056A respectively. Verification affordances 7022A and 7022B are affordances that the user selects to obtain more information about health records that the user is requested to verify.

Figure 8K:
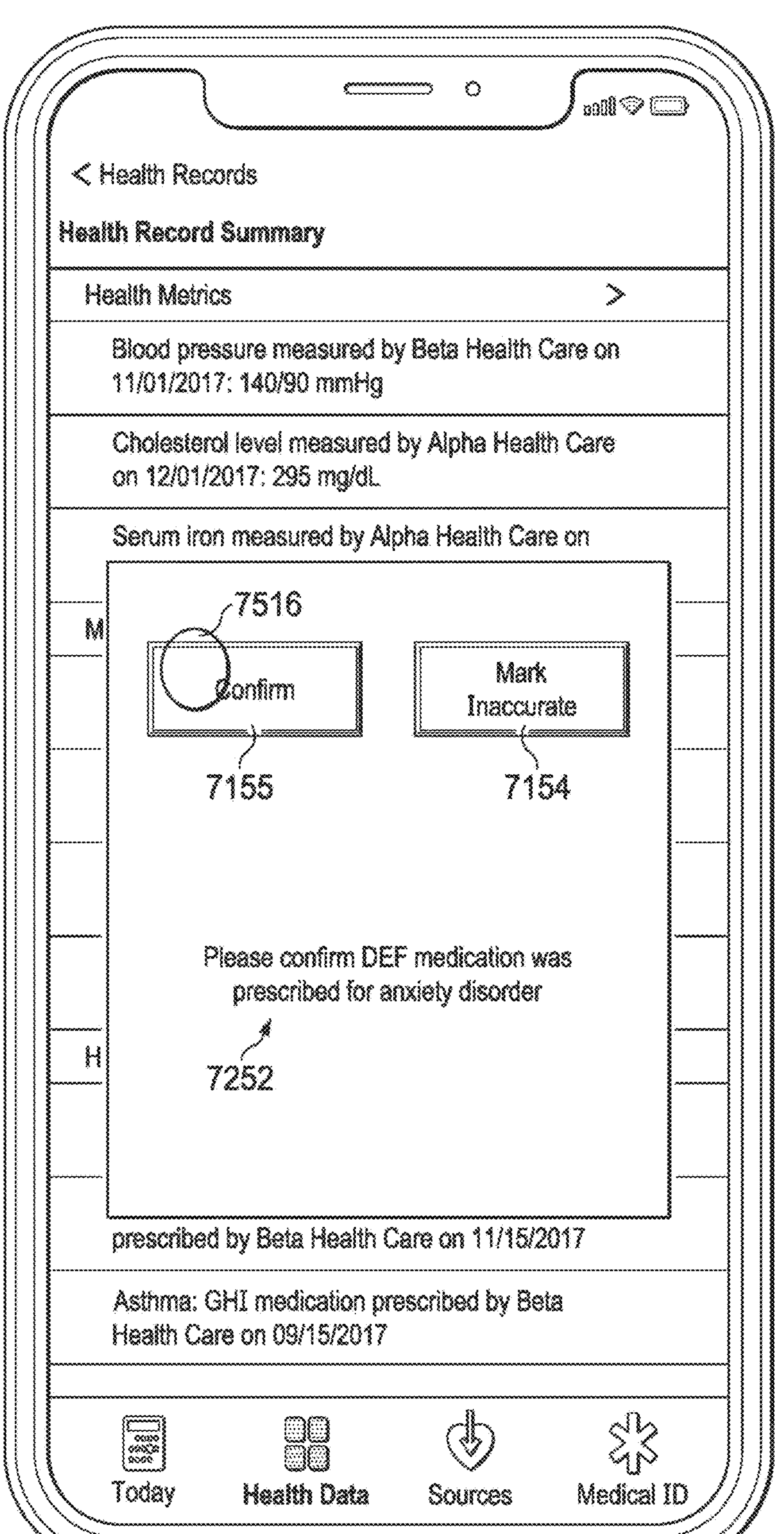

FIG. 8J further illustrates detecting a tap gesture with contact 7514 on verification affordance 7022B and, in response to the tap gesture, displaying a notification 7252 in FIG. 8K about the information in health condition record 7056A (anxiety disorder) that the user is requested to verify. In one embodiment, notification 7252 is overlaid on the dashboard of the health record summary of FIG. 8J as illustrated in FIG. 8K. Notification 7252 contains text requesting the user to confirm that DEF medication was prescribed for anxiety disorder. Notification 7252 also contains a confirm affordance 7155 and a mark inaccurate affordance 7154. The user interacts with confirm affordance 7155 to confirm the accuracy of the corresponding health record. Alternatively, the user interacts with mark inaccurate affordance 7154 to indicate that the information is inaccurate. FIG. 8K further illustrates detecting a tap gesture with contact 7516 on confirm affordance 7155. In some embodiments, in response to detecting tap gesture with contact 7516 on confirm affordance 7155, device 100 designates the information in both medication record 7054B (DEF medication) and health condition record 7056A illustrated in FIG. 8J as accurate and removes verification affordances 7022A and 7022B from the dashboard of the health records summary illustrated in FIG. 8J.

Figure 8L:
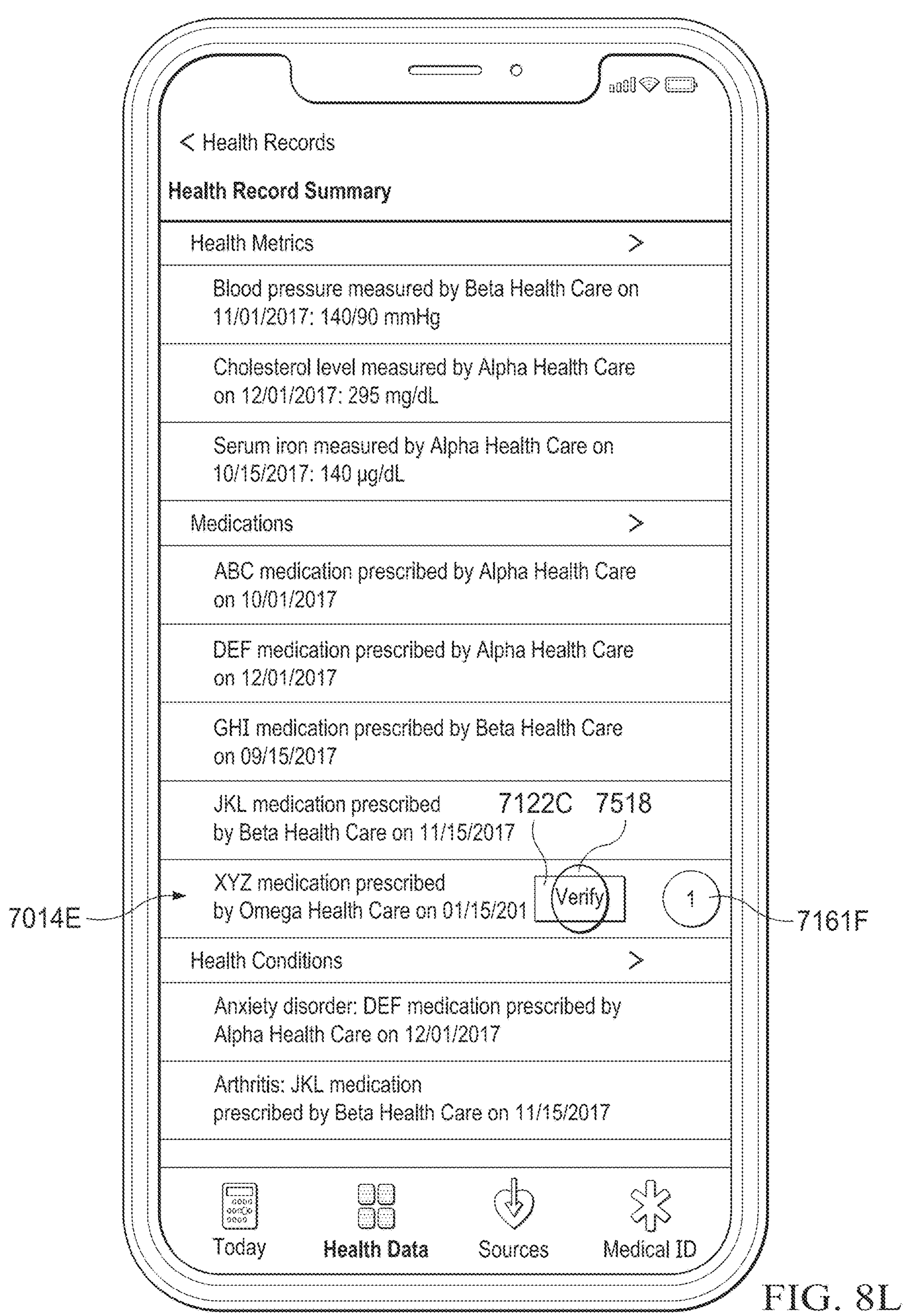

Similar to FIG. 8J, FIG. 8L also displays a health record summary after receiving an update to the user's health records. In the embodiment illustrated in FIG. 8L, an update of a new medication record 7014E is received of XYZ medication prescribed by Omega Health Care and is displayed with update badge 7161F. Although health record 7014E is not missing any information, device 100, upon a determination that the user has never been prescribed a medication by Omega Health Care, displays verification badge 7122C to notify the user that the user should verify the accuracy of health record 7014E.

Figure 8M:
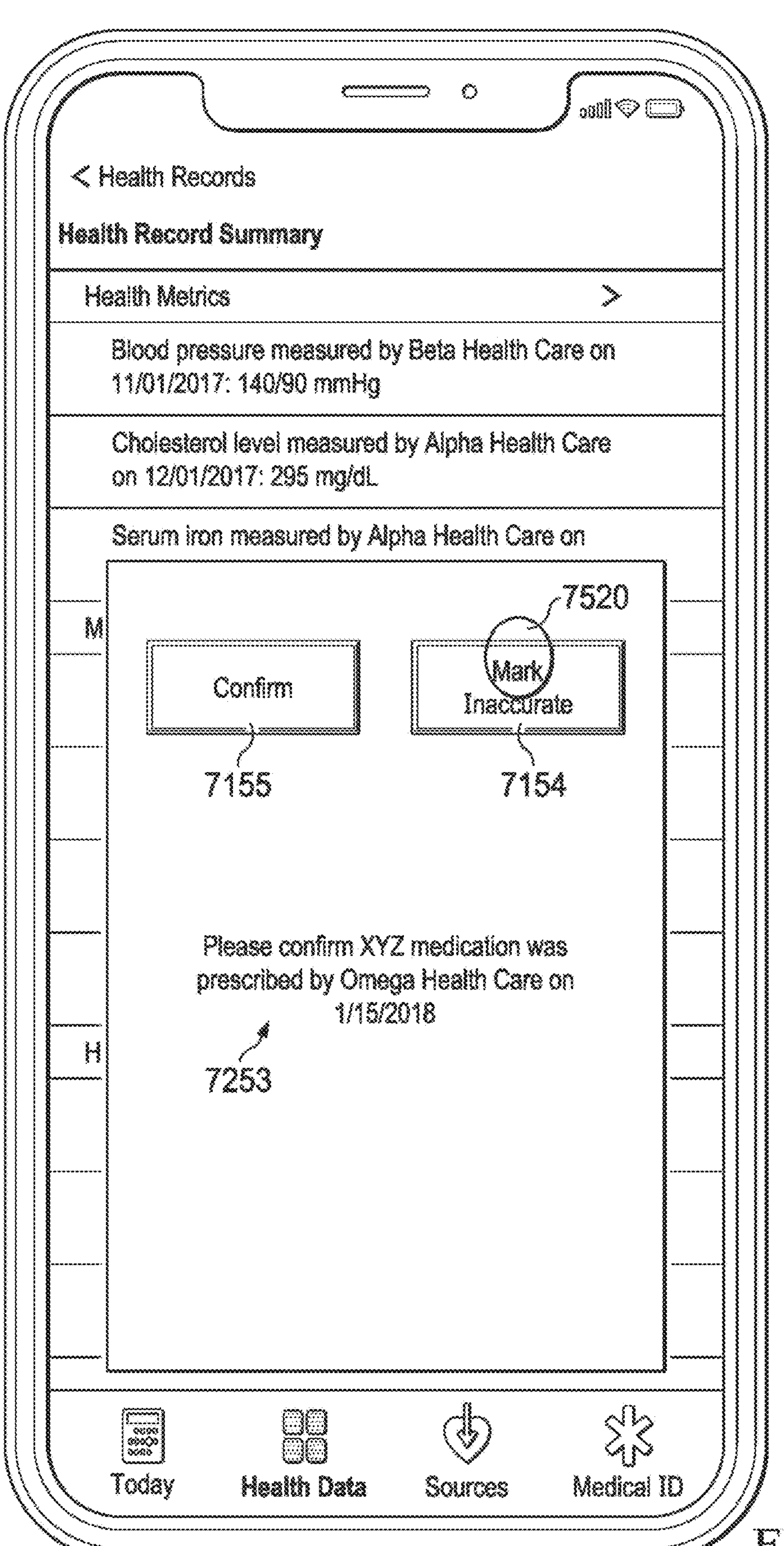
Figure 8N:
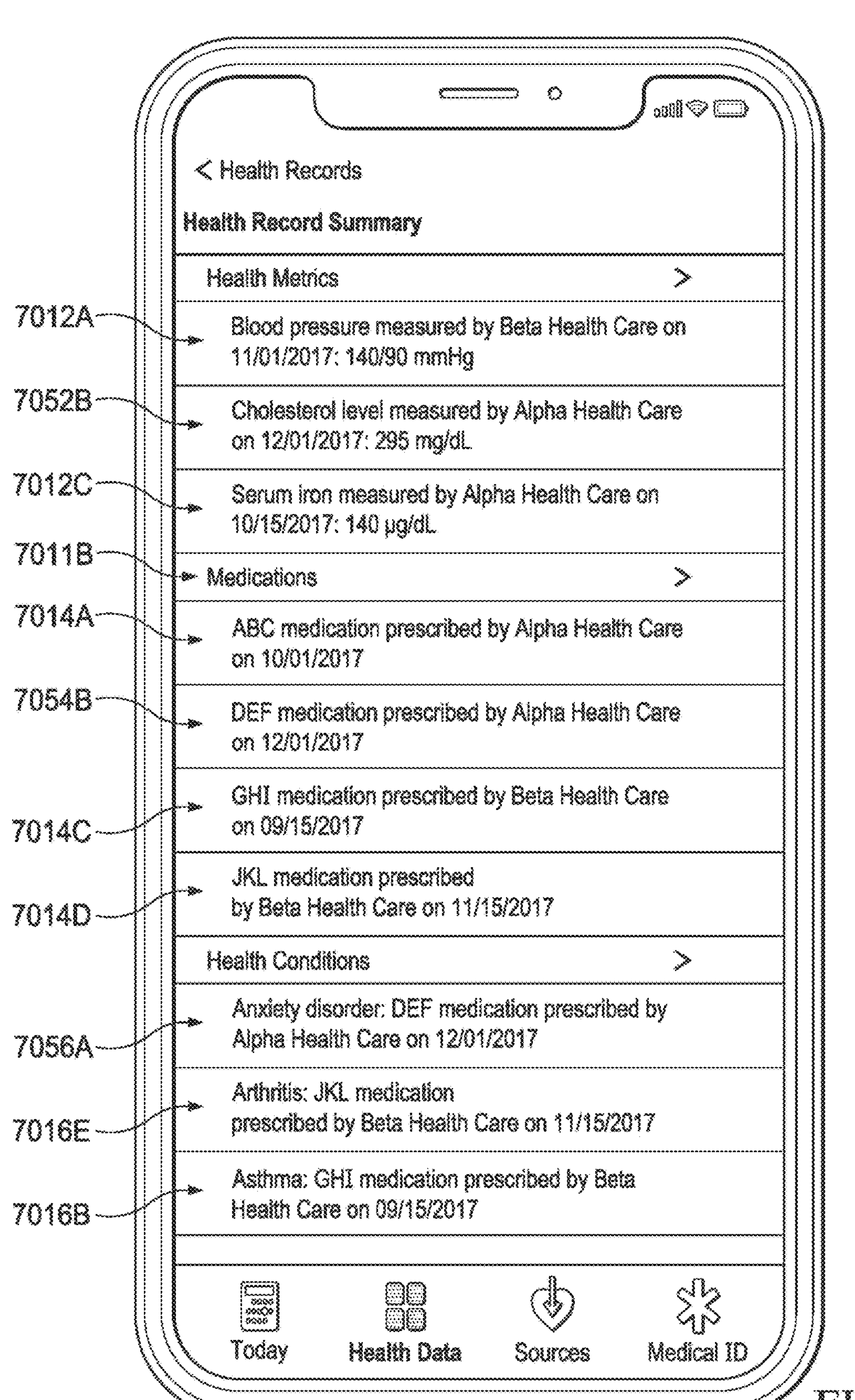

FIG. 8L further illustrates detecting a tap gesture with contact 7518 on verification affordance 7122C and, in response to the tap gesture, displaying a notification 7253 in FIG. 8M about the information in health condition record 7014E (XYZ medication) of FIG. 8L that the user is requested to verify. In the illustrated embodiment, notification 7253 is overlaid on the dashboard of the health record summary of FIG. 8L as illustrated in FIG. 8M. Notification 7253 contains text requesting the user to confirm that XYZ medication was prescribed by Omega Health Care on Jan. 15, 2018. Notification 7253 also contains confirm affordance 7155 and mark inaccurate affordance 7154. FIG. 8M further illustrates detecting a tap gesture from a user with contact 7520 on mark inaccurate affordance 7154. In some embodiments, in response to detecting tap gesture with contact 7520 on mark inaccurate affordance 7154, device 100 designates medication record 7014E as inaccurate and removes medication record 7014E from the dashboard of the health record summary in FIG. 8N. As illustrated in FIG. 8N, medication record 7014E of FIG. 8L is no longer displayed in the health record summary. In some embodiments, health records that have been marked by the user as inaccurate remain included in the health record archive. In that regard, the user may interact with medications affordance 7011B of FIG. 8N to review medication record 7014E.

FIGS. 9A-9D are flow diagrams illustrating a method for displaying dashboard user interfaces having aggregated health records using an electronic device in accordance with some embodiments. More particularly, FIGS. 9A-9D are flow diagrams illustrating a method for displaying current and historical health records of a user, using, for example, the user interfaces of FIGS. 8A-8N. As described in reference to FIGS. 8A-8N, method 900 can be utilized to display dashboard user interfaces for displaying current as well as historical health records of the user. Method 900 is performed at a device, (e.g., device 100, 300, 500 illustrated in FIGS. 1, 3, and 5A respectively). In one of such embodiments, display 112 is a touch screen display and the touch-sensitive surface is on or integrated with display 112. In some embodiments, display 112 is separate from the touch-sensitive surface. In other embodiments, the processes described herein may be implemented with devices having physical user-interfaces, voice interfaces, or other suitable interfaces. Some operations in the method 900 are, optionally, combined. Additionally, the order of some operations is, optionally, changed.

As described below, method 900 provides an intuitive way for displaying dashboard user interfaces having aggregated health records of the user. Method 900 also provides an intuitive way for displaying current as well as historical health records of the user. The method reduces the cognitive burden on a user when the user is browsing current health records and historical health records, thereby creating a more efficient human-machine interface. For battery-operated computing devices, enabling a user to browse through the user's current and historical health records faster and more efficiently conserves power and increases the time between battery charges.

Method 900 also provides an intuitive way for displaying representations of certain health conditions of the user to indicate the severity of such conditions. The method reduces the cognitive burden on a user by allowing the user to determine the severity of certain health conditions from the displayed representations of the health conditions, thereby creating a more efficient human-machine interface. The method increases the user's efficiency by reducing the amount of time required for a user to comprehend the severity of the user's health conditions. For battery-operated computing devices, allowing a user to comprehend the severity of the user's health conditions faster and more efficiently conserves power and increases the time between battery charges.

Device 100, while being associated with health data for a first user that includes a plurality of health record items of a first type and a plurality of health record items of a second type that is different from the first type, receives (902), via the one or more input devices, a request to display health record summary information for the user. FIG. 8A, for example, shows detecting a tap gesture with contact 7502 on health record summary representation 7005.

Device 100, in response to receiving the request, displays (904), on the display, health record summary information for the first user that includes concurrently displaying a plurality of health record items. FIG. 8B, for example, shows displaying, in response to detecting the tap gesture with contact 7502 on health record summary representation 7505 as illustrated in FIG. 8A, a health record summary containing health metric records 7012A-7012C (blood pressure level, cholesterol level, and serum iron level), medication records 7014A-7014C (ABC medication, DEF medication, and GHI medication, respectively), and health condition records 7016A-7016D (anxiety disorder, asthma, high cholesterol, and migraines, respectively).

The plurality of health record items include a first health record item of the first type that has a first date, where health record summary information excludes a plurality of health record items of the first type with dates earlier than the first date (906). FIG. 8B, for example, shows displaying health metric record 7012A (blood pressure level) in the health record summary. Health metric record 7012A contains a measurement of the user's blood pressure measured on Nov. 1, 2017. Prior measurements of the user's blood pressure are not included in the health record summary.

In some embodiments, the first health record item includes a representation of a severity of a condition of the first user (908). FIG. 8B,' also shows displaying health metric record 7012A (blood pressure level) in the health record summary. In the illustrated embodiment, health metric record 7012A includes chart 7712, which illustrates the user's blood pressure level within a range of blood pressure levels. The method reduces the cognitive burden on a user by providing the user with a representation (such as in image, a graph, or a chart) that allows the user to determine a severity of a health condition based on the representation, thereby creating a more efficient human-machine interface. The method also increases efficiency of the user by allowing the user to quickly identify the severity of the condition from the representation. For battery-operated computing devices, enabling a user to identify a severity of a condition faster and more efficiently conserves power and increases the time between battery charges.

In some embodiments, the first health record item includes a representation of a condition of the first user over a period of time (910). FIG. 8D, for example, shows displaying graph 7021, which is a graph of the user's cholesterol level over two years. In some embodiments, health metric record 7012A (blood pressure level) of FIG. 8B also contains graph 7021. Providing a graph of the user's condition over time allows the user to determine whether the user's condition has changed over time without having to navigate through multiple user interfaces to access data indicative of the user's condition from different periods of time, thereby reducing the cognitive burden on the user and creating a more efficient human-machine interface. For battery-operated computing devices, enabling a user to identify a condition of the user over time faster and more efficiently conserves power and increases the time between battery charges.

The plurality of health record items also includes a second health record item of the second type that has a second date that is different from the first date, where health record summary information excludes a plurality of health record items of the second type that have a date that is earlier than the second date (912). FIG. 8B for example, shows displaying medication record 7014A. Medication record 7014A is a health record of the user's prescription for ABC medication, which was prescribed to the user on Oct. 1, 2017. Prior prescriptions of ABC medication that predates Oct. 1, 2017 are not included in the health record summary.

In some embodiments, the health data for the first user includes a plurality of health record items of a third type that is different from the first type and the second type (914). FIG. 8B, for example, shows displaying health condition record 7016D. Health condition record 7016D is a health record of the user's migraines condition. In some embodiments, device 100 concurrently displays (914) the first health record item, the second health record item, and a third health record item of the third type that has a third date in the health record summary information. FIG. 8B, for example, shows concurrently displaying health metric record 7012A (blood pressure level), medication record 7014A (ABC medication), and health condition record 7016D (migraines) in the health record summary. Further, in some embodiments, the health record summary information excludes a plurality of health record items of the third type with dates earlier than the third date (914). Health condition record 7016D contains information about ABC medication, which was prescribed to the user on Oct. 1, 2017. Prior health condition records about the user's migraine condition are not included in the health record summary. Similarly, medication record 7014C of FIG. 8B is a health record of the user's prescription for GHI medication, which was prescribed to the user on Sep. 15, 2017. Prior prescriptions of GHI medication that predates Sep. 15, 2017 are also not included in the health record summary. Displaying multiple types of health records in a common interface allows the user to browse multiple types of health records without having to navigate between multiple user interfaces, thereby creating a more efficient human-machine interface. For battery-operated computing devices, enabling a user to browse through the user's records faster and more efficiently conserves power and increases the time between battery charges.

In some embodiments, the health data includes health data associated with a plurality of health care providers of the first user, where the first health record item is associated with a first health care provider of the plurality of health care providers, and where the second health record item is associated with a second health care provider of the plurality of providers (916). FIG. 8B, for example, shows that health metric record 7012A (blood pressure level) was obtained from Beta Health Care and medication record 7014A (ABC medication) was obtained from Alpha Health Care. Displaying multiple health records from multiple health care providers in a common interface allows the user to browse records from different health care providers without having to navigate between multiple user interfaces, thereby creating a more efficient human-machine interface. For battery-operated computing devices, enabling a user to browse through the user's health records faster and more efficiently conserves power and increases the time between battery charges.

In some embodiments, the plurality of health record items include a fourth health record item of a fourth type that has a fourth date, where the first health record item and the fourth health record item are associated with a first health care provider, and where the first date and the fourth date are dates of first and second visits to the first health care provider (918). FIG. 8B, for example, shows health metric record 7012A (blood pressure level) and health condition record 7016B (asthma). Both health records were obtained from Beta Health Care. Further, health metric record 7012A was obtained during a Nov. 1, 2017 visitation with Beta Health Care and health condition record 7016B was obtained during a Sep. 15, 2017 visitation with Beta Health Care. Displaying multiple health records obtained on different dates in a common interface allows the user to browse health records obtained on different dates without having to navigate between multiple user interfaces, thereby creating a more efficient human-machine interface. For battery-operated computing devices, enabling a user to browse through the user's health records faster and more efficiently conserves power and increases the time between battery charges.

In some embodiments, device 100, after displaying the health record that includes the first health record item and the second health record item, receives (920) third health record item of the first type with a third date that is after the first date. Device 100 received health metric record 7052A (blood pressure level measured on Dec. 1, 2017) illustrated in FIG. 8C after the health record summary (containing medication record 7014A of ABC medication prescribed on Oct. 1, 2017 and health metric record 7012A of blood pressure level measured on Nov. 1, 2017) illustrated in FIG. 8B was displayed. However, Health metric record 7052A was received before device 100 displayed the health record summary illustrated in FIG. 8C. In some embodiments, device 100, after receiving the third health record item, receives (920), via the one or more input devices, a second request to display health record summary information for the first user. In some embodiments, the user interface illustrated in FIG. 8A is displayed on display 112 at the time device 100 received health metric record 7052A. In such embodiments, the user performs a gesture similar to the tap gesture shown in FIG. 8A (with contact on health record summary representation 7005) to view the health record summary illustrated in FIG. 8C.

Further, in some embodiments, device 100, in response to receiving the second request, displays (920), on the display 112, an updated health record summary for the first user that includes concurrently displaying the second health record item and the third health record item without displaying the first health record item. FIG. 8C, for example, shows an updated health record summary containing health metric record 7052A (blood pressure level). Health metric record 7052A contains a measurement of the user's blood pressure, measured on Dec. 1, 2017. Health metric record 7012A also contains a measurement of the user's blood pressure, but measured on an earlier date. Device 100, after receiving a more up-to-date measurement of the user's blood pressure, displays health metric record 7052A instead of health metric record 7012A in the updated health record summary. Displaying a health record summary that is updated over time to include updates to existing health records of the user allows the user to access user's updates in a common interface without having to navigate through multiple user interfaces to obtain the up-to-date health records of the user. The method also reduces the cognitive burden on a user by allowing the user to access current health records through the health record summary, thereby creating a more efficient human-machine interface. The method increases the user's efficiency by allowing the user to access the user's current health records through the health record summary. For battery-operated computing devices, allowing a user to view the user's current health records faster and more efficiently conserves power and increases the time between battery charges.

In some embodiments, device 100, after displaying the health record that includes the first health record item and the second health record item, receives (922) a new health record item of the health data for the first user, where the new health record item has a date that is more recent than the first date and the second date. In some embodiments, device 100, receives medication record 7014D (JKL medication) illustrated in FIG. 8H prior to displaying medication record 7014D in the health record summary illustrated in FIG. 8H. In some embodiments, device 100, after receiving the new health record item, receives (922), via the one or more input devices, a third request to display health record summary information for the first user. In some embodiments, the user interface illustrated in FIG. 8A is displayed on display 112 at the time device 100 received medication record 7014D. In such embodiments, the user performs a gesture similar to the tap gesture shown in FIG. 8A to view the health record summary illustrated in FIG. 8H.

In some embodiments, device 100, in response to receiving the third request, displays (922) on the display, an updated health record summary for the first user that includes concurrently displaying the first health record item, the second health record item, and the new health record item. FIG. 8H, for example, shows displaying an updated health record summary containing health metric record 7012A (blood pressure level), medication record 7014A (ABC medication), and medication record 7014D (JKL medication). Displaying a health record summary that is updated over time to include new health records of the user allows the user to access user's updates in a common interface without having to navigate through multiple user interfaces to obtain the up-to-date health records of the user. The method also reduces the cognitive burden on a user by allowing the user to access current health records through the health record summary, thereby creating a more efficient human-machine interface. The method increases the user's efficiency by allowing the user to access the user's current health records through the health record summary. For battery-operated computing devices, allowing a user to view the user's current health records faster and more efficiently conserves power and increases the time between battery charges.

In some embodiments, device (100) receives (924), via the one or more input devices, a first request to display the plurality of health record items of the first type that are not displayed in the summary. FIG. 8C', for example, shows a tap gesture with contact 7506 on health metric record 7052B (cholesterol level). In some embodiments, device (100), in response to receiving the first request to display the plurality of health record items of the first type that are not displayed in the summary, displays (924) on the display, a plurality of health record items of the first type with dates earlier than the first date. FIG. 8D, for example, shows displaying health metric records 7056A-7056C (cholesterol levels) in response to detecting the tap gesture illustrated in FIG. 8C'. Health metric records 7056A-7056C contain measurements of the user's cholesterol level measured on Sep. 15, 2017, Sep. 1, 2016, and Jan. 1, 2016 made by an employee of Alpha Health Care or Beta Health Care. Health metric records 7056A-7056C all predate health metric record 7052B. Further, none of health metric records 7056A-7056C are displayed in health metric record 7012B (cholesterol level) illustrated in FIG. 8H. The method reduces the number of inputs required to obtain historical health records by allowing the user to access the user's historical health records through the health record summary, thereby creating a more efficient human-machine interface. The method increases the user's efficiency by allowing the user to access the user's historical health records through the health record summary. For battery-operated computing devices, allowing a user to view the user's historical health records faster and more efficiently conserves power and increases the time between battery charges.

In some embodiments, device (100) in response to receiving the first request to display the plurality of health record items of the first type that are not displayed in the summary, displays (926), on display 112, a health record archive for the first user that includes concurrently displaying a health record item of the first type with a most recent date and one or more of the plurality of health record items of the first type with dates earlier than the first date. FIG. 8D, for example, illustrates concurrently displaying health metric record 7052B, which contains the user's most recent cholesterol measurement measured on Dec. 1, 2017 and health metric records 7056A-7056C, which contain earlier measurements of the user's cholesterol level. Concurrently displaying the user's current and historical health records avoids the need to navigate through multiple user interfaces in order to obtain both the user's current health records and the user's historical health records. The method reduces the cognitive burden on a user by allowing the user to view the user's current and historical health records in one user interface, thereby creating a more efficient human-machine interface. The method increases the user's efficiency by allowing the user to view the user's current and historical health records without having to navigate to different user interfaces to view current and historical health records. For battery-operated computing devices, allowing a user to view the user's current and historical health records faster and more efficiently conserves power and increases the time between battery charges.

In some embodiments, device 100, in response to receiving the first request to display the plurality of health record items of the first type not displayed in the summary, displays (928), on display 112, a fourth health record item of the first type in the health record archive. FIG. 8D, for example, illustrates displaying graph 7021 of the user's cholesterol level over time in response to detecting the tap gesture illustrated in FIG. 8C'. In some embodiments, the fourth health record item includes a representation of a health metric measured on a fourth date earlier than the first date (928). Graph 7021 includes current and previous measurements of the user's cholesterol level. In other embodiments, one or more of health metric records 7056A-7056C (cholesterol levels) illustrated in FIG. 8D also contain a representation (such as a bar graph, or a scale) of the user's prior cholesterol level. Displaying a representation of a historical health metric allows the user to determine the user's health metric over time without having to contact the user's health care provider, thereby freeing up communications systems, reducing bandwidth on networks, and preserving energy. For battery-operated computing devices, allowing a user to obtain historical information about the user's health metric faster and more efficiently conserves power and increases the time between battery charges.

In some embodiments, device 100, after displaying health record summary information with the first health record and the second health record, receives (930) a third health record item of a third type that has a third date that is more recent than the first date and the second date. Health condition record 7016E (JKL medication) of FIG. 8H was received by device 100 after device 100 received health metric record 7012A (blood pressure level) and medication record 7014A (ABC medication) of FIG. 8B. Health condition record 7016E contains information about the user's arthritis condition and information about JKL medication, which was prescribed to the user on Nov. 15, 2017. The date of health condition record 7016E is more recent than the date of health metric record 7012A (Nov. 1, 2017) and the date of medication record 7014A (Oct. 1, 2017). In some embodiments, device 100, in response to a request to view health record summary information, updates (930) health record summary information to include the third health record item, where the first health record item, the second health record item, and the third health record item are concurrently displayed in health record summary information. As shown in FIG. 8N, health metric record 7012A (e.g., first health record item), medication record 7014A (e.g., second health record item), and health condition record 7016E (e.g., third health record item) are concurrently displayed in the health record summary. Displaying a health record summary that contains multiple types of health records allows the user to view multiple types of health records in a common interface without having to navigate through multiple user interfaces, thereby reducing the cognitive burden on a user and also creating a more efficient human-machine interface. The method also increases the user's efficiency by allowing the user to access multiple types of health records from a common interface. For battery-operated computing devices, allowing a user to view the user's current health records faster and more efficiently conserves power and increases the time between battery charges.

In some embodiments, device 100, in response to the request to display health record summary information, in accordance with a determination that a health record item of the health data for the first user is incomplete, displays (932) an incomplete record affordance in health record summary information. FIG. 8H, for example, shows displaying incomplete affordance 7020A with medication record 7014D (JKL medication) after determining that medication record 7014D is missing information. The method reduces the number of mistakes caused by the user relying on records that are missing information. The method reduces the cognitive burden on a user by identifying, to the user, health records that are missing information. The method increases the user's efficiency by allowing the user to optionally ignore records that are missing information while the user reviews the user's health records. For battery-operated computing devices, allowing a user to review the user's health records faster and more efficiently conserves power and increases the time between battery charges.

In some embodiments, device 100, receives (934), via the one or more input devices, a user verification of an accuracy of a health record item of the plurality of health record items displayed in health record summary information. FIG. 8K, for example, shows detection of a tap gesture with contact 7516 on confirm affordance 7155 to confirm that DEF medication was prescribed for anxiety disorder. Device 100, in response to receiving the user verification of the accuracy of the health record item, provides (934) the user verification to a health care provider associated with the health record item. In some embodiments, device 100, in response to detecting the user's input illustrated in FIG. 8J, automatically notifies Alpha Health Care that DEF medication has been verified by the user as a medication the user is taking to treat the user's anxiety disorder. The method reduces the cognitive burden on a user by allowing the user to verify the accuracy of a health record. The method increases the user's efficiency by allowing the user to verify the accuracy of certain health records without waiting for a verification from a health care provider. The method also reduces a need to request the health care provider to verify the health record, which saves bandwidth required to transmit the request to an electronic system of the health care provider. The method also reduces the burden of the electronic system of the health provider to process the request, which in turn also reduces the power expenditure of the electronic system. Automatically notifying an electronic system of a health care provider that a health record from the health care provider has been verified by the user reduces a need for the health care provider to contact (through the electronic system or through other means of telecommunication) the user or the user's device to verify the accuracy or completeness of the health record. The foregoing frees up communications systems, reduces bandwidth on networks, and preserves energy.

In some embodiments, device 100, receives (936), via the one or more input devices, a first user indication that a health record item of the plurality of health record items included in health record summary information is inaccurate. FIG. 8M, for example, shows detection of a tap gesture with contact 7520 on mark inaccurate affordance 7154 to mark medication record 7014E (XYZ medication) of FIG. 8L as inaccurate. In some embodiments, device 100, in response to receiving the first user indication, excludes (936) the health record item from health record summary information, where the health record item is no longer included in health record summary information after being excluded from health record summary information. FIG. 8N, for example, shows an updated health record summary after the tap gesture illustrated in FIG. 8M was performed. As shown in FIG. 8N, medication record 7014E of FIG. 8L is not displayed in the updated health record summary. The method reduces the cognitive burden on a user by allowing the user to ignore inaccurate or incomplete health records. The method increases the user's efficiency by reducing the amount of time a user spends on reviewing inaccurate or incomplete records. For battery-operated computing devices, allowing a user to review the user's health records faster and more efficiently conserves power and increases the time between battery charges. The method also reduces the number of user mistakes caused by the user relying on an incomplete or inaccurate health record.

In some embodiments, device 100, in response to receiving the first user indication, automatically, without further user input, transmits (938) to a request for updated information for the health record item from a health care provider computer system. In some embodiments, device 100, upon detecting an interaction with mark as inaccurate affordance 7154 of FIG. 8K to designate a health record as an inaccurate health record, automatically transmits a request to the health care provider of the health record. Automatically notifying an electronic system of a health care provider that a health record from the health care provider is inaccurate reduces a need for the user to manually contact (using the device or other telecommunication means) the health care provider to request the health care provider to update the inaccurate health record. The foregoing frees up communications systems, reduces bandwidth on networks, and preserves energy. Further, updated information may also be received from the health care provider before the user has an option to update the missing information. For battery-operated computing devices, updating inaccurate health records faster and more efficiently conserves power and increases the time between battery charges.

In some embodiments, device 100, receives (940), via the one or more input devices, information updating the first health record item. FIG. 8I, for example, shows user making edits to health metric record 7014D (JKL medication). In some embodiments, device 100 receives the edits to health metric record 7014D after user performs the tap gesture shown in FIG. 8I with contact 7512 over edit affordance 7152 of FIG. 8I. In some embodiments, device 100, after receiving the information updating the first health record item, receives (940) a second request to display health record summary information for the first user. In some embodiments, the user, after editing health metric record 7014D, selects health record summary representation 7005 to view the health record summary. In other embodiments, a tap gesture with a contact over edit affordance 7152 or dismiss affordance 7153 of FIG. 8I also constitutes as a request to display the health record summary. In some embodiments, device 100, in response to receiving the request to display health record summary information for the first user, displays (940) an updated health record summary for the first user including concurrently displaying an updated first health record item that reflects the changes to the first health record item and the second health record item. FIG. 8J, for example, shows an updated health record summary containing information about medication record 7014D that was previously missing from the health record summary illustrated in FIG. 8H. Displaying updates to health records with other current health records in a common interface allows the user to view the user's current health records in a common interface without having to navigate through different user interfaces to obtain updates to different health records, thereby creating a more efficient human-machine interface. For battery-operated computing devices, enabling a user to browse through the user's health records faster and more efficiently conserves power and increases the time between battery charges.

The particular order in which the operations in FIGS. 9A-9D have been described is merely exemplary and is not intended to indicate that the described order is the only order in which the operations could be performed. One of ordinary skill in the art would recognize various ways to reorder the operations described herein. Additionally, details of the processes described above with respect to method 900 (e.g., FIGS. 9A-9D) are also applicable in an analogous manner to the methods described above and below. For example, methods 700 and 1100 optionally include one or more of the characteristics of the various methods described above with reference to method 900. For example, the methods for displaying a health record summary containing current health records and displaying historical records in other user interfaces described above with reference to 900 are optionally used by method 700 to display aggregated health records, and are optionally used by method 1100 for displaying health records in a health record manager. For brevity, these details are not repeated below.

FIGS. 10A-10Q illustrate an exemplary health record manager in accordance with some embodiments. More particularly, 10A-10Q illustrate the display of a health record manager that allows the user to designate the status of and manage activities associated with certain health records through the health record manager. The user interfaces in these figures are used to illustrate the processes described below, including the processes in FIGS. 11A-11E.

Although some of the examples that follow will be given with reference to inputs on a touch-screen display (where the touch-sensitive surface and the display are combined), in some embodiments, the device detects inputs on a touch-sensitive surface 451 that is separate from the display 450, as shown in FIG. 4B. In other embodiments, the processes described herein may be implemented with devices having physical user-interfaces, voice interfaces, or other suitable interfaces. For convenience of explanation, the embodiments described below will be discussed with reference to operations performed on a device with a touch-sensitive display system 112. In such embodiments, a focus selector is, optionally: a respective finger or stylus contact, a representative point corresponding to a finger or stylus contact (e.g., a centroid of a respective contact or a point associated with a respective contact), or a centroid of two or more contacts detected on the touch-sensitive display system 112. However, analogous operations are, optionally, performed on a device with a display 450 and a separate touch-sensitive surface 451 in response to detecting the contacts on the touch-sensitive surface 451 while displaying the user interfaces discussed below, along with a focus selector.

As used herein, in one or more embodiments of FIGS. 10A-10Q, active health records are health records designated by a user or a health care provider as being current, associated with an active medical condition of the user being treated by a health care provider, or associated with a health condition that the user is currently monitoring. For example, in one embodiment active health records may be the most recent of each type of health record for the user, such as the results of a blood test from the user's latest annual physical or other latest visit to a health care provider or the current prescription records of the user. In another embodiment, active health records may be the most recent record of particular health conditions that the user is monitoring such as blood pressure and cholesterol level. In another embodiment, active health records may only be health records associated with an acute or chronic health condition for which the user is actually being treated by a health care provider. In yet another embodiment, active health records may be any health records that are not older than a period of time set by the user or automatically determined by device 100. In one embodiment, all health records are designated as active when first received by device 100 from a health care provider. However, in the illustrated embodiments, a user may designate any health record as active.

As used herein, in one or more embodiments of FIGS. 10A-10Q, an inactive health record is any health record other than an active health record. Optionally, health records designated by the user as inactive are hidden in a dashboard user interface of the health record manager, but are displayed in other user interfaces of the health record manager that contain more detailed information about the user's health records, whereas active health records are displayed in the dashboard user interface of the health record manager. The status of health records may be changed by the user from active to inactive, such as when asthma symptoms of the user are no longer present. Similarly, the status of health records may be changed by the user from inactive to active, such as when asthma symptoms of the user return. In one embodiment, in response to a change in status of a health record from active to inactive, a notification is automatically generated and transmitted by device 100 to a health care provider of the user. Similarly, in response to a change in status of a health record from inactive to active, a notification is also automatically generated and transmitted by device to a health care provider of the user.

The health record manager also allows the user to set reminders to perform a variety of tasks related to certain health records. The reminders may be used, for example, to remind the user to take medications prescribed to the user at predetermined times, to refill medications prescribed to the user, or track upcoming appointments with physicians or other health care professionals. Although the embodiments of FIGS. 10A-10Q are described relative to the management of health records, and more particularly health condition records, in some embodiments representations of health information other than health records may be used to manage the health information of a user. Similarly, other categories of health records may also be used to manage the health information of a user such as lab records, clinical records, or allergy records.

Similar to FIG. 8B, FIG. 10A illustrates displaying a dashboard of a health record summary that includes health record summary information containing multiple types of health records on display 112. Health records in the illustrated embodiment are current health records obtained from both Alpha Health Care and Beta Health Care. In the illustrated embodiment, the health metric summary includes health metric records 9012A-9012C (blood pressure, cholesterol level, and serum iron level, respectively), medication records 9014A-9014D (ABC medication, DEF medication, GHI medication, and LMN medication, respectively), and health condition records 9016A-9016D (anxiety disorder, asthma, high cholesterol, and migraines, respectively). FIG. 10A also illustrates displaying a health metrics affordance 9011A, a medications affordance 9011B, and a health conditions affordance 9011C. In the illustrated embodiment, each of health metrics affordance 9011A, medications affordance 9011B, and health conditions affordance 9011C is selectable by the user to view a health metrics archive, a medications archive, and a health conditions archive respectively. In the embodiments illustrated in FIGS. 10A-10Q, each of the health metrics archive, medications archive, and health conditions archive is a health record archive that contains current health records and historical health records belonging to the corresponding category.

In the embodiment illustrated by FIG. 10A, health metric records 9012A-9012C are displayed in alphabetical order based on the type of health metric record. Health metric record 9012A contains a current measurement of the user's blood pressure measured on Nov. 1, 2017 by Beta Health Care. Health metric record 9012B contains a current measurement of the user's cholesterol level measured on Oct. 1, 2017 by Alpha Health Care. Health metric record 9012C contains a current measurement of the user's serum iron level measured on Oct. 15, 2017 by Alpha Health Care.

In the embodiment illustrated by FIG. 10A, medication records 9014A-9014D are displayed in alphabetical order based on the type of medication. Medication health records 9014A-9014D are the user's current medication prescriptions for ABC medication, DEF medication, GHI medication, and LMN medication respectively. Each of medication health records 9014A-9014D also identifies a prescription date for the corresponding medication and the health care provider that prescribed the medication.

In the embodiment illustrated by FIG. 10A, health condition records 9016A-9016D are displayed in alphabetical order based on the type of health condition. Health condition records 9016A-9016D include information about current health conditions of the user, including anxiety disorder, asthma, high cholesterol, and migraines respectively. In some embodiments, health condition records 9016A-9016D also include information on medications most recently prescribed for the corresponding health conditions (anxiety disorder, asthma, high cholesterol, and migraines), even if such medications are separately identified in a medications group. FIG. 10A further illustrates detecting a tap gesture with contact 9502 on health conditions affordance 9011C and, in response to the tap gesture, displaying a health conditions archive 9058 in FIG. 10B.

Figure 10B:
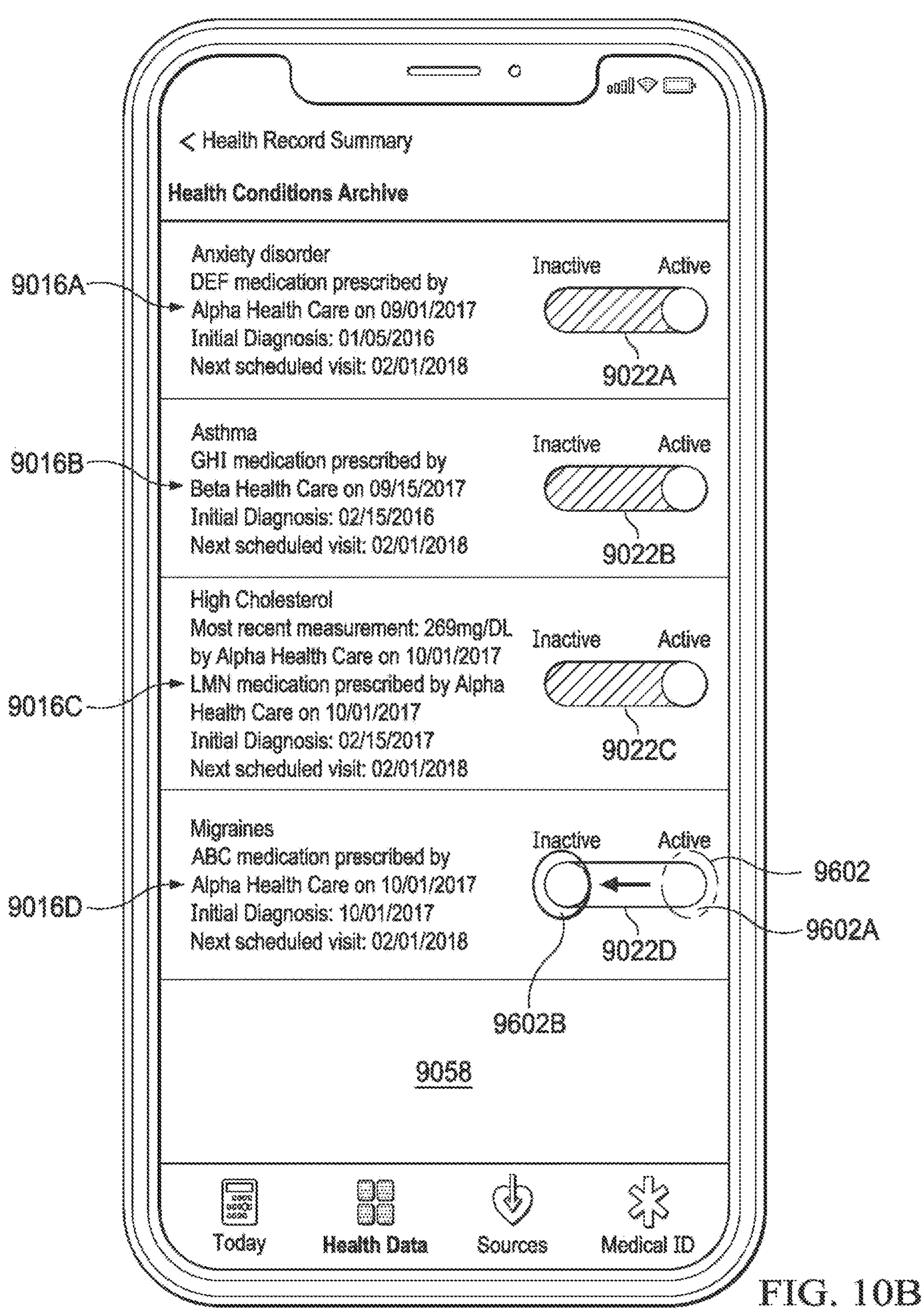

FIG. 10B illustrates an embodiment of a health conditions archive 9058 containing health records of the user's health conditions and status toggles to designate the health records as active or inactive. In the illustrated embodiment, health conditions archive 9058 contains health condition records 9016A-9016D (anxiety disorder, asthma, high cholesterol, and migraines, respectively). In the illustrated embodiment, health condition record 9016A contains information about the user's anxiety disorder, the medication (DEF medication) prescribed to treat the user's anxiety disorder, the date of the initial diagnosis, and the next scheduled visit with Alpha Health Care regarding the user's anxiety disorder. Health condition record 9016B contains information about the user's asthma, the medication (GHI medication) prescribed to treat the user's asthma, the date of the initial diagnosis, and the next scheduled visit with Beta Health Care regarding the user's asthma. Health condition record 9016C contains information about the user's high cholesterol, the level of cholesterol measured and the date the cholesterol test was given, the medication (LMN medication) prescribed to treat the user's high cholesterol, the date of the initial diagnosis, and the next scheduled visit with Alpha Health Care regarding the user's high cholesterol. Health condition record 9016D contains information about the user's migraines, the medication (ABC medication) prescribed to treat the user's migraines, the date of the initial diagnosis, and the next scheduled visit with Alpha Health Care regarding the user's Migraines. In other embodiments, each of health condition records 9016A-9016D contains additional information about the corresponding health condition, such as names of medications previously prescribed for the health condition, the name(s) of physician(s) or other health care professionals the user consults regarding the health condition, a list of symptoms of the health condition, as well as other useful information related to the health condition.

As illustrated in FIG. 10B, health condition records 9016A-9016D (anxiety disorder, asthma, high cholesterol, and migraines, respectively) also contain status toggles 9022A-9022D respectively, which are affordances that the user interacts with to designate the status of certain health conditions. In the illustrated embodiment, each of status toggles 9022A-9022D allows the user to designate the corresponding health condition as active or inactive. In other embodiments, each of health condition records 9016A-9016D also contain other types of status toggles that allow the user to designate other conditions, such as to set up a reminder to take a medication for the corresponding health condition, set up a reminder to visit with a physician regarding the health condition, or set up options to receive notifications or updates regarding the health condition.

In some embodiments, status toggles 9022A-9022D (for anxiety disorder, asthma, high cholesterol, and migraines, respectively) are not displayed in health conditions archive 9058. In one or more of such embodiments, health conditions archive 9058 contains a designate status affordance (not shown), which is an affordance the user interacts with to access status toggles 9022A-9022D. For example, device 100, in response to detecting a gesture to select the designate status affordance, overlays another user interface containing status toggles 9022A-9022D on a portion of the user interface displayed in FIG. 10B. In other embodiments, status toggles are displayed with the corresponding health records in the health record summary to allow the user to designate the status of particular health conditions without having to drill down to health conditions archive 9058. In yet another embodiment, a user selects an individual health condition record such as one of health condition records 9016A-9016D (anxiety disorder, asthma, high cholesterol, and migraines, respectively) in order to display a respective status toggle 9022A, 9022B, 9022C, or 9022D for such health condition record. In one or more of such embodiments, after the user interacts with a status toggle that is displayed in the health record summary, a notification, similar to the notification requesting the user to confirm the change in the status of the corresponding health condition is displayed. In such embodiments, device 100 changes the status of the health condition after detecting an input confirming the change in the status of the health condition to avoid accidental inputs.

Figure 10C:
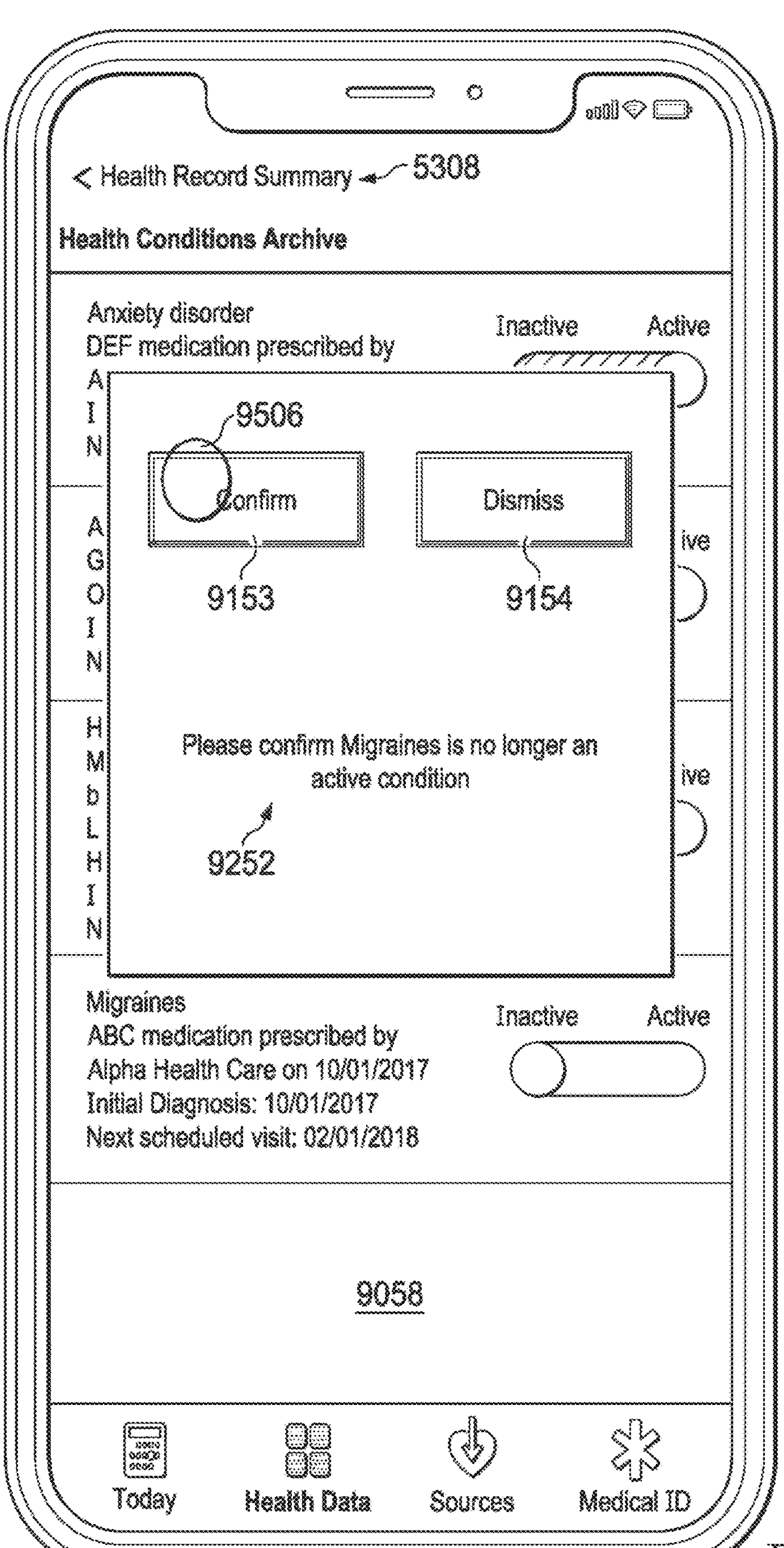

In the illustrated embodiment, status toggles 9022A-9022C (for anxiety disorder, asthma, and high cholesterol, respectively) indicate that the corresponding health conditions are active. FIG. 10B further illustrates detecting a swipe gesture with contact 9602 on status toggle 9022D (for migraines) and movement of contact from position 9602A to position 9602B to designate migraines as an inactive health condition. FIG. 10C illustrates displaying notification 9252 requesting the user to confirm the user's decision to designate migraines as an inactive condition. Notification 9252 contains a confirm affordance 9153, which is an affordance the user interacts with to confirm the designation of migraines as an inactive condition, and a dismiss affordance 9154, which is an affordance the user interacts with to cancel the designation of migraines as an inactive condition. FIG. 10C further illustrates detecting a tap gesture with contact 9506 on confirm affordance 9153 and, in response to the tap gesture, designating migraines as an inactive health condition in FIG. 10D.

Figure 10D:
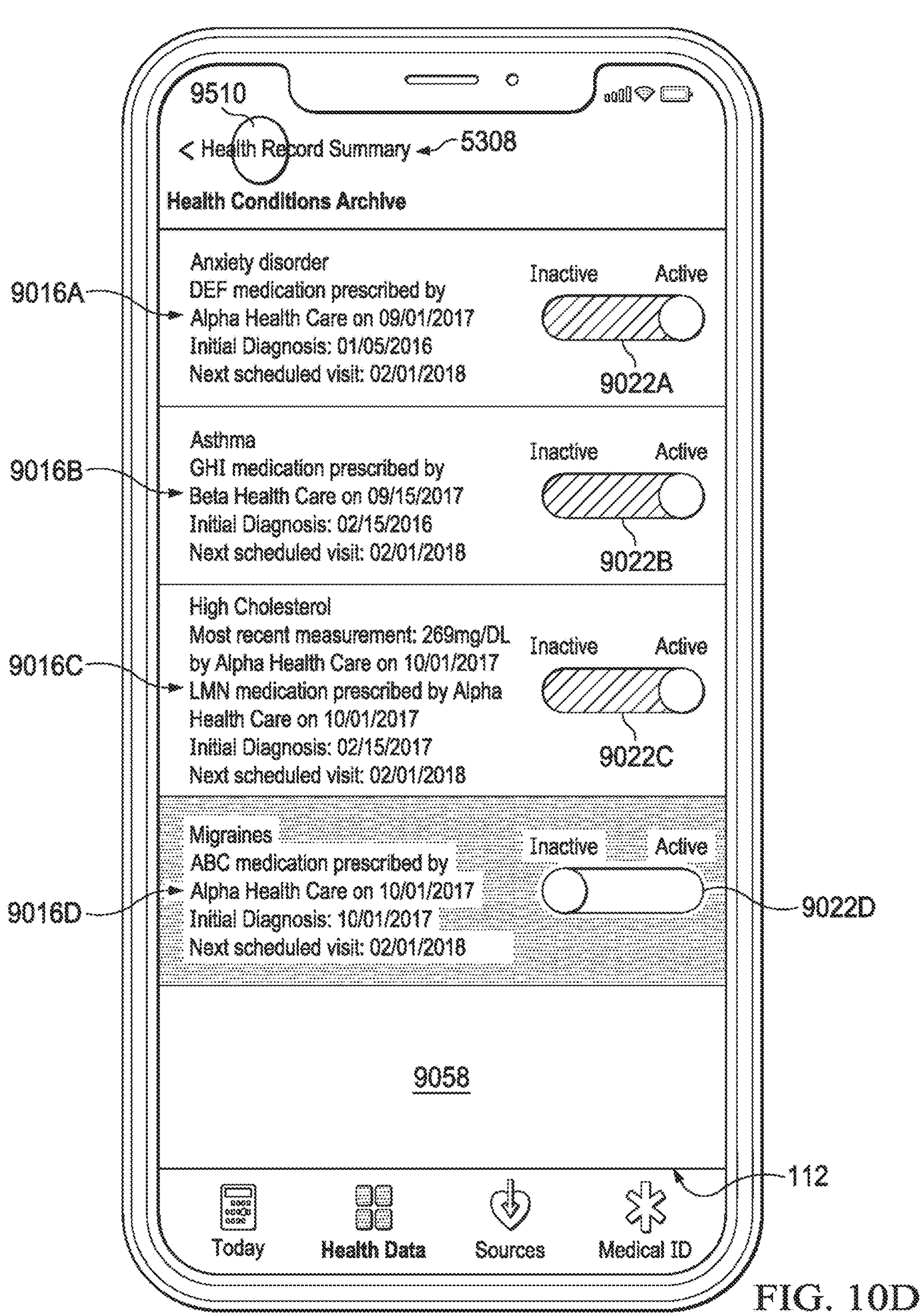

FIG. 10D illustrates an embodiment of health conditions archive 9058 after the user has designated migraines as an inactive health condition. In the illustrated embodiment, status toggle 9022D (for migraines) has been switched from active to inactive in response to the user's gestures illustrated in FIGS. 10B and 10C. In some embodiments, notification affordance 9252 illustrated in FIG. 10C is not displayed in response to the user's gestures illustrated in FIG. 10B. In such embodiments, health condition record 9016D (migraines) is designated as an inactive health condition in response to the swipe gesture performed in FIG. 10B. Health condition record 9016D is greyed out (or is displayed in a color that is different from the color of health conditions records 9016A-9016C) to indicate that migraines is no longer an active health condition. FIG. 10D further illustrates detecting a tap gesture with contact 9510 on health record summary affordance 5308 and, in response to the tap gesture, displaying the updated health record summary in FIG. 10E.

Figure 10E:
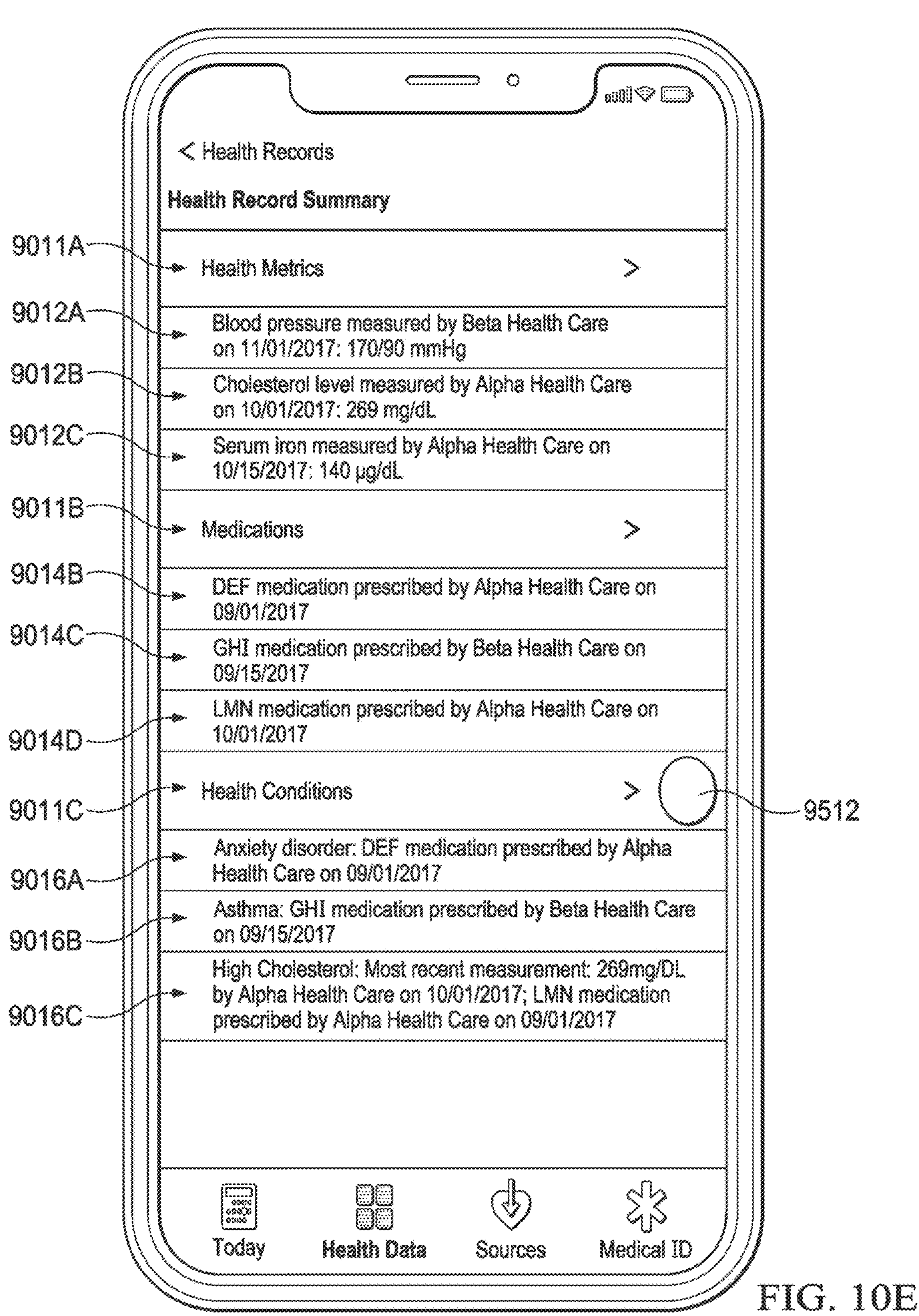

FIG. 10E illustrates displaying the updated health record summary on display 112. As illustrated in FIG. 10E, the updated health record summary does not contain medication record 9014A (ABC medication) illustrated in FIG. 10A, which contains information about medication prescribed to treat migraines, or health condition record 9016D (migraines) illustrated in FIG. 10A, which contains information about migraines. In the illustrated embodiment, health records that have been designated as inactive are not shown in the health record summary. In such embodiments, the user may access a health record archive of a category of health records (such as health conditions archive 9058 illustrated in FIG. 10B) to view inactive records belonging to the corresponding category. In other embodiments, such as the embodiment illustrated in FIG. 10H, the health record summary contains both active and inactive health records. However, inactive health records are greyed out or displayed in a different color than active health records. In further embodiments, the updated health record summary contains a view inactive health record affordance (not shown), which is an affordance the user interacts with to view all inactive health records, or a similar affordance that the user interacts with to view inactive health records in the health record summary. In one or more of such embodiments, device 100, after detecting a user interaction with the view inactive health records affordance, displays the inactive health records in the health record summary. FIG. 10E further illustrates detecting a tap gesture with contact 9512 on health conditions affordance 9011C and, in response to the tap gesture, displaying health conditions archive 9058 in FIG. 10F.

Figure 10F:
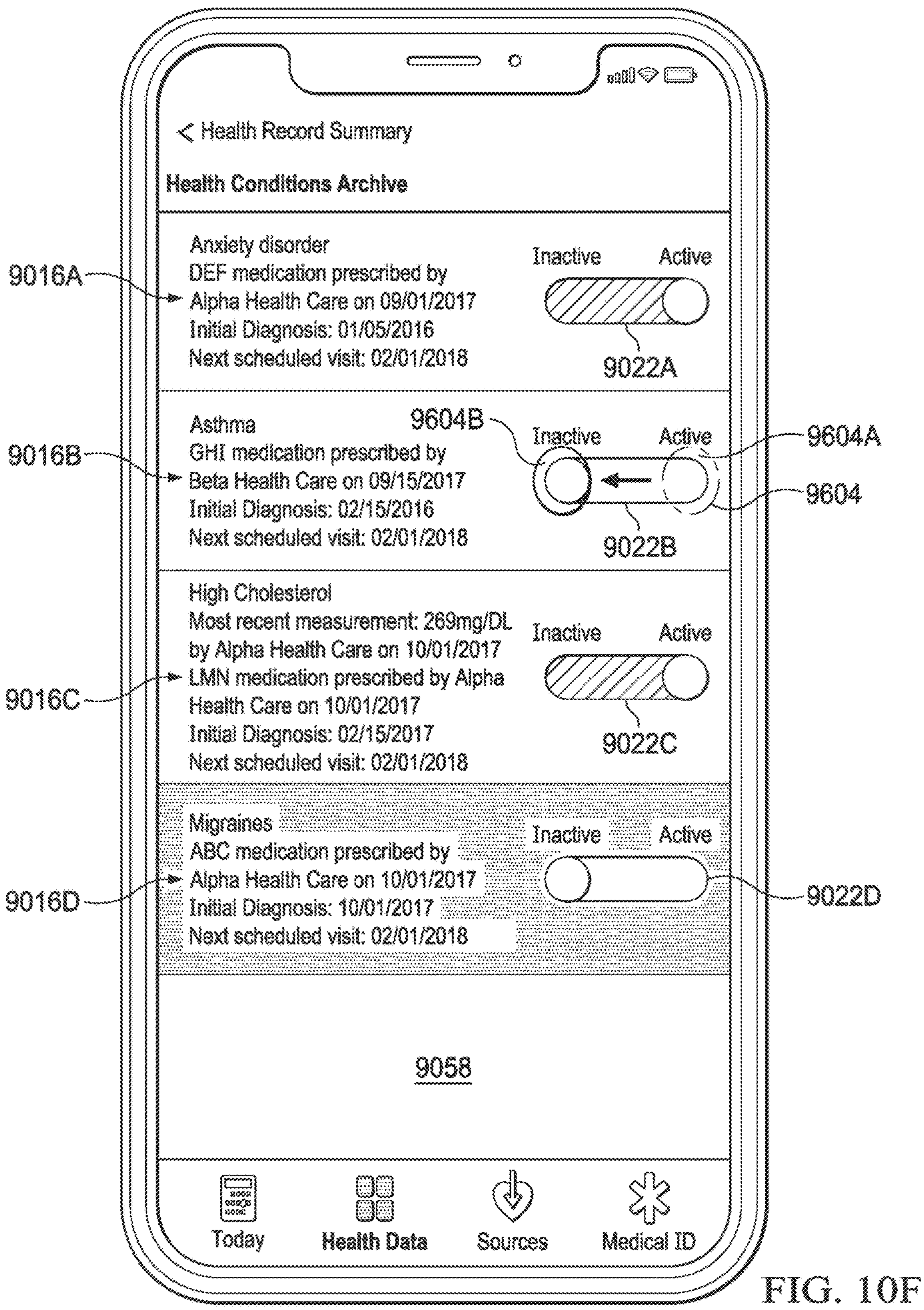

Similar to FIG. 10D, FIG. 10F also illustrates displaying health condition records 9016A-9016D (anxiety disorder, asthma, high cholesterol, and migraines, respectively) having status toggles 9022A-9022D in health conditions archive 9058. FIG. 10F further illustrates detecting a swipe gesture with contact 9604 on status toggle 9022B and movement of contact from position 9604A to position 9604B to designate asthma as an inactive health condition.

Figure 10G:
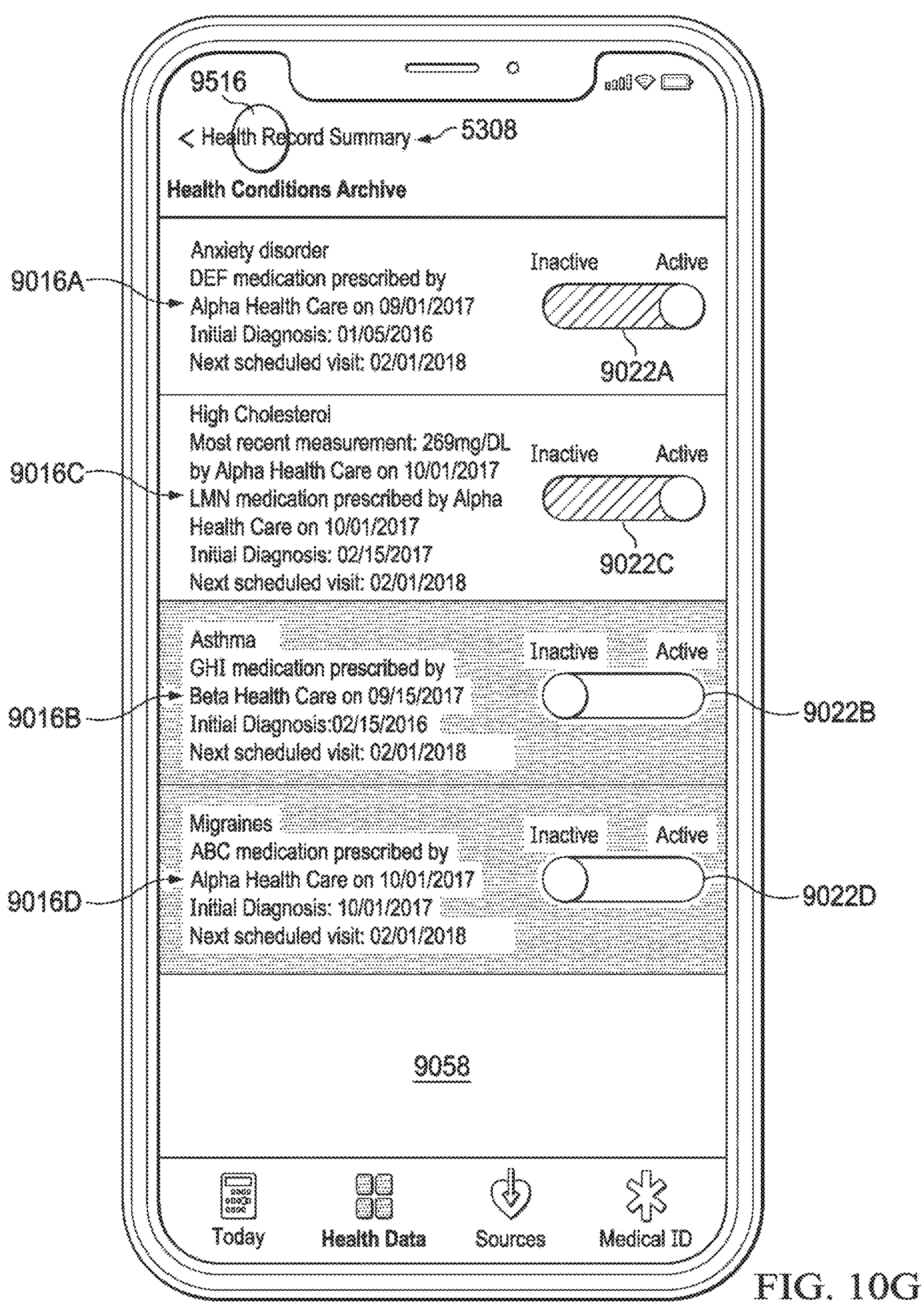

FIG. 10G is a continued view of FIG. 10F after the swipe gesture with contact 9604 on status toggle 9022B (for asthma) and movement of contact from position 9604A to position 9604B to designate asthma as an inactive health condition. In the embodiment of FIG. 10G, the order of health condition records 9016A-9016D (anxiety disorder, asthma, high cholesterol, and migraines, respectively) has been shifted to display the group of active health condition records (health condition records 9016A and 9016C) before the group of inactive health condition records (health condition records 9016B and 9016D), thereby presenting health condition records in a different order from the order of FIG. 10F. Further, health condition records within each group are organized in an alphabetical order based on the name of the health condition. FIG. 10G further illustrates detecting a tap gesture with contact 9516 on health record summary 5308 and, in response to the tap gesture, displaying an updated health record summary in FIG. 10H.

Figure 10H:
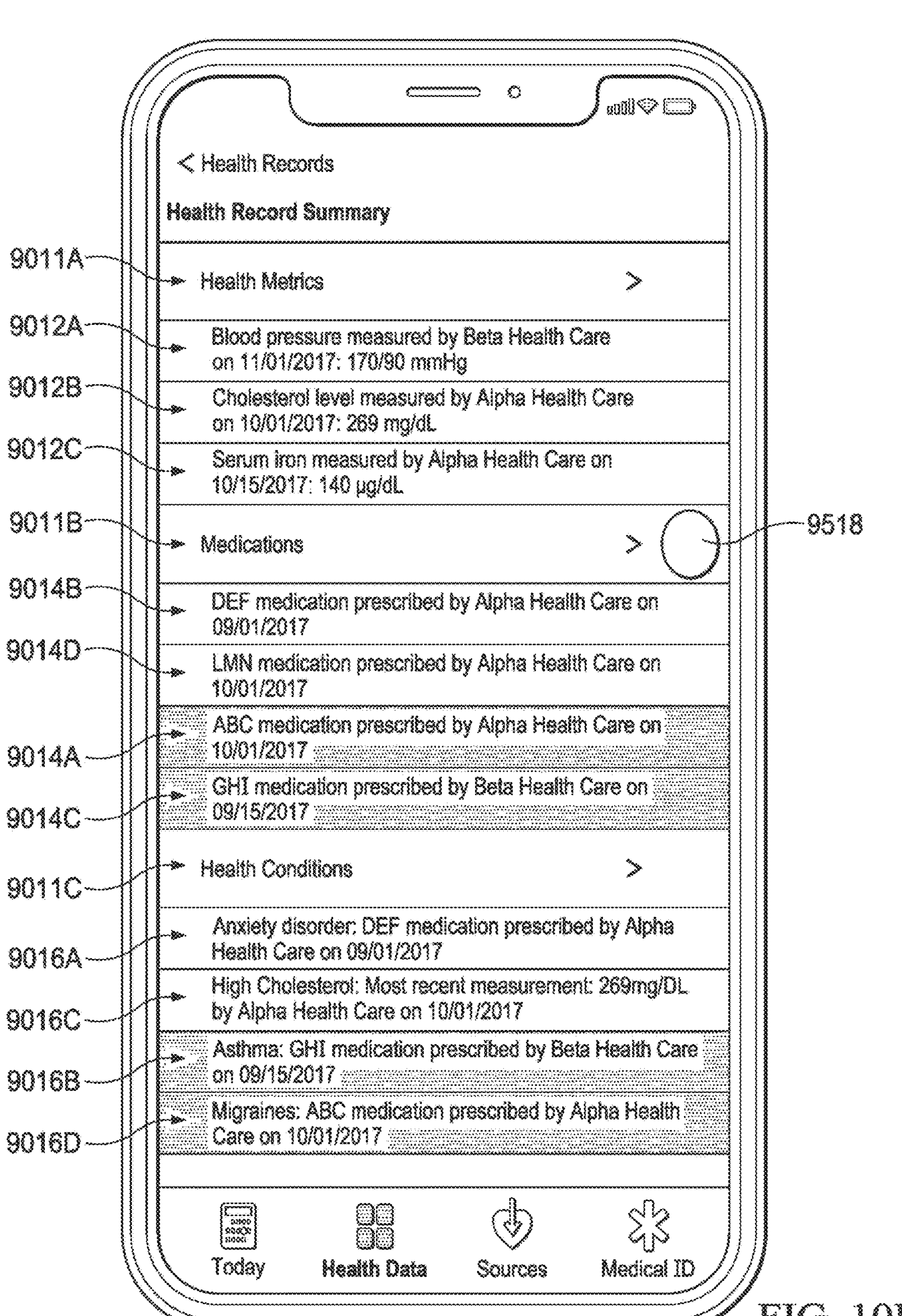

Similar to FIG. 10E, FIG. 10H also illustrates displaying an updated health record summary after the user has designated a health record as an inactive health record. Contrary to the embodiment of FIG. 10E, medication records 9014A and 9014C (ABC medication and GHI medication), and health condition records 9016B and 9016D (asthma and migraines), which have all been designated as inactive health records, are concurrently displayed with active health records. In the illustrated embodiment, the displayed order of medication records 9014A-9014D (ABC medication, DEF medication, GHI medication, and LMN medication, respectively) and the order of health condition records 9016A-9016D (anxiety disorder, asthma, high cholesterol, and migraines, respectively) have been rearranged to group active health records together and to group inactive health records together. Further, health records within each group are arranged in an alphabetical order by the names of the corresponding medications (for medication records) or by the names of the corresponding health conditions (for health condition records). In other embodiments, all inactive health records are grouped together regardless of the category, or are grouped in another order or identified in another manner that allows the user to differentiate active health records from inactive health records. FIG. 10H further illustrates detecting a tap gesture with contact 9518 on medications affordance 9011B and, in response to the tap gesture, displaying a medications archive 9057 in FIG. 10I.

Figure 10I:
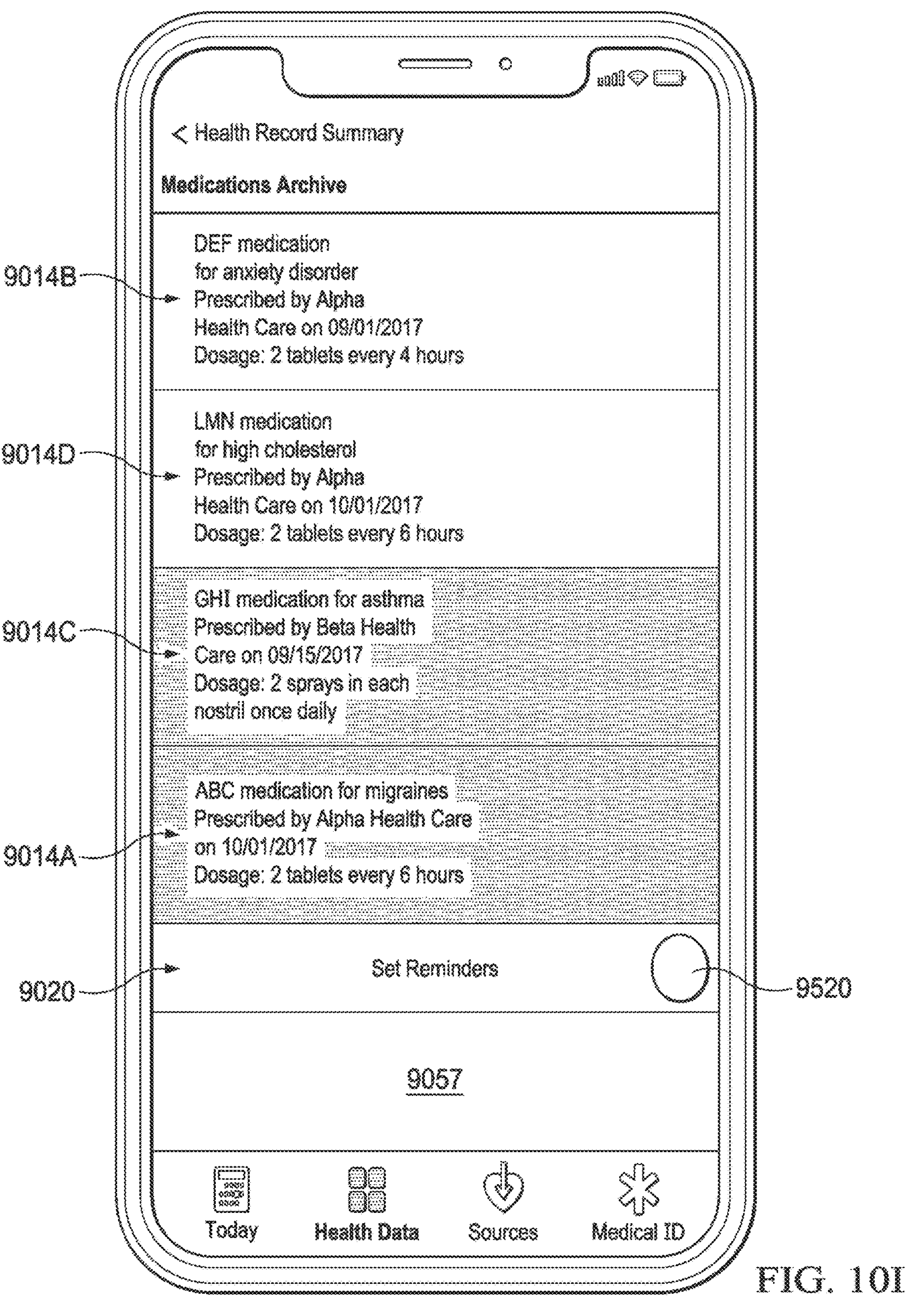

FIG. 10I illustrates medications archive 9057 containing medication records 9014A-9014D of ABC medication, DEF medication, GHI medication, and LMN medication respectively. Each of medication records 9014A-9014D also includes information about the health condition the medication is prescribed for, the health care provider that provided a prescription of the medication, and a recommended dosage amount. In some embodiments, medication records 9014A-9014D also include additional information about the corresponding medications, such as warnings, directions, locations of the nearest pharmacies, as well as other information about the medications. In the illustrated embodiment, medication records 9014A and 9014C are displayed together and greyed out to indicate that ABC medication and GHI medication are prescribed for inactive health conditions. In the illustrated embodiment, inactive medication records 9014A and 9014C are displayed together and ordered alphabetically by the name of the corresponding health conditions. In other embodiments, inactive medication records are organized alphabetically by the name of the medications, or by other methods that help the user identify inactive health records.

In some embodiments of medications archive 9057, the user may directly designate medication records 9014A-9014D (ABC medication, DEF medication, GHI medication, and LMN medication, respectively) as active or inactive. For example, although DEF medication is prescribed for an active health condition (anxiety disorder), the user may designate DEF medication as an inactive medication if the user is no longer taking DEF medication (such as due to an allergic reaction to DEF medication, receiving a prescription for an alternative medication to treat anxiety, or due to any other reason). In one or more of such embodiments, status toggles similar to toggle status toggles 9022A-9022D (for anxiety disorder, asthma, high cholesterol, and migraines, respectively) illustrated in FIG. 10B are displayed with medication records 9014A-9014D. In such embodiments, the user may toggle one or more status toggles to designate the corresponding medication record as an active health record or an inactive health record. In the illustrated embodiment, medications archive 9057 also includes a set reminders affordance 9020, which is an affordance the user selects to designate reminders about certain health records. FIG. 10I further illustrates detecting a tap gesture with contact 9520 on set reminders affordance 9020 and, in response to the tap gesture, displaying medication records 9014A-9014D in FIG. 10J.

Figure 10J:
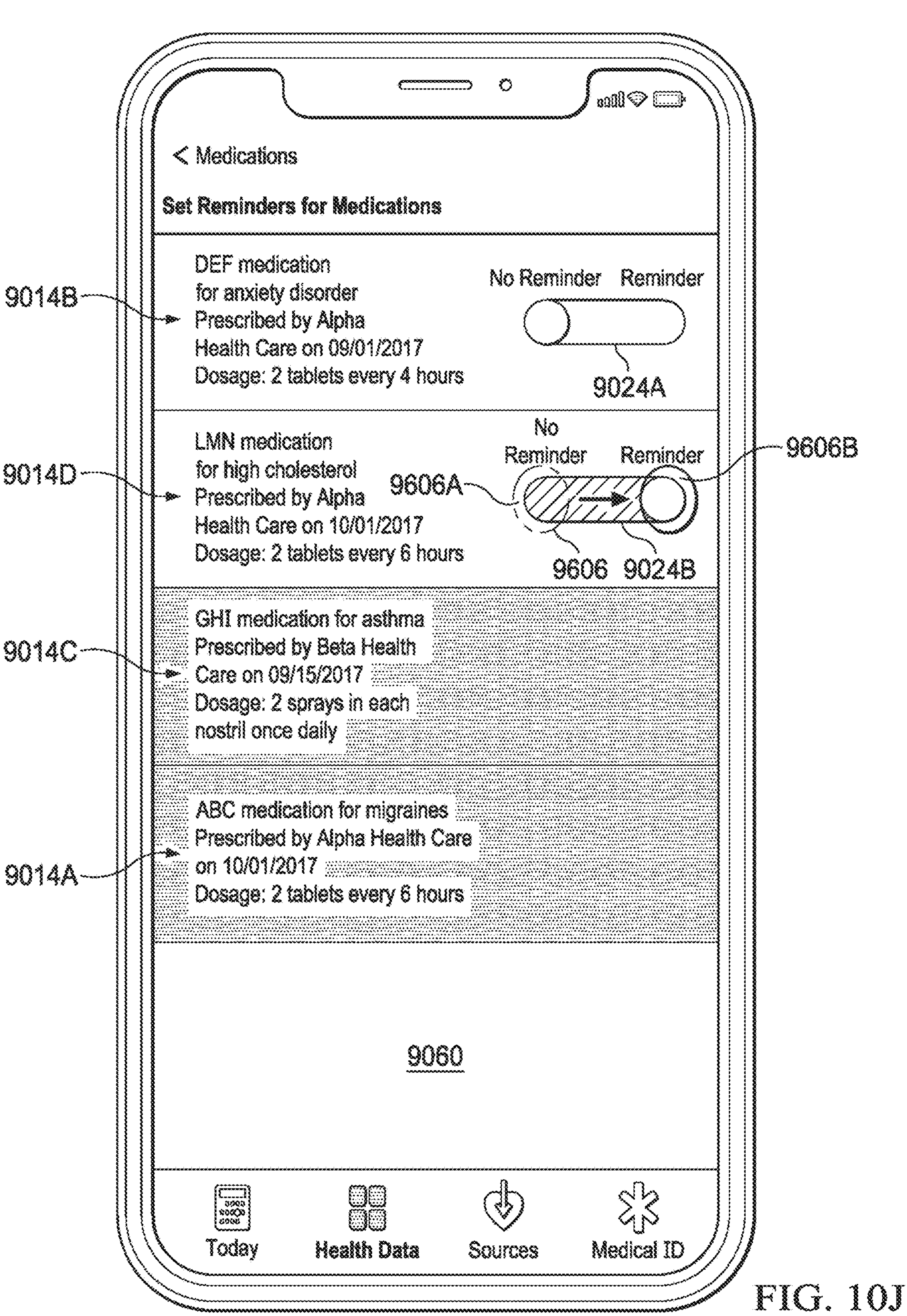

FIG. 10J illustrates the display of medication records 9014A-9014D (ABC medication, DEF medication, GHI medication, and LMN medication, respectively) to allow the user to set reminders for medications. Medication records 9014B and 9014D are displayed with reminder toggles 9024A and 9024B. As used herein, a reminder toggle is an affordance the user selects to set up one or more types of reminders about a corresponding health record. Examples of types of reminders include, reminders to take a medication, reminders to refill a medication, reminders to schedule an appointment with a physician, reminders to submit an insurance claim, reminders about an upcoming appointment with a physician, reminders to have lab tests done, or any other suitable reminder regarding a corresponding health record. In the illustrated embodiment, reminder toggles are not displayed with medication records 9014A and 9014C as medication records 9014A and 9014C are designated as inactive health records. In other embodiments, reminder toggles are also displayed with inactive medication records to allow the user to set reminders for corresponding medications (such as a reminder to renew an expired prescription or a reminder to contact a physician about a health condition associated with an expired prescription). FIG. 10J illustrates displaying medication records 9014A-9014D and reminder toggles 9024A and 9024B in a user interface 9060 that is separate from the medications archive shown in FIG. 10I. In other embodiments, medication records in medications archive 9057 contains medication records and corresponding reminder toggles. FIG. 10J further illustrates detecting a swipe gesture with contact 9606 on reminder toggle 9024B and movement of contact from position 9606A to position 9606B to set a reminder for LMN medication in FIG. 10K.

Figure 10K:
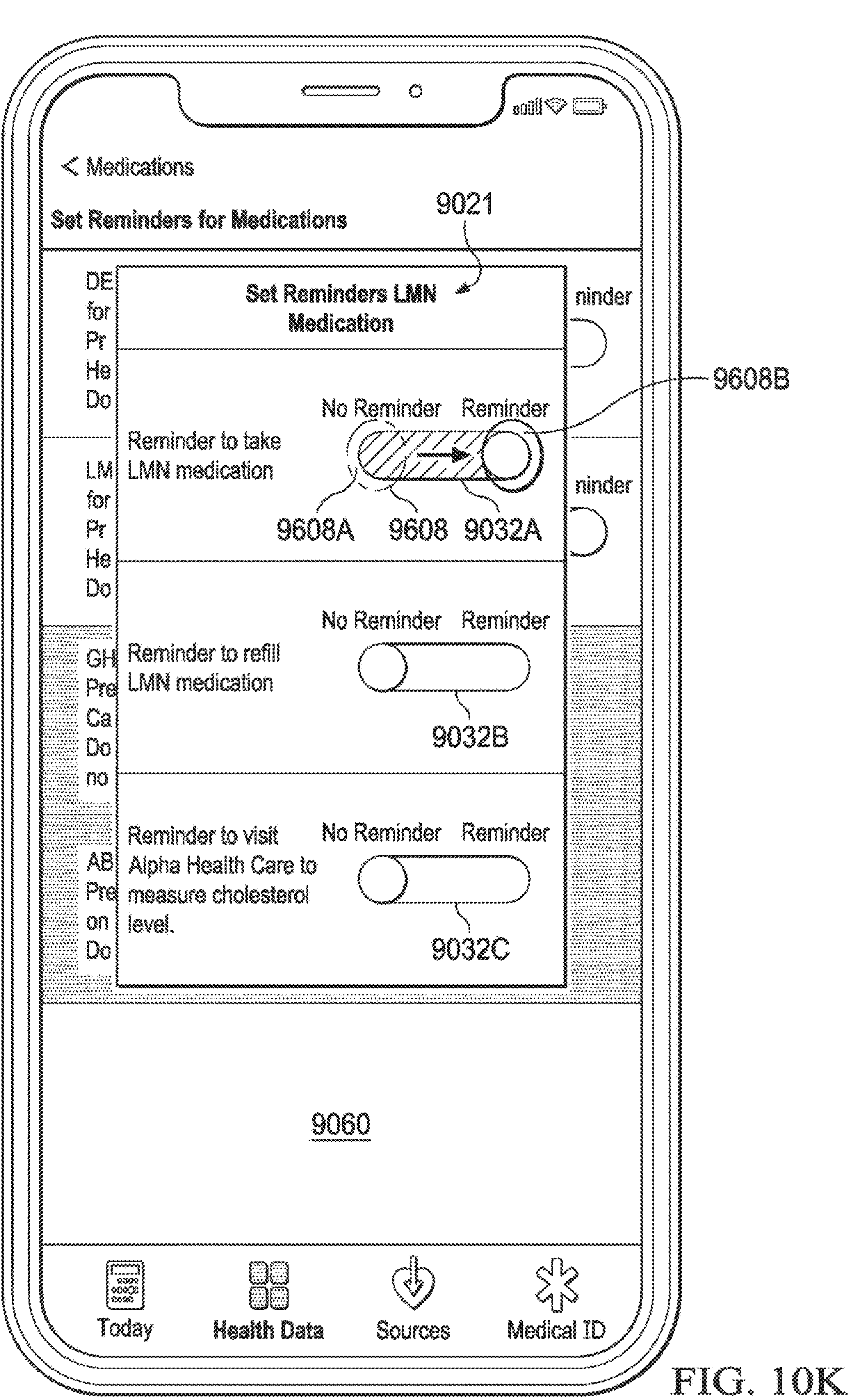

FIG. 10K illustrates one embodiment of displaying a set reminders notification 9021 to set one or more reminders for LMN medication. In the illustrated embodiment, set reminders notification 9021 is overlaid on a portion of user interface 9060 of FIG. 10J and includes a reminder toggle 9032A to set a reminder to take LMN medication, a reminder toggle 9032B to set a reminder to refill LMN medication, and a reminder toggle 9032C to set up a reminder to visit Alpha Health Care (or a physician at Alpha Health Care) about the user's cholesterol level, which is a health condition LMN medication is prescribed to treat. In other embodiments, each of reminder toggles 9032A-9032C and text describing the corresponding reminders are displayed directly in user interface 9060 for each medication instead of displaying reminder toggles 9024A and 9024B (for DEF medication and LMN medication) in FIG. 10J. In further embodiments, medications archive 9057 displays each of reminder toggles 9032A-9032C for each medication, avoiding the need for set reminders affordance 9020 of FIG. 10I, user interface 9060 of FIG. 10J, and set reminders notification 9021 of FIG. 10K.

FIG. 10K further illustrates detecting a swipe gesture with contact 9608 on reminder toggle 9032A and movement of contact from position 9608A to position 9608B to set a reminder to take LMN medication. In some embodiments, the user also specifies a time (or multiple times) during a day to receive a reminder. In other embodiments, where the user has not specified a time to display a reminder, device 100 automatically determines a suitable time for displaying the reminder a default such as 10 p.m. or 15 minutes after a user's daily alarm goes off in the morning. In one or more of such embodiments, where LMN medication is prescribed to be taken multiple times a day, device 100, after receiving a designated time to display a reminder to take LMN medication, automatically calculates other suitable times for displaying reminders to take LMN medication. For example, if a medication is supposed to be taken three times a day and the user sets 11 p.m. for a first reminder, device 100 will automatically designate 7 a.m. and 3 p.m. for additional reminders. In further embodiments, device 100 has access to the user's calendar schedule and automatically designates a time (or multiple times) to display reminders to the user based on such calendar schedule. In some embodiments, device 100, upon receiving a designated time to display a reminder to take LMN medication, continues to display the reminder at the designated time until the user changes such time or until the corresponding health record has been designated as an inactive health record.

Figure 10L:
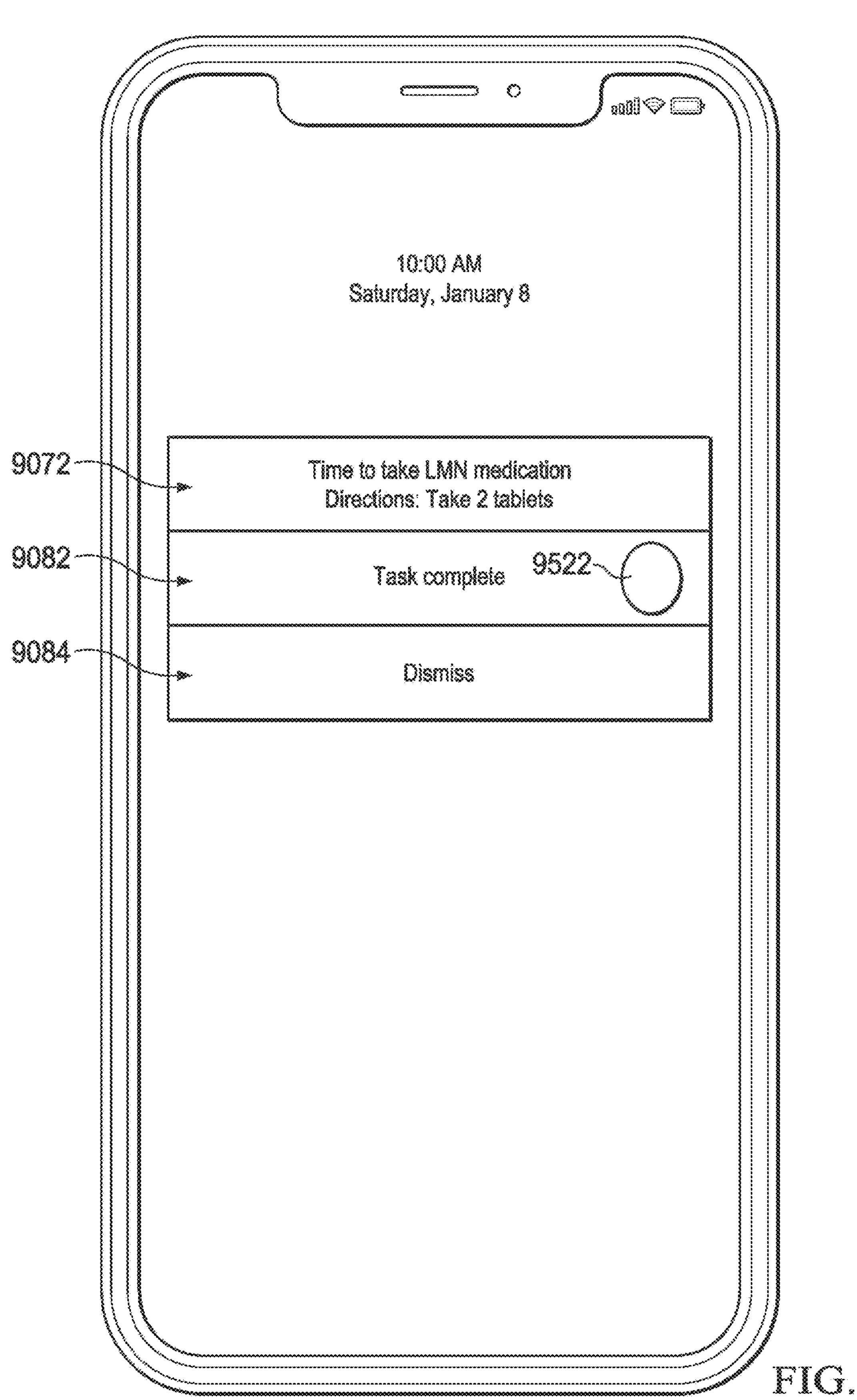

FIG. 10L illustrates displaying a notification 9072 in response to the user setting a reminder to take LMN medication as described in FIG. 10K. Notifications such as notification 9072 (and each of notifications 9074, 9076, and 9078 illustrated in FIGS. 10N, 10O, and 10Q respectively) can be displayed on a lock screen, on an overlay over any application the user happens to be reviewing at the time designated for such reminder, as a text message or other alert generated by device 100, as a notification badge in a border of a user interface, as a voice announcement from a digital assistant, another text-to-voice announcement, or using any other combination of audio or visual notifications. In the illustrated embodiment, notification 9072 contains directions for taking LMN medication including the prescribed dosage. In other embodiments, notification 9072 also contains additional information about LMN medication, such as warnings, drug facts, ingredients, or other useful information about LMN medication. Notification 9072 also includes a task complete affordance 9082, which is an affordance the user selects to indicate that the user has taken LMN medication, and a dismiss affordance 9084, which dismisses notification 9072. FIG. 10L further illustrates detecting a tap gesture with contact 9522 on task complete affordance 9082. In some embodiments, device 100 automatically keeps track of the amount of LMN medication left. In one of such embodiments, device 100, in response to detecting the tap gesture with contact 9522 on task complete affordance 9082, automatically deducts the amount of remaining LMN medication by the prescribed dosage (2 tablets). In some embodiments, the user performs another tap gesture with contact on dismiss affordance 9084 to dismiss notification 9072. In other embodiments, device 100 dismisses notification 9072 in response to detecting a tap gesture with contact on notification 9072 or a tap gesture in a region of display 112 not covered by notification 9072. In the illustrated embodiment, notification 9072 is displayed at 10:00 am on Saturday, January 8th. In other embodiments, if a user is unable to take the medication at the time of a reminder, the user may use notification 9072 to delay or designate a different time (not shown) to receive notification 9072. In further embodiments, device 100, determines the user's schedule and delays a scheduled notification to a time that is convenient for the user.

Figure 10M:
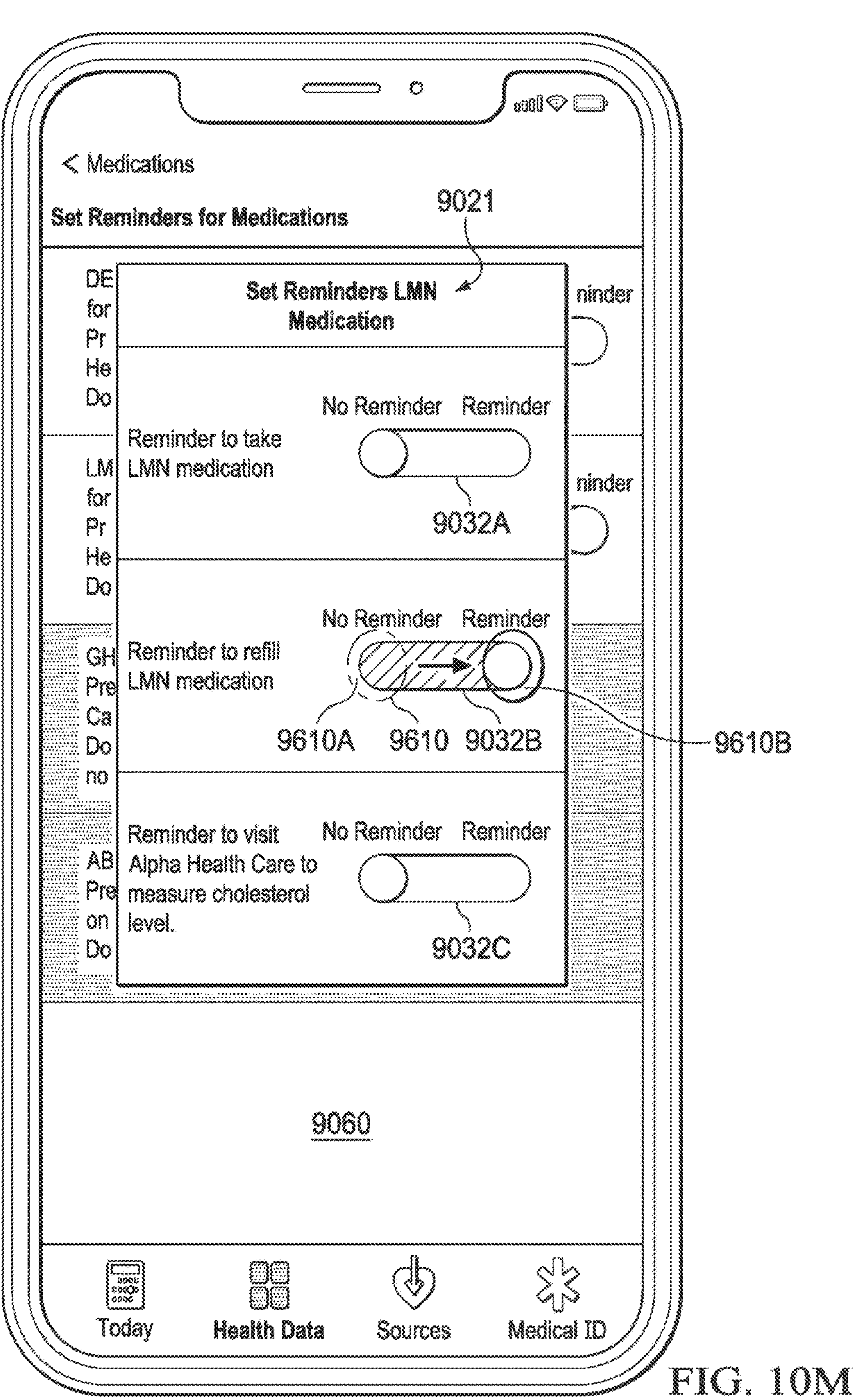

Similar to FIG. 10K, FIG. 10M illustrates displaying set reminders notification 9021 overlaid on a portion of user interface 9060. FIG. 10M further illustrates detecting a swipe gesture with contact 9610 on reminder toggle 9032B and movement of contact from position 9610A to position 9610B to set up a reminder to refill LMN medication. In some embodiments, device 100, in response to detecting a gesture to set a reminder to refill LMN medication, calculates an estimated remaining amount of LMN medication based on the last date the prescription was filled, the number of daily dosages provided in the medication, and the number of days since such prescription date based on the assumption that the user has taken the prescribed dosage since the date the LMN medication was prescribed to the user. Alternatively, device 100 calculates an estimated remaining amount of LMN medication each time the user selects task complete affordance 9082 of FIG. 10L to indicate that the user has taken the prescribed dosage, in each case based on the number of prescribed dosages provided in the medication and the date the medication was last filled. In either of the foregoing embodiments, device 100 estimates a date on which the medication will run out based on such calculation and determines one or more predetermined times to remind the user to refill the prescription before or on such estimated date. In further embodiments, device 100 periodically queries the user to determine the amount of remaining LMN medication. In one embodiment, the user sets how far in advance of the date on which such medication is estimated to run out such reminder is to be given.

Figure 10N:
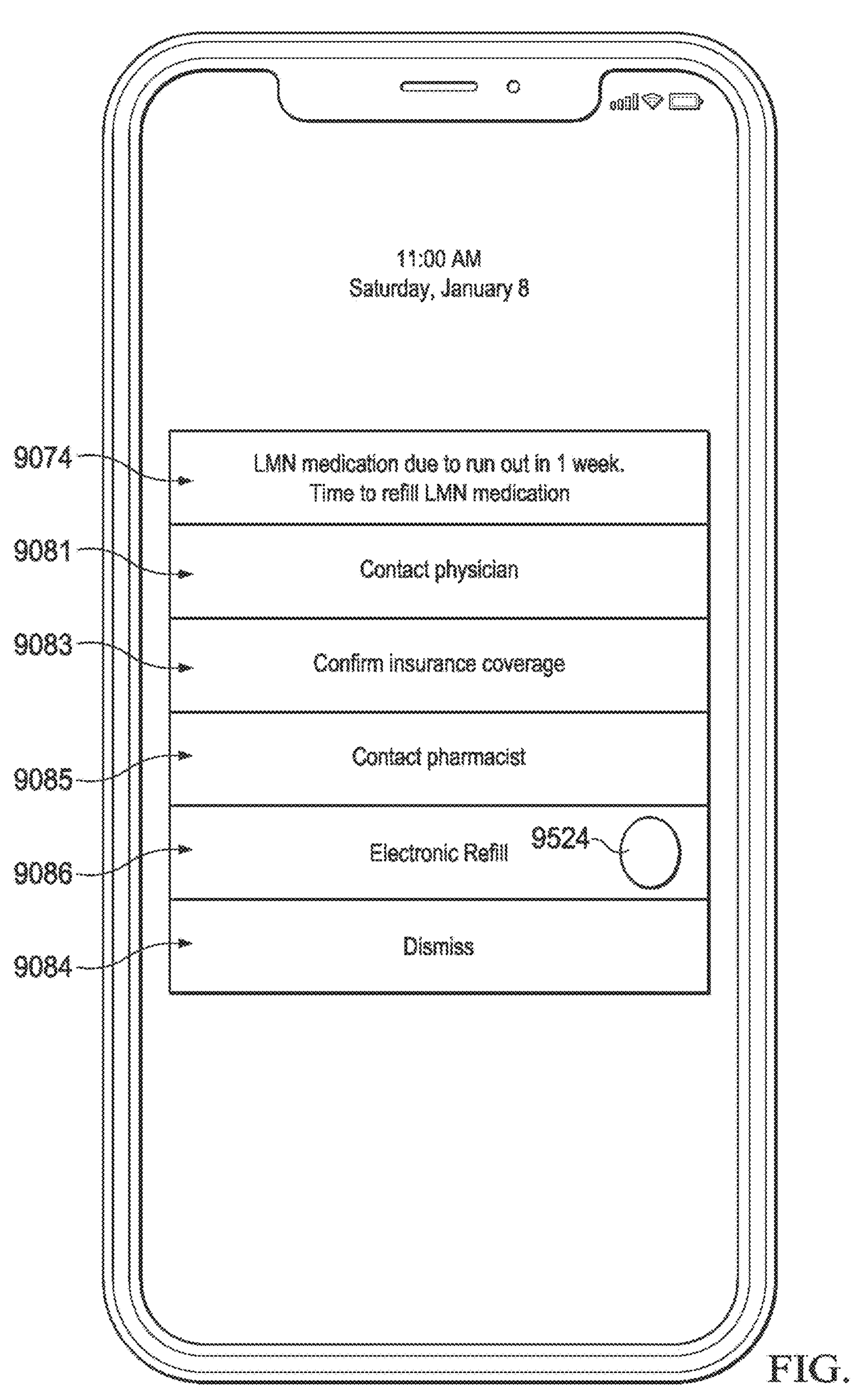
Figure 10O:
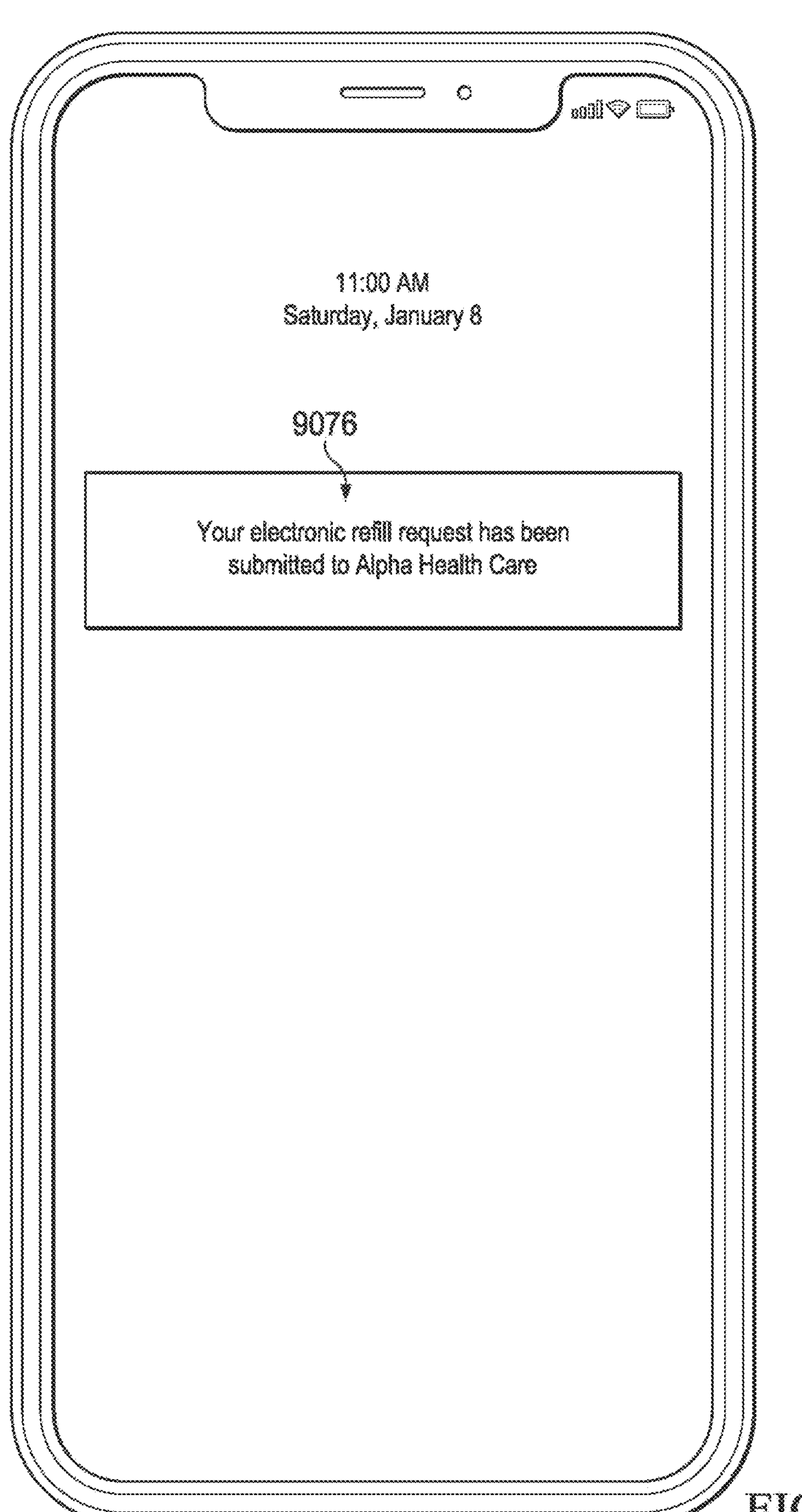

FIG. 10N illustrates displaying a notification 9074 reminding the user to refill LMN medication in response to the user setting a refill reminder as described in FIG. 10M. Notification 9074 contains multiple affordances the user may interact with to refill LMN medication or to obtain more information about LMN medication before refilling LMN medication. In the illustrated embodiment, the user may select contact physician affordance 9081 to contact a physician who prescribed LMN medication. Further, the user may select confirm insurance coverage affordance 9083 to determine the user's insurance coverage and the cost of refilling LMN medication. The user may also select contact pharmacist affordance 9085 to contact a pharmacist to refill LMN medication or to determine the nearest pharmacy with LMN medication available for pick-up. The user may select electronic refill affordance 9086 to initiate an alternate process to refill LMN medication. The user may also select dismiss affordance 9084 to dismiss notification 9074 without refilling LMN medication. In some embodiments, notification 9074 contains other types of affordances that the user may interact with to perform other tasks related to refilling LMN medication. In the illustrated embodiment, notification 9074 is displayed on device 100 one week prior to the date on which LMN medication is estimated to run out. In other embodiments, the user may designate a different time to receive notification 9074 (such as two weeks before LMN medication is estimated to run out) as well as the frequency at which the user wishes to receive notification 9074 (such as, for example, once a day, once a week, or any other period of time).

FIG. 10N further illustrates detecting a tap gesture with contact 9524 on electronic refill affordance 9086 to refill LMN medication. In some embodiments, device 100 automatically initiates the electronic refill process after detecting a tap gesture with contact on electronic refill affordance 9086. In such embodiments, in response to detecting the tap gesture with contact 9524 on electronic refill affordance 9086 in FIG. 10N, device 100 displays notification 9076 in FIG. 10O indicating that an electronic refill request has been processed. In other embodiments, device 100, in response to detecting the tap gesture, displays a user interface through which the user may initiate the electronic refill process.

Figure 10P:
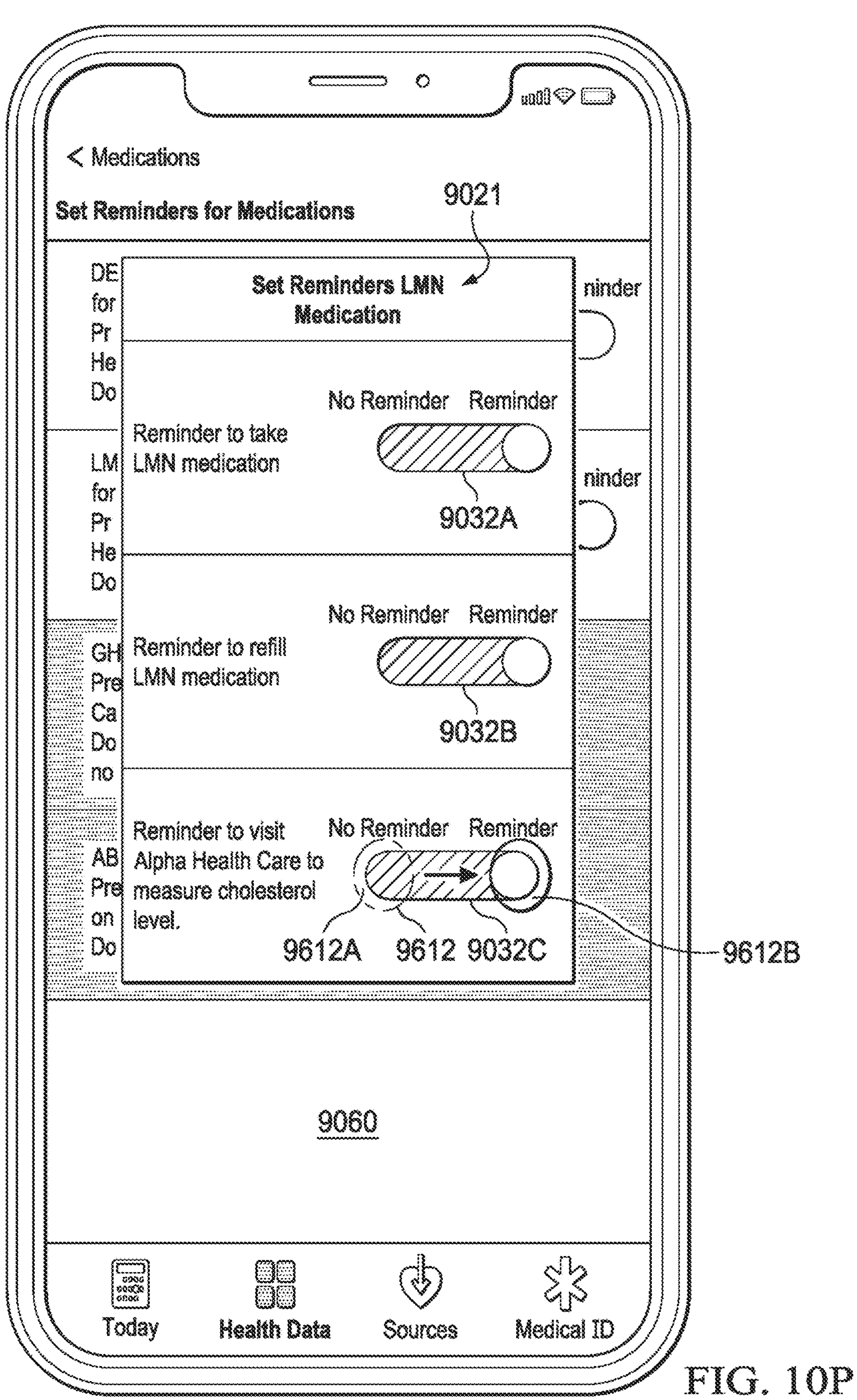
Figure 10Q:
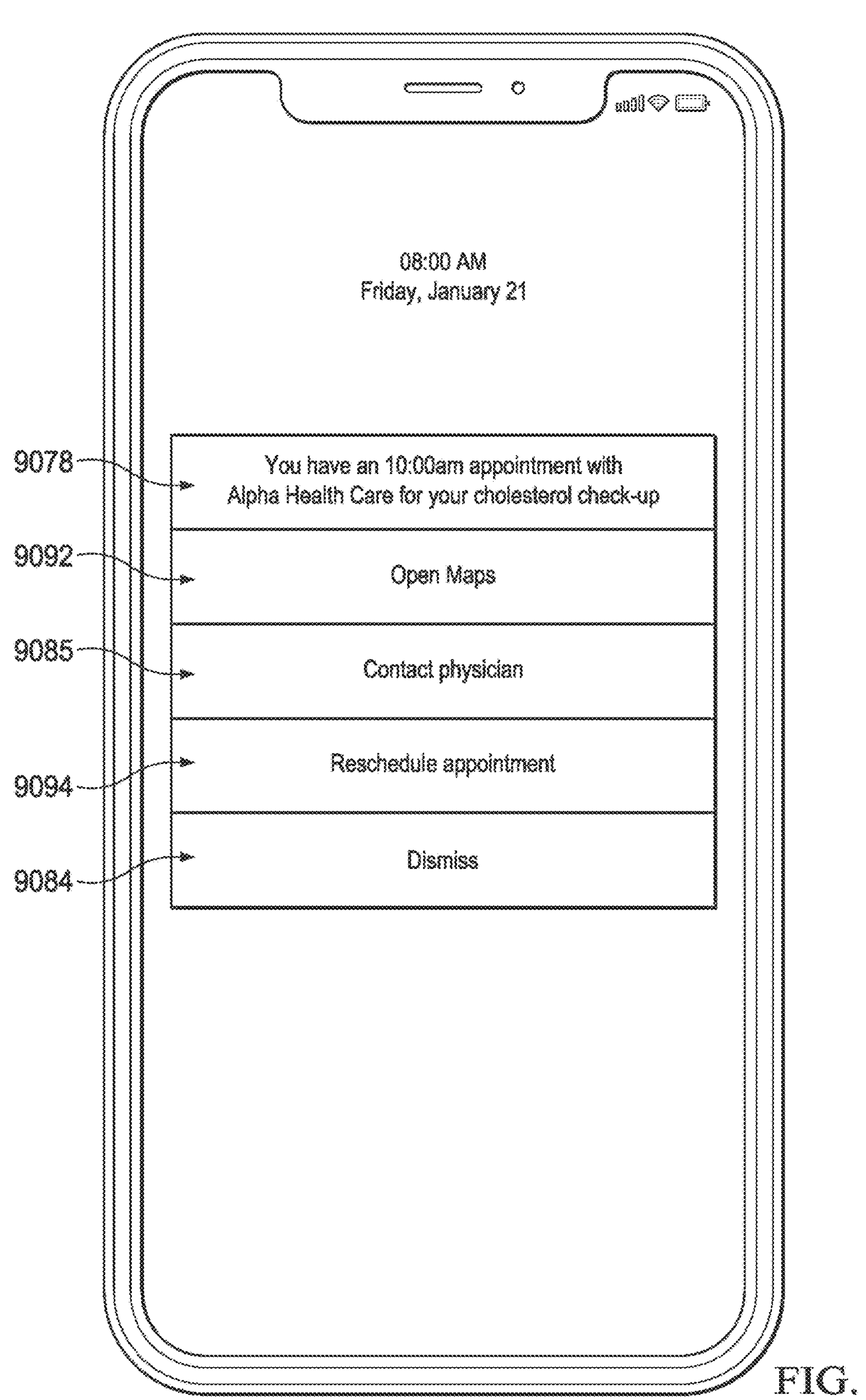

Similar to FIG. 10M, FIG. 10P illustrates displaying set reminders notification 9021 overlaid on a portion of user interface 9060. FIG. 10P further illustrates detecting a swipe gesture with contact 9612 on reminder toggle 9032C and movement of contact from position 9612A to position 9612B to set a reminder to visit Alpha Health Care at the time of a scheduled appointment. Alternatively, a reminder may be set to remind the user at a later time to schedule an appointment.

FIG. 10Q illustrates displaying a notification 9078 reminding the user about an upcoming appointment with (a physician at) Alpha Health Care in response to the user setting an appointment reminder as described in FIG. 10P. Notification 9078 contains multiple affordances that the user may interact with to obtain directions to the location of the appointment, contact a physician regarding the upcoming appointment, or reschedule the upcoming appointment. In the illustrated embodiment, the user may select maps affordance 9092 to open a map affordance containing directions to Alpha Health Care. The user may select contact physician affordance 9085 to contact the physician to discuss preparations for the upcoming appointment. Further, the user may select a reschedule appointment affordance 9094 to reschedule a time of the upcoming appointment. The user may also select dismiss affordance 9084 to dismiss notification 9078. In some embodiments, notification 9078 contains other types of affordances that the user may interact with to perform other tasks related to the upcoming appointment. In some embodiments, the user may designate a time to receive notification 9078 (such as one hour before the scheduled appointment). In other embodiments, where the user has not designated a time to receive notification 9078, device 100 automatically determines a time to display notification 9078. In one or more of such embodiments, device 100 delays notification 9078 or determines a time for notification 9078 based on the user's schedule. In other embodiments, where device 100 is authorized by the user to track the user's location, device 100 calculates an expected travel time from the user's current location to the location of the appointment. Device 100 then adds a threshold time as a cushion, deducts the expected travel time and threshold time from the appointment time to calculate a notification time, and displays notification 9078 at or before the notification time.

FIGS. 11A-11E are flow diagrams illustrating a method for using an electronic device to display a health record manager that allows the user to designate the status of and manage activities associated with certain health records through the health record manager in accordance with some embodiments. More particularly, FIGS. 11A-11E are flow diagrams illustrating a method for displaying a health record manager of the user, using, for example, the user interfaces of FIGS. 10A-10Q. As described in reference to FIGS. 10A-10Q, method 1100 can be utilized to display a health record manager that allows the user to designate the status of certain health records. Method 1100 is performed at a device, (e.g., device 100, 300, 500 illustrated in FIGS. 1, 3, and 5A respectively). In one of such embodiments, display 112 is a touch screen display and the touch-sensitive surface is on or integrated with display 112. In some embodiments, display 112 is separate from the touch-sensitive surface. In other embodiments, the processes described herein may be implemented with devices having physical user-interfaces, voice interfaces, or other suitable interfaces. Some operations in the method 1100 are, optionally, combined. Additionally, the order of some operations is, optionally, changed.

As described below, method 1100 provides an intuitive way for displaying a health record manager that allows the user to designate the status of and manage activities associated with certain health records through the health record manager. Optionally, health records designated by the user as inactive are hidden from a dashboard user interface of the health record manager, but are displayed in other user interfaces that contain more detailed information about the user's health records. The user may interact with inactive health records to update the status of the inactive health records. The method reduces the cognitive burden on a user by allowing the user to differentiate between active health records and inactive health records, thereby creating a more efficient human-machine interface. The method also increases efficiency of the user by allowing the user to quickly differentiate between active health records and inactive health records and by providing the user with reminders about certain health records of the user. For battery-operated computing devices, enabling a user to browse through the user's active and inactive health records faster and more efficiently conserves power and increases the time between battery charges.

Device 100, while being is associated with one or more health care providers of a user, displays (1102) a first representation of a first ongoing health condition of a plurality of ongoing health conditions of the user indicated by health record information from the one or more health care providers, where the plurality of ongoing health conditions include a second ongoing health condition and a third ongoing health condition. FIGS. 10A and 10B, for example, show four health condition records 9016A-9016D (anxiety disorder, asthma, high cholesterol, and migraines).

Device 100, while displaying the first representation of the first ongoing health condition, receives (1104), via the one or more input devices, a request to mark the first ongoing health condition as inactive for the user. FIG. 10B, for example, shows a swipe gesture with contact with contact 9602 on status toggle 9022D (for migraines) and movement of contact from position 9602A to position 9602B to designate migraines as an inactive health condition. The swipe gesture is detected by device 100 and causes device 100 to perform actions illustrated in FIGS. 10C and 10D.

Device 100, after receiving the request to mark the first ongoing health condition as inactive, receives (1106), via the one or more input devices, a request to display ongoing health conditions for the user. FIGS. 10D and 10E for example, show detecting a tap gesture with contact 9510 on health record summary affordance 5308 and, in response to the tap gesture, displaying an updated health record summary on display 112. The tap gesture illustrated in FIG. 10D is one example of a request to display ongoing health conditions.

Device 100, in response to receiving the request to display ongoing health conditions for the user, concurrently displays (1108), on display 112, a second representation of the second ongoing health condition of the user from the plurality of ongoing health conditions indicated by health record information from the one or more health care providers and a third representation of the third ongoing health condition of the user from the plurality of ongoing health conditions indicated by health record information from the one or more health care providers without displaying the first representation of the first ongoing health condition of the user as an active health condition. FIG. 10E for example, shows concurrently displaying health condition records 9016A (anxiety disorder), 9016B (asthma), and 9016C (high cholesterol) without displaying health condition record 9016D (migraine) illustrated in FIG. 10A, which was designated by the user as an inactive health record.

In some embodiments, device 100, in response to receiving the request to mark the first ongoing health condition as inactive, displays (1110), on display 112, a visual indication that the first ongoing health condition as inactive. In some embodiments, where an inactive health condition is not displayed in the health record summary, device 100 displays an inactive health record affordance (not shown), which is an affordance the user interacts with to view inactive health records, or a similar affordance that the user interacts with to view inactive health records in the health record summary. In other embodiments, the health record summary includes a badge or another item that indicates one or more health records have been marked inactive and are not displayed in the health record summary. In one or more of such embodiments, a badge is appended to health metrics affordance 9011A of FIG. 10A if the inactive health record is a health metric record, is appended to medications affordance 9011B of FIG. 10A if the inactive health record is a medication record, or is appended to health conditions affordance 9011C of FIG. 10A if the inactive health record is a health condition record. In one or more embodiments, the badge contains a numerical value that indicates the number of inactive health records belonging to a category or the total number of inactive health records. The method reduces the cognitive burden on a user by allowing the user to keep track of inactive health records that are not displayed in a user interface. The method also increases efficiency of the user by allowing the user to quickly determine the status of health records displayed in a user interface and to determine whether certain health records of the user have been designated as inactive health records, thereby creating a more efficient human-machine interface.

Device 100, in response to receiving the request to display the plurality of ongoing health conditions for the user, concurrently displays (1112), on display 112 the visual indication that the first ongoing health condition is inactive, the second ongoing health condition of the user, and the third ongoing health condition of the user. In some embodiments, the view inactive health record affordance and the badge described in the foregoing paragraph is displayed in the health record summary illustrated in FIG. 10E with health condition records 9016A-9016C (anxiety disorder, asthma, and high cholesterol, respectively). The method reduces the cognitive burden on a user by keeping track of the current status of the health record, thereby creating a more efficient human-machine interface. The method avoids the need to navigate through multiple user interfaces to obtain active health records. The method also increases efficiency of the user by allowing the user to quickly determine the current status of the user's health records. For battery-operated computing devices, allowing the user to determine the status of the user's health records faster and more efficiently conserves power and increases the time between battery charges.

Device 100, after receiving the request to mark the first ongoing health condition as inactive, receives (1114), via the one or more input devices, a second request to mark the first health condition as active. In some embodiments, while health condition record 9016D (migraines) illustrated in FIG. 10D is marked as an inactive record, the user performs a swipe gesture with contact on status toggle 9022D (for migraines) and movement of contact in a direction that toggles status toggle 9022D from an inactive designation to an active designation. In some embodiments, device 100, in response to receiving the second request to mark the first health condition as active, updates (1114) the first representation of the first ongoing health condition to indicate that the first ongoing health condition is active. Continuing with the foregoing example, device 100, in response to detecting inputs containing the swipe gesture to toggle status toggle 9022D from an inactive designation to an active designation, updates health condition record 9016D as an active health condition.

In some embodiments, device 100, after updating the first representation of the first ongoing health condition as active, receives (1114) a second request to display the plurality of ongoing health conditions for the user. FIG. 10G, for example, shows a tap gesture with contact 9516 over health record summary affordance 5308. In some embodiments, device 100, in response to receiving the second request to display the plurality of ongoing health conditions for the user, concurrently displays (1114), on display 112, a representation of the updated first ongoing health condition, the second representation of the second ongoing health condition, and the third representation of the third ongoing health condition. Continuing with the foregoing example, where 9016D (migraines) has been marked as an active health condition, health records 9016A (anxiety disorder), 9016C (high cholesterol), and 9016D would be concurrently displayed in the health record summary illustrated in FIG. 10H.

In some embodiments, device 100, in response to receiving the request to mark the first ongoing health condition as inactive, sends (1116), to a computer system associated with a health care provider that is associated with the first ongoing health condition, with information indicative of an inactive status of the first ongoing health condition. In some embodiments, device 100, after detecting inputs including the swipe gesture illustrated in FIG. 10B, transmits, to a computer system of Alpha Health Care, an indication that health condition record 9016D (migraines) illustrated in FIG. 10B has been designated as an inactive record. The method reduces a need for the user to communicate with a health care provider about the status of a health record updated by the user, thereby reducing the strain on existing network, which frees up communications systems, reduces bandwidth on networks, and preserves energy. The method also increases efficiency of the user by automatically providing the status of a health record to an electronic system of a health care provider, thereby creating a more efficient human-machine interface.

In some embodiments, device 100, after receiving an update to the first ongoing health condition, receives (1118), via the one or more input devices, a third request to display ongoing health conditions for the user. In some embodiments, while health condition record 9016D (migraines) is designated as an inactive health record, device 100 receives a request from the user to update the status of health condition record 9016D. In other embodiments, device 100 receives an update from a health care provider updating the status of the health record (such as updating the prescription of a previously expired prescription for a medication). In some embodiments, device 100, in response to receiving the third request to display the plurality of ongoing health conditions for the user, concurrently displays (1118), on display 112, a representation of the updated first ongoing health condition, the second representation of the second ongoing health condition, and the third representation of the third ongoing health condition. Continuing with the foregoing example, where 9016D has been marked as an active health condition, health records 9016A (anxiety disorder), 9016C (high cholesterol), and 9016D would be concurrently displayed in the health record summary illustrated in FIG. 10H. The method reduces the cognitive burden on a user by keeping track of updates to health records. The method also increases efficiency of the user by allowing the user to quickly determine the current status of the user's health records, thereby creating a more efficient human-machine interface. For battery-operated computing devices, allowing the user to determine the status of the user's health records faster and more efficiently conserves power and increases the time between battery charges.

In some embodiments, device 100, in response to receiving the update to the first ongoing health condition, marks (1120) the first ongoing health condition as an active health condition. Continuing with the foregoing examples, device 100, in response to receiving an update from the user or from the health care provider associated with the ongoing health condition (Alpha Health Care), marks health condition record 9016D (migraines) as an active health record. The method reduces the cognitive burden on a user by displaying, in response to a user input, an updated status of an ongoing health condition. For battery-operated computing devices, allowing a user to review the user's up-to-date health records faster and more efficiently conserves power and increases the time between battery charges.

In some embodiments, device 100, in response to receiving the update to the first ongoing health condition, sends (1122) the update to a computer system associated with a health care provider that is associated with the first ongoing health condition. In some embodiments, device 100, after receiving an update provided by the user, transmits, to a computer system of Alpha Health Care, an indication that health condition record 9016D (migraines) has been updated. In other embodiments, device 100 also transmits data indicative of the update to the computer system. The method reduces a need for the user to communicate with a health care provider about the status of a health record updated by the user, thereby reducing the strain on the existing network, which frees up communications systems, reduces bandwidth on networks, and preserves energy. The method also increases efficiency of the user by automatically providing the status of a health record to an electronic system of a health care provider, thereby creating a more efficient human-machine interface.

In some embodiments, device 100, in response to a determination of a set of dates associated with the second ongoing health condition, displays (1124), on display 112, a notification regarding the second ongoing health condition on each date of the set of dates. FIG. 10L, for example, shows displaying notification 9072 reminding the user to take LMN medication after detecting the swipe gesture illustrated in FIG. 10K. In the embodiment of FIG. 10L, where the recommended dosage is two tablets every six hours, device 100 displays notification 9072 on display 112 at least once a day, every day. The method reduces the cognitive burden on a user by keeping track of a set of days associated with the health condition and by automatically displaying the notification on the days associated with the health condition. The method also increases efficiency of the user by helping the user keep track of days associated with the health condition, and by automatically providing notifications on the days associated with the health condition, thereby creating a more efficient human-machine interface.

In some embodiments, the set of dates associated with the second ongoing health condition includes a first date, where the first date is a date on which a prescription for the second ongoing health condition is scheduled to be refilled, and where the notification includes a reminder to refill the prescription (1126). FIG. 10N, for example, shows displaying a notification 9074 reminding the user to refill LMN medication after detecting the swipe gesture illustrated in FIG. 10M. In the illustrated embodiment, notification 9074 is provided to the user one week prior to the date LMN medication is scheduled to run out. In other embodiments, where a refill request has been processed, a similar notification reminding the user to pick up LMN medication is displayed on the scheduled pick up date. The method reduces the cognitive burden on a user by anticipating when a medication is below a threshold. The method also increases efficiency of the user by helping the user to determine when to refill a prescription, thereby creating a more efficient human-machine interface. The method also reduces the strain on an electronic system of a health care provider tasked to remind the user to refill the user's prescription, thereby freeing up communication systems, reducing bandwidth on networks, and preserving energy.

In some embodiments, device 100 anticipates (1128) a date when a remaining amount of a prescription for the second ongoing health condition will be below a threshold, where the set of dates associated with the second ongoing health condition includes a second date, where the second date is a date on which the prescription is anticipated to be below a threshold, and where the notification includes a reminder to refill the prescription. In some embodiments, device 100 keeps track of the remaining dosage of LMN medication. In the embodiment of FIG. 10L, device 100, in response to detecting a tap gesture over task complete affordance 9082, subtracts the recommended dosage from the remaining dosage. In other embodiments, device 100 assumes that the user takes the recommended dosage and estimates the remaining amount based on the recommended dosage. FIG. 10N, for example, shows displaying notification 9074 reminding the user to refill LMN medication after detecting the swipe gesture illustrated in FIG. 10M. In the illustrated embodiment, notification 9074 is provided to the user one week prior to the date LMN medication is scheduled to run out. In the illustrated example, the threshold is the amount of LMN medication that would last the user for more than one week. The method reduces the cognitive burden on a user by anticipating when a medication is below a threshold and automatically transmits a request to the health care provider to refill the prescription. The method also increases efficiency of the user by automatically submitting a request to refill a prescription without requiring the user to keep track of the remaining amount of the prescription, thereby creating a more efficient human-machine interface. Reducing the amount of time a user needs to spend on their device reduces power usages and improves battery life of the device.

In some embodiments, device 100, requests (1130), on the second date, a health care provider of the one or more health care providers to refill the prescription, where the health care provider is associated with the second ongoing health condition. FIG. 10N, for example, shows displaying notification 9074 reminding the user to refill LMN medication after detecting the swipe gesture illustrated in FIG. 10M. In the illustrated embodiment, notification 9074 is provided to the user one week prior to the date LMN medication is scheduled to run out. In the illustrated embodiment, device 100 requests the health care provider to refill LMN prescription in response to detecting the gesture illustrated in FIG. 10N over electronic refill affordance 9086. In other embodiments, device 100 automatically initiates a request to refill LMN medication. The method reduces the cognitive burden on a user by automatically requesting a health care provider to refill a prescription. The method also increases efficiency of the user by reducing a need for the user to communicate with the health care provider, thereby creating a more efficient human-machine interface. For battery-operated computing devices, automatically requesting the health care provider to fill a prescription reduces a need for the user to use the device to perform such task via the device, thereby conserving power and increasing the time between battery charges.

In some embodiments, device 100, receives (1132), via the one or more input devices, an update to a remaining amount of a prescription for the second ongoing health condition. In some embodiments, device 100 periodically queries the user to provide an estimate of the amount of remaining prescription medication. In some embodiments, device 100, in accordance with a determination that the remaining amount of the prescription is below a threshold, displays (1132), on display 112, a notification to refill the prescription. In some embodiments, notification 9074 illustrated in FIG. 10N is displayed in response to a determination that a user inputted amount of remaining medication is under the threshold (such as less than or equal to one week). The method reduces the cognitive burden on a user by helping the user keep track of the remaining amount of the user's prescription, thereby creating a more efficient human-machine interface. The method also increases efficiency of the user by helping the user to determine when to refill a prescription, thereby creating a more efficient human-machine interface. The method also reduces the strain on an electronic system of a health care provider tasked to remind the user to refill the user's prescription, thereby freeing up communication systems, reducing bandwidth on networks, and preserving energy. For battery-operated computing devices, allowing the user to determine the remaining amount of a prescription faster and more efficiently conserves power and increases the time between battery charges.

In some embodiments, the set of dates associated with the second ongoing health condition includes a third date, where the third date is a scheduled date to visit a health care provider of the one or more health care providers, and where the health care provider is associated with the second ongoing health condition (1134). FIG. 10Q, for example, shows displaying notification 9078 reminding the user about a scheduled appointment with Alpha Health Care on the date of the appointment. The method reduces the cognitive burden on a user by keeping track of an upcoming appointment with a health care provider. The method also reduces power usage and improves battery life of the device by reducing the likelihood that the device would need to perform additional tasks to re-schedule an appointment with the health care provider. The method further reduces the need for the health care provider to remind the user about the upcoming appointment or to contact the user regarding a missed appointment, thereby freeing up communications systems, reducing bandwidth on networks, and preserving energy.

In some embodiments, device 100, displays (1136), on display 112, a first reminder affordance associated with the second ongoing health condition. FIG. 10K, for example, shows displaying reminder toggle 9032A to set up a reminder to take LMN medication. In some embodiments, device 100, while displaying the first reminder affordance, receives (1136), via the one or more input devices, a request to select the first reminder affordance. FIG. 10K, for example, further illustrates detecting the swipe gesture with contact 9608 on reminder toggle 9032A and movement of contact from position 9608A to position 9608B to set up a reminder to take LMN medication. The method reduces the cognitive burden on a user by helping a user set up reminder about a health condition of the user and by helping the user keep track of the health condition. The method also increases efficiency of the user by helping the user keep track of health condition, thereby creating a more efficient human-machine interface. The method also reduces the likelihood that the user forgets about the health condition, and reduces the likelihood that the user will experience complications caused by ignoring the health condition. For battery-operated computing devices, allowing the user to helping the user keep track of a health condition easier and more efficiently conserves power and increases the time between battery charges.

In some embodiments, device 100, in accordance with a determination that a reminder associated with the second ongoing health condition is also associated with a time, displays (1137), on display 112, and at the time, a notification regarding the reminder associated with the second ongoing health condition. In some embodiments, the user designates a time (such as 10:00 am) to receive reminders to take LMN medication. Device 100 then displays notifications to take LMN medication at the designated time. FIG. 10L, for example, shows displaying notification 9072 to take LMN medication at 10:00 am. The method reduces the cognitive burden on a user by reminding the user when to take the medication. The method also increases efficiency of the user by helping the user keep track of when to take the medication, thereby creating a more efficient human-machine interface. The method also reduces the likelihood that the user forgets to take the medication, or takes the medication at the wrong time, and reduces the likelihood that the user will experience complications caused by not taking the medication. For battery-operated computing devices, allowing the user to determine when to take the medication faster and more efficiently conserves power and increases the time between battery charges.

In some embodiments, the reminder associated with the second ongoing health condition is a recurring reminder associated with an interval of time at which the user is instructed to take a prescription for the second ongoing health condition, and where the notification is a reminder to take a prescribed dosage of the prescription (1138). In the illustrated embodiment of FIG. 10L, LMN medication is scheduled to be taken every day. As such, notification 9072 to take LMN medication is a recurring notification. In some embodiments, notification 9072 is displayed on display 112 at 10:00 am and at 4:00 pm each day. The method reduces the cognitive burden on a user by reminding the user when to take the medication. The method also increases efficiency of the user by helping the user keep track of when to take the medication, thereby creating a more efficient human-machine interface. The method also reduces the likelihood that the user forgets to take the medication, or takes the medication at the wrong time, and reduces the likelihood that the user will experience complications caused by not taking the medication. For battery-operated computing devices, allowing the user to determine when to take the medication faster and more efficiently conserves power and increases the time between battery charges.

In some embodiments, the notification includes a second reminder affordance associated with the reminder (1140). In some embodiments, reminder affordance is an affordance the user selects to indicate that the user has taken the prescribed dosage. Notification 9072 contains task complete affordance 9072. Device 100, receives (1140), via the one or more input devices, a request to select the second reminder affordance. FIG. 10L, for example, shows detecting a tap gesture with contact 9522 on task complete affordance 9082. Device 100, in response to receiving the request to select the second reminder affordance, calculates a remaining amount of the prescription (1140). In some embodiments, device 100 automatically keeps track of the amount of remaining LMN medication. In one of such embodiments, device 100, in response to detecting the gesture illustrated in FIG. 10L, automatically deducts the amount of remaining LMN medication by the prescribed dosage (two tablets). In some embodiments, device 100, in accordance with a determination that the remaining amount of the prescription is below a threshold, displays (1140), on display 112, a second notification regarding the second ongoing health condition, where the second notification is a reminder to refill the prescription. In some embodiments, device 100, after determining that the remaining amount of LMN prescription is below the threshold (more than one week of supply), displays notification 9074 illustrated in FIG. 10N to remind the user to refill LMN medication. The method reduces the cognitive burden on a user by helping the user keep track of the remaining amount of the user's prescription, thereby creating a more efficient human-machine interface. The method also increases efficiency of the user by helping the user to determine when to refill a prescription, thereby creating a more efficient human-machine interface. The method also reduces the strain on an electronic system of a health care provider tasked to remind the user to refill the user's prescription, thereby freeing up communication systems, reducing bandwidth on networks, and preserving energy. For battery-operated computing devices, allowing the user to determine the remaining amount of a prescription faster and more efficiently conserves power and increases the time between battery charges.

In some embodiments, the user is a patient and device 100 is a device of the patient. Device 100 is a user device. In some embodiments, device 100 is the device of a patient. In some embodiments, while the patient device is associated with one or more health care providers of the patient, device 100 displays (1142) on display 112 of the patient device, the first representation of the first ongoing health condition. FIGS. 10A and 10B, for example, show four health condition records 9016A-9016D (anxiety disorder, asthma, high cholesterol, and migraines, respectively). In some embodiments, device 100, while displaying the representation of the first ongoing health condition on the patient device, receives (1142) from the patient, via the one or more input devices, a request from the patient to mark the first ongoing health condition as inactive for the patient. FIG. 10B, for example, shows a swipe gesture with contact 9602 on status toggle 9022D (for migraines) and movement of contact from position 9602A to position 9602B to designate migraines as an inactive health condition. The swipe gesture is detected by device 100 and causes device 100 to perform actions illustrated in FIGS. 10C and 10D.

In some embodiments, device 100, after receiving the request from the patient to mark the first ongoing health condition as inactive, receives (1142), via the one or more input devices, a request from the patient to display ongoing health conditions for the patient. FIGS. 10D and 10E for example, show detecting a tap gesture with contact 9510 on health record summary affordance 5308 and, in response to the tap gesture, displaying an updated health record summary on display 112. The tap gesture illustrated in FIG. 10D is one example of a request to display ongoing health conditions. In some embodiments, device 100, in response to receiving the request from the patient to display ongoing health conditions for the patient, concurrently displays (1142), on display 112 of the patient device, the second representation of the second ongoing health condition and the third representation of the third ongoing health condition, without displaying the representation of the first ongoing health condition. FIG. 10E for example, shows concurrently displaying health condition records 9016A, 9016B, and 9016C (anxiety disorder, asthma, and high cholesterol, respectively) without displaying health condition record 9016D (migraines), which was designated by the user as an inactive health record. The method reduces the cognitive burden on a patient by allowing the patient to differentiate between active health records and inactive health records, thereby creating a more efficient human-machine interface. For battery-operated computing devices, enabling a patient to browse through the user's active and inactive health records faster and more efficiently conserves power and increases the time between battery charges.

The particular order in which the operations in FIGS. 11A-11E have been described is merely exemplary and is not intended to indicate that the described order is the only order in which the operations could be performed. One of ordinary skill in the art would recognize various ways to reorder the operations described herein. Additionally, details of the processes described above with respect to method 1100 (e.g., FIGS. 11A-11E) are also applicable in an analogous manner to the methods described above. For example, methods 700 and 900 optionally include one or more of the characteristics of the various methods described above with reference to method 1100. For example, the methods for displaying health records designated by the user as active or inactive described above with reference to 1100 are optionally used by method 700 to display aggregated health records, and are optionally used by method 900 to display health records in dashboard user interfaces. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. A method, comprising:

at an electronic device with a display and one or more input devices:

while the electronic device is associated with a first health care provider and not associated with a second health care provider, receiving, via the one or more input devices, a first request to display health records of a first user of the electronic device;

in response to receiving the first request to display health records of the first user, displaying, on the display, a plurality of categories of health records, including:

a first representation of a first category of the plurality of categories, wherein selection of the first representation of the first category while the electronic device is associated with the first health care provider and not associated with the second health care provider causes the electronic device to display, on the display:

a plurality of health records in the first category from the first health care provider; and a graph indicative of a health condition of the first user over a period of time based on data from the first health care provider; and a second representation of a second category of the plurality of categories, wherein selection of the second representation of the second category while the electronic device is associated with the first health care provider and not associated with the second health care provider causes the electronic device to display, on the display, a plurality of health records in the second category from the first health care provider;

after displaying the plurality of categories of health records and after the electronic device is associated with the second health care provider, receiving, via the one or more input devices, a second request to display health records of the first user;

in response to receiving the second request to display health records of the first user, displaying, on the display, the plurality of categories of health records, including:

the first representation of the first category of the plurality of categories, wherein selection of the first representation of the first category while the electronic device is associated with the first health care provider and the second health care provider causes the electronic device to display, on the display:

one or more health records in the first category from the first health care provider and one or more health records in the first category from the second health care provider; and a second graph indicative of the health condition of the first user over a second period of time based on the data from the first health care provider and data from the second health care provider; and the second representation of the second category of the plurality of categories, wherein selection of the second representation of the second category while the electronic device is associated with the first health care provider and the second health care provider causes the electronic device to display, on the display, one or more health records in the second category from the first health care provider and one or more health records in the second category from the second health care provider;

receiving an update to a health record of the first category of the plurality of categories, wherein the update to the health record of the first category includes a first update from the first health care provider, and wherein the update to the health record of the first category includes a second update from the second health care provider;

after receiving the update to the health record of the first category, displaying, on the display, a first update badge associated with the first category of the plurality of categories and a second update badge associated with at least two categories of the plurality of categories, wherein the first update badge, the second update badge, and the first representation of the first category of the plurality of categories are concurrently displayed in a first region of the display;

while concurrently displaying the first update badge associated with the first category of the plurality of categories, the second update badge associated with the at least two categories of the plurality of categories, and the first representation of the first category of the plurality of categories, receiving, via the one or more input devices, a request to select the first update badge associated with the first category; and in response to receiving the request to select the first update badge associated with the first category:

ceasing to display the first representation of the first category of the plurality of categories that was displayed concurrently with the first update badge and the second update badge; and displaying, on the display, the update to the health record of the first category of the plurality of categories, wherein displaying, on the display, the update to the health record comprises concurrently displaying the first update from the first health care provider and the second update from the second health care provider.

2. The method of claim 1, further comprising:

receiving, via the one or more input devices, a first selection of the first representation of the first category, in response to receiving the first selection, displaying, on the display, a plurality of subcategories of health records of the first category, including:

a first representation of a first subcategory of the first category, wherein selection of the first representation of the first subcategory of the first category causes the electronic device to display, on the display, a plurality of health records in the first subcategory of the first category from the first health care provider; and a second representation of a second subcategory of the first category, wherein selection of the second representation of the second subcategory of the first category causes the electronic device to display, on the display, a plurality of health records in the second subcategory of the first category from the first health care provider.

3. The method of claim 1, wherein health records of a first type are displayed in a first color and health records of a second type are displayed in a second color that is different from the first color.

4. The method of claim 1, wherein displaying, on the display, the plurality of categories of health records further comprises:

displaying, on the display, first content summarizing the first category and a first category information affordance associated with the first category, wherein selection of the first category information affordance causes the electronic device to display, on the display, additional content associated with the first category that is not included in the first content; and displaying, on the display, second content summarizing the second category and a second category information affordance of the second category, wherein selection of the second category information affordance causes the electronic device to display, on the display, additional content associated with the second category that is not included in the second content.

5. The method of claim 1, wherein:

the plurality of health records in the first category are displayed in a chronological order; and the plurality of health records in the second category are displayed in a chronological order.

6. The method of claim 1, wherein:

the plurality of health records in the first category from the first health care provider comprise a first health record in the first category from the first health care provider and a second health record in the first category from the first health care provider, the plurality of health records in the second category from the first health care provider comprise a third health record in the second category from the first health care provider and a fourth health record in the second category from the first health care provider, the first health record in the first category from the first health care provider and the third health record in the second category from the first health care provider are records of a first visit to the first health care provider, the second health record in the first category from the first health care provider and the fourth health record in the second category from the first health care provider are records of a second visit to the first health care provider, and the method further comprises:

in response to receiving the first request to display health records of the first user, concurrently displaying, on the display, the first health record and the third health record in a first group, wherein the first group is identified on the display by a first date of the first visit; and in response to receiving the first request to display health records of the first user, concurrently displaying, on the display, the second health record and the fourth health record in a second group, wherein the second group is identified on the display by a second date of the second visit, wherein the first date is different from the second date.

7. The method of claim 6, wherein:

the one or more health records in the first category from the second health care provider comprise a fifth health record in the first category from the second health care provider, the one or more of health records in the second category from the second health care provider comprise a sixth health record in the second category from the second health care provider, the fifth health record in the first category from the second health care provider and the sixth health record in the second category from the second health care provider are records of a third visit to the second health care provider, and the method further comprises:

in response to receiving the second request to display health records of the first user, concurrently displaying, on the display, the fifth health record and the sixth health record in a third group, wherein:

the third group is identified on the display by a third date of the third visit to the second health care provider, and the first group, the second group, and the third group are concurrently displayed on the display.

8. The method of claim 6, wherein:

the first health record in the first category from the first health care provider and the second health record in the first category from the first health care provider are displayed in a first color, and the third health record in the second category from the first health care provider and the fourth health record in the second category from the first health care provider are displayed in a second color that is different from the first color.

9. The method of claim 1, further comprising:

in response to receiving the first request to display health records of the first user, displaying, on the display, first content identifying an identity and location of the first health care provider; and in response to receiving the second request to display health records of the first user, displaying, on the display, second content identifying an identity and location of the second health care provider.

10. The method of claim 1, including:

detecting selection of the first representation of the first category while the electronic device is associated with the first health care provider; and in response to detecting the selection of the first representation of the first category while the electronic device is associated with the first health care provider displaying, on the display, a second representation of a second health record of the plurality of health records in the first category from the first health care provider, wherein:

the second representation of the second health record comprises a numerical value within a range of numerical values, and the numerical value is indicative of the health condition of the first user, and wherein the range of numerical values is indicative of normal range of values for the health condition.

11. The method of claim 10, further comprising:

displaying the numerical value with a color selected based on a severity of the health condition of the first user.

12. The method of claim 1, further comprising:

displaying a third representation of a third health record of the plurality of health records in the first category from the first health care provider, wherein the third representation of the third health record comprises an image indicative of a medical record of the first user.

13. The method of claim 1, wherein the first update badge is visually associated with the first representation of the first category.

14. The method of claim 1, wherein selection of the first representation of the first category while the electronic device is associated with the first health care provider causes the electronic device to display, on the display, a representation of a health record of the first category of the plurality of categories, and wherein the first update badge is visually associated with the representation of the health record of the first category of the plurality of categories.

15. The method of claim 1, wherein displaying, on the display, the first update badge comprises displaying content of the update to a health record on the first update badge.

16. The method of claim 1, further comprising:

in response to receiving the update to the health record:

in accordance with a determination that a significance of the update is greater than a threshold value, displaying, on the display, a notification of the update; and in accordance with a determination that a significance of the update is less than the threshold value, forgoing displaying, on the display, the notification of the update.

17. The method of claim 1, wherein selection of the first representation of the first category while the electronic device is associated with the first health care provider and not associated with the second health care provider causes the electronic device to display, on the display, historical health records associated with the first category from the first health care provider, and wherein the historical health records associated with the first category comprise the plurality of health records in the first category from the first health care provider, wherein selection of the second representation of the second category while the electronic device is associated with the first health care provider and not associated with the second health care provider causes the electronic device to display, on the display, historical health records associated with the second category from the first health care provider, and wherein the historical health records associated with the second category comprise the plurality of health records in the second category from the first health care provider, wherein selection of the first representation of the first category while the electronic device is associated with the first health care provider and the second health care provider causes the electronic device to display, on the display, historical health records associated with the first category from the first health care provider and the second health care provider, and wherein the historical health records associated with the first category comprise the one or more health records in the first category from the first health care provider and the one or more health records in the first category from the second health care provider, and wherein selection of the second representation of the second category while the electronic device is associated with the first health care provider and the second health care provider causes the electronic device to display, on the display, historical health records associated with the second category from the first health care provider and from the second health care provider, and wherein the historical health records associated with the second category are the one or more health records in the second category from the first health care provider and the one or more health records in the second category from the second health care provider.

18. An electronic device, comprising:

a display;

one or more input devices;

one or more processors;

a memory; and one or more programs, wherein the one or more programs are stored in the memory and configured to be executed by the one or more processors, the one or more programs including instructions for:

while the electronic device is associated with a first health care provider and not associated with a second health care provider, receiving, via the one or more input devices, a first request to display health records of a first user of the electronic device;

in response to receiving the first request to display health records of the first user, displaying, on the display, a plurality of categories of health records, including:

a first representation of a first category of the plurality of categories, wherein selection of the first representation of the first category while the electronic device is associated with the first health care provider and not associated with the second health care provider causes the electronic device to display, on the display:

a plurality of health records in the first category from the first health care provider; and a graph indicative of a health condition of the first user over a period of time based on data from the first health care provider; and a second representation of a second category of the plurality of categories, wherein selection of the second representation of the second category while the electronic device is associated with the first health care provider and not associated with the second health care provider causes the electronic device to display, on the display, a plurality of health records in the second category from the first health care provider;

after displaying the plurality of categories of health records and after the electronic device is associated with the second health care provider, receiving, via the one or more input devices, a second request to display health records of the first user;

in response to receiving the second request to display health records of the first user, displaying, on the display, the plurality of categories of health records, including:

the first representation of the first category of the plurality of categories, wherein selection of the first representation of the first category while the electronic device is associated with the first health care provider and the second health care provider causes the electronic device to display, on the display:

one or more health records in the first category from the first health care provider and one or more health records in the first category from the second health care provider; and a second graph indicative of the health condition of the first user over a second period of time based on the data from the first health care provider and data from the second health care provider; and the second representation of the second category of the plurality of categories, wherein selection of the second representation of the second category while the electronic device is associated with the first health care provider and the second health care provider causes the electronic device to display, on the display, one or more health records in the second category from the first health care provider and one or more health records in the second category from the second health care provider;

receiving an update to a health record of the first category of the plurality of categories, wherein the update to the health record of the first category includes a first update from the first health care provider, and wherein the update to the health record of the first category includes a second update from the second health care provider;

after receiving the update to the health record of the first category, displaying, on the display, a first update badge associated with the first category of the plurality of categories and a second update badge associated with at least two categories of the plurality of categories, wherein the first update badge, the second update badge, and the first representation of the first category of the plurality of categories are concurrently displayed in a first region of the display;

while concurrently displaying the first update badge associated with the first category of the plurality of categories, the second update badge associated with the at least two categories of the plurality of categories, and the first representation of the first category of the plurality of categories, receiving, via the one or more input devices, a request to select the first update badge associated with the first category; and in response to receiving the request to select the first update badge associated with the first category:

ceasing to display the first representation of the first category of the plurality of categories that was displayed concurrently with the first update badge and the second update badge; and displaying, on the display, the update to the health record of the first category of the plurality of categories, wherein displaying, on the display, the update to the health record comprises concurrently displaying the first update from the first health care provider and the second update from the second health care provider.

19. A non-transitory computer readable storage medium storing one or more programs, the one or more programs comprising instructions which, when executed by one or more processors of an electronic device with a display and one or more input devices, cause the electronic device to:

while the electronic device is associated with a first health care provider and not associated with a second health care provider, receive, via the one or more input devices, a first request to display health records of a first user of the electronic device;

in response to receiving the first request to display health records of the first user, display, on the display, a plurality of categories of health records, including:

a first representation of a first category of the plurality of categories, wherein selection of the first representation of the first category while the electronic device is associated with the first health care provider and not associated with the second health care provider causes the electronic device to display, on the display:

a plurality of health records in the first category from the first health care provider; and a graph indicative of a health condition of the first user over a period of time based on data from the first health care provider; and a second representation of a second category of the plurality of categories, wherein selection of the second representation of the second category while the electronic device is associated with the first health care provider and not associated with the second health care provider causes the electronic device to display, on the display, a plurality of health records in the second category from the first health care provider;

after displaying the plurality of categories of health records and after the electronic device is associated with the second health care provider, receive, via the one or more input devices, a second request to display health records of the first user;

in response to receiving the second request to display health records of the first user, display, on the display, the plurality of categories of health records, including:

the first representation of the first category of the plurality of categories, wherein selection of the first representation of the first category while the electronic device is associated with the first health care provider and the second health care provider causes the electronic device to display, on the display:

one or more health records in the first category from the first health care provider and one or more health records in the first category from the second health care provider; and a second graph indicative of the health condition of the first user over a second period of time based on the data from the first health care provider and data from the second health care provider; and the second representation of the second category of the plurality of categories, wherein selection of the second representation of the second category while the electronic device is associated with the first health care provider and the second health care provider causes the electronic device to display, on the display, one or more health records in the second category from the first health care provider and one or more health records in the second category from the second health care provider;

receive an update to a health record of the first category of the plurality of categories, wherein the update to the health record of the first category includes a first update from the first health care provider, and wherein the update to the health record of the first category includes a second update from the second health care provider;

after receiving the update to the health record of the first category, display, on the display, a first update badge associated with the first category of the plurality of categories and a second update badge associated with at least two categories of the plurality of categories, wherein the first update badge, the second update badge, and the first representation of the first category of the plurality of categories are concurrently displayed in a first region of the display;

while concurrently displaying the first update badge associated with the first category of the plurality of categories, the second update badge associated with the at least two categories of the plurality of categories, and the first representation of the first category of the plurality of categories, receive, via the one or more input devices, a request to select the first update badge associated with the first category; and in response to receiving the request to select the first update badge associated with the first category:

cease to display the first representation of the first category of the plurality of categories that was displayed concurrently with the first update badge and the second update badge; and display, on the display, the update to the health record of the first category of the plurality of categories, wherein displaying, on the display, the update to the health record comprises concurrently displaying the first update from the first health care provider and the second update from the second health care provider.

20. The electronic device of claim 18, the one or more programs further including instructions for:

receiving, via the one or more input devices, a first selection of the first representation of the first category, in response to receiving the first selection, displaying, on the display, a plurality of subcategories of health records of the first category, including:

a first representation of a first subcategory of the first category, wherein selection of the first representation of the first subcategory of the first category causes the electronic device to display, on the display, a plurality of health records in the first subcategory of the first category from the first health care provider; and a second representation of a second subcategory of the first category, wherein selection of the second representation of the second subcategory of the first category causes the electronic device to display, on the display, a plurality of health records in the second subcategory of the first category from the first health care provider.

21. The electronic device of claim 18, wherein health records of a first type are displayed in a first color and health records of a second type are displayed in a second color that is different from the first color.

22. The electronic device of claim 18, wherein displaying, on the display, the plurality of categories of health records further comprises:

displaying, on the display, first content summarizing the first category and a first category information affordance associated with the first category, wherein selection of the first category information affordance causes the electronic device to display, on the display, additional content associated with the first category that is not included in the first content; and displaying, on the display, second content summarizing the second category and a second category information affordance of the second category, wherein selection of the second category information affordance causes the electronic device to display, on the display, additional content associated with the second category that is not included in the second content.

23. The electronic device of claim 18, wherein:

the plurality of health records in the first category are displayed in a chronological order; and the plurality of health records in the second category are displayed in a chronological order.

24. The electronic device of claim 18, wherein:

the plurality of health records in the first category from the first health care provider comprise a first health record in the first category from the first health care provider and a second health record in the first category from the first health care provider, the plurality of health records in the second category from the first health care provider comprise a third health record in the second category from the first health care provider and a fourth health record in the second category from the first health care provider, the first health record in the first category from the first health care provider and the third health record in the second category from the first health care provider are records of a first visit to the first health care provider, the second health record in the first category from the first health care provider and the fourth health record in the second category from the first health care provider are records of a second visit to the first health care provider, and the one or more programs further including instructions for:

in response to receiving the first request to display health records of the first user, concurrently displaying, on the display, the first health record and the third health record in a first group, wherein the first group is identified on the display by a first date of the first visit; and in response to receiving the first request to display health records of the first user, concurrently displaying, on the display, the second health record and the fourth health record in a second group, wherein the second group is identified on the display by a second date of the second visit, wherein the first date is different from the second date.

25. The electronic device of claim 24, wherein:

the one or more health records in the first category from the second health care provider comprise a fifth health record in the first category from the second health care provider, the one or more health records in the second category from the second health care provider comprise a sixth health record in the second category from the second health care provider, the fifth health record in the first category from the second health care provider and the sixth health record in the second category from the second health care provider are records of a third visit to the second health care provider, and the one or more programs further including instructions for:

in response to receiving the second request to display health records of the first user, concurrently displaying, on the display, the fifth health record and the sixth health record in a third group, wherein:

the third group is identified on the display by a third date of the third visit to the second health care provider, and the first group, the second group, and the third group are concurrently displayed on the display.

26. The electronic device of claim 24, wherein:

the first health record in the first category from the first health care provider and the second health record in the first category from the first health care provider are displayed in a first color, and the third health record in the second category from the first health care provider and the fourth health record in the second category from the first health care provider are displayed in a second color that is different from the first color.

27. The electronic device of claim 18, the one or more programs further including instructions for:

in response to receiving the first request to display health records of the first user, displaying, on the display, first content identifying an identity and location of the first health care provider; and in response to receiving the second request to display health records of the first user, displaying, on the display, second content identifying an identity and location of the second health care provider.

28. The electronic device of claim 18, including:

detecting selection of the first representation of the first category while the electronic device is associated with the first health care provider; and in response to detecting the selection of the first representation of the first category while the electronic device is associated with the first health care provider displaying, on the display, a second representation of a second health record of the plurality of health records in the first category from the first health care provider, wherein:

the second representation of the second health record comprises a numerical value within a range of numerical values, and the numerical value is indicative of the health condition of the first user, and wherein the range of numerical values is indicative of normal range of values for the health condition.

29. The electronic device of claim 28, the one or more programs further including instructions for:

displaying the numerical value with a color selected based on a severity of the health condition of the first user.

30. The electronic device of claim 18, the one or more programs further including instructions for:

displaying a third representation of a third health record of the plurality of health records in the first category from the first health care provider, wherein the third representation of the third health record comprises an image indicative of a medical record of the first user.

31. The electronic device of claim 18, wherein the first update badge is visually associated with the first representation of the first category.

32. The electronic device of claim 18, wherein selection of the first representation of the first category while the electronic device is associated with the first health care provider causes the electronic device to display, on the display, a representation of a health record of the first category of the plurality of categories, and wherein the first update badge is visually associated with the representation of the health record of the first category of the plurality of categories.

33. The electronic device of claim 18, wherein displaying, on the display, the first update badge comprises displaying content of the update to a health record on the first update badge.

34. The electronic device of claim 18, the one or more programs further including instructions for:

in response to receiving the update to the health record:

in accordance with a determination that a significance of the update is greater than a threshold value, displaying, on the display, a notification of the update; and in accordance with a determination that a significance of the update is less than the threshold value, forgoing displaying, on the display, the notification of the update.

35. The electronic device of claim 18, wherein selection of the first representation of the first category while the electronic device is associated with the first health care provider and not associated with the second health care provider causes the electronic device to display, on the display, historical health records associated with the first category from the first health care provider, and wherein the historical health records associated with the first category comprise the plurality of health records in the first category from the first health care provider, wherein selection of the second representation of the second category while the electronic device is associated with the first health care provider and not associated with the second health care provider causes the electronic device to display, on the display, historical health records associated with the second category from the first health care provider, and wherein the historical health records associated with the second category comprise the plurality of health records in the second category from the first health care provider, wherein selection of the first representation of the first category while the electronic device is associated with the first health care provider and the second health care provider causes the electronic device to display, on the display, historical health records associated with the first category from the first health care provider and the second health care provider, and wherein the historical health records associated with the first category comprise the one or more health records in the first category from the first health care provider and the one or more health records in the first category from the second health care provider, and wherein selection of the second representation of the second category while the electronic device is associated with the first health care provider and the second health care provider causes the electronic device to display, on the display, historical health records associated with the second category from the first health care provider and from the second health care provider, and wherein the historical health records associated with the second category are the one or more health records in the second category from the first health care provider and the one or more health records in the second category from the second health care provider.

36. The non-transitory computer readable storage medium of claim 19, the one or more programs further comprising instructions which cause the electronic device to:

receive, via the one or more input devices, a first selection of the first representation of the first category, in response to receiving the first selection, display, on the display, a plurality of subcategories of health records of the first category, including:

a first representation of a first subcategory of the first category, wherein selection of the first representation of the first subcategory of the first category causes the electronic device to display, on the display, a plurality of health records in the first subcategory of the first category from the first health care provider; and a second representation of a second subcategory of the first category, wherein selection of the second representation of the second subcategory of the first category causes the electronic device to display, on the display, a plurality of health records in the second subcategory of the first category from the first health care provider.

37. The non-transitory computer readable storage medium of claim 19, wherein health records of a first type are displayed in a first color and health records of a second type are displayed in a second color that is different from the first color.

38. The non-transitory computer readable storage medium of claim 19, wherein displaying, on the display, the plurality of categories of health records further comprises:

displaying, on the display, first content summarizing the first category and a first category information affordance associated with the first category, wherein selection of the first category information affordance causes the electronic device to display, on the display, additional content associated with the first category that is not included in the first content; and displaying, on the display, second content summarizing the second category and a second category information affordance of the second category, wherein selection of the second category information affordance causes the electronic device to display, on the display, additional content associated with the second category that is not included in the second content.

39. The non-transitory computer readable storage medium of claim 19, wherein:

the plurality of health records in the first category are displayed in a chronological order; and the plurality of health records in the second category are displayed in a chronological order.

40. The non-transitory computer readable storage medium of claim 19, wherein:

the plurality of health records in the first category from the first health care provider comprise a first health record in the first category from the first health care provider and a second health record in the first category from the first health care provider, the plurality of health records in the second category from the first health care provider comprise a third health record in the second category from the first health care provider and a fourth health record in the second category from the first health care provider, the first health record in the first category from the first health care provider and the third health record in the second category from the first health care provider are records of a first visit to the first health care provider, the second health record in the first category from the first health care provider and the fourth health record in the second category from the first health care provider are records of a second visit to the first health care provider, and the one or more programs further comprising instructions which cause the electronic device to:

in response to receiving the first request to display health records of the first user, concurrently display, on the display, the first health record and the third health record in a first group, wherein the first group is identified on the display by a first date of the first visit; and in response to receiving the first request to display health records of the first user, concurrently display, on the display, the second health record and the fourth health record in a second group, wherein the second group is identified on the display by a second date of the second visit, wherein the first date is different from the second date.

41. The non-transitory computer readable storage medium of claim 40, wherein:

the one or more health records in the first category from the second health care provider comprise a fifth health record in the first category from the second health care provider, the one or more health records in the second category from the second health care provider comprise a sixth health record in the second category from the second health care provider, the fifth health record in the first category from the second health care provider and the sixth health record in the second category from the second health care provider are records of a third visit to the second health care provider, and the one or more programs further comprising instructions which cause the electronic device to:

in response to receiving the second request to display health records of the first user, concurrently display, on the display, the fifth health record and the sixth health record in a third group, wherein:

the third group is identified on the display by a third date of the third visit to the second health care provider, and the first group, the second group, and the third group are concurrently displayed on the display.

42. The non-transitory computer readable storage medium of claim 40, wherein:

the first health record in the first category from the first health care provider and the second health record in the first category from the first health care provider are displayed in a first color, and the third health record in the second category from the first health care provider and the fourth health record in the second category from the first health care provider are displayed in a second color that is different from the first color.

43. The non-transitory computer readable storage medium of claim 19, the one or more programs further comprising instructions which cause the electronic device to:

in response to receiving the first request to display health records of the first user, display, on the display, first content identifying an identity and location of the first health care provider; and in response to receiving the second request to display health records of the first user, display, on the display, second content identifying an identity and location of the second health care provider.

44. The non-transitory computer readable storage medium of claim 19, including:

detecting selection of the first representation of the first category while the electronic device is associated with the first health care provider; and in response to detecting the selection of the first representation of the first category while the electronic device is associated with the first health care provider displaying, on the display, a second representation of a second health record of the plurality of health records in the first category from the first health care provider, wherein:

the second representation of the second health record comprises a numerical value within a range of numerical values, and the numerical value is indicative of the health condition of the first user, and wherein the range of numerical values is indicative of normal range of values for the health condition.

45. The non-transitory computer readable storage medium of claim 44, the one or more programs further comprising instructions which cause the electronic device to:

display the numerical value with a color selected based on a severity of the health condition of the first user.

46. The non-transitory computer readable storage medium of claim 19, the one or more programs further comprising instructions which cause the electronic device to:

display a third representation of a third health record of the plurality of health records in the first category from the first health care provider, wherein the third representation of the third health record comprises an image indicative of a medical record of the first user.

47. The non-transitory computer readable storage medium of claim 19, wherein the first update badge is visually associated with the first representation of the first category.

48. The non-transitory computer readable storage medium of claim 19, wherein selection of the first representation of the first category while the electronic device is associated with the first health care provider causes the electronic device to display, on the display, a representation of a health record of the first category of the plurality of categories, and wherein the first update badge is visually associated with the representation of the health record of the first category of the plurality of categories.

49. The non-transitory computer readable storage medium of claim 19, wherein displaying, on the display, the first update badge comprises displaying content of the update to a health record on the first update badge.

50. The non-transitory computer readable storage medium of claim 19, the one or more programs further comprising instructions which cause the electronic device to:

in response to receiving the update to the health record:

in accordance with a determination that a significance of the update is greater than a threshold value, display, on the display, a notification of the update; and in accordance with a determination that a significance of the update is less than the threshold value, forgo displaying, on the display, the notification of the update.

51. The non-transitory computer readable storage medium of claim 19, wherein selection of the first representation of the first category while the electronic device is associated with the first health care provider and not associated with the second health care provider causes the electronic device to display, on the display, historical health records associated with the first category from the first health care provider, and wherein the historical health records associated with the first category comprise the plurality of health records in the first category from the first health care provider, wherein selection of the second representation of the second category while the electronic device is associated with the first health care provider and not associated with the second health care provider causes the electronic device to display, on the display, historical health records associated with the second category from the first health care provider, and wherein the historical health records associated with the second category comprise the plurality of health records in the second category from the first health care provider, wherein selection of the first representation of the first category while the electronic device is associated with the first health care provider and the second health care provider causes the electronic device to display, on the display, historical health records associated with the first category from the first health care provider and the second health care provider, and wherein the historical health records associated with the first category comprise the one or more health records in the first category from the first health care provider and the one or more health records in the first category from the second health care provider, and wherein selection of the second representation of the second category while the electronic device is associated with the first health care provider and the second health care provider causes the electronic device to display, on the display, historical health records associated with the second category from the first health care provider and from the second health care provider, and wherein the historical health records associated with the second category are the one or more health records in the second category from the first health care provider and the one or more health records in the second category from the second health care provider.

* * * * *